(12) United States Patent
Campbell

(10) Patent No.: US 10,150,764 B2
(45) Date of Patent: Dec. 11, 2018

(54) SUBSTITUTED BENZENE COMPOUNDS

(71) Applicant: Epizyme, Inc., Cambridge, MA (US)

(72) Inventor: John Emmerson Campbell, Cambridge, MA (US)

(73) Assignee: Epizyme, Inc., Cambridge, MA (US)

( * ) Notice: Subject to any disclaimer, the term of this patent is extended or adjusted under 35 U.S.C. 154(b) by 0 days.

(21) Appl. No.: 14/904,801

(22) PCT Filed: Jul. 18, 2014

(86) PCT No.: PCT/US2014/047238
§ 371 (c)(1),
(2) Date: Jan. 13, 2016

(87) PCT Pub. No.: WO2015/010049
PCT Pub. Date: Jan. 22, 2015

(65) Prior Publication Data
US 2016/0194316 A1  Jul. 7, 2016

Related U.S. Application Data

(60) Provisional application No. 61/856,512, filed on Jul. 19, 2013, provisional application No. 61/953,305, filed on Mar. 14, 2014.

(51) Int. Cl.

| | | |
|---|---|---|
| *C07D 471/04* | (2006.01) | |
| *C07D 231/20* | (2006.01) | |
| *C07D 413/12* | (2006.01) | |
| *C07D 405/12* | (2006.01) | |
| *C07D 413/14* | (2006.01) | |
| *C07D 405/14* | (2006.01) | |
| *C07D 487/04* | (2006.01) | |
| *C07D 231/30* | (2006.01) | |
| *C07D 498/04* | (2006.01) | |

(52) U.S. Cl.
CPC ......... *C07D 471/04* (2013.01); *C07D 231/20* (2013.01); *C07D 231/30* (2013.01); *C07D 405/12* (2013.01); *C07D 405/14* (2013.01); *C07D 413/12* (2013.01); *C07D 413/14* (2013.01); *C07D 487/04* (2013.01); *C07D 498/04* (2013.01)

(58) Field of Classification Search
CPC .. C07D 471/04; C07D 231/20; C07D 231/30; C07D 405/12; C07D 413/12; C07D 413/14; C07D 487/04; C07D 498/04; C07D 405/14

USPC .......................................................... 544/106
See application file for complete search history.

(56) References Cited

U.S. PATENT DOCUMENTS

| | | | |
|---|---|---|---|
| 8,410,088 B2 | 4/2013 | Kuntz et al. | |
| 8,598,167 B1 | 12/2013 | Kuntz et al. | |
| 8,765,732 B2 | 7/2014 | Kuntz et al. | |
| 8,962,620 B2 | 2/2015 | Kuntz et al. | |
| 9,006,242 B2 | 4/2015 | Kuntz et al. | |
| 9,045,477 B2 | 6/2015 | Campbell et al. | |
| 9,089,575 B2 | 7/2015 | Kuntz et al. | |
| 9,090,562 B2 | 7/2015 | Kuntz et al. | |
| 9,206,157 B2 | 12/2015 | Kuntz et al. | |
| 9,243,001 B2 | 1/2016 | Campbell et al. | |
| 2009/0163545 A1* | 6/2009 | Goldfarb ............. | A61K 31/122 514/312 |
| 2014/0142083 A1 | 5/2014 | Kuntz et al. | |
| 2014/0352119 A1 | 12/2014 | Kaltenrieder et al. | |
| 2015/0065483 A1 | 3/2015 | Kuntz et al. | |
| 2015/0353494 A1 | 12/2015 | Kuntz et al. | |
| 2016/0022693 A1 | 1/2016 | Kuntz et al. | |
| 2016/0024081 A1 | 1/2016 | Campbell et al. | |
| 2016/0031907 A1 | 2/2016 | Campbell et al. | |

FOREIGN PATENT DOCUMENTS

| | | | | |
|---|---|---|---|---|
| DE | 1197464 B | * | 7/1965 | .......... C07D 231/50 |
| ES | 458604 A1 | * | 2/1978 | |
| WO | WO 2012/118812 A2 | | 9/2012 | |
| WO | WO 2012/142504 A1 | | 10/2012 | |
| WO | WO 2012/142513 A1 | | 10/2012 | |
| WO | WO 2014/062732 A1 | | 4/2014 | |
| WO | WO 2014/144747 A1 | | 9/2014 | |
| WO | WO 2014/172044 A1 | | 10/2014 | |

OTHER PUBLICATIONS

Segura-Cabrera et al., Integrative computational protocol for the discovery of inhibitors of the Helicobacter pylori nickel response regulator (NikR), 2011, J Mol Model, 17:3075-3084.*

* cited by examiner

*Primary Examiner* — Kristin A Vajda
(74) *Attorney, Agent, or Firm* — Cooley LLP; Heidi A. Erlacher; Xixi Sun

(57) ABSTRACT

The present invention relates to substituted benzene compounds. The present invention also relates to pharmaceutical compositions containing these compounds and methods of treating cancer by administering these compounds and pharmaceutical compositions to subjects in need thereof. The present invention also relates to the use of such compounds for research or other non-therapeutic purposes.

19 Claims, No Drawings
Specification includes a Sequence Listing.

SUBSTITUTED BENZENE COMPOUNDS

RELATED APPLICATIONS

This application is a U.S. National Phase application, filed under 35 U.S.C. § 371, of International Application No. PCT/US2014/047238, filed Jul. 18, 2014, which claims priority to, and the benefit of, U.S. provisional application Nos. 61/856,512, filed Jul. 19, 2013, and 61/953,305, filed Mar. 14, 2014, the contents of each of which are incorporated herein by reference in their entireties.

INCORPORATION-BY-REFERENCE OF SEQUENCE LISTING

The contents of the text file named "EPIZ-025N01US-ST25.txt", which was created on Jan. 7, 2015 and is 2 KB in size, are hereby incorporated by reference in their entireties.

BACKGROUND OF THE INVENTION

There is an ongoing need for new agents as inhibitors of EZH2, which can be used for treating an EZH2-mediated disorder (e.g., cancer).

SUMMARY OF THE INVENTION

In one aspect, the present invention features a substituted benzene compound of Formula (I) below or a pharmaceutically acceptable salt thereof.

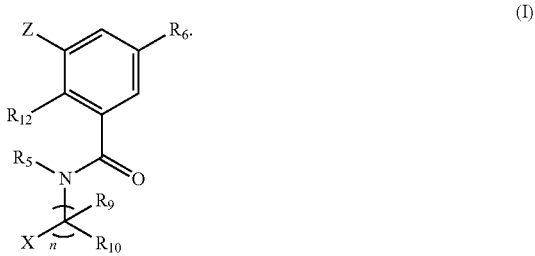

In this Formula,
X is

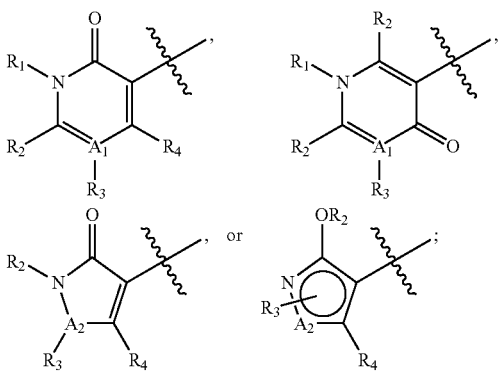

$A_1$ is C or N and when $A_1$ is N, $R_3$ is absent;
$A_2$ is N, O, or S and when $A_2$ is O or S, $R_3$ is absent;
Z is $NR_7R_8$, $OR_7$, $S(O)_aR_7$, or $CR_7R_8R_{14}$, in which a is 0, 1, or 2;

$R_1$ is $-Q_0-T_0$, in which $Q_0$ is $NR_{1a}$, O or S, $R_{1a}$ being H, OH, $C_1-C_6$ alkyl, or $C_1-C_6$ alkoxyl, and $T_0$ is H or $R_{S0}$, in which $R_{S0}$ is $C_1-C_6$ alkyl, $C_2-C_6$ alkenyl, $C_2-C_6$ alkynyl, $C_3-C_8$ cycloalkyl, $C_6-C_{10}$ aryl, 4 to 12-membered heterocycloalkyl, or 5- or 6-membered heteroaryl, and $R_{S0}$ is optionally substituted with one or more substituents selected from the group consisting of halo, hydroxyl, oxo, C(O)OH, C(O)O—$C_1-C_6$ alkyl, cyano, $C_1-C_6$ alkyl, $C_1-C_6$ alkoxyl, amino, mono-$C_1-C_6$ alkylamino, di-$C_1-C_6$ alkylamino, $C_3-C_8$ cycloalkyl, $C_6-C_{10}$ aryl, 4 to 12-membered heterocycloalkyl, and 5- or 6-membered heteroaryl;

each of $R_2$, $R_3$, and $R_4$, independently, is -$Q_1$-$T_1$, in which $Q_1$ is a bond or $C_1-C_3$ alkyl linker optionally substituted with halo, cyano, hydroxyl or $C_1-C_6$ alkoxy, and $T_1$ is H, halo, hydroxyl, C(O)OH, cyano, azido, or $R_{S1}$, in which $R_{S1}$ is $C_1-C_3$ alkyl, $C_2-C_6$ alkenyl, $C_2-C_6$ alkynyl, $C_1-C_6$ alkoxyl, $C_1-C_6$ thioalkyl, C(O)O—$C_1-C_6$ alkyl, $CONH_2$, $SO_2NH_2$, —C(O)—NH($C_1-C_6$ alkyl), —C(O)—N($C_1-C_6$ alkyl)$_2$, —$SO_2$—NH($C_1-C_6$ alkyl), —$SO_2$—N($C_1-C_6$ alkyl)$_2$, $C_3-C_8$ cycloalkyl, $C_6-C_{10}$ aryl, $C_6-C_{10}$ aryloxy, amino, mono-$C_1$-$C_6$ alkylamino, di-$C_1-C_6$ alkylamino, 4 to 12-membered heterocycloalkyl, or 5- or 6-membered heteroaryl, and $R_{S1}$ is optionally substituted with one or more substituents selected from the group consisting of halo, hydroxyl, oxo, C(O)OH, C(O)O—$C_1-C_6$ alkyl, cyano, $C_1-C_6$ alkyl, $C_1-C_6$ alkoxyl, amino, mono-$C_1-C_6$ alkylamino, di-$C_1-C_6$ alkylamino, $C_3-C_8$ cycloalkyl, $C_6-C_{10}$ aryl, 4 to 12-membered heterocycloalkyl, and 5- or 6-membered heteroaryl; or neighboring $R_1$ and $R_2$, together with the atoms to which they are attached, form a 5- or 6-membered heteroaryl having 0 to 2 additional heteroatoms or a 5 to 12-membered heterocycloalkyl ring having 0 to 2 additional heteroatoms; or neighboring $R_1$ and $R_4$, together with the atoms to which they are attached, form a 5- or 6-membered heteroaryl having 0 to 2 additional heteroatoms or a 5 to 12-membered heterocycloalkyl ring having 0 to 2 additional heteroatoms; or neighboring $R_2$ and $R_3$, together with the atoms to which they are attached, form $C_5-C_8$ cycloalkyl, $C_6-C_{10}$ aryl, or a 5- or 6-membered heteroaryl having 1 to 3 heteroatoms, or a 5 to 12-membered heterocycloalkyl ring having 1 to 3 heteroatoms; or neighboring $R_3$ and $R_4$, together with the atoms to which they are attached, form $C_5-C_8$ cycloalkyl, $C_6-C_{10}$ aryl, or a 5- or 6-membered heteroaryl having 1 to 3 heteroatoms, or a 5 to 12-membered heterocycloalkyl ring having 1 to 3 heteroatoms; in which each of the ring structures formed by $R_1$ and $R_2$, by $R_1$ and $R_4$, by $R_2$ and $R_3$, or by $R_3$ and $R_4$, independently is optionally substituted with one or more substituents selected from the group consisting of halo, hydroxyl, oxo, $C_1-C_6$ alkyl, $C_1-C_6$ haloalkyl, C(O)OH, C(O)O—$C_1-C_6$ alkyl, C(O)O—$C_1-C_6$ haloalkyl, cyano, $C_1-C_6$ alkoxyl, $C_1-C_6$ haloalkoxyl, amino, mono-$C_1-C_6$ alkylamino, di-$C_1-C_6$ alkylamino, $C_3-C_8$ cycloalkyl, $C_6-C_{10}$ aryl, 4 to 12-membered heterocycloalkyl, and 5- or 6-membered heteroaryl;

each of $R_5$, $R_9$, and $R_{10}$, independently, is H or $C_1-C_6$ alkyl optionally substituted with one or more substituents selected from the group consisting of halo, hydroxyl, COOH, C(O)O—$C_1-C_6$ alkyl, cyano, $C_1-C_6$ alkoxyl, amino, mono-$C_1-C_6$ alkylamino, di-$C_1-C_6$ alkylamino, $C_3-C_8$ cycloalkyl, $C_6-C_{10}$ aryl, 4 to 12-membered heterocycloalkyl, and 5- or 6-membered heteroaryl;

$R_6$ is H, halo, cyano, azido, $OR_a$, —$NR_aR_b$, —$C(O)R_a$, —$C(O)OR_a$, —$C(O)NR_aR_b$, —$NR_bC(O)R_a$, —$S(O)_bR_a$, —$S(O)_bNR_aR_b$, or $R_{S2}$, in which $R_{S2}$ is $C_1-C_6$ alkyl, $C_2-C_6$ alkenyl, $C_2-C_6$ alkynyl, $C_3-C_8$ cycloalkyl, $C_6-C_{10}$ aryl, 5- or 6-membered heteroaryl, or 4 to 12-membered heterocycloalkyl, b is 0, 1, or 2, each of $R_a$ and $R_b$, independently is H or $R_{S3}$, and $R_{S3}$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 12-membered heterocycloalkyl, or 5- or 6-membered heteroaryl; or $R_a$ and $R_b$, together with the N atom to which they are attached, form a 4 to 12-membered heterocycloalkyl ring having 0 or 1 additional heteroatom; and each of $R_{S2}$, $R_{S3}$, and the 4 to 12-membered heterocycloalkyl ring formed by $R_a$ and $R_b$, is optionally substituted with one or more -$Q_2$-$T_2$, wherein $Q_2$ is a bond or $C_1$-$C_3$ alkyl linker each optionally substituted with halo, cyano, hydroxyl or $C_1$-$C_6$ alkoxy, and $T_2$ is H, halo, cyano, —$OR_c$, —$NR_cR_d$, —$C(O)R_c$, —$C(O)OR_c$, —$C(O)NR_cR_d$, —$NR_dC(O)R_c$, —$NR_dC(O)OR_c$, —$S(O)_2R_c$, —$S(O)_2NR_cR_d$, or $R_{S4}$, in which each of $R_c$ and $R_d$, independently is H or $R_{S5}$, each of $R_{S4}$ and $R_{S5}$, independently, is $C_1$-$C_6$ alkyl, $C_3$-$C_8$ cycloalkyl, $C_6$-$C_{10}$ aryl, 4 to 12-membered heterocycloalkyl, or 5- or 6-membered heteroaryl, or $R_c$ and $R_d$, together with the N atom to which they are attached, form a 4 to 12-membered heterocycloalkyl ring having 0 or 1 additional heteroatom, and each of $R_{S4}$, $R_{S5}$, and the 4 to 12-membered heterocycloalkyl ring formed by $R_c$ and $R_d$, is optionally substituted with one or more -$Q_3$-$T_3$, wherein $Q_3$ is a bond or $C_1$-$C_3$ alkyl linker each optionally substituted with halo, cyano, hydroxyl or $C_1$-$C_6$ alkoxy, and $T_3$ is selected from the group consisting of H, halo, cyano, $C_1$-$C_6$ alkyl, $C_3$-$C_8$ cycloalkyl, $C_6$-$C_{10}$ aryl, 4 to 12-membered heterocycloalkyl, 5- or 6-membered heteroaryl, $OR_e$, $C(O)OR_e$, —$S(O)_2R_e$, —$NR_eR_f$, and —$C(O)NR_eR_f$, each of $R_e$ and $R_f$ independently being H or $C_1$-$C_6$ alkyl optionally substituted with OH, O—$C_1$-$C_6$ alkyl, or NH—$C_1$-$C_6$ alkyl, or -$Q_3$-$T_3$ is oxo; or -$Q_2$-$T_2$ is oxo; or any two neighboring -$Q_2$-$T_2$, when $R_6$ is $C_6$-$C_{10}$ aryl or 5- or 6-membered heteroaryl, together with the atoms to which they are attached form a 5- or 6-membered ring optionally containing 1-4 heteroatoms selected from N, O and S and optionally substituted with one or more substituents selected from the group consisting of halo, hydroxyl, C(O)OH, C(O)O—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl;

$R_7$ is -$Q_4$-$T_4$, in which $Q_4$ is a bond, $C_1$-$C_4$ alkyl linker, or $C_2$-$C_4$ alkenyl linker, each linker optionally substituted with halo, cyano, hydroxyl or $C_1$-$C_6$ alkoxy, and $T_4$ is H, halo, cyano, $NR_gR_h$, —$OR_g$, —$C(O)R_g$, —$C(O)OR_g$, —$C(O)NR_gR_h$, —$C(O)NR_gOR_h$, —$NR_gC(O)R_h$, —$S(O)_2R_g$, or $R_{S6}$, in which each of $R_g$ and $R_h$, independently is H or $R_{S7}$, each of $R_{S6}$ and $R_{S7}$, independently is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 14-membered heterocycloalkyl, or 5- or 6-membered heteroaryl, and each of $R_{S6}$ and $R_{S7}$ is optionally substituted with one or more -$Q_5$-$T_5$, wherein $Q_5$ is a bond, C(O), C(O)$NR_k$, $NR_kC(O)$, $NR_k$, $S(O)_2$, $NR_kS(O)_2$, or $C_1$-$C_3$ alkyl linker, $R_k$ being H or $C_1$-$C_6$ alkyl, and $T_5$ is H, halo, $C_1$-$C_6$ alkyl, $C_2$-$C_6$ alkenyl, $C_2$-$C_6$ alkynyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_1$-$C_6$ alkylene-$C_3$-$C_8$ cycloalkyl, $C_6$-$C_{10}$ aryl, $C_1$-$C_6$ alkylene-$C_6$-$C_{10}$ aryl, 4 to 12-membered heterocycloalkyl, $C_1$-$C_6$ alkylene-4 to 12-membered heterocycloalkyl, 5- or 6-membered heteroaryl, $C_1$-$C_6$ alkylene-5- or 6-membered heteroaryl, or $S(O)_qR_q$ in which q is 0, 1, or 2 and $R_q$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 12-membered heterocycloalkyl, or 5- or 6-membered heteroaryl, and $T_5$ is optionally substituted with one or more substituents selected from the group consisting of halo, $C_1$-$C_6$ alkyl, hydroxyl, cyano, $C_1$-$C_6$ alkoxyl, O—$C_1$-$C_4$ alkylene-$C_1$-$C_4$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl except when $T_5$ is H, halo, hydroxyl, or cyano; or -Q-$T_5$ is oxo;

each of $R_8$, and $R_{12}$, independently, is H, halo, hydroxyl, C(O)OH, cyano, $R_{S8}$, $OR_{S8}$, or $C(O)OR_{S8}$, in which $R_{S8}$ is $C_1$-$C_6$ alkyl, $C_2$-$C_6$ alkenyl, $C_2$-$C_6$ alkynyl, $C_3$-$C_8$ cycloalkyl, 4 to 12-membered heterocycloalkyl, amino, mono-$C_1$-$C_6$ alkylamino, or di-$C_1$-$C_6$ alkylamino, and $R_{S8}$ is optionally substituted with one or more substituents selected from the group consisting of halo, hydroxyl, C(O)OH, C(O)O—$C_1$-$C_6$ alkyl, cyano, $C_1$-$C_6$ alkoxyl, amino, mono-$C_1$-$C_6$ alkylamino, and di-$C_1$-$C_6$ alkylamino; or $R_7$ and $R_8$, together with the N atom to which they are attached, form a 4 to 12-membered heterocycloalkyl ring having 0 to 2 additional heteroatoms, or $R_7$ and $R_8$, together with the atom to which they are attached, form $C_3$-$C_8$ cycloalkyl or a 4 to 12-membered heterocycloalkyl ring having 1 to 3 heteroatoms, and each of the 4 to 12-membered heterocycloalkyl rings or $C_3$-$C_8$ cycloalkyl formed by $R_7$ and $R_8$ is optionally substituted with one or more -$Q_6$-$T_6$, wherein $Q_6$ is a bond, C(O), C(O)$NR_m$, $NR_mC(O)$, $S(O)_2$, or $C_1$-$C_3$ alkyl linker, $R_m$ being H or $C_1$-$C_6$ alkyl, and $T_6$ is H, halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, 5- or 6-membered heteroaryl, or $S(O)_pR_p$ in which p is 0, 1, or 2 and $R_p$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 12-membered heterocycloalkyl, or 5- or 6-membered heteroaryl, and $T_6$ is optionally substituted with one or more substituents selected from the group consisting of halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl except when $T_6$ is H, halo, hydroxyl, or cyano; or -$Q_6$-$T_6$ is oxo;

$R_{14}$ is absent, H, or $C_1$-$C_6$ alkyl optionally substituted with one or more substituents selected from the group consisting of halo, hydroxyl, C(O)OH, C(O)O—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl; and n is 0, 1, 2, 3, 4, or 5.

One subset of the compounds of Formula (I) includes those of Formula (Ia):

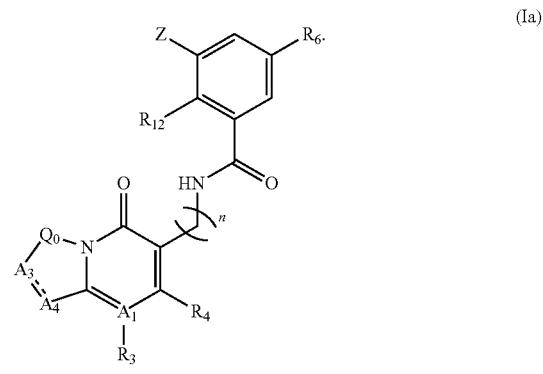

(Ia)

Another subset of the compounds of Formula (I) includes those of Formula (Ib):

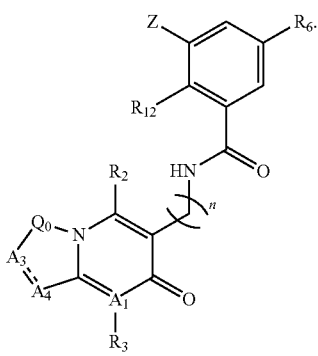

(Ib)

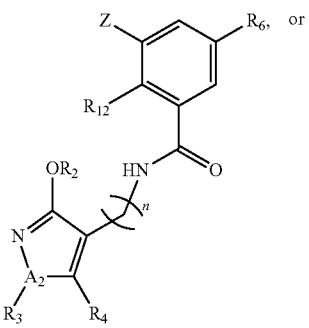

(Id1)

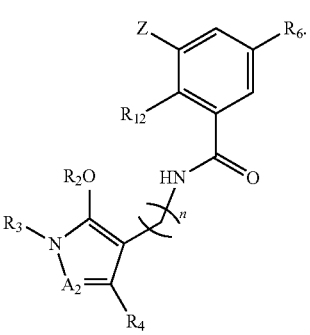

(Id2)

In each of Formulae (Ia) and (Ib), $Q_0$ is NH or O; ==== between $A_3$ and $A_4$ is a single or double bond; each of $A_3$ and $A_4$, independently, is $CR_{15}R_{16}$, $NR_{15}$, O, or S; each of $R_{15}$ and $R_{16}$, independently is absent, H, halo, hydroxyl, $C_1$-$C_6$ alkyl, $C_1$-$C_6$ haloalkyl, C(O)OH, C(O)O—$C_1$-$C_6$ alkyl, C(O)O—$C_1$-$C_6$ haloalkyl, cyano, $C_1$-$C_6$ alkoxyl, $C_1$-$C_6$ haloalkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, or 5- or 6-membered heteroaryl; and (i) when $Q_0$ is NH and ==== is a single bond, each of $A_3$ and $A_4$ independently is $CR_{15}R_{16}$, $NR_{15}$, O, or S; (ii) when $Q_0$ is NH and ==== is a double bond, each of $A_3$ and $A_4$ independently is $CR_{15}$ or N; (iii) when $Q_0$ is O and ==== is a single bond, each of $A_3$ and $A_4$ independently is $CR_{15}R_{16}$ or $NR_{15}$; or (iv) when $Q_0$ is O and ==== is a double bond, each of $A_3$ and $A_4$ independently is $CR_{15}$ or N.

Still another subset of the compounds of Formula (I) includes those of Formula (Ic):

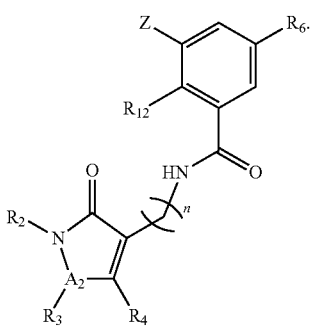

(Ic)

Still another subset of the compounds of Formula (I) includes those of Formula (Id), i.e., those of formula (Id1) or (Id2):

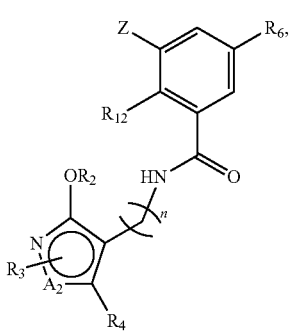

(Id)

In each of Formulae (Ic) and (Id), $A_2$ is N or O, and when $A_2$ is O, $R_3$ is absent; each of $R_2$, $R_3$, and $R_4$, independently, is -$Q_1$-$T_1$, in which $Q_1$ is a bond or $C_1$-$C_3$ alkyl linker optionally substituted with halo, and $T_1$ is H, halo, hydroxyl, C(O)OH, cyano, azido, or $R_{S1}$, in which $R_{S1}$ is $C_1$-$C_3$ alkyl, $C_1$-$C_6$ alkoxyl, $C_3$-$C_8$ cycloalkyl, $C_6$-$C_{10}$ aryl, $C_6$-$C_{10}$ aryloxy, amino, mono-$C_1$-$C_6$ alkylamino, di-$C_1$-$C_6$ alkylamino, 4 to 12-membered heterocycloalkyl, or 5- or 6-membered heteroaryl, and $R_{S1}$ is optionally substituted with one or more substituents selected from the group consisting of halo, hydroxyl, C(O)OH, C(O)O—$C_1$-$C_6$ alkyl, cyano, $C_1$-$C_6$ alkyl, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl; or neighboring $R_2$ and $R_3$, together with the atoms to which they are attached, form a 6 to 12-membered heterocycloalkyl ring having 2 to 3 heteroatoms; or neighboring $R_3$ and $R_4$, together with the atoms to which they are attached, form a 6-membered heteroaryl having 1 to 3 heteroatoms, or a 6 to 12-membered heterocycloalkyl ring having 1 to 3 heteroatoms; in which each of the ring structures formed by $R_2$ and $R_3$, or by $R_3$ and $R_4$, independently is optionally substituted with one or more substituents selected from the group consisting of halo, hydroxyl, oxo, $C_1$-$C_6$ alkyl, $C_1$-$C_6$ haloalkyl, cyano, $C_1$-$C_6$ alkoxyl, $C_1$-$C_6$ haloalkoxyl, amino, mono-$C_1$-$C_6$ alkylamino, or di-$C_1$-$C_6$ alkylamino.

The compounds of Formulae (I), (Ia), (Ib), (Ic) and (Id) can include one or more of the following features when applicable:

n is 1.
n is 2.
n is 0.
$A_1$ is C.
$A_1$ is N and $R_3$ is absent.
$A_2$ is N.
$A_2$ is O and $R_3$ is absent.
$A_2$ is S and $R_3$ is absent.

X is

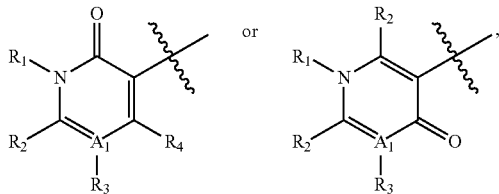

and $R_1$ is —OH.

X is

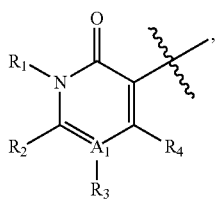

and $R_1$ is —NH-$T_0$, in which —NH-$T_0$ and $R_2$, together with the atoms to which they are attached, form a 5- or 6-membered heteroaryl having 0 to 2 additional heteroatoms or a 5 to 12-membered heterocycloalkyl ring having 0 to 2 additional heteroatoms.

X is

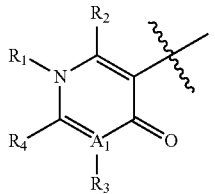

and $R_1$ is —NH-$T_0$, in which —NH-$T_0$ and $R_4$, together with the atoms to which they are attached, form a 5- or 6-membered heteroaryl having 0 to 2 additional heteroatoms or a 5 to 12-membered heterocycloalkyl ring having 0 to 2 additional heteroatoms.

X is

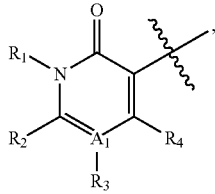

and $R_1$ is —O-$T_0$, in which —O-$T_0$ and $R_2$, together with the atoms to which they are attached, form a 5- or 6-membered heteroaryl having 0 to 2 additional heteroatoms or a 5 to 12-membered heterocycloalkyl ring having 0 to 2 additional heteroatoms.

X is

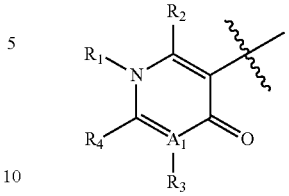

and $R_1$ is —O-$T_0$, in which —O-$T_0$ and $R_4$, together with the atoms to which they are attached, form a 5- or 6-membered heteroaryl having 0 to 2 additional heteroatoms or a 5 to 12-membered heterocycloalkyl ring having 0 to 2 additional heteroatoms.

Z is $NR_7R_8$.
Z is $CR_7R_8R_{14}$.
Z is $OR_7$.
Z is $S(O)_aR_7$, in which a is 0, 1, or 2.
Z is $SR_7$.

$R_6$ is $C_6$-$C_{10}$ aryl or 5- or 6-membered heteroaryl, each of which is optionally, independently substituted with one or more -$Q_2$-$T_2$, wherein $Q_2$ is a bond or $C_1$-$C_3$ alkyl linker, and $T_2$ is H, halo, cyano, —$OR_c$, —$NR_cR_d$, —C(O)$NR_cR_d$, —$NR_dC(O)R_c$, —$S(O)_2R_c$, —$S(O)_2NR_cR_d$, or $R_{S4}$, in which each of $R_c$ and $R_d$, independently is H or $R_{S5}$, each of $R_{S4}$ and $R_{S5}$, independently, is $C_1$-$C_6$ alkyl, or $R_c$ and $R_d$, together with the N atom to which they are attached, form a 4 to 7-membered heterocycloalkyl ring having 0 or 1 additional heteroatom, and each of $R_{S4}$, $R_{S5}$, and the 4 to 7-membered heterocycloalkyl ring formed by $R_c$ and $R_d$, is optionally, independently substituted with one or more -$Q_3$-$T_3$, wherein $Q_3$ is a bond or $C_1$-$C_3$ alkyl linker and $T_3$ is selected from the group consisting of H, halo, $C_1$-$C_6$ alkyl, 4 to 7-membered heterocycloalkyl, $OR_e$, —$S(O)_2R_e$, and —$NR_eR_f$, each of $R_e$ and $R_f$ independently being H or $C_1$-$C_6$ alkyl optionally substituted with OH, O—$C_1$-$C_6$ alkyl, or NH—$C_1$-$C_6$ alkyl, or -$Q_3$-$T_3$ is oxo; or any two neighboring -$Q_2$-$T_2$, together with the atoms to which they are attached form a 5- or 6-membered ring optionally containing 1-4 heteroatoms selected from N, O and S.

$R_c$ and $R_d$, together with the N atom to which they are attached, form a 4 to 7-membered heterocycloalkyl ring having 0 or 1 additional heteroatoms to the N atom and the ring is optionally substituted with one or more -$Q_3$-$T_3$, wherein the heterocycloalkyl is azetidinyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, or morpholinyl.

$R_6$ is phenyl or 5- or 6-membered heteroaryl substituted with O—$C_{1-6}$ alkyl or NH—$C_{1-6}$ alkyl, each of which is optionally substituted with hydroxyl, O—$C_{1-3}$ alkyl or NH—$C_{1-3}$ alkyl, each of the O—$C_{1-3}$ alkyl and NH—$C_{1-3}$ alkyl being optionally further substituted with O—$C_{1-3}$ alkyl or NH—$C_{1-3}$ alkyl.

$R_6$ is

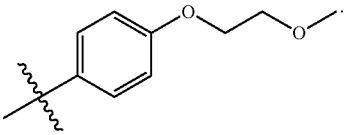 [SMILES: *c1ccc(OCCOC)cc1]

$R_6$ is halo, $C_1$-$C_3$ alkyl, $C_1$-$C_3$ alkoxyl, $C_2$-$C_6$ alkenyl, $C_3$-$C_6$ cycloalkyl, C(O)H, or —C(O)$R_a$, in which $R_a$ is $C_1$-$C_6$ alkyl or 4 to 12-membered (e.g., 4 to 7-membered) heterocycloalkyl.

$R_6$ is F, Br, or Cl.

$R_6$ is Cl.

$R_6$ is ethynyl substituted with one or more -$Q_2$-$T_2$, in which $Q_2$ is a bond or $C_1$-$C_3$ alkyl linker and $T_2$ is $C_1$-$C_6$ alkyl, $C_3$-$C_6$ cycloalkyl, or 4 to 7-membered heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyranyl, 1,4-diazepanyl, 1,4-oxazepanyl, 2-oxa-5-azabicyclo[2.2.1]heptanyl, 2,5-diazabicyclo[2.2.1]heptanyl, and morpholinyl, and the like) optionally substituted with one or more -$Q_3$-$T_3$.

$R_6$ is

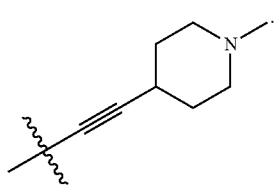 [SMILES: *C#CC1CCN(C)CC1]

$R_7$ is $C_3$-$C_8$ cycloalkyl or 4 to 7-membered heterocycloalkyl, each optionally substituted with one or more -$Q_5$-$T_5$.

$R_7$ is piperidinyl, tetrahydropyran, tetrahydro-2H-thiopyranyl, piperazinyl, cyclopentyl, cyclohexyl, pyrrolidinyl, or cycloheptyl, each optionally substituted with one or more -$Q_5$-$T_5$.

$R_8$ is H or $C_1$-$C_6$ alkyl which is optionally substituted with one or more substituents selected from the group consisting of halo, hydroxyl, C(O)OH, C(O)O—$C_1$-$C_6$ alkyl, cyano, $C_1$-$C_6$ alkoxyl, amino, mono-$C_1$-$C_6$ alkylamino, and di-$C_1$-$C_6$ alkylamino.

$R_7$ is piperidinyl, tetrahydropyran, cyclopentyl, or cyclohexyl, each optionally substituted with one -$Q_5$-$T_5$ and $R_8$ is ethyl.

$R_7$ is tetrahydropyran of

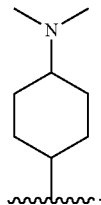

$R_7$ is

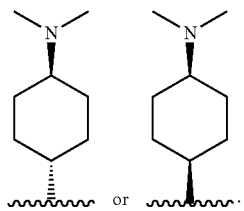

$R_7$ is

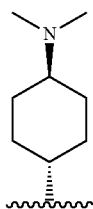

$R_7$ is

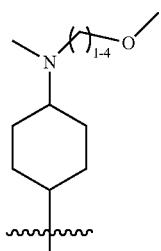 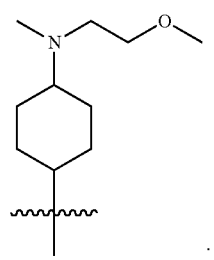, e.g., $R_7$ is

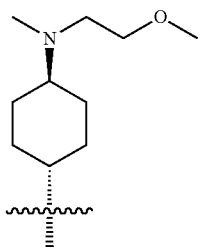 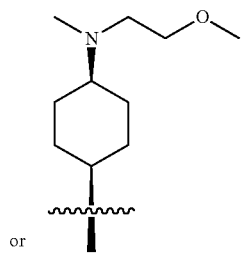 or $R_7$ is

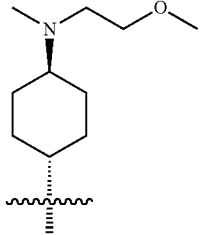

$R_7$ is

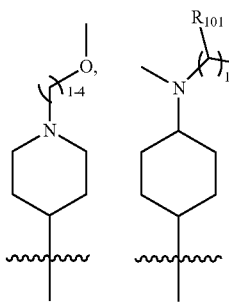 or 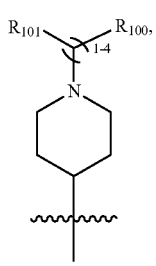, wherein $R_{100}$ is phenyl, 5- or 6-membered heteroaryl, or 4 to 12-membered heterocycloalkyl, each optionally substituted with one or more $T_{5a}$ in which each $T_{5a}$ is independently $C_1$-$C_6$ alkoxyl or O—$C_1$-$C_4$ alkylene-$C_1$-$C_4$ alkoxy, and $R_{101}$ is H or $C_1$-$C_4$ alkyl.
$R_7$ is
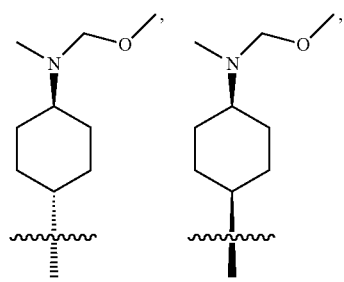
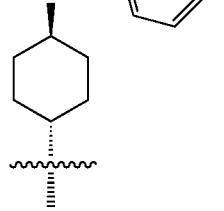
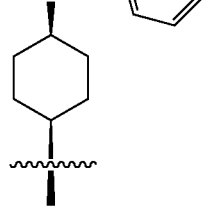
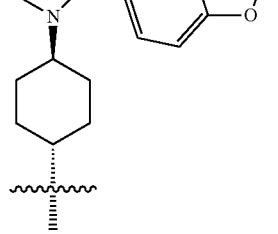
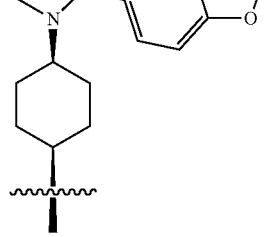
-continued
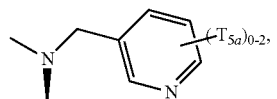
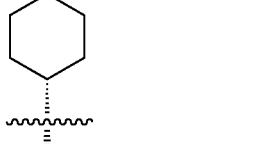
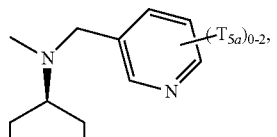
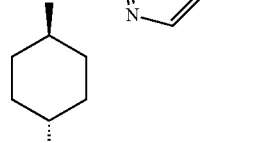
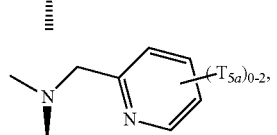
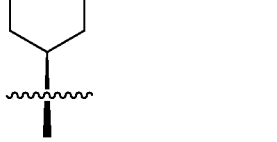
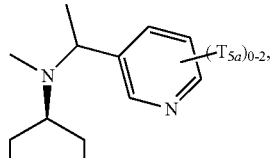
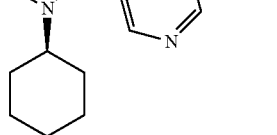

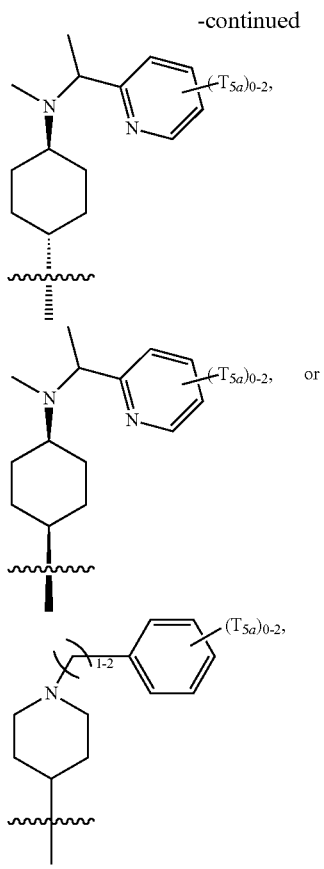

wherein each $T_{5a}$ is independently $C_1$-$C_3$ alkoxyl or O—$C_1$-$C_3$ alkylene-$C_1$-$C_2$ alkoxy.

Each of $R_9$ and $R_{10}$ is H.

The present invention also provides pharmaceutical compositions comprising one or more pharmaceutically acceptable carriers and one or more compounds selected from those of any of the Formulae described herein.

The present invention also provides compounds as described in any Formula herein or a pharmaceutically acceptable salt thereof for use in a method of treating cancer.

The present invention also provides compounds as described in any Formula herein or a pharmaceutically acceptable salt thereof for use in a method of treating lymphoma, leukemia or melanoma.

The present invention also provides compounds as described in any Formula herein or a pharmaceutically acceptable salt thereof for use in a method of treating diffuse large B-cell lymphoma (DLBCL), non-Hodgkin's lymphoma (NHL), follicular lymphoma or diffuse large B-cell lymphoma, chronic myelogenous leukemia (CML), acute myeloid leukemia, acute lymphocytic leukemia or mixed lineage leukemia, or myelodysplastic syndromes (MDS).

The present invention also provides compounds as described in any Formula herein or a pharmaceutically acceptable salt thereof for use in a method of treating malignant rhabdoid tumor or INI1-defecient tumor.

Another aspect of this invention is a method of treating or preventing an EZH2-mediated disorder. The method includes administering to a subject in need thereof a therapeutically effective amount of one or more compounds selected from those of any of the Formulae described herein. The EZH2-mediated disorder is a disease, disorder, or condition that is mediated at least in part by the activity of EZH2. In one embodiment, the EZH2-mediated disorder is related to an increased EZH2 activity. In one embodiment, the EZH2-mediated disorder is a cancer. The EZH2-mediated cancer may be lymphoma, leukemia or melanoma, for example, diffuse large B-cell lymphoma (DLBCL), non-Hodgkin's lymphoma (NHL), follicular lymphoma, chronic myelogenous leukemia (CML), acute myeloid leukemia, acute lymphocytic leukemia, mixed lineage leukemia, or myelodysplastic syndromes (MDS). In one embodiment the EZH2-mediated cancer may be a malignant rhabdoid tumor or INI1-defecient tumor. The histologic diagnosis of malignant rhabdoid tumor depends on identification of characteristic rhabdoid cells (large cells with eccentrically located nuclei and abundant, eosinophilic cytoplasm) and immunohistochemistry with antibodies to vimentin, keratin and epithelial membrane antigen. In most malignant rhabdoid tumors, the SMARCB1/INI1 gene, located in chromosome band 22q11.2, is inactivated by deletions and/or mutations. In one embodiment, the malignant rhabdoid tumors may be INI1-defecient tumors.

Unless otherwise stated, any description of a method of treatment includes use of the compounds to provide such treatment or prophylaxis as is described herein, as well as use of the compounds to prepare a medicament to treat or prevent such condition. The treatment includes treatment of human or non-human animals including rodents and other disease models. Methods described herein may be used to identify suitable candidates for treating or preventing EZH2-mediated disorders. For example, the invention also provides methods of identifying an inhibitor of a wild-type EZH2, a mutant EZH2 (e.g., a Y641, A677, and/or A687 mutant EZH2), or both.

For example, the method comprises the step of administering to a subject having a cancer with aberrant H3-K27 methylation an effective amount of one or more compounds of Formulae described herein, wherein the compound(s) inhibits histone methyltransferase activity of EZH2, thereby treating the cancer. Examples of aberrant H3-K27 methylation may include a global increase in and/or altered distribution of H3-K27 di or tri-methylation within the cancer cell chromatin.

For example, the cancer is selected from the group consisting of cancers that overexpress EZH2 or other PRC2 subunits, contain loss-of-function mutations in H3-K27 demethylases such as UTX, or overexpress accessory proteins such as PHF19/PCL3 capable of increasing and or mislocalizing EZH2 activity (see references in Sneeringer et al. *Proc Natl Acad Sci USA* 107(49):20980-5, 2010).

For example, the method comprises the step of administering to a subject having a cancer overexpressing EZH2 a therapeutically effective amount of one or more compounds of Formulae described herein, wherein the compound(s) inhibits histone methyltransferase activity of EZH2, thereby treating the cancer.

For example, the method comprises the step of administering to a subject having a cancer with a loss-of-function mutation in the H3-K27 demethylase UTX a therapeutically effective amount of one or more compounds of Formulae described herein, wherein the compound(s) inhibits histone methyltransferase activity of EZH2, thereby treating the cancer.

For example, the method comprises the step of administering to a subject having a cancer overexpressing an accessory component(s) of the PRC2, such as PHF19/PCL3, a therapeutically effective amount of one or more compounds of Formulae described herein, wherein the compound(s) inhibits histone methyltransferase activity of EZH2, thereby treating the cancer.

In still another aspect, this invention relates to a method of modulating the activity of the wild-type EZH2, the catalytic subunit of the PRC2 complex which catalyzes the mono-through tri-methylation of lysine 27 on histone H3 (H3-K27). For example, the present invention relates to a method of inhibiting the activity of EZH2 in a cell. This method can be conducted either in vitro or in vivo.

In yet another aspect, this invention features to a method of inhibiting in a subject conversion of H3-K27 to trimethylated H3-K27. The method comprises administering to a subject a therapeutically effective amount of one or more of the compounds of Formulae described herein to inhibit histone methyltransferase activity of EZH2, thereby inhibiting conversion of H3-K27 to trimethylated H3-K27 in the subject.

For example, the method comprises the step of administering to a subject having a cancer expressing a mutant EZH2 (e.g., a Y641, A677, and/or A687 mutant of EZH2) a therapeutically effective amount of one or more compounds of Formulae described herein, wherein the compound(s) inhibits histone methyltransferase activity of EZH2, thereby treating the cancer.

For example, the cancer is selected from the group consisting of follicular lymphoma and diffuse large B-cell lymphoma (DLBCL) of germinal center B cell-like (GCB) subtype. For example, the cancer is lymphoma, leukemia or melanoma. Preferably, the lymphoma is non-Hodgkin's lymphoma (NHL), follicular lymphoma or diffuse large B-cell lymphoma. Alternatively, the leukemia is chronic myelogenous leukemia (CML), acute myeloid leukemia, acute lymphocytic leukemia or mixed lineage leukemia.

For example, the lymphoma is a germinal center-derived lymphoma. For example, the germinal center-derived lymphoma is an EZH2 wild type germinal center B-cell lymphoma. For example, the germinal center-derived lymphoma is an EZH2 mutant germinal center B-cell lymphoma. For example, the germinal center-derived lymphoma is diffuse large B-cell lymphoma, follicular lymphoma, Burkitt's lymphoma or Non-Hodgkin's Lymphoma of germinal center B cell subtype.

For example, the precancerous condition is myelodysplastic syndromes (MDS, formerly known as preleukemia).

For example, the cancer is a hematological cancer.

For example, the cancer is selected from the group consisting of brain and central nervous system (CNS) cancer, head and neck cancer, kidney cancer, ovarian cancer, pancreatic cancer, leukemia, lung cancer, lymphoma, myeloma, sarcoma, breast cancer, and prostate cancer. Preferably, a subject in need thereof is one who had, is having or is predisposed to developing brain and CNS cancer, kidney cancer, ovarian cancer, pancreatic cancer, leukemia, lymphoma, myeloma, and/or sarcoma. Exemplary brain and central CNS cancer includes medulloblastoma, oligodendroglioma, atypical teratoid/rhabdoid tumor, choroid plexus carcinoma, choroid plexus papilloma, ependymoma, glioblastoma, meningioma, neuroglial tumor, oligoastrocytoma, oligodendroglioma, and pineoblastoma. Exemplary ovarian cancer includes ovarian clear cell adenocarcinoma, ovarian endomethrioid adenocarcinoma, and ovarian serous adenocarcinoma. Exemplary pancreatic cancer includes pancreatic ductal adenocarcinoma and pancreatic endocrine tumor. Exemplary sarcoma includes chondrosarcoma, clear cell sarcoma of soft tissue, Ewing sarcoma, gastrointestinal stromal tumor, osteosarcoma, rhabdomyosarcoma, and not otherwise specified (NOS) sarcoma. Alternatively, cancers to be treated by the compounds of the present invention are non NHL cancers.

For example, the cancer is selected from the group consisting of medulloblastoma, oligodendroglioma, ovarian clear cell adenocarcinoma, ovarian endomethrioid adenocarcinoma, ovarian serous adenocarcinoma, pancreatic ductal adenocarcinoma, pancreatic endocrine tumor, malignant rhabdoid tumor, astrocytoma, atypical teratoid/rhabdoid tumor, choroid plexus carcinoma, choroid plexus papilloma, ependymoma, glioblastoma, meningioma, neuroglial tumor, oligoastrocytoma, oligodendroglioma, pineoblastoma, carcinosarcoma, chordoma, extragonadal germ cell tumor, extrarenal rhabdoid tumor, schwannoma, skin squamous cell carcinoma, chondrosarcoma, clear cell sarcoma of soft tissue, Ewing sarcoma, gastrointestinal stromal tumor, osteosarcoma, rhabdomyosarcoma, and not otherwise specified (NOS) sarcoma. Preferably, the cancer is medulloblastoma, ovarian clear cell adenocarcinoma, ovarian endomethrioid adenocarcinoma, pancreatic ductal adenocarcinoma, malignant rhabdoid tumor, atypical teratoid/rhabdoid tumor, choroid plexus carcinoma, choroid plexus papilloma, glioblastoma, meningioma, pineoblastoma, carcinosarcoma, extrarenal rhabdoid tumor, schwannoma, skin squamous cell carcinoma, chondrosarcoma, ewing sarcoma, epithelioid sarcoma, renal medullary carcinoma, diffuse large B-cell lymphoma, follicular lymphoma and/or NOS sarcoma. More preferably, the cancer is malignant rhabdoid tumor, medulloblastoma and/or atypical teratoid/rhabdoid tumor. Malignant rhabdoid tumors are high-grade neoplasms of the central nervous system (CNS), kidneys and soft tissue that usually occur in children. The histologic diagnosis of malignant rhabdoid tumor depends on identification of characteristic rhabdoid cells (large cells with eccentrically located nuclei and abundant, eosinophilic cytoplasm) and immunohistochemistry with antibodies to vimentin, keratin and epithelial membrane antigen. In most malignant rhabdoid tumors, the SMARCB1/INI1 gene, located in chromosome band 22q11.2, is inactivated by deletions and/or mutations. In one embodiment, the malignant rhabdoid tumors are INI1-defecient tumor.

For example, the method comprises the step of administering to a subject having a cancer expressing a mutant EZH2 (e.g., a Y641, A677, and/or A687 mutant of EZH2) a therapeutically effective amount of one or more compounds of Formulae described herein, wherein the compound(s) inhibits activity (e.g., histone methyltransferase activity) of the mutant EZH2, the wild-type EZH2, or both, thereby treating the cancer.

For example, the method further comprises the steps of performing an assay to detect the presence or absence of a mutant EZH2 in a sample comprising cancer cells from a subject in need thereof.

In another aspect, the invention features a method of selecting a therapy for a patient having a disease associated with EZH2-mediated protein methylation. The method includes the steps of determining the presence or absence of gene mutation in the EZH2 gene of the subject; and selecting, based on the presence or absence of a gene mutation in the EZH2 gene a therapy for treating the disease. In one embodiment, the therapy includes the administration of one or more of the compounds of the invention. In one embodiment, the method further includes administrating one or more of the compounds of the invention to the subject. In one embodiment, the disease is cancer (such as lymphoma) and the mutation is a Y641, A677, and/or A687 mutation. In another embodiment, the disease is an EZH2 wild type germinal center B-cell lymphoma, e.g., the germinal center B-cell lymphoma cells having non-mutated, wild-type EZH2 protein.

In yet another aspect, a method of treatment is provided for a patient in need thereof, the method comprising the steps of determining the presence or absence of gene mutation in the EZH2 gene and treating the patient in need thereof, based on the presence or absence of a gene mutation in the EZH2 gene, with a therapy that includes the administration of the compounds of the invention. In one embodiment, the patient is a cancer patient and the mutation is a Y641, A677, and/or A687 mutation. In another embodiment, the patient has an EZH2 wild type germinal center B-cell lymphoma, e.g., the germinal center B-cell lymphoma cells having non-mutated, wild-type EZH2 protein.

In still another aspect, this invention relates to a method of modulating the activity of the wild-type and mutant histone methyltransferase EZH2, the catalytic subunit of the PRC2 complex which catalyzes the mono- through tri-methylation of lysine 27 on histone H3 (H3-K27). For example, the present invention relates to a method of inhibiting the activity of certain mutant forms of EZH2 in a cell. The mutant forms of EZH2 include a substitution of another amino acid residue for tyrosine 641 (Y641, also Tyr641) of wild-type EZH2. The method includes contacting the cell with an effective amount of one or more of the compounds of any Formula described herein. This method can be conducted either in vitro or in vivo.

In yet another aspect, this invention features to a method of inhibiting in a subject conversion of H3-K27 to trimethylated H3-K27. The method comprises administering to a subject expressing a mutant EZH2 (e.g., a Y641, A677, and/or A687 mutant of EZH2) a therapeutically effective amount of one or more of the compounds of any Formula described herein to inhibit histone methyltransferase activity of EZH2, thereby inhibiting conversion of H3-K27 to trimethylated H3-K27 in the subject. For example, the histone methyltransferase activity inhibited is that of the Y641 mutant of EZH2. For example, the compound of this invention selectively inhibits histone methyltransferase activity of the Y641 mutant of EZH2. For example, the Y641 mutant of EZH2 is selected from the group consisting of Y641C, Y641F, Y641H, Y641N, and Y641S.

The method of inhibiting in a subject conversion of H3-K27 to trimethylated H3-K27 may also comprise performing an assay to detect a mutant EZH2 (e.g., a Y641, A677, and/or A687 mutant of EZH2) in a sample from a subject before administering to the subject expressing a mutant EZH2 a therapeutically effective amount of one or more of the compounds of any Formula described herein. For example, performing the assay to detect the mutant EZH2 includes whole-genome resequencing or target region resequencing that detects a nucleic acid encoding the mutant EZH2. For example, performing the assay to detect the mutant EZH2 includes contacting the sample with an antibody that binds specifically to a polypeptide or fragment thereof characteristic of the mutant EZH2. For example, performing the assay to detect the mutant EZH2 includes contacting the sample under highly stringent conditions with a nucleic acid probe that hybridizes to a nucleic acid encoding a polypeptide or fragment thereof characteristic of the mutant EZH2.

Further, the invention also relates to a method of identifying an inhibitor of a mutant EZH2, the wild-type EZH2, or both. The method comprises the steps of combining an isolated EZH2 with a histone substrate, a methyl group donor, and a test compound, wherein the histone substrate comprises a form of H3-K27 selected from the group consisting of unmethylated H3-K27, monomethylated H3-K27, dimethylated H3-K27, and any combination thereof; and performing an assay to detect methylation of H3-K27 (e.g., formation of trimethylated H3-K27) in the histone substrate, thereby identifying the test compound as an inhibitor of the EZH2 when methylation of H3-K27 (e.g., formation of trimethylated H3-K27) in the presence of the test compound is less than methylation of H3-K27 (e.g., formation of trimethylated H3-K27) in the absence of the test compound.

In one embodiment, performing the assay to detect methylation of H3-K27 in the histone substrate comprises measuring incorporation of labeled methyl groups.

In one embodiment, the labeled methyl groups are isotopically labeled methyl groups.

In one embodiment, performing the assay to detect methylation of H3-K27 in the histone substrate comprises contacting the histone substrate with an antibody that binds specifically to trimethylated H3-K27.

Also within the scope of the invention is a method of identifying a selective inhibitor of a mutant EZH2. The method comprises the steps of combining an isolated mutant EZH2 with a histone substrate, a methyl group donor, and a test compound, wherein the histone substrate comprises a form of H3-K27 selected from the group consisting of monomethylated H3-K27, dimethylated H3-K27, and a combination of monomethylated H3-K27 and dimethylated H3-K27, thereby forming a test mixture; combining an isolated wild-type EZH2 with a histone substrate, a methyl group donor, and a test compound, wherein the histone substrate comprises a form of H3-K27 selected from the group consisting of monomethylated H3-K27, dimethylated H3-K27, and a combination of monomethylated H3-K27 and dimethylated H3-K27, thereby forming a control mixture; performing an assay to detect trimethylation of the histone substrate in each of the test mixture and the control mixture; calculating the ratio of (a) trimethylation with the mutant EZH2 and the test compound (M+) to (b) trimethylation with the mutant EZH2 without the test compound (M−); calculating the ratio of (c) trimethylation with wild-type EZH2 and the test compound (WT+) to (d) trimethylation with wild-type EZH2 without the test compound (WT−); comparing the ratio (a)/(b) with the ratio (c)/(d); and identifying the test compound as a selective inhibitor of the mutant EZH2 when the ratio (a)/(b) is less than the ratio (c)/(d).

The present invention further provides a method of identifying a subject as a candidate for treatment with one or more compounds of the invention. The method comprises the steps of performing an assay to detect a mutant EZH2 in a sample from a subject; and identifying a subject expressing a mutant EZH2 as a candidate for treatment with one or more compounds of the invention, wherein the compound(s) inhibits histone methyltransferase activity of EZH2.

In one embodiment, the method comprises: (i) providing a nucleic acid sample from a biological sample obtained from a subject; (ii) contacting the nucleic acid sample with at least one primer that specifically hybridizes to a nucleic acid sequence of EZH2, or a complement thereof, characterized with nucleotides encoding a mutation that increases EZH2 trimethylation of H3-K27; (iii) detecting the presence of the mutation in the nucleic acid sample by detecting the presence of a nucleic acid characterized with nucleotides encoding a mutation that increases EZH2 trimethylation of H3-K27; and (iv) identifying the subject as a candidate for treatment. The method can further comprise (v) administering a therapeutically effective amount of an EZH2 inhibitor to the subject identified in step (iv), wherein the EZH2 inhibitor inhibits the conversion of H3-K27 to trimethylated H3-K27.

In one embodiment, the method comprises: (i) providing a nucleic acid sample from a biological sample obtained from a subject; (ii) contacting the nucleic acid sample with at least two primers that specifically hybridize to a nucleic acid sequence of EZH2, or a complement thereof, characterized with nucleotides encoding a mutation that increases EZH2 trimethylation of H3-K27; (iii) amplifying the nucleic acid sequence, or the complement thereof, characterized with nucleotides encoding the mutation that increases EZH2 trimethylation of H3-K27; (iv) detecting the presence of the mutation by detecting the presence of the amplified nucleic acid; and (v) identifying the subject as a candidate for treatment. The method can further comprise (vi) administering a therapeutically effective amount of an EZH2 inhibitor to the subject identified in step (v), wherein the EZH2 inhibitor inhibits the conversion of H3-K27 to trimethylated H3-K27.

In one embodiment, the method comprises: (i) providing a nucleic acid sample from a biological sample obtained from a subject; (ii) contacting the nucleic acid sample with at least one primer that specifically hybridizes to a nucleic acid sequence, or a complement thereof, characterized with nucleotides encoding a mutation at the position Tyr641 (Y641), A677, and/or A687 of EZH2, wherein the mutation increases EZH2 trimethylation of H3-K27; (iii) detecting the presence of the mutation at the nucleotides encoding Y641, A677, and/or A687 in the nucleic acid sample by detecting the presence of a nucleic acid encoding the mutation at Y641, A677, and/or A687; and (iv) identifying the subject as a candidate for treatment. The method can further comprise (v) selecting a therapy that includes the administration of a therapeutically effective amount of an EZH2 inhibitor to the subject identified in step (iv), wherein the EZH2 inhibitor inhibits the conversion of H3-K27 to trimethylated H3-K27.

In one embodiment, the method comprises: (i) providing a nucleic acid sample from a biological sample obtained from a subject; (ii) contacting the nucleic acid sample with at least two primers that specifically hybridize to a nucleic acid sequence, or a complement thereof, characterized with nucleotides encoding a mutation at the position Y641, A677, and/or A687 of EZH2, wherein the mutation increases EZH2 trimethylation of H3-K27; (iii) amplifying the nucleic acid sequence, or the complement thereof, characterized with the mutation at the nucleotides encoding position Y641, A677, and/or A687; (iv) detecting the presence of the mutation at the nucleotides encoding Y641, A677, and/or A687 by detecting the presence of the amplified nucleic acid; and (v) identifying the subject as a candidate for treatment. The method can further comprise (vi) selecting a therapy that includes the administration of a therapeutically effective amount of an EZH2 inhibitor to the subject identified in step (v), wherein the EZH2 inhibitor inhibits the conversion of H3-K27 to trimethylated H3-K27.

Still another aspect of the invention is a method of inhibiting conversion of H3-K27 to trimethylated H3-K27. The method comprises the step of contacting a mutant EZH2, the wild-type EZH2, or both, with a histone substrate comprising H3-K27 and an effective amount of a compound of the present invention, wherein the compound inhibits histone methyltransferase activity of EZH2, thereby inhibiting conversion of H3-K27 to trimethylated H3-K27.

Further, the compounds or methods described herein can be used for research (e.g., studying epigenetic enzymes) and other non-therapeutic purposes.

Unless otherwise defined, all technical and scientific terms used herein have the same meaning as commonly understood by one of ordinary skill in the art to which this invention belongs. In the specification, the singular forms also include the plural unless the context clearly dictates otherwise. Although methods and materials similar or equivalent to those described herein can be used in the practice or testing of the present invention, suitable methods and materials are described below. All publications, patent applications, patents and other references mentioned herein are incorporated by reference. The references cited herein are not admitted to be prior art to the claimed invention. In the case of conflict, the present specification, including definitions, will control. In addition, the materials, methods and examples are illustrative only and are not intended to be limiting. In the case of conflict between the chemical structures and names of the compounds disclosed herein, the chemical structures will control.

Other features and advantages of the invention will be apparent from the following detailed description and claims.

DETAILED DESCRIPTION OF THE INVENTION

The present invention provides novel substituted benzene compounds, synthetic methods for making the compounds, pharmaceutical compositions containing them and various uses of the compounds.

The present invention provides the compounds of Formula (I):

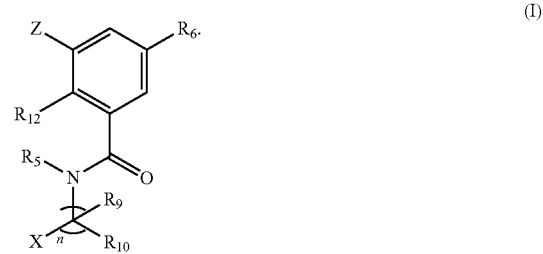

In this Formula,
X is

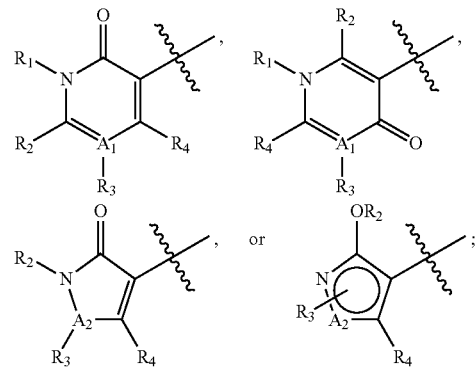

$A_1$ is C or N and when $A_1$ is N, $R_3$ is absent;
$A_2$ is N, O, or S and when $A_2$ is O or S, $R_3$ is absent;
Z is $NR_7R_8$, $OR_7$, $S(O)_aR_7$, or $CR_7R_8R_{14}$, in which a is 0, 1, or 2;

$R_1$ is $-Q_0-T_0$, in which $Q_0$ is $NR_{1a}$, O or S, $R_{1a}$ being H, OH, $C_1-C_6$ alkyl, or $C_1-C_6$ alkoxyl, and $T_0$ is H or $R_{S0}$, in which $R_{S0}$ is $C_1-C_6$ alkyl, $C_2-C_6$ alkenyl, $C_2-C_6$ alkynyl, $C_3-C_8$ cycloalkyl, $C_6-C_{10}$ aryl, 4 to 12-membered heterocycloalkyl, or 5- or 6-membered heteroaryl, and $R_{S0}$ is optionally substituted with one or more substituents selected from the group consisting of halo, hydroxyl, oxo, C(O)OH, C(O)O—$C_1$-$C_6$ alkyl, cyano, $C_1-C_6$ alkyl, $C_1-C_6$ alkoxyl, amino, mono-$C_1-C_6$ alkylamino, di-$C_1-C_6$ alkylamino, $C_3-C_8$ cycloalkyl, $C_6-C_{10}$ aryl, 4 to 12-membered heterocycloalkyl, and 5- or 6-membered heteroaryl;

each of $R_2$, $R_3$, and $R_4$, independently, is $-Q_1-T_1$, in which $Q_1$ is a bond or $C_1-C_3$ alkyl linker optionally substituted with halo, cyano, hydroxyl or $C_1-C_6$ alkoxy, and $T_1$ is H, halo, hydroxyl, C(O)OH, cyano, azido, or $R_{S1}$, in which $R_{S1}$ is $C_1-C_3$ alkyl, $C_2-C_6$ alkenyl, $C_2-C_6$ alkynyl, $C_1-C_6$ alkoxyl, $C_1-C_6$ thioalkyl, C(O)O—$C_1-C_6$ alkyl, $CONH_2$, $SO_2NH_2$, —C(O)—NH($C_1-C_6$ alkyl), —C(O)—N($C_1-C_6$ alkyl)$_2$, —$SO_2$—NH($C_1-C_6$ alkyl), —$SO_2$—N($C_1-C_6$ alkyl)$_2$, $C_3-C_8$ cycloalkyl, $C_6-C_{10}$ aryl, $C_6-C_{10}$ aryloxy, amino, mono-$C_1$-$C_6$ alkylamino, di-$C_1-C_6$ alkylamino, 4 to 12-membered heterocycloalkyl, or 5- or 6-membered heteroaryl, and $R_{S1}$ is optionally substituted with one or more substituents selected from the group consisting of halo, hydroxyl, oxo, C(O)OH, C(O)O—$C_1-C_6$ alkyl, cyano, $C_1-C_6$ alkyl, $C_1-C_6$ alkoxyl, amino, mono-$C_1-C_6$ alkylamino, di-$C_1-C_6$ alkylamino, $C_3-C_8$ cycloalkyl, $C_6-C_{10}$ aryl, 4 to 12-membered heterocycloalkyl, and 5- or 6-membered heteroaryl; or neighboring $R_1$ and $R_2$, together with the atoms to which they are attached, form a 5- or 6-membered heteroaryl having 0 to 2 additional heteroatoms or a 5 to 12-membered heterocycloalkyl ring having 0 to 2 additional heteroatoms; or neighboring $R_1$ and $R_4$, together with the atoms to which they are attached, form a 5- or 6-membered heteroaryl having 0 to 2 additional heteroatoms or a 5 to 12-membered heterocycloalkyl ring having 0 to 2 additional heteroatoms; or neighboring $R_2$ and $R_3$, together with the atoms to which they are attached, form $C_5-C_8$ cycloalkyl, $C_6-C_{10}$ aryl, or a 5- or 6-membered heteroaryl having 1 to 3 heteroatoms, or a 5 to 12-membered heterocycloalkyl ring having 1 to 3 heteroatoms; or neighboring $R_3$ and $R_4$, together with the atoms to which they are attached, form $C_5-C_8$ cycloalkyl, $C_6-C_{10}$ aryl, or a 5- or 6-membered heteroaryl having 1 to 3 heteroatoms, or a 5 to 12-membered heterocycloalkyl ring having 1 to 3 heteroatoms; in which each of the ring structures formed by $R_1$ and $R_2$, by $R_1$ and $R_4$, by $R_2$ and $R_3$, or by $R_3$ and $R_4$, independently is optionally substituted with one or more substituents selected from the group consisting of halo, hydroxyl, oxo, $C_1-C_6$ alkyl, $C_1-C_6$ haloalkyl, C(O)OH, C(O)O—$C_1-C_6$ alkyl, C(O)O—$C_1-C_6$ haloalkyl, cyano, $C_1-C_6$ alkoxyl, $C_1-C_6$ haloalkoxyl, amino, mono-$C_1-C_6$ alkylamino, di-$C_1-C_6$ alkylamino, $C_3-C_8$ cycloalkyl, $C_6-C_{10}$ aryl, 4 to 12-membered heterocycloalkyl, and 5- or 6-membered heteroaryl;

each of $R_5$, $R_9$, and $R_{10}$, independently, is H or $C_1-C_6$ alkyl optionally substituted with one or more substituents selected from the group consisting of halo, hydroxyl, COOH, C(O)O—$C_1-C_6$ alkyl, cyano, $C_1-C_6$ alkoxyl, amino, mono-$C_1-C_6$ alkylamino, di-$C_1-C_6$ alkylamino, $C_3-C_8$ cycloalkyl, $C_6-C_{10}$ aryl, 4 to 12-membered heterocycloalkyl, and 5- or 6-membered heteroaryl;

$R_6$ is H, halo, cyano, azido, $OR_a$, $-NR_aR_b$, $-C(O)R_a$, $-C(O)OR_a$, $-C(O)NR_aR_b$, $-NR_bC(O)R_a$, $-S(O)_bR_a$, $-S(O)_bNR_aR_b$, or $R_{S2}$, in which $R_{S2}$ is $C_1-C_6$ alkyl, $C_2-C_6$ alkenyl, $C_2-C_6$ alkynyl, $C_3-C_8$ cycloalkyl, $C_6-C_{10}$ aryl, 5- or 6-membered heteroaryl, or 4 to 12-membered heterocycloalkyl, b is 0, 1, or 2, each of $R_a$ and $R_b$, independently is H or $R_{S3}$, and $R_{S3}$ is $C_1-C_6$ alkyl, $C_2-C_6$ alkenyl, $C_2-C_6$ alkynyl, $C_3-C_8$ cycloalkyl, $C_6-C_{10}$ aryl, 4 to 12-membered heterocycloalkyl, or 5- or 6-membered heteroaryl; or $R_a$ and $R_b$, together with the N atom to which they are attached, form a 4 to 12-membered heterocycloalkyl ring having 0 or 1 additional heteroatom; and each of $R_{S2}$, $R_{S3}$, and the 4 to 12-membered heterocycloalkyl ring formed by $R_a$ and $R_b$, is optionally substituted with one or more $-Q_2-T_2$, wherein $Q_2$ is a bond or $C_1-C_3$ alkyl linker each optionally substituted with halo, cyano, hydroxyl or $C_1-C_6$ alkoxy, and $T_2$ is H, halo, cyano, $-OR_c$, $-NR_cR_d$, $-C(O)R_c$, $-C(O)OR_c$, $-C(O)NR_cR_d$, $-NR_dC(O)R_c$, $-NR_dC(O)OR_c$, $-S(O)_2R_c$, $-S(O)_2NR_cR_d$, or $R_{S4}$, in which each of $R_c$ and $R_d$, independently is H or $R_{S5}$, each of $R_{S4}$ and $R_{S5}$, independently, is $C_1-C_6$ alkyl, $C_3-C_8$ cycloalkyl, $C_6-C_{10}$ aryl, 4 to 12-membered heterocycloalkyl, or 5- or 6-membered heteroaryl, or $R_c$ and $R_d$, together with the N atom to which they are attached, form a 4 to 12-membered heterocycloalkyl ring having 0 or 1 additional heteroatom, and each of $R_{S4}$, $R_{S5}$, and the 4 to 12-membered heterocycloalkyl ring formed by $R_c$ and $R_d$, is optionally substituted with one or more $-Q_3-T_3$, wherein $Q_3$ is a bond or $C_1-C_3$ alkyl linker each optionally substituted with halo, cyano, hydroxyl or $C_1-C_6$ alkoxy, and $T_3$ is selected from the group consisting of H, halo, cyano, $C_1-C_6$ alkyl, $C_3-C_8$ cycloalkyl, $C_6-C_{10}$ aryl, 4 to 12-membered heterocycloalkyl, 5- or 6-membered heteroaryl, $OR_e$, $C(O)OR_e$, $-S(O)_2R_e$, $-NR_eR_f$, and $-C(O)NR_eR_f$, each of $R_e$ and $R_f$ independently being H or $C_1-C_6$ alkyl optionally substituted with OH, O—$C_1-C_6$ alkyl, or NH—$C_1-C_6$ alkyl, or $-Q_3-T_3$ is oxo; or $-Q_2-T_2$ is oxo; or any two neighboring $-Q_2-T_2$, when $R_6$ is $C_6-C_{10}$ aryl or 5- or 6-membered heteroaryl, together with the atoms to which they are attached form a 5- or 6-membered ring optionally containing 1-4 heteroatoms selected from N, O and S and optionally substituted with one or more substituents selected from the group consisting of halo, hydroxyl, C(O)OH, C(O)O—$C_1$-$C_6$ alkyl, cyano, $C_1-C_6$ alkoxyl, amino, mono-$C_1-C_6$ alkylamino, di-$C_1-C_6$ alkylamino, $C_3-C_8$ cycloalkyl, $C_6-C_{10}$ aryl, 4 to 12-membered heterocycloalkyl, and 5- or 6-membered heteroaryl;

$R_7$ is $-Q_4-T_4$, in which $Q_4$ is a bond, $C_1-C_4$ alkyl linker, or $C_2-C_4$ alkenyl linker, each linker optionally substituted with halo, cyano, hydroxyl or $C_1-C_6$ alkoxy, and $T_4$ is H, halo, cyano, $NR_gR_h$, $-OR_g$, $-C(O)R_g$, $-C(O)OR_g$, $-C(O)NR_gR_h$, $-C(O)NR_gOR_h$, $-NR_gC(O)R_h$, $-S(O)_2R_g$, or $R_{S6}$, in which each of $R_g$ and $R_h$, independently is H or $R_{S7}$, each of $R_{S6}$ and $R_{S7}$, independently is $C_1-C_6$ alkyl, $C_2-C_6$ alkenyl, $C_2-C_6$ alkynyl, $C_3-C_8$ cycloalkyl, $C_6-C_{10}$ aryl, 4 to 14-membered heterocycloalkyl, or 5- or 6-membered heteroaryl, and each of $R_{S6}$ and $R_{S7}$ is optionally substituted with one or more $-Q_5-T_5$, wherein $Q_5$ is a bond, C(O), C(O)$NR_k$, $NR_kC(O)$, $NR_k$, $S(O)_2$, $NR_kS(O)_2$, or $C_1-C_3$ alkyl linker, $R_k$ being H or $C_1-C_6$ alkyl, and $T_5$ is H, halo, $C_1-C_6$ alkyl, $C_2-C_6$ alkenyl, $C_2-C_6$ alkynyl, hydroxyl, cyano, $C_1-C_6$ alkoxyl, amino, mono-$C_1-C_6$ alkylamino, di-$C_1-C_6$ alkylamino, $C_3-C_8$ cycloalkyl, $C_1-C_6$ alkylene-$C_3-C_8$ cycloalkyl, $C_6-C_{10}$ aryl, $C_1-C_6$ alkylene-$C_6-C_{10}$ aryl, 4 to 12-membered heterocycloalkyl, $C_1-C_6$ alkylene-4 to 12-membered heterocycloalkyl, 5- or 6-membered heteroaryl, $C_1-C_6$ alkylene-5- or 6-membered heteroaryl, or $S(O)_qR_q$ in which q is 0, 1, or 2 and $R_q$ is $C_1-C_6$ alkyl, $C_2-C_6$ alkenyl, $C_2-C_6$ alkynyl, $C_3-C_8$ cycloalkyl, $C_6-C_{10}$ aryl, 4 to 12-membered heterocycloalkyl, or 5- or 6-membered heteroaryl, and $T_5$ is optionally substituted with one or more substituents selected from the group consisting of halo, $C_1-C_6$ alkyl, hydroxyl, cyano, $C_1-C_6$ alkoxyl, O—$C_1-C_4$ alkylene-$C_1-C_4$ alkoxy, amino, mono-$C_1-C_6$ alkylamino, di-$C_1-C_6$ alkylamino, $C_3-C_8$ cycloalkyl, $C_6$-$C_{10}$ aryl, 4 to 12-membered heterocycloalkyl, and 5- or 6-membered heteroaryl except when $T_5$ is H, halo, hydroxyl, or cyano; or -$Q_5$-$T_5$ is oxo;

each of $R_8$, and $R_{12}$, independently, is H, halo, hydroxyl, C(O)OH, cyano, $R_{S8}$, $OR_{S8}$, or $C(O)OR_{S8}$, in which $R_{S8}$ is $C_1$-$C_6$ alkyl, $C_2$-$C_6$ alkenyl, $C_2$-$C_6$ alkynyl, $C_3$-$C_8$ cycloalkyl, 4 to 12-membered heterocycloalkyl, amino, mono-$C_1$-$C_6$ alkylamino, or di-$C_1$-$C_6$ alkylamino, and $R_{S8}$ is optionally substituted with one or more substituents selected from the group consisting of halo, hydroxyl, C(O)OH, C(O)O—$C_1$-$C_6$ alkyl, cyano, $C_1$-$C_6$ alkoxyl, amino, mono-$C_1$-$C_6$ alkylamino, and di-$C_1$-$C_6$ alkylamino; or $R_7$ and $R_8$, together with the N atom to which they are attached, form a 4 to 12-membered heterocycloalkyl ring having 0 to 2 additional heteroatoms, or $R_7$ and $R_8$, together with the atom to which they are attached, form $C_3$-$C_8$ cycloalkyl or a 4 to 12-membered heterocycloalkyl ring having 1 to 3 heteroatoms, and each of the 4 to 12-membered heterocycloalkyl rings or $C_3$-$C_8$ cycloalkyl formed by $R_7$ and $R_8$ is optionally substituted with one or more -$Q_6$-$T_6$, wherein $Q_6$ is a bond, C(O), $C(O)NR_m$, $NR_mC(O)$, $S(O)_2$, or $C_1$-$C_3$ alkyl linker, $R_m$ being H or $C_1$-$C_6$ alkyl, and $T_6$ is H, halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, 5- or 6-membered heteroaryl, or $S(O)_pR_p$ in which p is 0, 1, or 2 and $R_p$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 12-membered heterocycloalkyl, or 5- or 6-membered heteroaryl, and $T_6$ is optionally substituted with one or more substituents selected from the group consisting of halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl except when $T_6$ is H, halo, hydroxyl, or cyano; or -Q-$T_6$ is oxo;

$R_{14}$ is absent, H, or $C_1$-$C_6$ alkyl optionally substituted with one or more substituents selected from the group consisting of halo, hydroxyl, C(O)OH, C(O)O—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl; and n is 0, 1, 2, 3, 4, or 5.

The compounds of Formula (I) can have one or more of the following features when applicable:

For example, n is 1.
For example, n is 2.
For example, n is 0.
For example, $A_1$ is C.
For example, $A_1$ is N and $R_3$ is absent.
For example, $A_2$ is N.
For example, $A_2$ is O and $R_3$ is absent.
For example, $A_2$ is S and $R_3$ is absent.
For example, X is

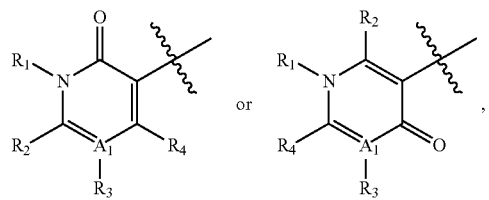

and $R_1$ is —OH.

For example, X is

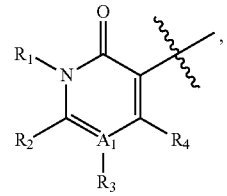

and $R_1$ is —NH-$T_0$, in which —NH-$T_0$ and $R_2$, together with the atoms to which they are attached, form a 5- or 6-membered heteroaryl having 0 to 2 additional heteroatoms or a 5 to 12-membered heterocycloalkyl ring having 0 to 2 additional heteroatoms.

For example, X is

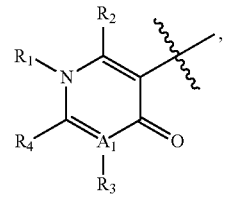

and $R_1$ is —NH-$T_0$, in which —NH-$T_0$ and $R_4$, together with the atoms to which they are attached, form a 5- or 6-membered heteroaryl having 0 to 2 additional heteroatoms or a 5 to 12-membered heterocycloalkyl ring having 0 to 2 additional heteroatoms.

For example, X is

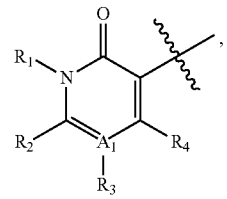

and $R_1$ is —O-$T_0$, in which —O-$T_0$ and $R_2$, together with the atoms to which they are attached, form a 5- or 6-membered heteroaryl having 0 to 2 additional heteroatoms or a 5 to 12-membered heterocycloalkyl ring having 0 to 2 additional heteroatoms.

For example, X is

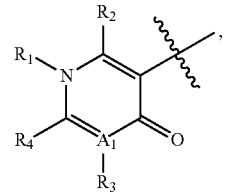

and $R_1$ is —O-$T_0$, in which —O-$T_0$ and $R_4$, together with the atoms to which they are attached, form a 5- or 6-membered heteroaryl having 0 to 2 additional heteroatoms or a 5 to 12-membered heterocycloalkyl ring having 0 to 2 additional heteroatoms.

For example, Z is $NR_7R_8$.
For example, Z is $CR_7R_8R_{14}$.
For example, Z is $OR_7$.
For example, Z is $S(O)_aR_7$, in which a is 0, 1, or 2.
For example, Z is $SR_7$.
For example, $R_6$ is unsubstituted $C_6-C_{10}$ aryl or unsubstituted 5- or 6-membered heteroaryl.
For example, $R_6$ is substituted $C_6-C_{10}$ aryl or substituted 5- or 6-membered heteroaryl.
For example, $R_6$ is $C_6-C_{10}$ aryl substituted with one or more -$Q_2$-$T_2$ or 5- or 6-membered heteroaryl substituted with one or more -$Q_2$-$T_2$.
For example, $R_6$ is unsubstituted or substituted phenyl.
For example, $R_6$ is phenyl substituted with one or more -$Q_2$-$T_2$.
For example, $R_6$ is 5 to 6-membered heteroaryl containing 1-3 additional heteroatoms selected from N, O, and S and optionally substituted with one or more -$Q_2$-$T_2$.
For example, $R_6$ is pyridinyl, pyrazolyl, pyrimidinyl, quinolinyl, tetrazolyl, oxazolyl, isoxazolyl, thiazolyl, isothiazolyl, furyl, or thienyl, each of which is optionally substituted with one or more -$Q_2$-$T_2$.
For example, $R_6$ is $C_6-C_{10}$ aryl or 5- or 6-membered heteroaryl, each of which is optionally, independently substituted with one or more -$Q_2$-$T_2$, wherein $Q_2$ is a bond or $C_1-C_3$ alkyl linker, and $T_2$ is H, halo, cyano, —$OR_c$, —$NR_cR_d$, —$C(O)NR_cR_d$, —$NR_dC(O)R_c$, —$S(O)_2R_c$, —$S(O)_2NR_cR_d$, or $R_{S4}$, in which each of $R_c$ and $R_d$, independently is H or $R_{S5}$, each of $R_{S4}$ and $R_{S5}$, independently, is $C_1-C_6$ alkyl, or $R_c$ and $R_d$, together with the N atom to which they are attached, form a 4 to 7-membered heterocycloalkyl ring having 0 or 1 additional heteroatom, and each of $R_{S4}$, $R_{S5}$, and the 4 to 7-membered heterocycloalkyl ring formed by $R_c$ and $R_d$, is optionally, independently substituted with one or more -$Q_3$-$T_3$, wherein $Q_3$ is a bond or $C_1-C_3$ alkyl linker and $T_3$ is selected from the group consisting of H, halo, $C_1-C_6$ alkyl, 4 to 7-membered heterocycloalkyl, $OR_e$, —$S(O)_2R_e$, and —$NR_eR_f$, each of $R_e$ and $R_f$ independently being H or $C_1-C_6$ alkyl optionally substituted with OH, O—$C_1-C_6$ alkyl, or NH—$C_1-C_6$ alkyl, or -$Q_3$-$T_3$ is oxo; or any two neighboring -$Q_2$-$T_2$, together with the atoms to which they are attached form a 5- or 6-membered ring optionally containing 1-4 heteroatoms selected from N, O and S.
For example, $R_6$ is phenyl or 5- or 6-membered heteroaryl substituted with O—$C_{1-6}$ alkyl or NH—$C_{1-6}$ alkyl, each of which is optionally substituted hydroxyl, O—$C_{1-3}$ alkyl or NH—$C_{1-3}$ alkyl, each of the O—$C_{1-3}$ alkyl and NH—$C_{1-3}$ alkyl being optionally further substituted with O—$C_{1-3}$ alkyl or NH—$C_{1-3}$ alkyl.
For example, $R_6$ is

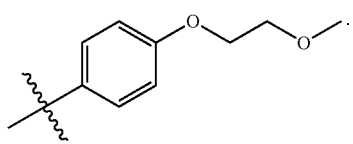 [SMILES: *c1ccc(OCCOC)cc1]

For example, $R_6$ is H.
For example, $R_6$ is halo (e.g., fluorine, chlorine, bromine, and iodine).
For example, $R_6$ is Cl.
For example, $R_6$ is $C_1-C_3$ alkyl optionally substituted with one or more -$Q_2$-$T_2$.
For example, $R_6$ is $CF_3$.

For example, $R_6$ is $C_2-C_6$ alkenyl, $C_2-C_6$ alkynyl, or $C_3-C_6$ cycloalkyl each optionally substituted with one or more -$Q_2$-$T_2$.
For example, $R_6$ is ethenyl.
For example, $R_6$ is ethynyl.
For example, $R_6$ is ethynyl substituted with one or more -$Q_2$-$T_2$, in which $Q_2$ is a bond or $C_1-C_3$ alkyl linker and $T_2$ is $C_1-C_6$ alkyl, $C_3-C_6$ cycloalkyl, or 4 to 7-membered heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyranyl, 1,4-diazepanyl, 1,4-oxazepanyl, 2-oxa-5-azabicyclo[2.2.1]heptanyl, 2,5-diazabicyclo[2.2.1]heptanyl, and morpholinyl, and the like) optionally substituted with one or more -$Q_3$-$T_3$.
For example, $R_6$ is azido.
For example, $R_6$ is cyano.
For example, $R_6$ is C(O)H.
For example, $R_6$ is $OR_a$ or —$C(O)R_a$.
For example, $R_a$ is $C_1-C_6$ alkyl or 4 to 7-membered heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyranyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, and morpholinyl, and the like), which is optionally substituted with one or more -$Q_2$-$T_2$.
For example, $R_6$ is 4 to 7-membered heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyranyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, and morpholinyl, and the like) optionally substituted with one or more -$Q_2$-$T_2$.
For example, $R_6$ is piperidinyl, 2,2,6,6-tetramethyl-piperidinyl, 1,2,3,6-tetrahydropyridinyl, 2,2,6,6-tetramethyl-1,2,3,6-tetrahydropyridinyl, piperazinyl, morpholinyl, tetrahydro-2H-pyranyl, 3,6-dihydro-2H-pyranyl, or pyrrolidinyl, each of which is optionally substituted with one or more -$Q_2$-$T_2$.
For example, $R_6$ is 4 to 7-membered heterocycloalkyl optionally substituted with one or more -$Q_2$-$T_2$, and -$Q_2$-$T_2$ is oxo or $Q_2$ is a bond and $T_2$ is —$OR_c$, —$NR_cR_d$, —$C(O)R_c$, —$C(O)OR_c$, —$S(O)_2R_c$, $C_1-C_6$ alkyl, or 4 to 7-membered heterocycloalkyl, each of which is optionally substituted with one or more -$Q_3$-$T_3$ when $R_c$ or $R_d$ is not H.
For example, $R_6$ is —$NR_aR_b$, —$C(O)R_a$, —$C(O)OR_a$, —$C(O)NR_aR_b$, —$NR_bC(O)R_a$, —$SR_a$, —$S(O)_2R_a$, or —$S(O)_2NR_aR_b$.
For example, each of $R_a$ and $R_b$, independently is H, $C_1-C_6$ alkyl or $C_3-C_8$ cycloalkyl optionally substituted with one or more -$Q_2$-$T_2$.
For example, one of $R_a$ and $R_b$ is H.
For example, $R_a$ and $R_b$, together with the N atom to which they are attached, form a 4 to 7-membered heterocycloalkyl ring having 0 or 1 additional heteroatoms to the N atom (e.g., azetidinyl, pyrrolidinyl, imidazolidinyl, pyrazolidinyl, oxazolidinyl, isoxazolidinyl, triazolidinyl, piperidinyl, 1,2,3,6-tetrahydropyridinyl, piperazinyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, and morpholinyl, and the like) and the ring is optionally substituted with one or more -$Q_2$-$T_2$.

For example, -$Q_2$-$T_2$ is not H.

For example, -$Q_2$-$T_2$ is oxo.

For example, $Q_2$ is a bond.

For example, $Q_2$ is an unsubstituted $C_1$-$C_3$ alkyl linker.

For example, $T_2$ is $C_1$-$C_6$ alkyl or $C_6$-$C_{10}$ aryl, each optionally substituted with one or more -$Q_3$-$T_3$.

For example, $T_2$ is an unsubstituted substituted straight chain $C_1$-$C_6$ or branched $C_3$-$C_6$ alkyl, including but not limited to, methyl, ethyl, n-propyl, i-propyl, n-butyl, s-butyl, t-butyl, n-pentyl, s-pentyl and n-hexyl.

For example, $T_2$ is phenyl.

For example, $T_2$ is halo (e.g., fluorine, chlorine, bromine, and iodine).

For example, $T_2$ is 4 to 7-membered heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyranyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, and morpholinyl, and the like) optionally substituted with one or more -$Q_3$-$T_3$.

For example, $T_2$ is —$OR_c$, —$NR_cR_d$, —$C(O)R_c$, —$C(O)OR_c$, or —$S(O)_2R_c$.

For example, $R_c$ is $C_1$-$C_6$ alkyl or 4 to 7-membered heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyranyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, and morpholinyl, and the like), which is optionally substituted with one or more -$Q_3$-$T_3$.

For example, each of $R_c$ and $R_d$, independently is H or $C_1$-$C_6$ alkyl optionally substituted with one or more -$Q_3$-$T_3$.

For example, $R_c$ is H.

For example, $R_d$ is H.

For example, $R_c$ and $R_d$, together with the N atom to which they are attached, form a 4 to 7-membered heterocycloalkyl ring having 0 or 1 additional heteroatoms to the N atom (e.g., azetidinyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, and morpholinyl, and the like) and the ring is optionally substituted with one or more -$Q_3$-$T_3$.

For example, $Q_2$ is a bond and $T_2$ is —$OR_c$, —$NR_cR_d$, —$C(O)R_c$, —$C(O)OR_c$, —$S(O)_2R_c$, $C_1$-$C_6$ alkyl, or 4 to 7-membered heterocycloalkyl, each of which is optionally substituted with one or more -$Q_3$-$T_3$ when $R_c$ or $R_d$ is not H.

For example, -$Q_3$-$T_3$ is oxo.

For example, $T_2$ is 4 to 7-membered heterocycloalkyl or $C_3$-$C_8$ cycloalkyl and one or more -$Q_3$-$T_3$ are oxo.

For example, $Q_3$ is a bond or unsubstituted or substituted $C_1$-$C_3$ alkyl linker.

For example, $T_3$ is H, halo, 4 to 7-membered heterocycloalkyl, $C_1$-$C_3$ alkyl, $OR_e$, $C(O)OR_e$, —$S(O)_2R_e$, —$NR_eR_f$, or —$C(O)NR_eR_f$.

For example, one of $R_d$ and $R_e$ is H.

For example, $Q_3$ is a bond or $C_1$-$C_3$ alkyl linker and $T_3$ is selected from the group consisting of $C_1$-$C_3$ alkyl, halo, $OR_e$, —$S(O)_2R_e$, —$NR_eR_f$, and —$C(O)NR_eR_f$.

For example, $Q_3$ is a bond or $C_1$-$C_3$ alkyl linker and $T_3$ is selected from the group consisting of $C_1$-$C_3$ alkyl, $OR_e$, —$S(O)_2R_e$, or —$NR_eR_f$.

For example, $R_e$ is H.

For example, $R_f$ is H.

For example, $R_6$ is selected from the group consisting of $CH_3$, $OCH_3$,

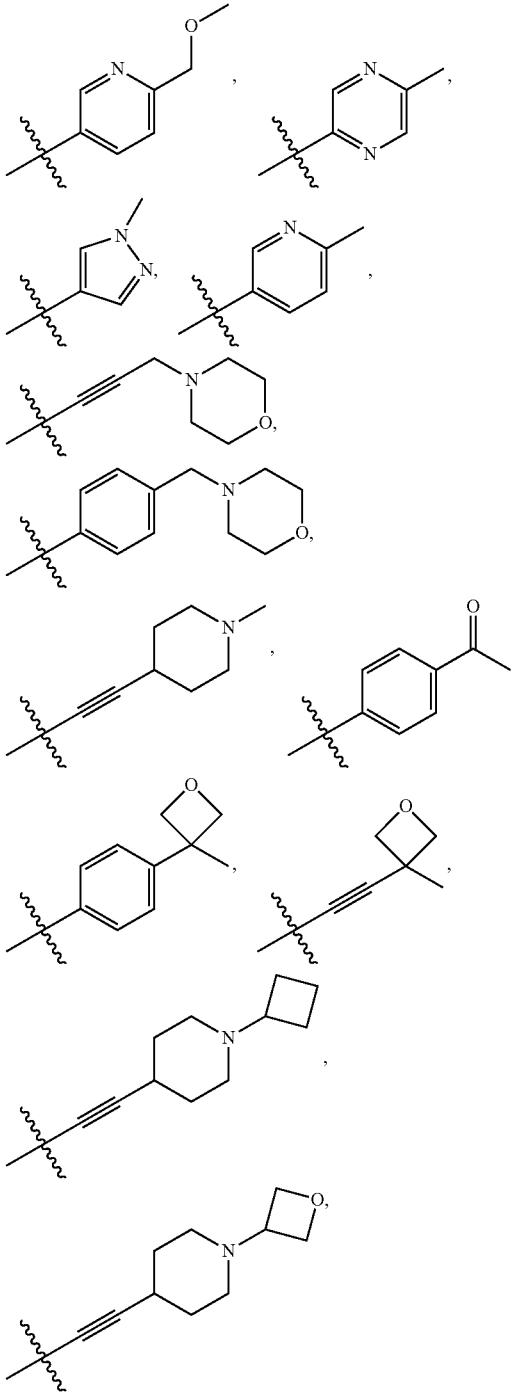

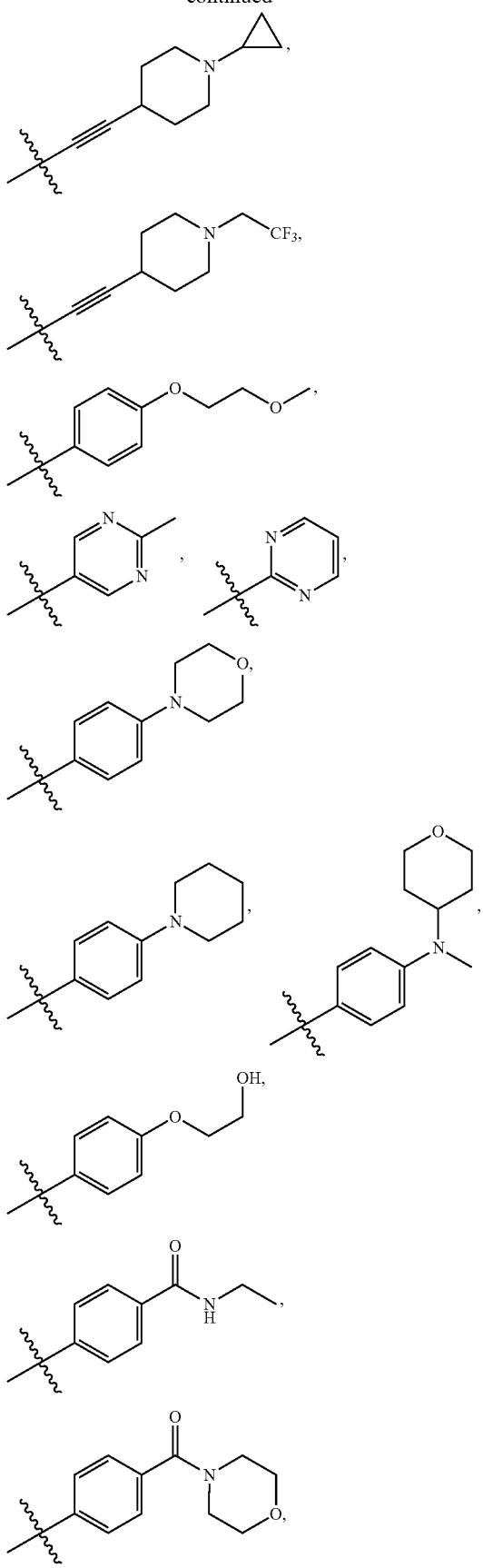
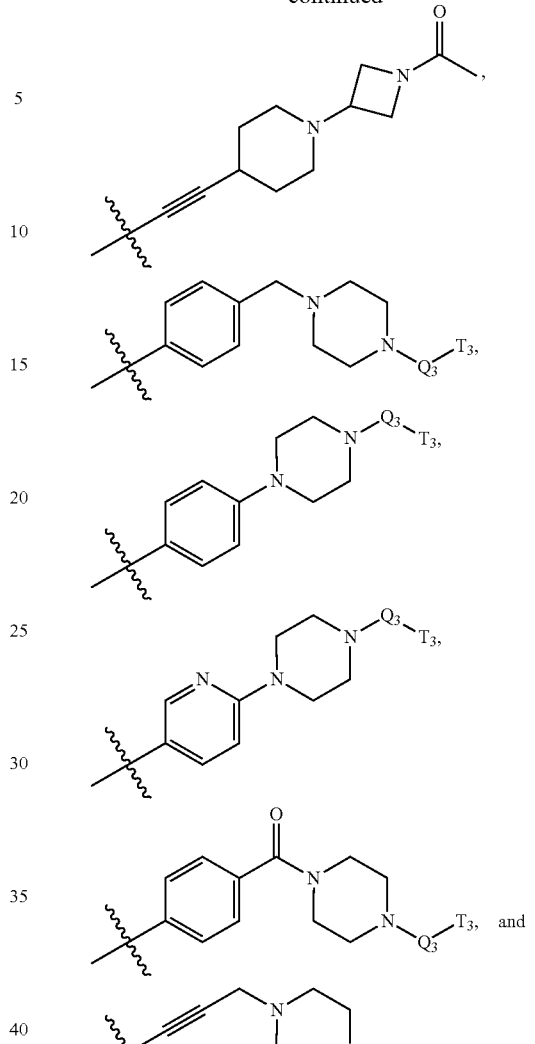

For example, $R_7$ is not H.

For example, $R_7$ is —C(O)$R_g$.

For example, $R_7$ is —C(O)$R_g$, in which $R_g$ is $C_3$-$C_8$ cycloalkyl, or 4 to 7-membered heterocycloalkyl, $C_3$-$C_8$ cycloalkyl.

For example, $R_7$ is $C_6$-$C_{10}$ aryl substituted with one or more -$Q_5$-$T_5$.

For example, $R_7$ is phenyl optionally substituted with one or more -$Q_5$-$T_5$.

For example, $R_7$ is $C_1$-$C_6$ alkyl optionally substituted with one or more -$Q_5$-$T_5$.

For example, $R_7$ is $C_3$-$C_8$ cycloalkyl optionally substituted with one or more -$Q_5$-$T_5$.

For example, $R_7$ is 4 to 7-membered heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyranyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, and morpholinyl, and the like) optionally substituted with one or more -$Q_5$-$T_5$.

For example, $R_7$ is 8 to 14-membered heterocycloalkyl such as 1,4-dioxaspiro[4.5]decanyl (e.g., 1,4-dioxaspiro[4.5]decan-8-yl), 1,4-dioxa-8-azaspiro[4.5]decanyl (e.g., 1,4-dioxa-8-azaspiro[4.5]decan-8-yl), 1-oxaspiro[4.5]decanyl (e.g., 1-oxaspiro[4.5]decan-8-yl or 1-oxaspiro[4.5]decan-2-one-8-yl), 1-azaspiro[4.5]decanyl (e.g., 1-azaspiro[4.5]decan-8-yl or 1-azaspiro[4.5]decan-2-one-8-yl), 3'H-spiro[cyclohexane-1,1'-isobenzofuran]-yl (e.g., 3'H-spiro[cyclohexane-1,1'-isobenzofuran]-4-yl or 3'H-spiro[cyclohexane-1,1'-isobenzofuran]-3'-one-4-yl), 7'H-spiro[cyclohexane-1,5'-furo[3,4-b]pyridin]-yl (e.g., 7'H-spiro[cyclohexane-1,5'-furo[3,4-b]pyridin]-4-yl or 7'H-spiro[cyclohexane-1,5'-furo[3,4-b]pyridin]-7'-one-4-yl), or 3'H-spiro[cyclohexane-1,1'-furo[3,4-c]pyridin]-yl (e.g., 3'H-spiro[cyclohexane-1,1'-furo[3,4-c]pyridin]-4-yl or 3'H-spiro[cyclohexane-1,1'-furo[3,4-c]pyridin]-3'-one-4-yl), each optionally substituted with one or more -$Q_5$-$T_5$.

For example, $R_7$ is 5 to 6-membered heterocycloalkyl optionally substituted with one or more -$Q_5$-$T_5$.

For example, $R_7$ is isopropyl.

For example, $R_7$ is piperidinyl, tetrahydropyran, tetrahydro-2H-thiopyranyl, piperazinyl, cyclopentyl, cyclohexyl, pyrrolidinyl, or cycloheptyl, each optionally substituted with one or more -$Q_5$-$T_5$.

For example, $R_7$ is piperidinyl, tetrahydropyran, cyclopentyl, or cyclohexyl, each optionally substituted with one -$Q_5$-$T_5$ and $R_8$ is ethyl.

For example, $R_7$ is tetrahydropyran or

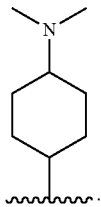

For example, $R_7$ is

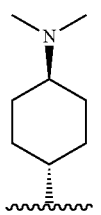 or 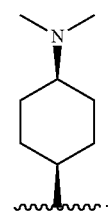

For example, $R_7$ is

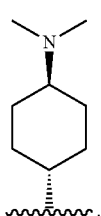

For example, $R_7$ is

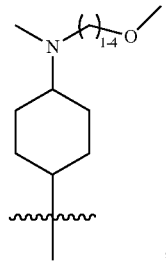, e.g., 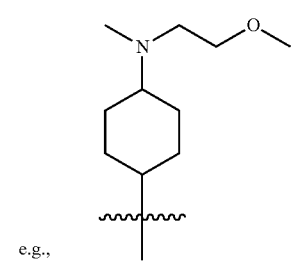

For example, $R_7$ is

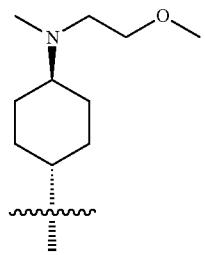 or 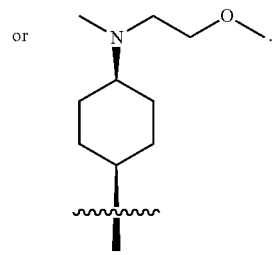

For example, $R_7$ is

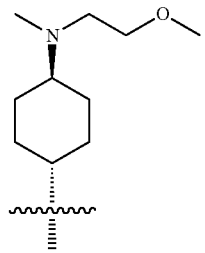

For example, $R_7$ is

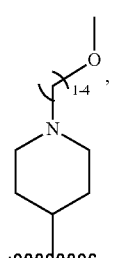 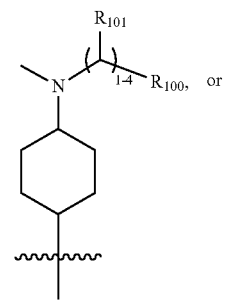

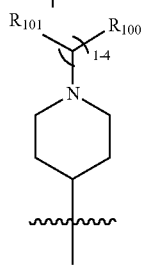

wherein $R_{100}$ is phenyl, 5- or 6-membered heteroaryl, or 4 to 12-membered heterocycloalkyl, each optionally substituted with one or more $T_{5a}$ in which each $T_{5a}$ is independently $C_1$-$C_6$ alkoxyl or O—$C_1$-$C_4$ alkylene-$C_1$-$C_4$ alkoxy, and $R_{101}$ is H or $C_1$-$C_4$ alkyl.
For example, $R_7$ is
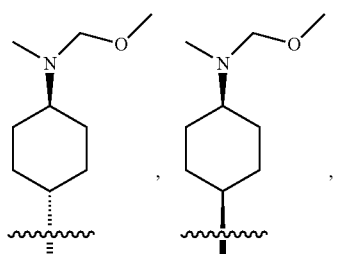,
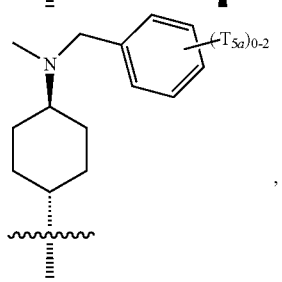,
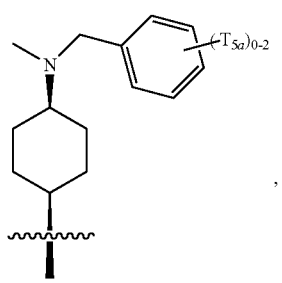,
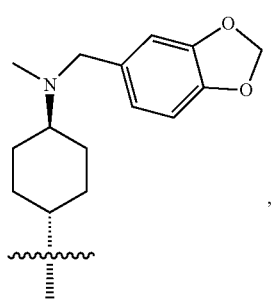,
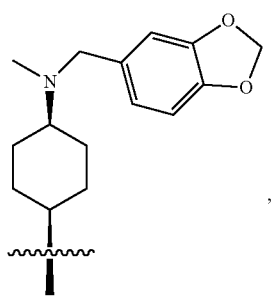,
-continued
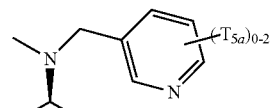,
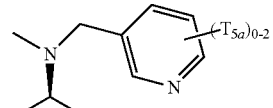,
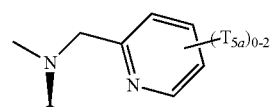,
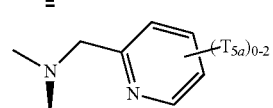,
,
,
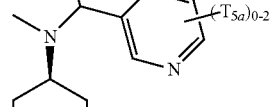,

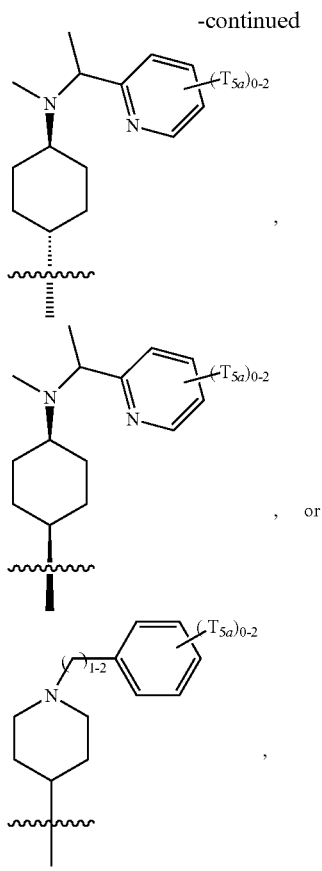

wherein each $T_{5a}$ is independently $C_1$-$C_3$ alkoxyl or O—$C_1$-$C_3$ alkylene-$C_1$-$C_2$ alkoxy.

For example, $R_7$ is cyclopentyl or cyclohexyl, each optionally substituted with one -$Q_5$-$T_5$.

For example, $Q_5$ is NHC(O) and $T_5$ is $C_1$-$C_6$ alkyl or $C_1$-$C_6$ alkoxy.

For example, -$Q_5$-$T_5$ is oxo.

For example, $T_4$ is 4 to 7-membered heterocycloalkyl or $C_3$-$C_8$ cycloalkyl or $C_6$-$C_{10}$ aryl, and one or more -$Q_5$-$T_5$ are oxo.

For example, $R_7$ is 1-oxide-tetrahydro-2H-thiopyranyl or 1,1-dioxide-tetrahydro-2H-thiopyranyl.

For example, $R_7$ is cyclohexanonyl, e.g., cyclohexanon-4-yl.

For example, $T_5$ is H, halo, $C_1$-$C_6$ alkyl, $C_1$-$C_6$ alkoxyl, $C_3$-$C_8$ cycloalkyl, $C_6$-$C_{10}$ aryl, or 4 to 7-membered heterocycloalkyl.

For example, $Q_5$ is a bond or $NR_k$ and $T_5$ is H, $C_1$-$C_6$ alkyl, $C_3$-$C_8$ cycloalkyl, $C_1$-$C_6$ alkylene-$C_3$-$C_8$ cycloalkyl, $C_6$-$C_{10}$ aryl, $C_1$-$C_6$ alkylene-$C_6$-$C_{10}$ aryl, 4 to 12-membered heterocycloalkyl, $C_1$-$C_6$ alkylene-4 to 12-membered heterocycloalkyl, 5- or 6-membered heteroaryl, $C_1$-$C_6$ alkylene-5- or 6-membered heteroaryl, amino, mono-$C_1$-$C_6$ alkylamino, or di-$C_1$-$C_6$ alkylamino, $T_5$ being optionally substituted with one or more substituents selected from the group consisting of halo, hydroxyl, $C_1$-$C_6$ alkoxyl, O—$C_1$-$C_4$ alkylene-$C_1$-$C_4$ alkoxy, and $C_3$-$C_8$ cycloalkyl.

For example, $Q_5$ is a bond or $NR_k$ and $T_5$ is $C_6$-$C_{10}$ aryl, $C_1$-$C_6$ alkylene-$C_6$-$C_{10}$ aryl, 5- or 6-membered heteroaryl, $C_1$-$C_6$ alkylene-5- or 6-membered heteroaryl, amino, mono-$C_1$-$C_6$ alkylamino, di-$C_1$-$C_6$ alkylamino, $T_5$ being optionally substituted with one or more substituents selected from the group consisting of halo, hydroxyl, $C_1$-$C_6$ alkoxyl, O—$C_1$-$C_4$ alkylene-$C_1$-$C_4$ alkoxy, and $C_3$-$C_8$ cycloalkyl.

For example, $Q_5$ is CO, $S(O)_2$, or NHC(O); and $T_5$ is $C_1$-$C_6$ alkyl, $C_1$-$C_6$ alkoxyl, $C_3$-$C_8$ cycloalkyl, or 4 to 7-membered heterocycloalkyl.

For example, $T_5$ is $C_1$-$C_6$ alkyl or $C_1$-$C_6$ alkoxyl, each optionally substituted with halo, hydroxyl, cyano, $C_1$-$C_6$ alkoxyl, amino, mono-$C_1$-$C_6$ alkylamino, di-$C_1$-$C_6$ alkylamino, or $C_3$-$C_8$ cycloalkyl.

For example, $Q_5$ is $C_1$-$C_3$ alkyl linker and $T_5$ is H or $C_6$-$C_{10}$ aryl.

For example, $Q_5$ is $C_1$-$C_3$ alkyl linker and $T_5$ is $C_3$-$C_8$ cycloalkyl, 4 to 7-membered heterocycloalkyl, or $S(O)_q R_q$.

For example, $R_6$ is halo (e.g., fluorine, chlorine, bromine, and iodine) and Z is $S(O)_a R_7$, in which a is 0, 1, or 2 and $R_7$ is $C_1$-$C_6$ alkyl (e.g., methyl, ethyl, n-propyl, i-propyl, butyl, or t-butyl), $C_3$-$C_8$ cycloalkyl (e.g., cyclopentyl, cyclohexyl, or cycloheptyl) or 4 to 14-membered heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyranyl, 1,4-diazepanyl, 1,4-oxazepanyl, 2-oxa-5-azabicyclo[2.2.1]heptanyl, 2,5-diazabicyclo[2.2.1]heptanyl, morpholinyl, 1,4-dioxaspiro[4.5]decanyl, 1,4-dioxa-8-azaspiro[4.5]decanyl, 1-oxaspiro[4.5]decanyl, 1-azaspiro[4.5]decanyl, 3'H-spiro[cyclohexane-1,1'-isobenzofuran]-yl, 7'H-spiro[cyclohexane-1,5'-furo[3,4-b]pyridin]-yl, or 3'H-spiro[cyclohexane-1,1'-furo[3,4-c]pyridin]-yl, and the like) and $R_7$ is optionally substituted with one or more -$Q_5$-$T_5$.

For example, $R_6$ is halo (e.g., fluorine, chlorine, bromine, and iodine) and Z is $OR_7$ in which $R_7$ is 4 to 14-membered heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyranyl, 1,4-diazepanyl, 1,4-oxazepanyl, 2-oxa-5-azabicyclo[2.2.1]heptanyl, 2,5-diazabicyclo[2.2.1]heptanyl, morpholinyl, 1,4-dioxaspiro[4.5]decanyl, 1,4-dioxa-8-azaspiro[4.5]decanyl, 1-oxaspiro[4.5]decanyl, 1-azaspiro[4.5]decanyl, 3'H-spiro[cyclohexane-1,1'-isobenzofuran]-yl, 7'H-spiro[cyclohexane-1,5'-furo[3,4-b]pyridin]-yl, or 3'H-spiro[cyclohexane-1,1'-furo[3,4-c]pyridin]-yl, and the like) and $R_7$ is optionally substituted with one or more -$Q_5$-$T_5$.

For example, each of $R_2$ and $R_4$, independently, is H, halo, or $C_1$-$C_6$ alkyl optionally substituted with amino, azido, halo, mono-$C_1$-$C_6$ alkylamino, di-$C_1$-$C_6$ alkylamino, or $C_6$-$C_{10}$ aryl.

For example, each of $R_2$ and $R_4$, independently is $C_1$-$C_3$ alkyl optionally substituted with $C_1$-$C_6$ alkoxyl.

For example, each of $R_2$ and $R_4$ is methyl.

For example, each of $R_2$ and $R_4$, independently is halo, e.g., F, Cl, or Br.

For example, each of $R_2$ and $R_4$, independently, is CN, mono-$C_1$-$C_6$ alkylamino, or di-$C_1$-$C_6$ alkylamino.

For example, each of $R_2$ and $R_4$, independently, is optionally substituted phenyl.

For example, each of $R_2$ and $R_4$, independently, is optionally substituted 5- or 6-membered heteroaryl (e.g., pyrrolyl, pyrazolyl, imidazolyl, pyridyl, pyrimidinyl, pyrazinyl, pyridazinyl, tetrazolyl, oxazolyl, isoxazolyl, thiazolyl, isothiazolyl, and the like).

For example, each of $R_2$ and $R_4$, independently, is optionally substituted 4 to 12-membered heterocycloalkyl (e.g., pyrrolidinyl, imidazolidinyl, pyrazolidinyl, oxazolidinyl, isoxazolidinyl, triazolidinyl, piperidinyl, 1,2,3,6-tetrahydropyridinyl, piperazinyl, 1,4-diazepanyl, 1,4-oxazepanyl, and morpholinyl, and the like).

For example, each of $R_2$ and $R_4$, independently, is $C_{1-6}$ alkoxyl or $C_6$-$C_{10}$ aryloxy, each optionally substituted with one or more halo.

For example, $R_2$ is $C_{1-6}$ alkoxyl or $C_6$-$C_{10}$ aryloxy, each optionally substituted with one or more halo.

For example, $R_4$ is halo, or $C_{1-4}$ alkyl or $C_{1-6}$ alkoxyl, each optionally substituted with one or more halo.

For example, $R_3$ is H, halo, or $C_{1-4}$ alkyl.

For example, $R_1$ is OH, SH, or NH($C_{1-4}$ alkyl).

For example, neighboring $R_1$ and $R_2$, together with the atoms to which they are attached, form a 5- or 6-membered heteroaryl having 0 to 2 additional heteroatoms (e.g., pyrrolyl, pyrazolyl, imidazolyl, pyridyl, pyrimidinyl, pyrazinyl, pyridazinyl, tetrazolyl, oxazolyl, isoxazolyl, thiazolyl, isothiazolyl, and the like), or a 5 to 12-membered heterocycloalkyl ring having 0 to 2 additional heteroatoms (e.g., pyrrolidinyl, imidazolidinyl, pyrazolidinyl, oxazolidinyl, isoxazolidinyl, triazolidinyl, piperidinyl, 1,2,3,6-tetrahydropyridinyl, piperazinyl, 1,4-diazepanyl, 1,4-oxazepanyl, and morpholinyl, and the like). Further, each of the ring structures formed by $R_1$ and $R_2$ mentioned above, independently, is optionally substituted with one or more substituents selected from the group consisting of halo, hydroxyl, oxo, $C_1$-$C_6$ alkyl, C(O)OH, C(O)O—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl.

For example, neighboring $R_1$ and $R_4$, together with the atoms to which they are attached, form a 5- or 6-membered heteroaryl having 0 to 2 additional heteroatoms (e.g., pyrrolyl, pyrazolyl, imidazolyl, pyridyl, pyrimidinyl, pyrazinyl, pyridazinyl, tetrazolyl, oxazolyl, isoxazolyl, thiazolyl, isothiazolyl, and the like), or a 5 to 12-membered heterocycloalkyl ring having 0 to 2 additional heteroatoms (e.g., pyrrolidinyl, imidazolidinyl, pyrazolidinyl, oxazolidinyl, isoxazolidinyl, triazolidinyl, piperidinyl, 1,2,3,6-tetrahydropyridinyl, piperazinyl, 1,4-diazepanyl, 1,4-oxazepanyl, and morpholinyl, and the like). Further, each of the ring structures formed by $R_1$ and $R_4$ mentioned above, independently, is optionally substituted with one or more substituents selected from the group consisting of halo, hydroxyl, oxo, $C_1$-$C_6$ alkyl, C(O)OH, C(O)O—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl.

For example, neighboring $R_3$ and $R_4$, together with the C atoms to which they are attached, form $C_5$-$C_8$ cycloalkyl (e.g., $C_5$-$C_6$ cycloalkyl), $C_6$-$C_{10}$ aryl (e.g., phenyl), or a 5- or 6-membered heteroaryl having 1 to 3 heteroatoms (e.g., pyrrolyl, pyrazolyl, imidazolyl, pyridyl, pyrimidinyl, pyrazinyl, pyridazinyl, tetrazolyl, oxazolyl, isoxazolyl, thiazolyl, isothiazolyl, and the like), or a 5 to 12-membered heterocycloalkyl ring having 1 to 3 heteroatoms (e.g., pyrrolidinyl, imidazolidinyl, pyrazolidinyl, oxazolidinyl, isoxazolidinyl, triazolidinyl, piperidinyl, 1,2,3,6-tetrahydropyridinyl, piperazinyl, 1,4-diazepanyl, 1,4-oxazepanyl, and morpholinyl, and the like). Further, each of the above-mentioned ring structures formed by $R_3$ and $R_4$, independently, is optionally substituted with one or more substituents selected from the group consisting of halo, hydroxyl, oxo, $C_1$-$C_6$ alkyl, C(O)OH, C(O)O—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl.

For example, $R_1$ is OH.

For example, $R_{12}$ is H, methyl, ethyl, ethenyl, or halo.

For example, $R_{12}$ is methyl.

For example, $R_{12}$ is ethyl or propenyl.

For example, $R_{12}$ is methoxyl.

For example, $R_{12}$ is ethenyl.

For example, $R_8$ is H, methyl, ethyl, or ethenyl.

For example, $R_8$ is methyl.

For example, $R_8$ is ethyl.

For example, $R_8$ is propyl.

For example, $R_8$ is ethenyl or propenyl.

For example, $R_8$ is $C_1$-$C_6$ alkyl substituted with one or more substituents selected from the group consisting of halo (e.g., F, Cl, or Br), hydroxyl, or $C_1$-$C_6$ alkoxyl.

For example, $R_8$ is 4 to 7-membered optionally substituted heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyranyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, and morpholinyl, and the like).

For example, $R_8$ is piperidinyl.

For example, $R_8$ is 4 to 7-membered optionally substituted heterocycloalkyl and $R_7$ is -$Q_4$-$T_4$, in which $Q_4$ is a bond or $C_1$-$C_4$ alkyl linker and $T_4$ is H, $C_1$-$C_6$ alkyl, $C_3$-$C_8$ cycloalkyl or 4 to 7-membered heterocycloalkyl.

For example, Z is $NR_7R_8$ or $CR_7R_8R_{14}$ wherein $R_7$ and $R_8$, together with the atom to which they are attached, form a 4 to 11-membered heterocycloalkyl ring having 1 to 3 heteroatoms (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyranyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, morpholinyl, 1,4-dioxa-8-azaspiro[4.5]decanyl, and the like) or $C_3$-$C_8$ cycloalkyl, each optionally substituted with one or more -$Q_6$-$T_6$.

For example, the ring formed by $R_7$ and $R_8$ is selected from the group consisting of azetidinyl, pyrrolidinyl, piperidinyl, morpholinyl, piperazinyl, 1,4-dioxa-8-azaspiro[4.5]decanyl, and cyclohexenyl, each optionally substituted with one -$Q_6$-$T_6$.

For example, Z is 1,4-dioxa-8-azaspiro[4.5]decan-8-yl, pyrrolidine-2,5-dione-1-yl, or piperidine-2,6-dione-1-yl.

For example, one or more -Q-$T_6$ is oxo.

For example, $T_6$ is H, halo, $C_1$-$C_6$ alkyl, $C_1$-$C_6$ alkoxyl, $C_3$-$C_8$ cycloalkyl, $C_6$-$C_{10}$ aryl, or 4 to 7-membered heterocycloalkyl.

For example, $Q_6$ is a bond and $T_6$ is $C_1$-$C_6$ alkyl, $C_3$-$C_8$ cycloalkyl, or 4 to 7-membered heterocycloalkyl.

For example, $Q_6$ is CO, $S(O)_2$, or NHC(O); and $T_6$ is $C_1$-$C_6$ alkyl, $C_1$-$C_6$ alkoxyl, $C_3$-$C_8$ cycloalkyl, or 4 to 7-membered heterocycloalkyl.

For example, $T_6$ is $C_1$-$C_6$ alkyl or $C_1$-$C_6$ alkoxyl, each optionally substituted with halo, hydroxyl, cyano, $C_1$-$C_6$ alkoxyl, amino, mono-$C_1$-$C_6$ alkylamino, di-$C_1$-$C_6$ alkylamino, or $C_3$-$C_8$ cycloalkyl.

For example, $Q_6$ is $C_1$-$C_3$ alkyl linker and $T_6$ is H or $C_6$-$C_{10}$ aryl.

For example, $Q_6$ is $C_1$-$C_3$ alkyl linker and $T_6$ is $C_3$-$C_8$ cycloalkyl, 4 to 7-membered heterocycloalkyl, or $S(O)_pR_p$.

For example, each of $R_p$ and $R_q$, independently, is $C_1$-$C_6$ alkyl.

For example, $R_6$ is —S(O)$_b$R$_a$ or azido, in which b is 0, 1, or 2 and $R_a$ is $C_1$-$C_6$ alkyl or $C_3$-$C_8$ cycloalkyl; and Z is NR$_7$R$_8$, in which $R_7$ is $C_3$-$C_8$ cycloalkyl (e.g., cyclopentyl, cyclohexyl, or cycloheptyl) or 4 to 14-membered heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyranyl, 1,4-diazepanyl, 1,4-oxazepanyl, 2-oxa-5-azabicyclo[2.2.1]heptanyl, 2,5-diazabicyclo[2.2.1]heptanyl, morpholinyl, 1,4-dioxaspiro[4.5]decanyl, 1,4-dioxa-8-azaspiro[4.5]decanyl, 1-oxaspiro[4.5]decanyl, 1-azaspiro[4.5]decanyl, 3'H-spiro[cyclohexane-1,1'-isobenzofuran]-yl, 7'H-spiro[cyclohexane-1,5'-furo[3,4-b]pyridin]-yl, or 3'H-spiro[cyclohexane-1,1'-furo[3,4-c]pyridin]-yl, and the like), each optionally substituted with one or more -Q$_5$-T$_5$; and $R_8$ is H or $C_1$-$C_6$ alkyl (e.g., methyl, ethyl, n-propyl, i-propyl, butyl, or t-butyl).

For example, $R_6$ is halo (e.g., fluorine, chlorine, bromine, and iodine) and Z is NR$_7$R$_8$ or CR$_7$R$_8$R$_{14}$ wherein $R_7$ and $R_8$, together with the atom to which they are attached, form a 4 to 11-membered heterocycloalkyl ring having 1 to 3 heteroatoms (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyranyl, 1,4-diazepanyl, 1,4-oxazepanyl, 2-oxa-5-azabicyclo[2.2.1]heptanyl, 2,5-diazabicyclo[2.2.1]heptanyl, morpholinyl, 2-oxa-6-azaspiro[3.3]heptanyl, 2,6-diazaspiro[3.3]heptanyl, 1,4-dioxa-8-azaspiro[4.5]decanyl, 1,4-dioxa-8-azaspiro[4.5]decan-8-yl, pyrrolidine-2,5-dione-1-yl, piperidine-2,6-dione-1-yl, and the like) or $C_3$-$C_8$ cycloalkyl, each optionally substituted with one or more -Q$_6$-T$_6$.

For example, $R_3$ is H.

For example, each of $R_5$, $R_9$, and $R_{10}$ is H.

For example, X is pyrazolo[1,5-a]pyridin-7(1H)-one-6-yl, [1,2,4]triazolo[1,5-a]pyridin-7(1H)-one-6-yl, [1,2,3]triazolo[1,5-a]pyridin-7(1H)-one-6-yl, tetrazolo[1,5-a]pyridin-7(1H)-one-6-yl, 2,3-dihydropyrazolo[1,5-a]pyridin-7(1H)-one-6-yl, 2,3-dihydro-[1,2,4]triazolo[1,5-a]pyridin-7(1H)-one-6-yl, 2,3-dihydro-[1,2,3]triazolo[1,5-a]pyridin-7(1H)-one-6-yl, or 2,3-dihydrotetrazolo[1,5-a]pyridin-7(1H)-one-6-yl; each of which is optionally substituted with one or more substituents selected from the group consisting of halo, hydroxyl, $C_1$-$C_6$ alkyl, $C_1$-$C_6$ haloalkyl, C(O)OH, C(O)O—$C_1$-$C_6$ alkyl, C(O)O—$C_1$-$C_6$ haloalkyl, cyano, $C_1$-$C_6$ alkoxyl, $C_1$-$C_6$ haloalkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl. For example X is substituted with one or more substituents selected from halo, hydroxyl, $C_1$-$C_6$ alkyl, and $C_1$-$C_6$ haloalkyl.

For example, X is pyrazolo[1,5-a]pyrimidin-7(1H)-one-6-yl, [1,2,4]triazolo[1,5-a]pyrimidin-7(1H)-one-6-yl, [1,2,3]triazolo[1,5-a]pyrimidin-7(1H)-one-6-yl, tetrazolo[1,5-a]pyrimidin-7(1H)-one-6-yl, 2,3-dihydropyrazolo[1,5-a]pyrimidin-7(1H)-one-6-yl, 2,3-dihydro-[1,2,4]triazolo[1,5-a]pyrimidin-7(1H)-one-6-yl, 2,3-dihydro-[1,2,3]triazolo[1,5-a]pyrimidin-7(1H)-one-6-yl, or 2,3-dihydrotetrazolo[1,5-a]pyrimidin-7(1H)-one-6-yl; each of which is optionally substituted with one or more substituents selected from the group consisting of halo, hydroxyl, $C_1$-$C_6$ alkyl, $C_1$-$C_6$ haloalkyl, C(O)OH, C(O)O—$C_1$-$C_6$ alkyl, C(O)O—$C_1$-$C_6$ haloalkyl, cyano, $C_1$-$C_6$ alkoxyl, $C_1$-$C_6$ haloalkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl. For example X is substituted with one or more substituents selected from halo, hydroxyl, $C_1$-$C_6$ alkyl, and $C_1$-$C_6$ haloalkyl.

For example, X is pyrazolo[1,5-a]pyridin-5(1H)-one-6-yl, [1,2,4]triazolo[1,5-a]pyridin-5(1H)-one-6-yl, [1,2,3]triazolo[1,5-a]pyridin-5(1H)-one-6-yl, tetrazolo[1,5-a]pyridin-5(1H)-one-6-yl, 2,3-dihydropyrazolo[1,5-a]pyridin-5(1H)-one-6-yl, 2,3-dihydro-[1,2,4]triazolo[1,5-a]pyridin-5(1H)-one-6-yl, 2,3-dihydro-[1,2,3]triazolo[1,5-a]pyridin-5(1H)-one-6-yl, or 2,3-dihydrotetrazolo[1,5-a]pyridin-5(1H)-one-6-yl; each of which is optionally substituted with one or more substituents selected from the group consisting of halo, hydroxyl, $C_1$-$C_6$ alkyl, $C_1$-$C_6$ haloalkyl, C(O)OH, C(O)O—$C_1$-$C_6$ alkyl, C(O)O—$C_1$-$C_6$ haloalkyl, cyano, $C_1$-$C_6$ alkoxyl, $C_1$-$C_6$ haloalkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl. For example X is substituted with one or more substituents selected from halo, hydroxyl, $C_1$-$C_6$ alkyl, and $C_1$-$C_6$ haloalkyl.

For example, X is pyrazolo[1,5-a]pyrimidin-5(1H)-one-6-yl, [1,2,4]triazolo[1,5-a]pyrimidin-5(1H)-one-6-yl, [1,2,3]triazolo[1,5-a]pyrimidin-5(1H)-one-6-yl, tetrazolo[1,5-a]pyrimidin-5(1H)-one-6-yl, 2,3-dihydropyrazolo[1,5-a]pyrimidin-5(1H)-one-6-yl, 2,3-dihydro-[1,2,4]triazolo[1,5-a]pyrimidin-5(1H)-one-6-yl, 2,3-dihydro-[1,2,3]triazolo[1,5-a]pyrimidin-5(1H)-one-6-yl, or 2,3-dihydrotetrazolo[1,5-a]pyrimidin-5(1H)-one-6-yl; each of which is optionally substituted with one or more substituents selected from the group consisting of halo, hydroxyl, $C_1$-$C_6$ alkyl, $C_1$-$C_6$ haloalkyl, C(O)OH, C(O)O—$C_1$-$C_6$ alkyl, C(O)O—$C_1$-$C_6$ haloalkyl, cyano, $C_1$-$C_6$ alkoxyl, $C_1$-$C_6$ haloalkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl. For example X is substituted with one or more substituents selected from halo, hydroxyl, $C_1$-$C_6$ alkyl, and $C_1$-$C_6$ haloalkyl.

For example, X is 7H-isoxazolo[2,3-a]pyridin-7-one-6-yl, 7H-[1,3,4]oxadiazolo[3,2-a]pyridin-7-one-6-yl, 5H-[1,3,4]oxadiazolo[3,2-a]pyridin-5-one-6-yl, 7H-isoxazolo[2,3-a]pyrimidin-7-one-6-yl, 7H-[1,3,4]oxadiazolo[3,2-a]pyrimidin-7-one-6-yl, 5H-[1,3,4]oxadiazolo[3,2-a]pyrimidin-5-one-6-yl, 2,3-dihydro-7H-isoxazolo[2,3-a]pyridin-7-one-6-yl, 2,3-dihydro-7H-[1,3,4]oxadiazolo[3,2-a]pyridin-7-one-6-yl, 2,3-dihydro-5H-[1,3,4]oxadiazolo[3,2-a]pyridin-5-one-6-yl, 2,3-dihydro-7H-isoxazolo[2,3-a]pyrimidin-7-one-6-yl, 2,3-dihydro-7H-[1,3,4]oxadiazolo[3,2-a]pyrimidin-7-one-6-yl, 2,3-dihydro-5H-[1,3,4]oxadiazolo[3,2-a]pyrimidin-5-one-6-yl, 1H-[1,2,3]oxadiazolo[3,4-a]pyridin-7(3H)-one-6-yl, or 1H-[1,2,3]oxadiazolo[3,4-a]pyridin-5(3H)-one-6-yl; each of which is optionally substituted with one or more substituents selected from the group consisting of halo, hydroxyl, $C_1$-$C_6$ alkyl, $C_1$-$C_6$ haloalkyl, C(O)OH, C(O)O—$C_1$-$C_6$ alkyl, C(O)O—$C_1$-$C_6$ haloalkyl, cyano, $C_1$-$C_6$ alkoxyl, $C_1$-$C_6$ haloalkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl. For example X is substituted with one or more substituents selected from halo, hydroxyl, $C_1$-$C_6$ alkyl, and $C_1$-$C_6$ haloalkyl.

For example, X is 7H-isothiazolo[2,3-a]pyridin-7-one-6-yl, 7H-[1,3,4]thiadiazolo[3,2-a]pyridin-7-one-6-yl, 5H-[1,3,4]thiadiazolo[3,2-a]pyridin-5-one-6-yl, 7H-isothiazolo[2,3-a]pyrimidin-7-one-6-yl, 7H-[1,3,4]thiadiazolo[3,2-a]pyrimidin-7-one-6-yl, 5H-[1,3,4]thiadiazolo[3,2-a]

pyrimidin-5-one-6-yl, 2,3-dihydro-7H-isothiazolo[2,3-a]pyridin-7-one-6-yl, 2,3-dihydro-7H-[1,3,4]thiadiazolo[3,2-a]pyridin-5-one-6-yl, 2,3-dihydro-5H-[1,3,4]thiadiazolo[3,2-a]pyridin-5-one-6-yl, 2,3-dihydro-7H-isothiazolo[2,3-a]pyrimidin-7-one-6-yl, 2,3-dihydro-7H-[1,3,4]thiadiazolo[3,2-a]pyrimidin-7-one-6-yl, 2,3-dihydro-5H-[1,3,4]thiadiazolo[3,2-a]pyrimidin-5-one-6-yl, 1H-[1,2,3]thiadiazolo[3,4-a]pyrimidin-7(3H)-one-6-yl, or 1H-[1,2,3]thiadiazolo[3,4-a]pyridin-5(3H)-one-6-yl; each of which is optionally substituted with one or more substituents selected from the group consisting of halo, hydroxyl, $C_1$-$C_6$ alkyl, $C_1$-$C_6$ haloalkyl, C(O)OH, C(O)O—$C_1$-$C_6$ alkyl, C(O)O—$C_1$-$C_6$ haloalkyl, cyano, $C_1$-$C_6$ alkoxyl, $C_1$-$C_6$ haloalkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl. For example X is substituted with one or more substituents selected from halo, hydroxyl, $C_1$-$C_6$ alkyl, and $C_1$-$C_6$ haloalkyl.

For example, X is 1-hydroxy-pyridin-2(1H)-one-3-yl or 1-hydroxy-pyridin-4(1H)-one-3-yl, each of which is optionally substituted with one or more substituents selected from the group consisting of halo, hydroxyl, $C_1$-$C_6$ alkyl, $C_1$-$C_6$ haloalkyl, C(O)OH, C(O)O—$C_1$-$C_6$ alkyl, C(O)O—$C_1$-$C_6$ haloalkyl, cyano, $C_1$-$C_6$ alkoxyl, $C_1$-$C_6$ haloalkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl. For example X is substituted with one or more substituents selected from halo, hydroxyl, $C_1$-$C_6$ alkyl, and $C_1$-$C_6$ haloalkyl. For example, X is 1-hydroxy-2,6-dimethylpyridin-4(1H)-one-3-yl or 1-hydroxy-4,6-dimethylpyridin-2(1H)-one-3-yl.

For example, X is 1,2-dihydro-3H-pyrazol-3-one-4-yl or isoxazol-3(2H)-one-4-yl, each of which is optionally substituted with one or more -$Q_1$-$T_1$, in which $Q_1$ is a bond or $C_1$-$C_3$ alkyl linker and $T_1$ is selected from the group consisting of halo, hydroxyl, $C_1$-$C_3$ alkyl, $C_1$-$C_6$ haloalkyl, cyano, $C_1$-$C_6$ alkoxyl, $C_1$-$C_6$ haloalkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl.

For example, X is 4,5,6,7-tetrahydropyrazolo[1,5-a]pyrimidin-2(1H)-one-3-yl, 4,5,6,7-tetrahydropyrazolo[1,5-a]pyridin-2(1H)-one-3-yl, 5,6,7,8-tetrahydro-1H-pyrazolo[1,2-a]pyridazin-1-one-2-yl, 1H-pyrazol-5-ol-4-yl, 5-methoxy-1H-pyrazol-4-yl, pyrazolo[1,5-a]pyrimidin-2-ol-3-yl, pyrazolo[1,5-a]pyrimidin-2(1H)-one-3-yl, 2-methoxypyrazolo[1,5-a]pyrimidin-3-yl, or 2-methoxy-4,5,6,7-tetrahydropyrazolo[1,5-a]pyrimidin-3-yl, each of which is optionally substituted with one or more substituents selected from halo, hydroxyl, $C_1$-$C_6$ alkyl, $C_1$-$C_6$ alkoxyl, $C_1$-$C_6$ haloalkoxyl, and $C_1$-$C_6$ haloalkyl.

The present invention provides a compound of Formula (Ia) or (Ib):

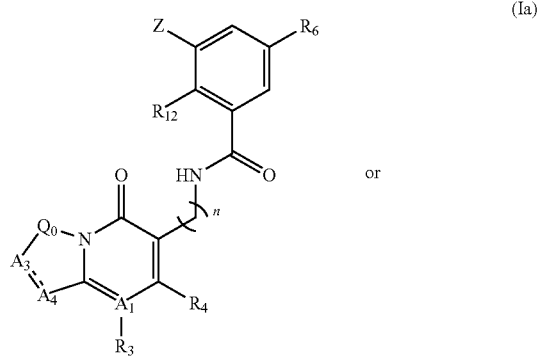

(Ia)

or

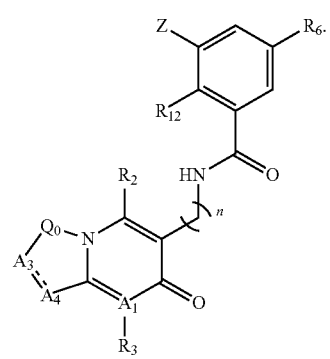

(Ib)

In each of Formulae (Ia) and (Ib), $Q_0$ is NH, O, or S; ==== between $A_3$ and $A_4$ is a single or double bond; each of $A_3$ and $A_4$, independently, is $CR_{15}R_{16}$, $NR_{15}$, O, or S; each of $R_{15}$ and $R_{16}$, independently is absent, H, halo, hydroxyl, $C_1$-$C_6$ alkyl, $C_1$-$C_6$ haloalkyl, C(O)OH, C(O)O—$C_1$-$C_6$ alkyl, C(O)O—$C_1$-$C_6$ haloalkyl, cyano, $C_1$-$C_6$ alkoxyl, $C_1$-$C_6$ haloalkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, or 5- or 6-membered heteroaryl; and (i) when $Q_0$ is NH and ==== is a single bond, each of $A_3$ and $A_4$ independently is $CR_{15}R_{16}$, $NR_{15}$, O, or S; (ii) when $Q_0$ is NH and ==== is a double bond, each of $A_3$ and $A_4$ independently is $CR_{15}$ or N; (iii) when $Q_0$ is O or S and ==== is a single bond, each of $A_3$ and $A_4$ independently is $CR_{15}R_{16}$ or $NR_{15}$; or (iv) when $Q_0$ is O or S and ==== is a double bond, each of $A_3$ and $A_4$ independently is $CR_{15}$ or N. Other variables are as defined herein for Formula (I) above.

The compounds of Formulae (Ia) and (Ib), in addition to the features described for Formula (I), when applicable, can further have one or more of the following features:

For example, $Q_0$ is NH.

For example, $Q_0$ is O.

For example, ==== between $A_3$ and $A_4$ is a double bond. For example, both $A_3$ and $A_4$ are $CR_{15}$, e.g., CH or C($CH_3$). For example, both $A_3$ and $A_4$ are N. For example, $A_3$ is $CR_{15}$, e.g., CH or C($CH_3$), and $A_4$ is N. For example, $A_3$ is N and $A_4$ is $CR_{15}$, e.g., CH or C($CH_3$).

For example, ==== between $A_3$ and $A_4$ is a single bond and $Q_0$ is NH. For example, each of $A_3$ and $A_4$ independently is $CR_{15}R_{16}$, e.g., $CH_2$ or CH($CH_3$). For example, each of $A_3$ and $A_4$ independently is $NR_{15}$, e.g., NH or N($CH_3$). For example, $A_3$ is $CR_{15}R_{16}$, e.g., $CH_2$ or CH($CH_3$), and $A_4$ is $NR_{15}$, e.g., NH or N($CH_3$). For example, $A_3$ is $NR_{15}$, e.g., NH or N($CH_3$), and $A_4$ is $CR_{15}R_{16}$, e.g., $CH_2$ or CH($CH_3$). For example, $A_3$ is $CR_{15}R_{16}$, e.g., $CH_2$ or CH($CH_3$), and $A_4$ is O or S. For example, $A_3$ is $NR_{15}$, e.g., NH or N($CH_3$), and $A_4$ is O or S. For example, $A_4$ is $CR_{15}R_{16}$, e.g., $CH_2$ or CH($CH_3$), and $A_3$ is O or S. For example, $A_4$ is $NR_{15}$, e.g., NH or N($CH_3$), and $A_3$ is O or S.

For example, ==== between $A_3$ and $A_4$ is a single bond and $Q_0$ is O. For example, each of $A_3$ and $A_4$ independently is $CR_{15}R_{16}$, e.g., $CH_2$ or CH($CH_3$). For example, each of $A_3$ and $A_4$ independently is $NR_{15}$, e.g., NH or N($CH_3$). For example, $A_3$ is $CR_{15}R_{16}$, e.g., $CH_2$ or CH($CH_3$), and $A_4$ is $NR_{15}$, e.g., NH or N($CH_3$). For example, $A_3$ is $NR_{15}$, e.g., NH or N($CH_3$), and $A_4$ is $CR_{15}R_{16}$, e.g., $CH_2$ or CH($CH_3$).

For example, each $R_{15}$, when present, is independently H, halo (e.g., F, Cl, Br, or I), cyano, $C_1$-$C_6$ alkyl, or $C_1$-$C_6$ haloalkyl (e.g., $CF_3$, $CH_2CF_3$, or $CH_2CH_2Cl$).

For example, each $R_{15}$, when present, is independently hydroxyl, $C_1$-$C_6$ alkoxyl, or $C_1$-$C_6$ haloalkoxyl (e.g., $OCF_3$, $OCH_2CF_3$, or $OCH_2CH_2Cl$).

For example, each $R_{15}$, when present, is independently $C_3$-$C_8$ cycloalkyl, $C_6$-$C_{10}$ aryl, 4 to 7-membered heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyranyl, 1,4-diazepanyl, 1,4-oxazepanyl, 2-oxa-5-azabicyclo[2.2.1]heptanyl, 2,5-diazabicyclo[2.2.1]heptanyl, and morpholinyl, and the like), or 5- or 6-membered heteroaryl (e.g., pyrrolyl, pyrazolyl, imidazolyl, pyridyl, pyrimidinyl, pyrazinyl, pyridazinyl, tetrazolyl, oxazolyl, isoxazolyl, thiazolyl, isothiazolyl, and the like).

For example, each $R_{16}$, when present, is independently H, halo (e.g., F, Cl, Br, or I), cyano, $C_1$-$C_6$ alkyl, or $C_1$-$C_6$ haloalkyl (e.g., $CF_3$, $CH_2CF_3$, or $CH_2CH_2Cl$).

For example, each $R_{16}$, when present, is independently hydroxyl, $C_1$-$C_6$ alkoxyl, or $C_1$-$C_6$ haloalkoxyl (e.g., $OCF_3$, $OCH_2CF_3$, or $OCH_2CH_2Cl$).

For example, each $R_{16}$, when present, is independently $C_3$-$C_8$ cycloalkyl, $C_6$-$C_{10}$ aryl, 4 to 7-membered heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyranyl, 1,4-diazepanyl, 1,4-oxazepanyl, 2-oxa-5-azabicyclo[2.2.1]heptanyl, 2,5-diazabicyclo[2.2.1]heptanyl, and morpholinyl, and the like), or 5- or 6-membered heteroaryl (e.g., pyrrolyl, pyrazolyl, imidazolyl, pyridyl, pyrimidinyl, pyrazinyl, pyridazinyl, tetrazolyl, oxazolyl, isoxazolyl, thiazolyl, isothiazolyl, and the like).

For example, $R_2$ is $C_1$-$C_3$ alkyl optionally substituted with $C_1$-$C_6$ alkoxyl.

For example, $R_2$ is methyl.

For example, $R_2$ is halo, e.g., F, Cl, or Br.

For example, $R_2$ is CN, $NH_2$, mono-$C_1$-$C_6$ alkylamino, or di-$C_1$-$C_6$ alkylamino.

For example, $R_2$ is $C_{1-6}$ alkoxyl or $C_6$-$C_{10}$ aryloxy, each optionally substituted with one or more halo.

For example, $R_4$ is $C_1$-$C_3$ alkyl optionally substituted with $C_1$-$C_6$ alkoxyl.

For example, $R_4$ is methyl.

For example, $R_4$ is halo, e.g., F, Cl, or Br.

For example, $R_4$ is CN, $NH_2$, mono-$C_1$-$C_6$ alkylamino, or di-$C_1$-$C_6$ alkylamino.

For example, $R_4$ is $C_{1-6}$ alkoxyl or $C_6$-$C_{10}$ aryloxy, each optionally substituted with one or more halo.

For example, $R_3$ is H.

The present invention provides a compound of Formula (Ic), (Id1), or (Id2):

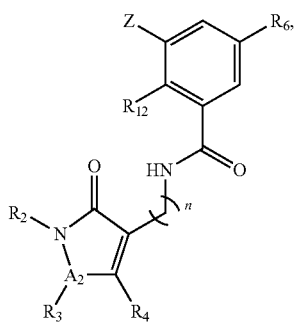

(Ic)

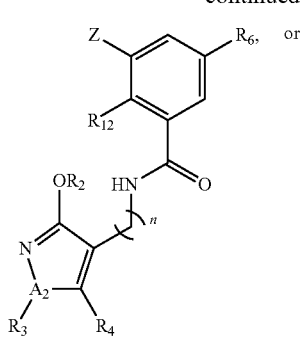

(Id1)

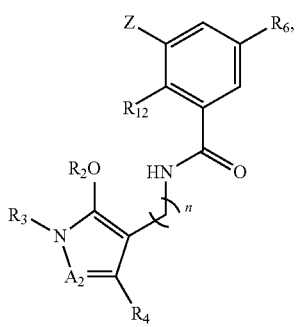

(Id2)

or a pharmaceutically acceptable salt thereof, wherein: $A_2$ is N, O, or S, and when $A_2$ is O or S, $R_3$ is absent; each of $R_2$, $R_3$, and $R_4$, independently, is -$Q_1$-$T_1$, in which $Q_1$ is a bond or $C_1$-$C_3$ alkyl linker optionally substituted with halo, and $T_1$ is H, halo, hydroxyl, C(O)OH, cyano, azido, or $R_{S1}$, in which $R_{S1}$ is $C_1$-$C_3$ alkyl, $C_1$-$C_6$ alkoxyl, $C_3$-$C_8$ cycloalkyl, $C_6$-$C_{10}$ aryl, $C_6$-$C_{10}$ aryloxy, amino, mono-$C_1$-$C_6$ alkylamino, di-$C_1$-$C_6$ alkylamino, 4 to 12-membered heterocycloalkyl, or 5- or 6-membered heteroaryl, and $R_{S1}$ is optionally substituted with one or more substituents selected from the group consisting of halo, hydroxyl, C(O)OH, C(O)O—$C_1$-$C_6$ alkyl, cyano, $C_1$-$C_6$ alkyl, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl; or neighboring $R_2$ and $R_3$, together with the atoms to which they are attached, form a 6 to 12-membered heterocycloalkyl ring having 2 to 3 heteroatoms; or neighboring $R_3$ and $R_4$, together with the atoms to which they are attached, form a 6-membered heteroaryl having 1 to 3 heteroatoms, or a 6 to 12-membered heterocycloalkyl ring having 1 to 3 heteroatoms; in which each of the ring structures formed by $R_2$ and $R_3$, or by $R_3$ and $R_4$, independently is optionally substituted with one or more substituents selected from the group consisting of halo, hydroxyl, oxo, $C_1$-$C_6$ alkyl, $C_1$-$C_6$ haloalkyl, cyano, $C_1$-$C_6$ alkoxyl, $C_1$-$C_6$ haloalkoxyl, amino, mono-$C_1$-$C_6$ alkylamino, or di-$C_1$-$C_6$ alkylamino. Other variables are as defined herein for Formula (I).

The compounds of Formulae (Ic), (Id1) and (Id2), in addition to the features described for Formula (I), when applicable, can further have one or more of the following features:

For example, $A_2$ is N.

For example, $A_2$ is O.

For example, when the compound is of Formula (Ic), both $R_2$ and $R_3$ are H. For example, $R_4$ is $C_1$-$C_3$ alkyl optionally substituted with $C_1$-$C_6$ alkoxyl. For example, $R_4$ is methyl. For example, $R_4$ is halo, e.g., F, Cl, or Br. For example, $R_4$ is CN, $NH_2$, mono-$C_1$-$C_6$ alkylamino, or di-$C_1$-$C_6$ alkylamino. For example, $R_4$ is $C_{1-6}$ alkoxyl (e.g., methoxyl) or $C_6$-$C_{10}$ aryloxy, each optionally substituted with one or more halo. For example, $R_4$ is $C_6$-$C_{10}$ aryl or 5- or 6-membered heteroaryl, each optionally substituted with one or more substituents selected from OH, $C_1$-$C_6$ alkyl, $C_1$-$C_6$ alkoxyl, and halo. For example, $R_4$ is —$C_{1-3}$ alkylene-$C_{3-8}$ cycloalkyl or —$C_{1-3}$ alkylene-4 to 7-membered heterocycloalkyl, each optionally substituted with one or more substituents selected from $C_1$-$C_6$ alkyl, OH, $C_1$-$C_6$ alkoxyl, and halo.

For example, when the compound is of Formula (Ic), one of $R_2$ and $R_3$ is H and the other is -$Q_1$-$T_1$, in which $Q_1$ is a bond or $C_1$-$C_3$ alkyl linker optionally substituted with halo, and $T_1$ is halo, hydroxyl, or $R_{S1}$, in which $R_{S1}$ is $C_1$-$C_3$ alkyl, $C_1$-$C_6$ alkoxyl, $C_3$-$C_8$ cycloalkyl, or 4 to 12-membered heterocycloalkyl. For example, $R_4$ is $C_1$-$C_3$ alkyl optionally substituted with $C_1$-$C_6$ alkoxyl. For example, $R_4$ is methyl. For example, $R_4$ is halo, e.g., F, Cl, or Br. For example, $R_4$ is CN, $NH_2$, mono-$C_1$-$C_6$ alkylamino, or di-$C_1$-$C_6$ alkylamino. For example, $R_4$ is $C_{1-6}$ alkoxyl (e.g., methoxyl) or $C_6$-$C_{10}$ aryloxy, each optionally substituted with one or more halo. For example, $R_4$ is $C_6$-$C_{10}$ aryl or 5- or 6-membered heteroaryl, each optionally substituted with one or more substituents selected from OH, $C_1$-$C_6$ alkyl, $C_1$-$C_6$ alkoxyl, and halo. For example, $R_4$ is —$C_{1-3}$ alkylene-$C_{3-8}$ cycloalkyl or —$C_{1-3}$ alkylene-4 to 7-membered heterocycloalkyl, each optionally substituted with one or more substituents selected from $C_1$-$C_6$ alkyl, OH, $C_1$-$C_6$ alkoxyl, and halo.

For example, when the compound is of Formula (Ic), $R_2$ and $R_3$ together with the atoms to which they are attached, form an optionally substituted 6 to 12-membered heterocycloalkyl ring having 2 to 3 heteroatoms (e.g., 3,4,5,6-tetrahydropyridazine ring). For example, $R_4$ is $C_1$-$C_3$ alkyl optionally substituted with $C_1$-$C_6$ alkoxyl. For example, $R_4$ is methyl. For example, $R_4$ is halo, e.g., F, Cl, or Br. For example, $R_4$ is CN, $NH_2$, mono-$C_1$-$C_6$ alkylamino, or di-$C_1$-$C_6$ alkylamino. For example, $R_4$ is $C_{1-6}$ alkoxyl (e.g., methoxyl) or $C_6$-$C_{10}$ aryloxy, each optionally substituted with one or more halo. For example, $R_4$ is $C_6$-$C_{10}$ aryl or 5- or 6-membered heteroaryl, each optionally substituted with one or more substituents selected from OH, $C_1$-$C_6$ alkyl, $C_1$-$C_6$ alkoxyl, and halo. For example, $R_4$ is —$C_{1-3}$ alkylene-$C_{3-8}$ cycloalkyl or —$C_{1-3}$ alkylene-4 to 7-membered heterocycloalkyl, each optionally substituted with one or more substituents selected from $C_1$-$C_6$ alkyl, OH, $C_1$-$C_6$ alkoxyl, and halo.

For example, when the compound is of Formula (Ic), $R_4$ and $R_3$ together with the atoms to which they are attached, for an optionally substituted 6-membered heteroaryl having 1 to 3 heteroatoms, or an optionally substituted 6 to 12-membered heterocycloalkyl ring having 1 to 3 heteroatoms. For example, $R_2$ is H or $C_1$-$C_3$ alkyl optionally substituted with $C_1$-$C_6$ alkoxyl. For example, $R_2$ is methyl. For example, $R_2$ is $C_1$-$C_6$ haloalkyl, e.g., $CH_2CF_3$. For example, $R_2$ is —$C_{1-3}$ alkylene-$C_{3-8}$ cycloalkyl or —$C_{1-3}$ alkylene-4 to 7-membered heterocycloalkyl, each optionally substituted with one or more substituents selected from $C_1$-$C_6$ alkyl, OH, $C_1$-$C_6$ alkoxyl, and halo.

For example, when the compound is of Formula (Id1) or (Id2), $R_2$ is not H. For example, $R_2$ is $C_1$-$C_6$ alkyl. For example, $R_4$ and $R_3$ together with the atoms to which they are attached, for an optionally substituted 6-membered heteroaryl having 1 to 3 heteroatoms, or an optionally substituted 6 to 12-membered heterocycloalkyl ring having 1 to 3 heteroatoms.

For example, when the compound is of Formula (Id1) or (Id2), $R_2$ is H and $R_4$ and $R_3$ together with the atoms to which they are attached, for an optionally substituted 6-membered heteroaryl having 1 to 3 heteroatoms, or an optionally substituted 6 to 12-membered heterocycloalkyl ring having 1 to 3 heteroatoms.

Another subset of the compounds of Formula (I) includes those of Formula (IIa), (IIb), or (IIc):

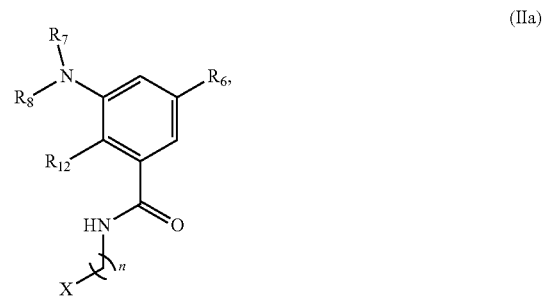

(IIa)

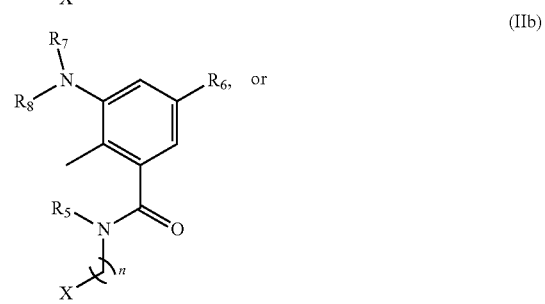

(IIb)

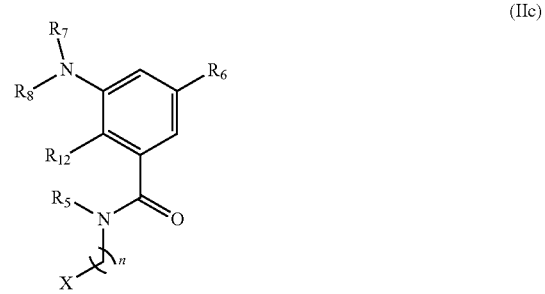

(IIc)

or pharmaceutically acceptable salts thereof, wherein, n, X, $R_5$, $R_6$, $R_7$, $R_8$, and $R_{12}$ are as defined herein for Formula (I) or for any of Formula (Ia)-(Id) when applicable.

Another subset of the compounds of Formula (I) includes those of Formula (III):

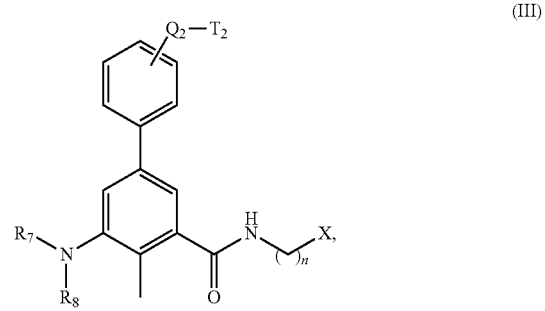

(III)

or pharmaceutically acceptable salts thereof, wherein $Q_2$ is a bond or methyl linker, $T_2$ is H, halo, —$OR_c$, —$NR_cR_d$, or —$S(O)_2NR_cR_d$ and n, X, $R_c$, $R_d$, $R_2$, $R_7$, and $R_8$ are defined herein for Formula (I) or for any of Formula (Ia)-(Id) when applicable.

Another subset of the compounds of Formula (I) includes those of Formula (IIa):

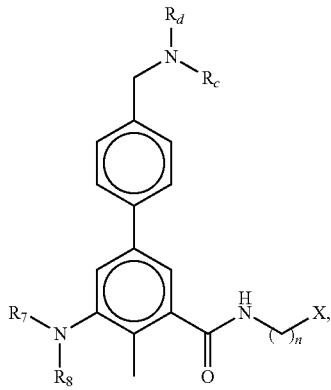

or pharmaceutically acceptable salts thereof, wherein n, X, $R_c$, $R_d$, $R_2$, $R_7$, and $R_8$ are defined herein for Formula (I) or for any of Formula (Ia)-(Id) when applicable.

Yet another subset of the compounds of Formula (I) includes those of Formula (IIIb):

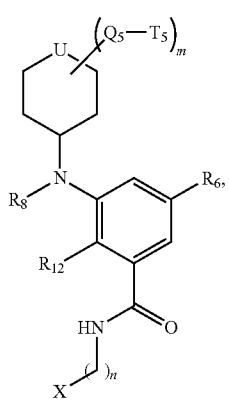

or pharmaceutically acceptable salts thereof, wherein m is 0, 1, or 2; U is O, S, N-$Q_5$-$T_5$, or CH-$Q_5$-$T_5$; $R_{12}$ is Cl, Br, or methyl; and n, X, $R_6$, $R_7$, $R_8$, $Q_5$, and $T_5$ are defined herein for Formula (I) or for any of Formula (Ia)-(Id) when applicable.

In addition to the above-described features of the compounds of this invention where applicable, the compounds of Formula (IIa), (IIb), (IIc), (III), (IIIa), or (IIIb) can include one or more of the following features:

For example, $Q_5$ is a bond or $NR_k$ and $T_5$ is H, $C_1$-$C_6$ alkyl, $C_3$-$C_8$ cycloalkyl, $C_1$-$C_6$ alkylene-$C_3$-$C_8$ cycloalkyl, $C_6$-$C_{10}$ aryl, $C_1$-$C_6$ alkylene-$C_6$-$C_{10}$ aryl, 4 to 12-membered heterocycloalkyl, $C_1$-$C_6$ alkylene-4 to 12-membered heterocycloalkyl, 5- or 6-membered heteroaryl, $C_1$-$C_6$ alkylene-5- or 6-membered heteroaryl, amino, mono-$C_1$-$C_6$ alkylamino, or di-$C_1$-$C_6$ alkylamino, $T_5$ being optionally substituted with one or more substituents selected from the group consisting of halo, hydroxyl, $C_1$-$C_6$ alkoxyl, O—$C_1$-$C_4$ alkylene-$C_1$-$C_4$ alkoxy, and $C_3$-$C_8$ cycloalkyl.

For example, $Q_5$ is CO, $S(O)_2$, or NHC(O); and $T_5$ is $C_1$-$C_6$ alkyl, $C_1$-$C_6$ alkoxyl, $C_3$-$C_8$ cycloalkyl, $C_1$-$C_6$ alkylene-$C_3$-$C_8$ cycloalkyl, $C_6$-$C_{10}$ aryl, $C_1$-$C_6$ alkylene-$C_6$-$C_{10}$ aryl, 4 to 12-membered heterocycloalkyl, $C_1$-$C_6$ alkylene-4 to 12-membered heterocycloalkyl, 5- or 6-membered heteroaryl, $C_1$-$C_6$ alkylene-5- or 6-membered heteroaryl.

For example, $Q_5$ is $C_1$-$C_3$ alkyl linker and $T_5$ is H or $C_6$-$C_{10}$ aryl.

For example, $Q_5$ is $C_1$-$C_3$ alkyl linker and $T_5$ is $C_3$-$C_8$ cycloalkyl, $C_1$-$C_6$ alkylene-$C_3$-$C_8$ cycloalkyl, $C_6$-$C_{10}$ aryl, $C_1$-$C_6$ alkylene-$C_6$-$C_{10}$ aryl, 4 to 12-membered heterocycloalkyl, $C_1$-$C_6$ alkylene-4 to 12-membered heterocycloalkyl, 5- or 6-membered heteroaryl, $C_1$-$C_6$ alkylene-5- or 6-membered heteroaryl, or $S(O)_qR_q$, $T_5$ being optionally substituted with one or more substituents selected from the group consisting of halo, hydroxyl, $C_1$-$C_6$ alkoxyl, 0-$C_1$-$C_4$ alkylene-$C_1$-$C_4$ alkoxy, and $C_3$-$C_8$ cycloalkyl.

For example, $Q_5$ is NHC(O) and $T_5$ is $C_1$-$C_6$ alkyl or $C_1$-$C_6$ alkoxy.

For example, one or more -$Q_5$-$T_5$ are oxo.

For example, U is CH-$Q_5$-$T_5$ and m is 0.

For example, one or more -$Q_6$-$T_6$ are oxo.

For example, $Q_6$ is a bond or C(O) and $T_6$ is $C_1$-$C_6$ alkyl or $C_1$-$C_6$ alkoxy.

Still another subset of the compounds of Formula (I) includes those of Formula (IV):

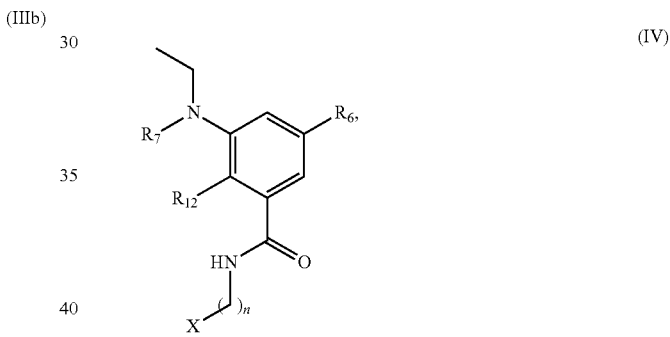

or pharmaceutically acceptable salts thereof, wherein $R_7$ is -$Q_4$-$T_4$, wherein $Q_4$ is a bond or methyl linker, $T_4$ is optionally substituted $C_3$-$C_8$ cycloalkyl or optionally substituted 4- to 14-membered heterocycloalkyl, and n, X, $R_6$, and $R_{12}$ are defined herein for Formula (I).

In addition to the above-described features of the compounds of this invention where applicable, the compounds of Formula (IV) can include one or more of the following features:

For example, $T_4$ is

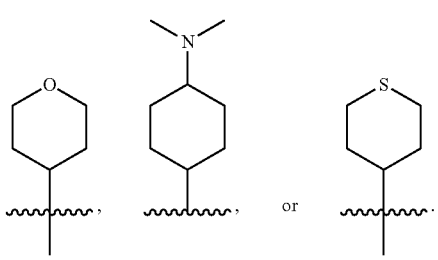

For example, $T_4$ is

[structures shown]

in which R''' is $T_5$, —C(O)$T_5$, or S(O)$_2T_5$, $T_5$ being as defined herein for Formula (I).

For example, $R_7$ is optionally substituted $C_3$-$C_8$ cycloalkyl or a 4- to 6-membered heterocycloalkyl.

For example, the compounds of Formula (IV) include those of Formula (IVa):

(IVa)

[structure shown]

or a pharmaceutically acceptable salt thereof; wherein
$n_5$ is 0, 1, or 2;
$R^{501}$ is C(H) or N;
$R^{504}$ is $C_{1-4}$ alkyl;
$R^{506}$ is $C_1$-$C_6$ alkyl, piperidine substituted by 1, 2, or 3 $R^{707}$ groups, or cyclohexyl substituted by N($R^{707}$)$_2$ wherein each $R^{707}$ is independently $C_{1-4}$ alkyl that is optionally substituted with (i) $C_{1-6}$ alkoxyl, (ii) 4 to 12-membered heterocycloalkyl, (iii) $C_6$-$C_{10}$ aryl that is optionally further substituted with $C_1$-$C_6$ alkoxyl or O—$C_1$-$C_4$ alkylene-$C_1$-$C_4$ alkoxy, or (iv) 5- or 6-membered heteroaryl that is optionally further substituted with $C_1$-$C_6$ alkoxyl or O—$C_1$-$C_4$ alkylene-$C_1$-$C_4$ alkoxy;

$R^{507}$ is morpholine, piperazine, piperidine, diazepane, pyrrolidine, azetidine, O—$C_{1-6}$ alkyl, NH—$C_{1-6}$ alkyl, or O-heterocycle, wherein the heterocycle is a 4-7 membered heterocycle containing an oxygen or nitrogen, or both, and wherein the nitrogen can optionally be substituted with $C_{1-3}$ alkyl; wherein the piperazine, piperidine, diazepane, pyrrolidine or azetidine groups can be optionally further substituted with OH, $C_{1-6}$ alkyl, or O—$C_{1-3}$ alkyl; wherein each of the O—$C_{1-6}$ alkyl and NH—$C_{1-6}$ alkyl is optionally substituted with hydroxyl, O—$C_{1-3}$ alkyl or NH—$C_{1-3}$ alkyl, each of the O—$C_{1-3}$ alkyl and NH—$C_{1-3}$ alkyl being optionally further substituted with O—$C_{1-3}$ alkyl or NH—$C_{1-3}$ alkyl; and each of n and X is as defined herein for Formula (I).

In addition to the above-described features of the compounds of this invention where applicable, the compounds of Formula (IVa) can include one or more of the following features.

In certain compounds of Formula (IVa), $R^{501}$ is C(H), and $R^{507}$ is piperidine; diazepane; pyrrolidine; azetidine; O—$C_{1-6}$ alkyl; or O-heterocycle, wherein the heterocycle is a 4-7 membered heterocycle containing an oxygen or nitrogen, or both, and wherein the nitrogen can optionally be substituted with $C_{1-3}$ alkyl; wherein the piperidine, diazepane, pyrrolidine or azetidine groups can be optionally further substituted with OH, $C_{1-6}$ alkyl, or O—$C_{1-3}$ alkyl.

In certain compounds of Formula (IVa), $R^{501}$ is C(H) and $R^{507}$ is piperidine, diazepane, pyrrolidine, azetidine or O—$C_{1-6}$ alkyl, wherein the piperidine, diazepane, pyrrolidine or azetidine groups can be optionally further substituted with OH or $C_{1-6}$ alkyl.

In certain compounds of Formula (IVa), $R^{501}$ is C(H), $R^{507}$ is piperazine optionally further substituted with $C_{1-6}$ alkyl, and $R^{506}$ is piperidine substituted by 1, 2, or 3 $C_{1-4}$ alkyl groups.

In certain compounds of Formula (IVa), $R^{501}$ is N, and $R^{507}$ is morpholine, piperidine, piperazine, diazepane, pyrrolidine, azetidine or O—$C_{1-6}$ alkyl, wherein the piperidine, piperazine, diazepane, pyrrolidine or azetidine groups can be optionally further substituted with OH or $C_{1-6}$ alkyl.

In certain compounds of Formula (IVa), $R^{504}$ is methyl.

In certain compounds of Formula (IVa), $R^{506}$ is

[structures shown] or [structure shown]

In certain compounds of Formula (IVa), $R^{506}$ is

[structures shown] or [structure shown].

In certain compounds of Formula (IVa), $R^{506}$ is

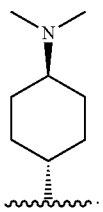.

In certain compounds of Formula (IVa), $R^{506}$ is

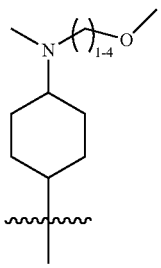, e.g., 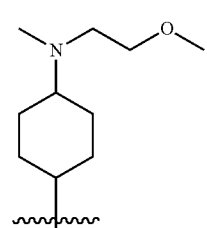.

In certain compounds of Formula (IVa), $R^{506}$ is

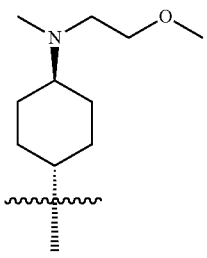 or 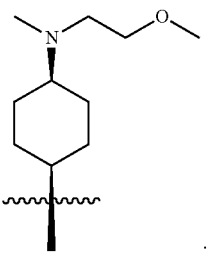.

In certain compounds of Formula (IVa), $R^{506}$ is

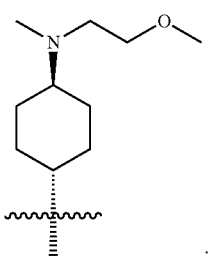.

In certain compounds of Formula (IVa), $R^{506}$ is

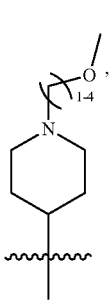, 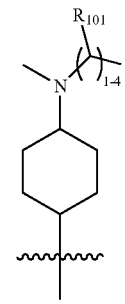, or 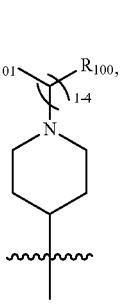, wherein $R_{100}$ is phenyl, 5- or 6-membered heteroaryl, or 4 to 12-membered heterocycloalkyl, each optionally substituted with one or more $T_{5a}$ in which each $T_{5a}$ is independently $C_1$-$C_6$ alkoxyl or O—$C_1$-$C_4$ alkylene-$C_1$-$C_4$ alkoxy, and $R_{101}$ is H or $C_1$-$C_4$ alkyl.

In certain compounds of Formula (IVa), $R^{506}$ is

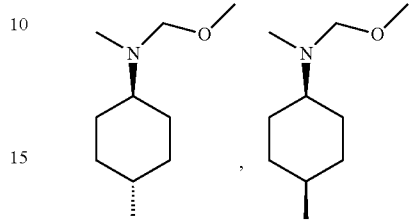

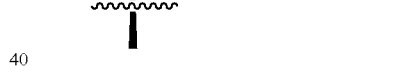

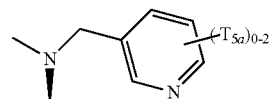

,

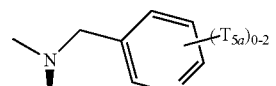

,

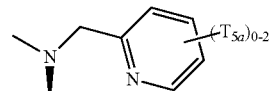

,


,

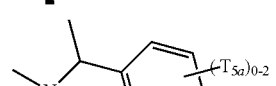

,

,

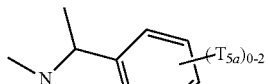

,

,

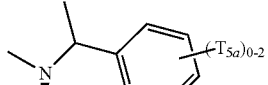

, or

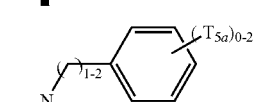

, wherein each $T_{5a}$ is independently $C_1$-$C_3$ alkoxyl or O—$C_1$-$C_3$ alkylene-$C_1$-$C_2$ alkoxy.

In certain compounds of Formula (IVa), when $R^{501}$ is C(H), $R^{507}$ is piperidine or diazepane, which are substituted with OH or $C_{1-6}$ alkyl, or when $R^{501}$ is N, $R^{507}$ is piperidine, piperazine, or diazepane, which are optionally further substituted with OH or $C_{1-6}$ alkyl.

In certain compounds of Formula (IVa), when $R^{501}$ is C(H), $R^{507}$ is piperidine substituted with $C_{1-6}$ alkyl, or when $R^{501}$ is N, $R^{507}$ is piperidine substituted with OH or piperazine substituted with $C_{1-6}$ alkyl.

In certain compounds of Formula (IVa), when $R^{501}$ is N, $R^{507}$ is unsubstituted piperazine.

In certain compounds of Formula (IVa), $n_5$ is 0 or 1.

In certain compounds of Formula (IVa), when $R^{501}$ is C(H) or N, $R^{507}$ is O—$C_{1-6}$ alkyl or O-heterocycle, and $n_5$ is 1.

In certain compounds of Formula (IVa), when $R^{501}$ is C(H), $R^{507}$ is unsubstituted piperazine and $R^{506}$ is piperidine substituted by 1, 2, or 3 $C_{1-4}$ alkyl groups.

In certain compounds of Formula (IVa), $R^{507}$ is O—$C_{2-3}$ alkyl substituted with O—$C_{1-2}$ alkyl, e.g., —OCH$_2$CH$_2$OCH$_3$.

For example, the compounds of Formula (IV) include those of Formula (IVb):

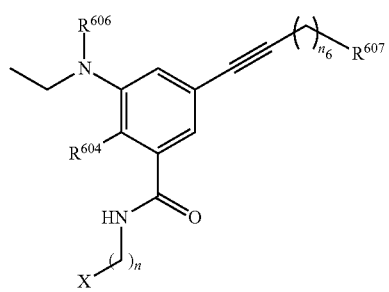

(IVb)

or a pharmaceutically acceptable salt thereof; wherein
$n_6$ is 0, 1 or 2;

$R^{604}$ is $C_{1-4}$ alkyl;

$R^{606}$ is $C_6$ alkyl, tetrahydropyranyl, piperidine substituted by 1, 2, or 3 $R^{707}$ groups, or cyclohexyl substituted by $N(R^{707})_2$ wherein each $R^{707}$ independently is $C_{1-4}$ alkyl that is optionally substituted with (i) $C_{1-6}$ alkoxyl, (ii) 4 to 12-membered heterocycloalkyl, (iii) $C_6$-$C_{10}$ aryl that is optionally further substituted with $C_1$-$C_6$ alkoxyl or O—$C_1$-$C_4$ alkylene-$C_1$-$C_4$ alkoxy, or (iv) 5- or 6-membered heteroaryl that is optionally further substituted with $C_1$-$C_6$ alkoxyl or O—$C_1$-$C_4$ alkylene-$C_1$-$C_4$ alkoxy;

$R^{607}$ is morpholine, piperidine, piperazine, pyrrolidine, diazepane, oxetane, azetidine or O—$C_{1-6}$ alkyl, wherein the piperidine, diazepane, oxetane or azetidine groups can be optionally further substituted with one or more $C_{1-6}$ alkyl, $C_{1-6}$ haloalkyl, $C_{3-8}$ cycloalkyl, or 4 to 6-membered heterocycloalkyl; and each of n and X is as defined herein for Formula (I).

In addition to the above-described features of the compounds of this invention where applicable, the compounds of Formula (IVb) can include one or more of the following features:

In certain compounds of Formula (IVb), $R^{604}$ is methyl.

In certain compounds of Formula (IVb), $R^{606}$ is

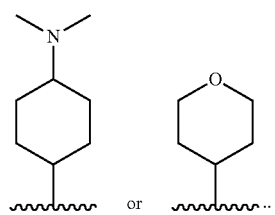

In certain compounds of Formula (IVb), $R^{606}$ is

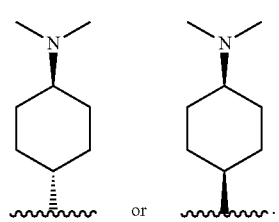

In certain compounds of Formula (IVb), $R^{606}$ is

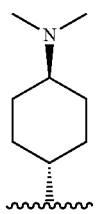

In certain compounds of Formula (IVb), $R^{606}$ is

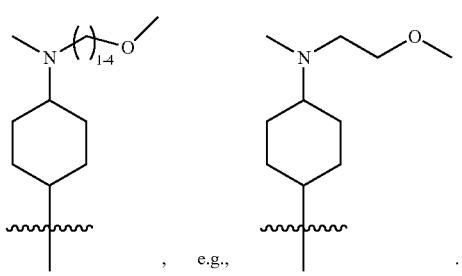

, e.g., .

In certain compounds of Formula (IVb), $R^{606}$ is

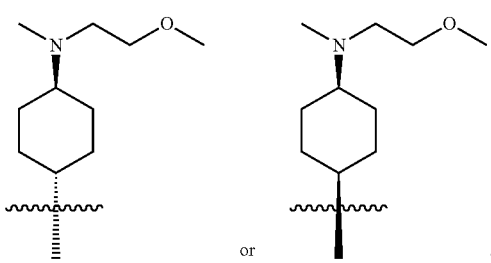

or .

In certain compounds of Formula (IVb), $R^{606}$ is

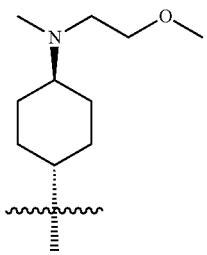

In certain compounds of Formula (IVb), $R^{606}$ is

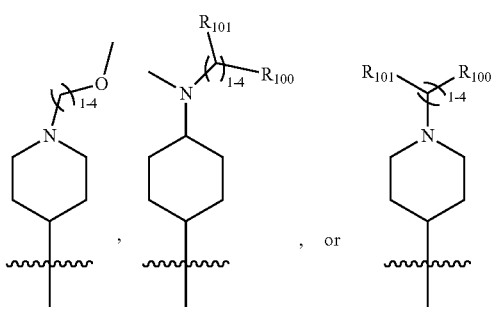

, , or wherein $R_{100}$ is phenyl, 5- or 6-membered heteroaryl, or 4 to 12-membered heterocycloalkyl, each optionally substituted with one or more $T_{5a}$ in which each $T_{5a}$ is independently $C_1$-$C_6$ alkoxyl or O—$C_1$-$C_4$ alkylene-$C_1$-$C_4$ alkoxy, and $R_{101}$ is H or $C_1$-$C_4$ alkyl.
In certain compounds of Formula (IVb), $R^{606}$
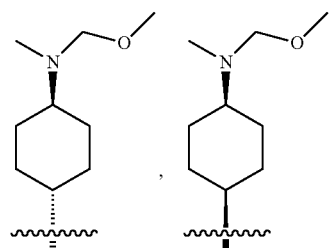
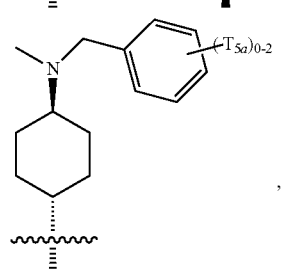
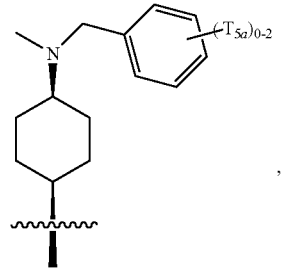
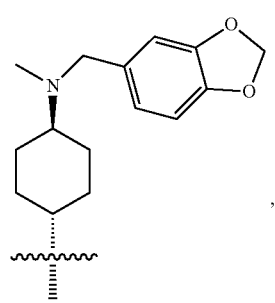
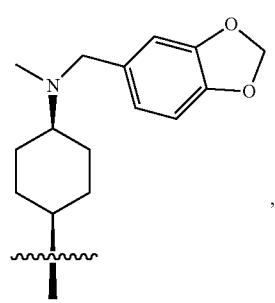
-continued
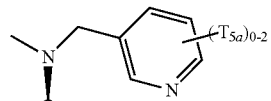
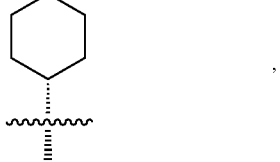
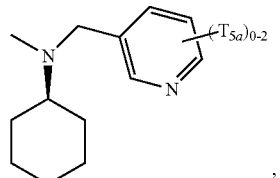
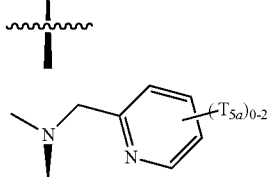
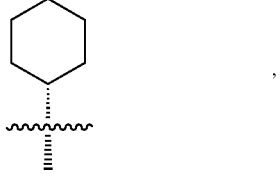
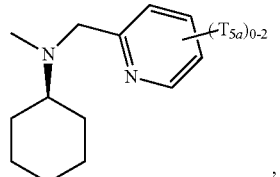
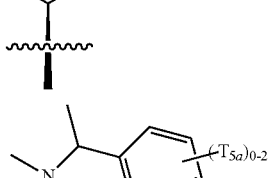
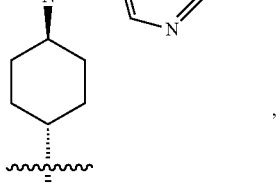
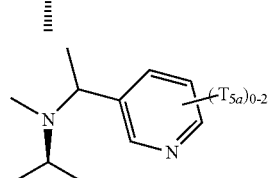
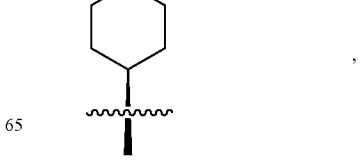

-continued

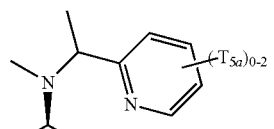

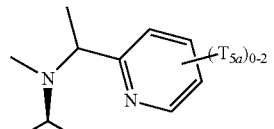, or

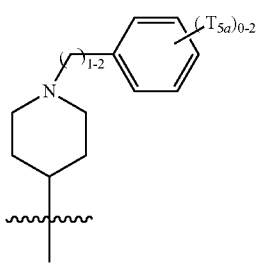, wherein each $T_{5a}$ is independently $C_1$-$C_3$ alkoxyl or O—$C_1$-$C_3$ alkylene-$C_1$-$C_2$ alkoxy.

In certain compounds of Formula (IVb), $R^{607}$ is piperidine or oxetane, each of which is substituted with $C_{1-6}$ alkyl.

In certain compounds of Formula (IVb), $R^{607}$ is piperidine substituted with $CH_2CF_3$, cyclopropyl, cyclobutyl, or oxetane.

In certain compounds of Formula (IVb), $n_6$ is 0 or 1.

For example, the compounds of Formula (IV) include those of Formula (IVc) or (IVd):

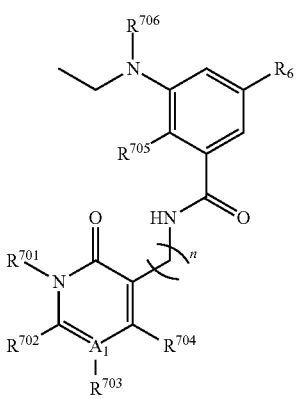

(IVc)

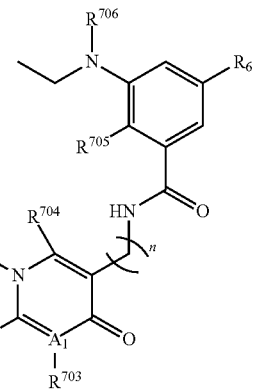

(IVd)

or a pharmaceutically acceptable salt thereof; wherein
$R^{701}$ is OH or —NH-$T_0$, in which —NH-$T_0$ and $R^{702}$, together with the atoms to which they are attached, form a 5- or 6-membered heteroaryl having 0 to 2 additional heteroatoms or a 5 to 12-membered heterocycloalkyl ring having 0 to 2 additional heteroatoms;
$A_1$ is C or N and when $A_1$ is N, $R^{703}$ is absent;
$R^{703}$ is H, halo, or $C_{1-4}$ alkyl;
$R^{704}$ is halo, $C_{1-4}$ alkyl or $C_{1-6}$ alkoxyl, where each $C_{1-4}$ alkyl or $C_{1-6}$ alkoxyl is optionally substituted with one or more halo;
$R^{705}$ is $C_{1-4}$ alkyl;
$R^{706}$ is tetrahydropyranyl, piperidine substituted by 1, 2, 3, 4, or 5 $R^{707}$ groups, or cyclohexyl substituted by $N(R^{707})_2$ wherein each $R^{707}$ is independently $C_{1-4}$ alkyl that is optionally substituted with (i) $C_{1-6}$ alkoxyl, (ii) 4 to 12-membered heterocycloalkyl, (iii) $C_6$-$C_{10}$ aryl that is optionally further substituted with $C_1$-$C_6$ alkoxyl or O—$C_1$-$C_4$ alkylene-$C_1$-$C_4$ alkoxy, or (iv) 5- or 6-membered heteroaryl that is optionally further substituted with $C_1$-$C_6$ alkoxyl or O—$C_1$-$C_4$ alkylene-$C_1$-$C_4$ alkoxy; and
each of n and $R_6$ is as defined herein for Formula (I).

In addition to the above-described features of the compounds of this invention where applicable, the compounds of Formula (IVc) or (IVd) can include one or more of the following features:

For example, $R^{705}$ is methyl.
For example, $R^{706}$ is

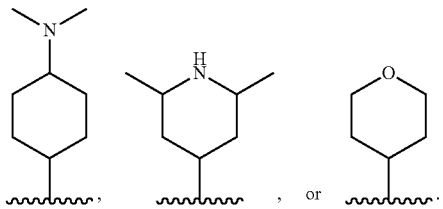

For example, $R^{706}$ is

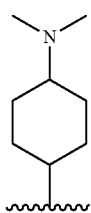

For example, $R^{706}$ is

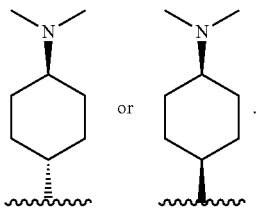

For example, $R^{706}$ is

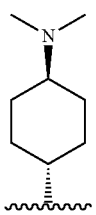

For example, $R^{706}$ is

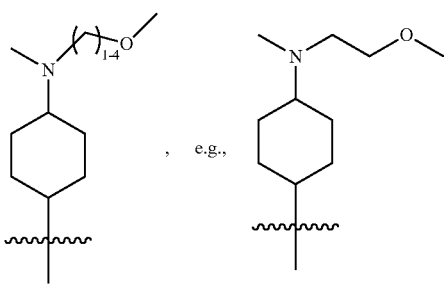

For example, $R^{706}$ is

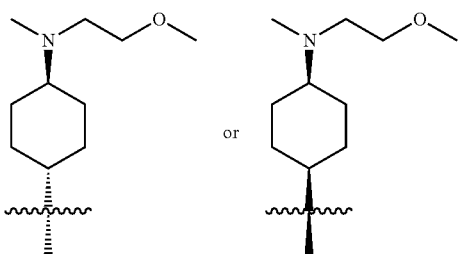

For example, $R^{706}$ is

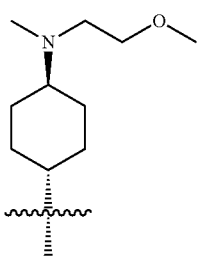

For example, $R^{706}$ is

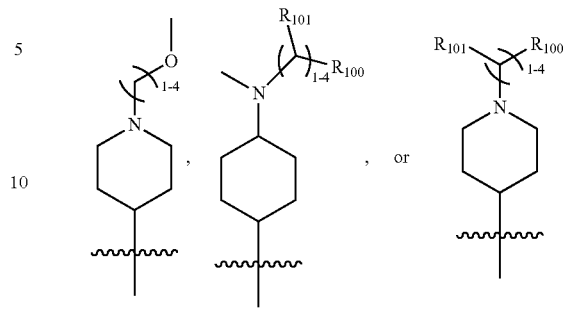

wherein $R_{100}$ is phenyl, 5- or 6-membered heteroaryl, or 4 to 12-membered heterocycloalkyl, each optionally substituted with one or more $T_{5a}$ in which each $T_{5a}$ is independently $C_1$-$C_6$ alkoxyl or O—$C_1$-$C_4$ alkylene-$C_1$-$C_4$ alkoxy, and $R_{101}$ is H or $C_1$-$C_4$ alkyl.

For example, $R^{706}$ is

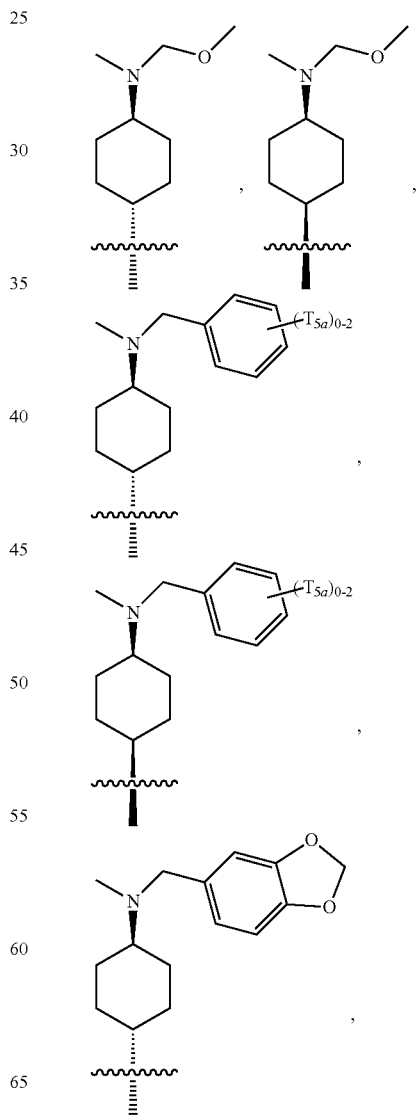

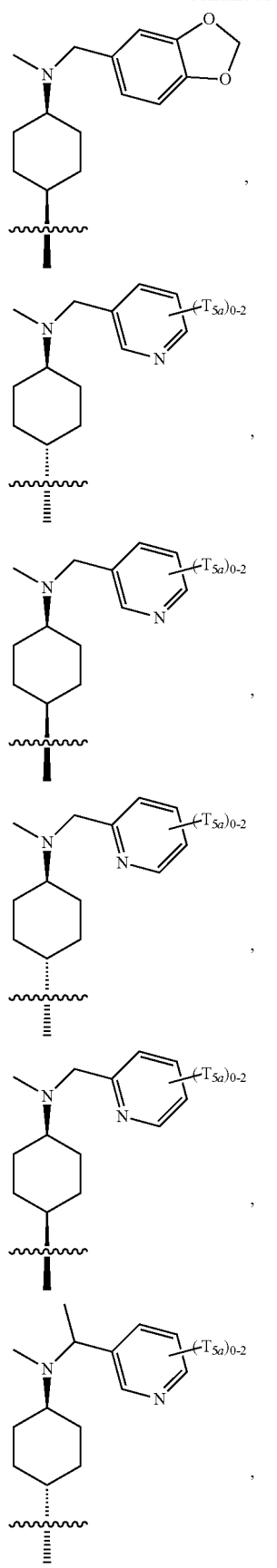
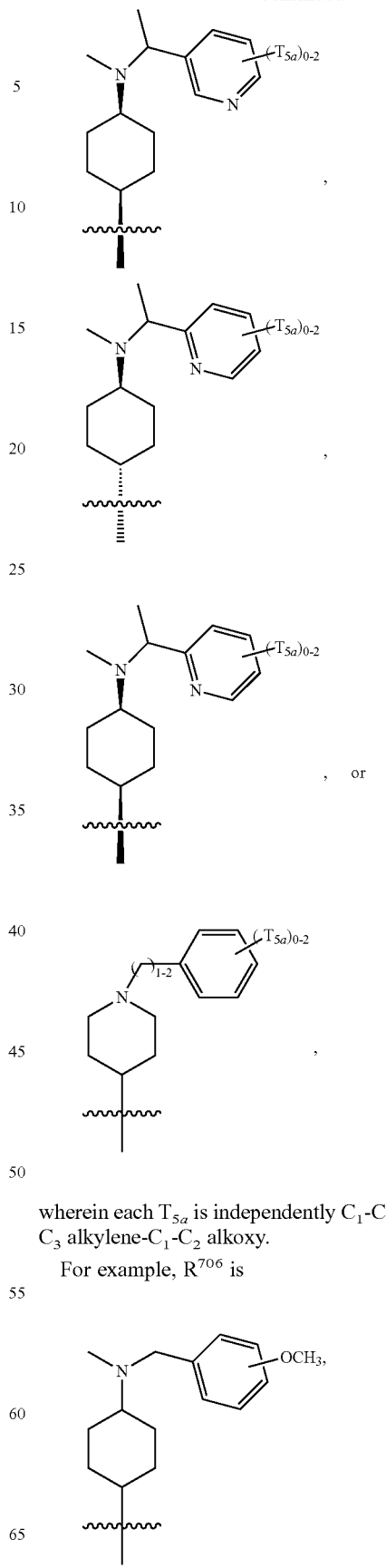
wherein each $T_{5a}$ is independently $C_1$-$C_3$ alkoxyl or O—$C_1$-$C_3$ alkylene-$C_1$-$C_2$ alkoxy.
For example, $R^{706}$ is
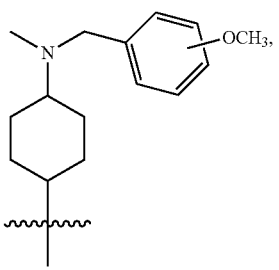

-continued

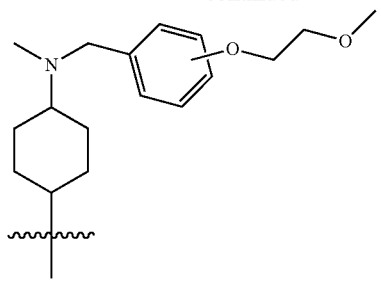,

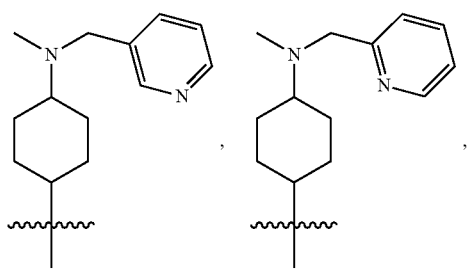,

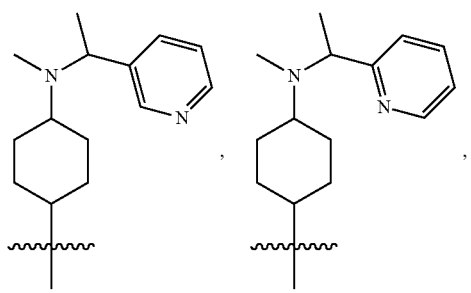,

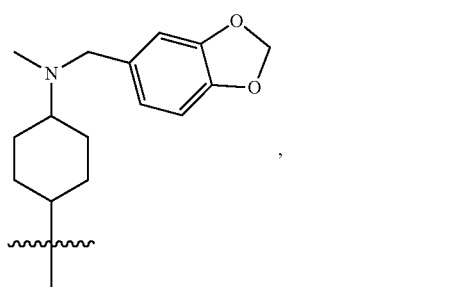,

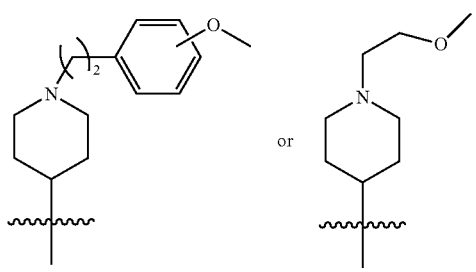 or .

For example, R$^{701}$ is H.

For example, R$^{702}$ is methoxy, ethoxy, —OCF$_3$, or phenoxy.

For example, R$^{703}$ is H.

For example, R$^{703}$ is F.

For example, R$^{704}$ is methyl, ethyl or CF$_3$.

For example, R$^{704}$ is methoxy or ethoxy.

For example, R$^{704}$ is F or Cl.

For example, R$^{701}$ and R$^{702}$, together with the atoms to which they are attached, form a 5- or 6-membered heteroaryl or 5 to 6-membered heterocycloalkyl ring, each having no additional heteroatom.

For example, R$^{701}$ and R$^{702}$, together with the atoms to which they are attached, form a 5- or 6-membered heteroaryl or a 5 to 6-membered heterocycloalkyl ring, each having an additional heteroatom selected from N and O.

For example, R$_6$ is halo, e.g., F, Cl, or Br.

For example, R$_6$ is Cl.

For example, R$_6$ is unsubstituted or substituted phenyl or 5- or 6-membered heteroaryl.

For example, R$_6$ is phenyl or 5- or 6-membered heteroaryl substituted with O—C$_{1-6}$ alkyl or NH—C$_{1-6}$ alkyl, each of which is optionally substituted with hydroxyl, O—C$_{1-3}$ alkyl or NH—C$_{1-3}$ alkyl, each of the O—C$_{1-3}$ alkyl and NH—C$_{1-3}$ alkyl being optionally further substituted with O—C$_{1-3}$ alkyl or NH—C$_{1-3}$ alkyl.

For example, R$_6$ is

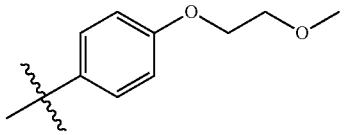

For example, A$_1$ is C.

For example, A$_1$ is N.

For example, n is 1.

For example, n is 2.

For example, n is 0.

Representative compounds of the present invention include compounds listed in Tables 1-5 and salts or tautomers thereof. For compounds containing the variables R$_2$, R$_3$, R$_4$, and R$_6$ in Table 3, each variable is as defined herein for Formula (I). In Table 4, except for R$_6$, variables such as n, X, Z, Q$_3$, T$_3$, and R$_{12}$ are as defined herein for Formula (I). In Table 5, R'" is T$_5$, —C(O)T$_5$, or S(O)$_2$T$_5$, and the other variables except for R$_7$, such as X, R$_6$, R$_8$, R$_{12}$, T$_5$ and T$_{5a}$ are as defined herein for Formula (I).

TABLE 1

| Compound Number | Structure | MS (M + 1)+ |
|---|---|---|
| 1 | 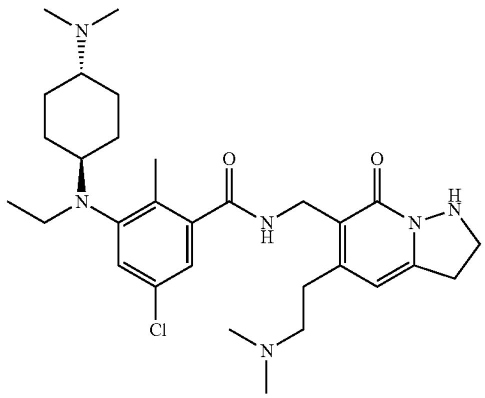 [SMILES: CCN(c1cc(Cl)cc(C(=O)NCc2c(CCN(C)C)cc3n(c2=O)NCC3)c1C)[C@H]1CC[C@H](N(C)C)CC1] | 557.45 |

TABLE 2

| Cpd No. | Structure |
|---|---|
| 2 | 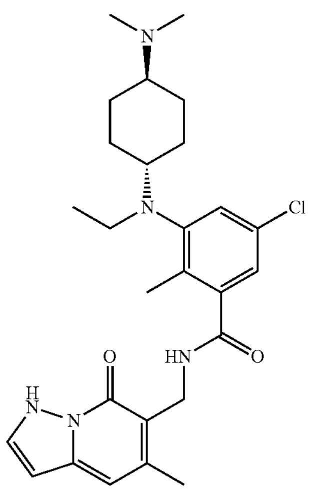 [SMILES: CCN(c1cc(Cl)cc(C(=O)NCc2c(C)cc3cc[nH]n3c2=O)c1C)[C@H]1CC[C@H](N(C)C)CC1] |
| 3 | 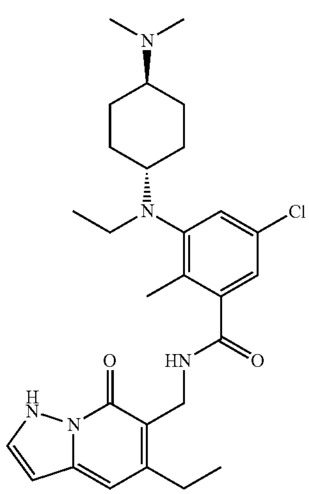 [SMILES: CCc1cc2cc[nH]n2c(=O)c1CNC(=O)c1cc(Cl)cc(N(CC)[C@H]2CC[C@H](N(C)C)CC2)c1C] |

TABLE 2-continued

| Cpd No. | Structure |
|---|---|
| 4 | 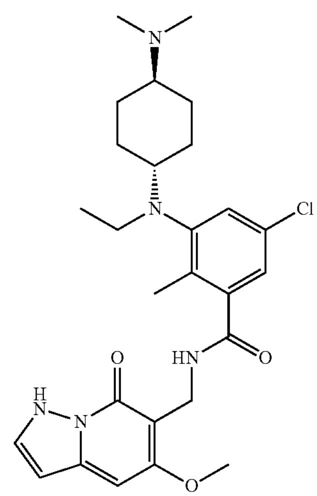 [SMILES: CCN(c1cc(Cl)cc(C(=O)NCc2c(OC)cc3cc[nH]n3c2=O)c1C)[C@H]1CC[C@H](N(C)C)CC1] |
| 5 | 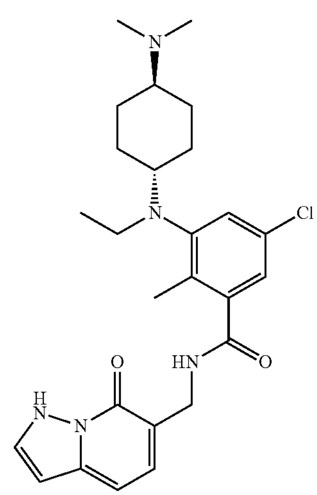 [SMILES: CCN(c1cc(Cl)cc(C(=O)NCc2ccc3cc[nH]n3c2=O)c1C)[C@H]1CC[C@H](N(C)C)CC1] |

TABLE 2-continued

| Cpd No. | Structure |
|---|---|
| 6 | (structure) |
| 7 | (structure) |
| 8 | (structure) |
| 9 | (structure) |
| 10 | (structure) |
| 11 | (structure) |

TABLE 2-continued
| Cpd No. | Structure |
|---|---|
| 12 | 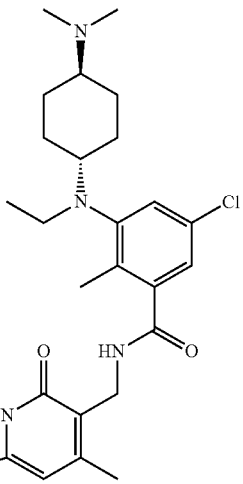 |
| 13 | 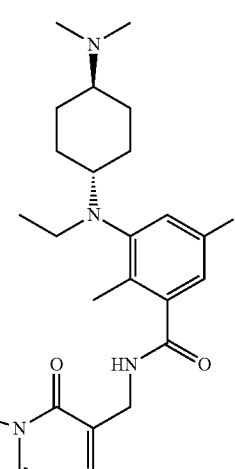 |
| 14 | 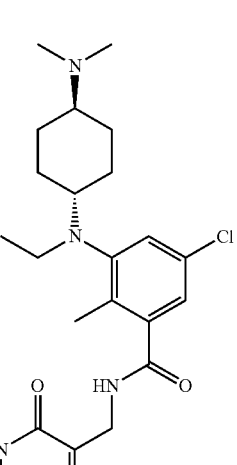 |
TABLE 2-continued
| Cpd No. | Structure |
|---|---|
| 15 | 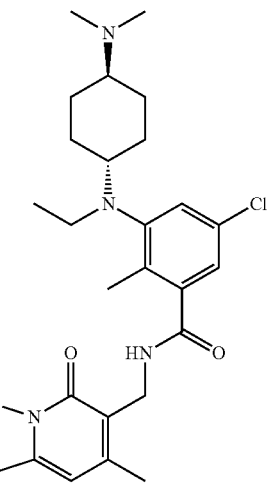 |
| 16 | 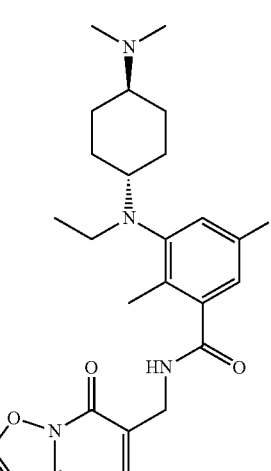 |
| 17 | 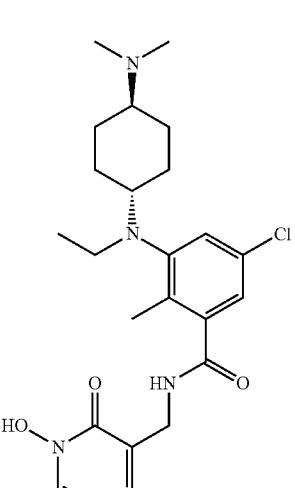 |

TABLE 2-continued

| Cpd No. | Structure |
|---|---|
| 18 | (chemical structure) |
| 19 | (chemical structure) |
| 20 | (chemical structure) |
| 21 | (chemical structure) |
| 22 | (chemical structure) |
| 23 | (chemical structure) |

TABLE 2-continued

| Cpd No. | Structure |
|---|---|
| 24 | *(chemical structure)* |
| 25 | *(chemical structure)* |
| 26 | *(chemical structure)* |
| 27 | *(chemical structure)* |
| 28 | *(chemical structure)* |
| 29 | *(chemical structure)* |

TABLE 2-continued
| Cpd No. | Structure |
|---|---|
| 30 | 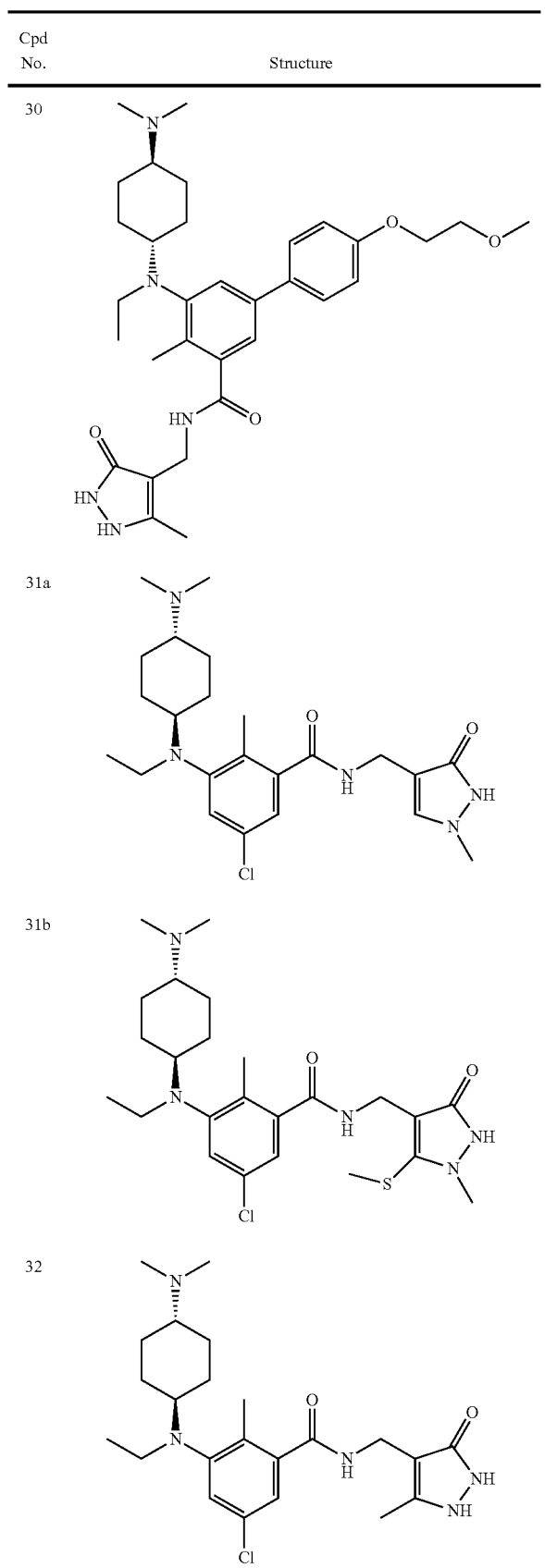 |
| 31a | 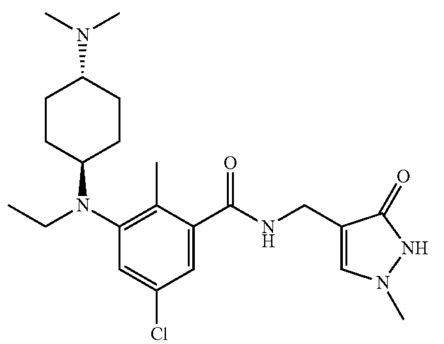 [SMILES: CCN(c1cc(Cl)cc(C(=O)NCc2cn(C)[nH]c2=O)c1C)[C@H]1CC[C@H](N(C)C)CC1] |
| 31b | 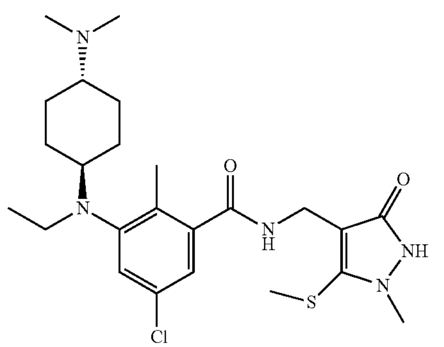 [SMILES: CCN(c1cc(Cl)cc(C(=O)NCc2c(SC)n(C)[nH]c2=O)c1C)[C@H]1CC[C@H](N(C)C)CC1] |
| 32 | 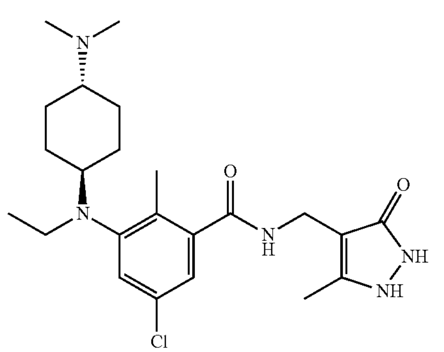 [SMILES: CCN(c1cc(Cl)cc(C(=O)NCc2c(C)[nH][nH]c2=O)c1C)[C@H]1CC[C@H](N(C)C)CC1] |
TABLE 2-continued
| Cpd No. | Structure |
|---|---|
| 33a | 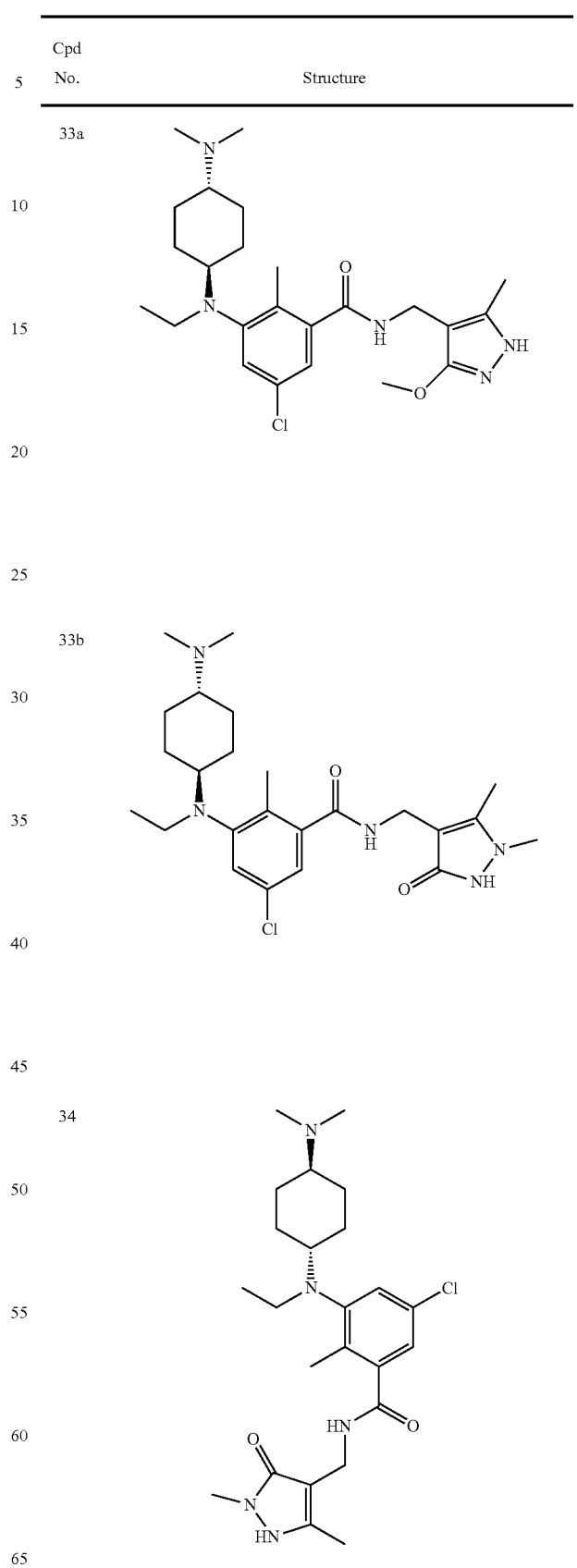 |
| 33b | 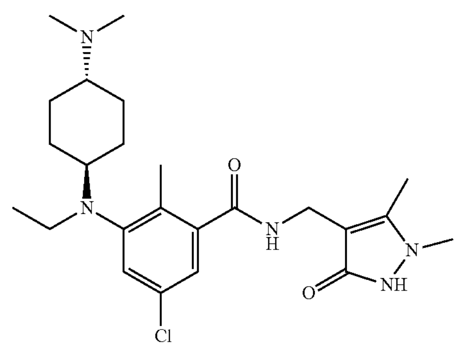 [SMILES: CCN(c1cc(Cl)cc(C(=O)NCc2c(C)n(C)[nH]c2=O)c1C)[C@H]1CC[C@H](N(C)C)CC1] |
| 34 | 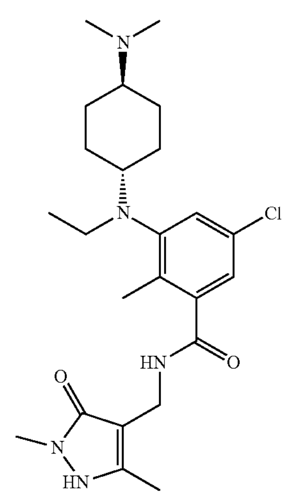 [SMILES: CCN(c1cc(Cl)cc(C(=O)NCc2c(C)[nH]n(C)c2=O)c1C)[C@H]1CC[C@H](N(C)C)CC1] |

TABLE 2-continued
| Cpd No. | Structure |
|---|---|
| 35 | 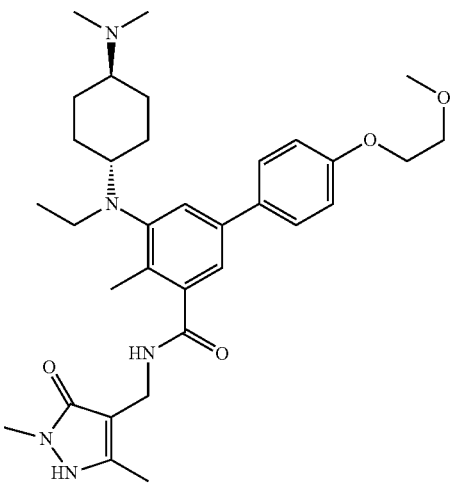 [SMILES: CCN(c1cc(-c2ccc(OCCOC)cc2)cc(C(=O)NCc2c(C)[nH]n(C)c2=O)c1C)[C@H]1CC[C@H](N(C)C)CC1] |
| 36 | 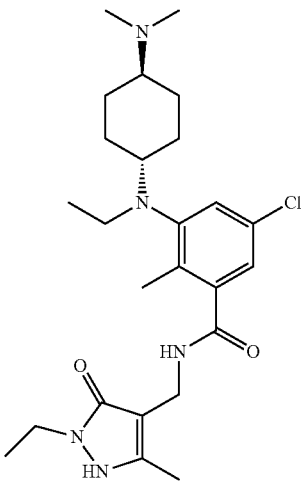 [SMILES: CCn1[nH]c(C)c(CNC(=O)c2cc(Cl)cc(N(CC)[C@H]3CC[C@H](N(C)C)CC3)c2C)c1=O] |
| 37 | 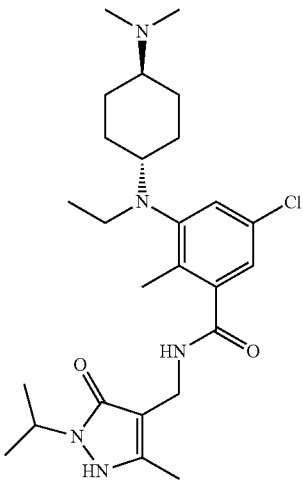 [SMILES: CCN(c1cc(Cl)cc(C(=O)NCc2c(C)[nH]n(C(C)C)c2=O)c1C)[C@H]1CC[C@H](N(C)C)CC1] |
TABLE 2-continued
| Cpd No. | Structure |
|---|---|
| 38 | 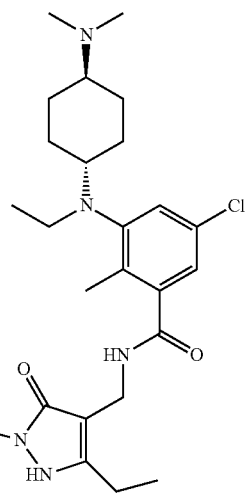 |
| 39 | 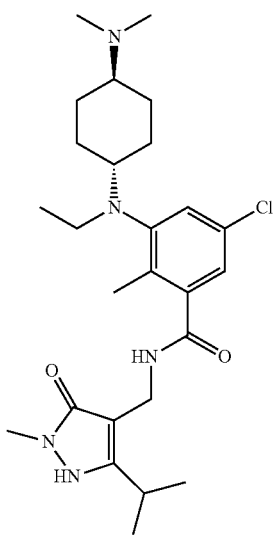 [SMILES: CCN(c1cc(Cl)cc(C(=O)NCc2c(C(C)C)[nH]n(C)c2=O)c1C)[C@H]1CC[C@H](N(C)C)CC1] |
| 40 | 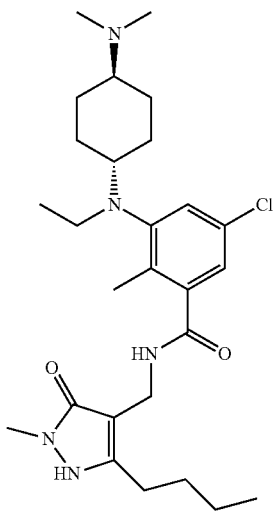 [SMILES: CCCCc1[nH]n(C)c(=O)c1CNC(=O)c1cc(Cl)cc(N(CC)[C@H]2CC[C@H](N(C)C)CC2)c1C] |

TABLE 2-continued

| Cpd No. | Structure |
|---|---|
| 41 | (structure) |
| 42 | (structure) |
| 43 | (structure) |
| 44 | (structure) |
| 45 | (structure) |
| 46 | (structure) |

TABLE 2-continued

| Cpd No. | Structure |
|---|---|
| 47 | (structure) |
| 48 | (structure) |
| 49 | (structure) |
| 50 | (structure) |
| 51 | (structure) |

TABLE 2-continued
| Cpd No. | Structure |
|---|---|
| 52 | 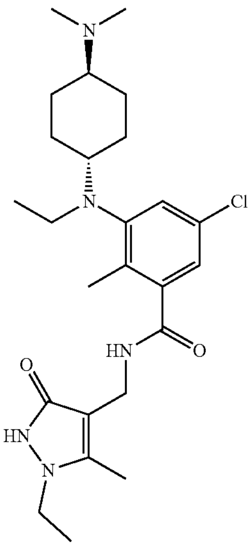 [SMILES: CCn1[nH]c(=O)c(CNC(=O)c2cc(Cl)cc(N(CC)[C@H]3CC[C@H](N(C)C)CC3)c2C)c1C] |
| 53 | 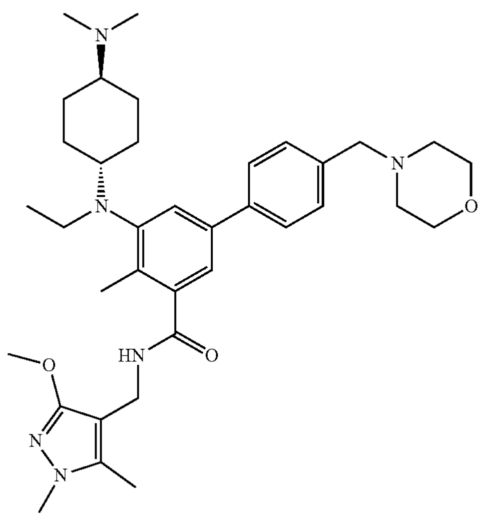 [SMILES: CCN(c1cc(-c2ccc(CN3CCOCC3)cc2)cc(C(=O)NCc2c(OC)nn(C)c2C)c1C)[C@H]1CC[C@H](N(C)C)CC1] |
| 54 | 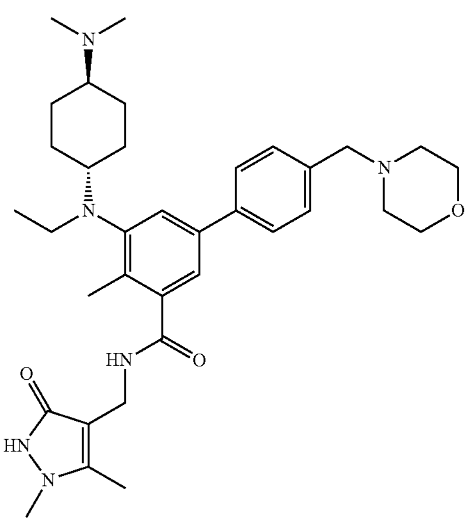 [SMILES: CCN(c1cc(-c2ccc(CN3CCOCC3)cc2)cc(C(=O)NCc2c(C)n(C)[nH]c2=O)c1C)[C@H]1CC[C@H](N(C)C)CC1] |
| 55 | |
| 56 | |
| 57 | |
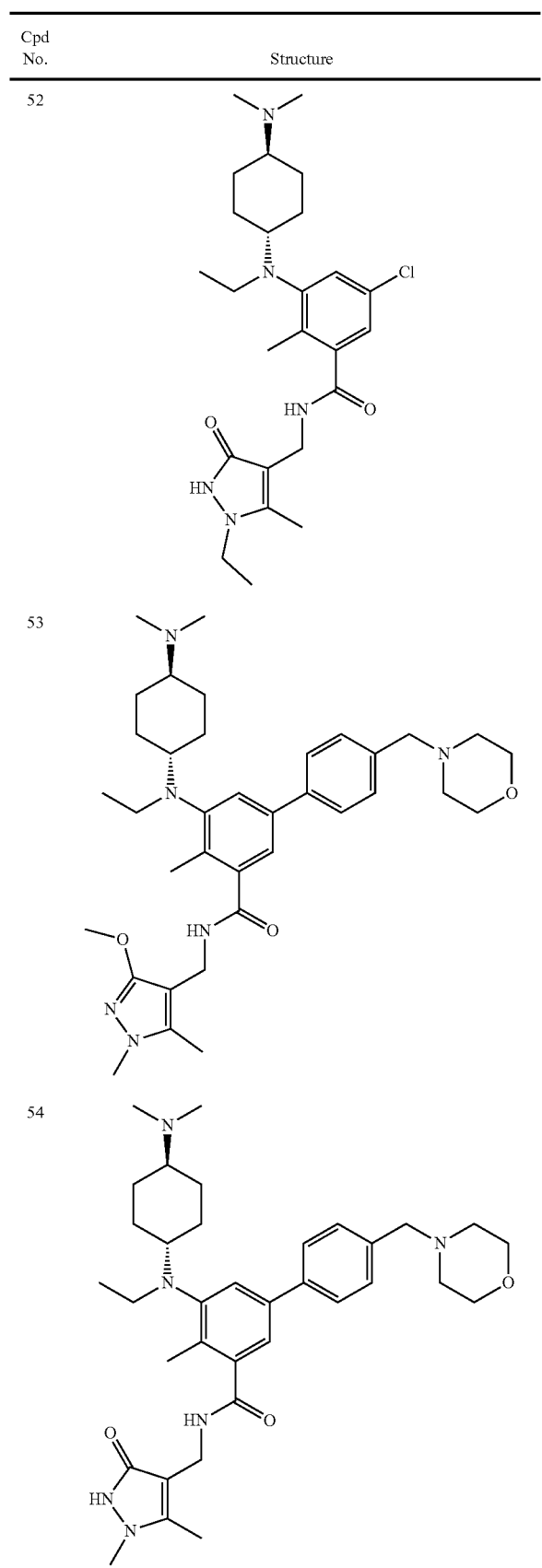
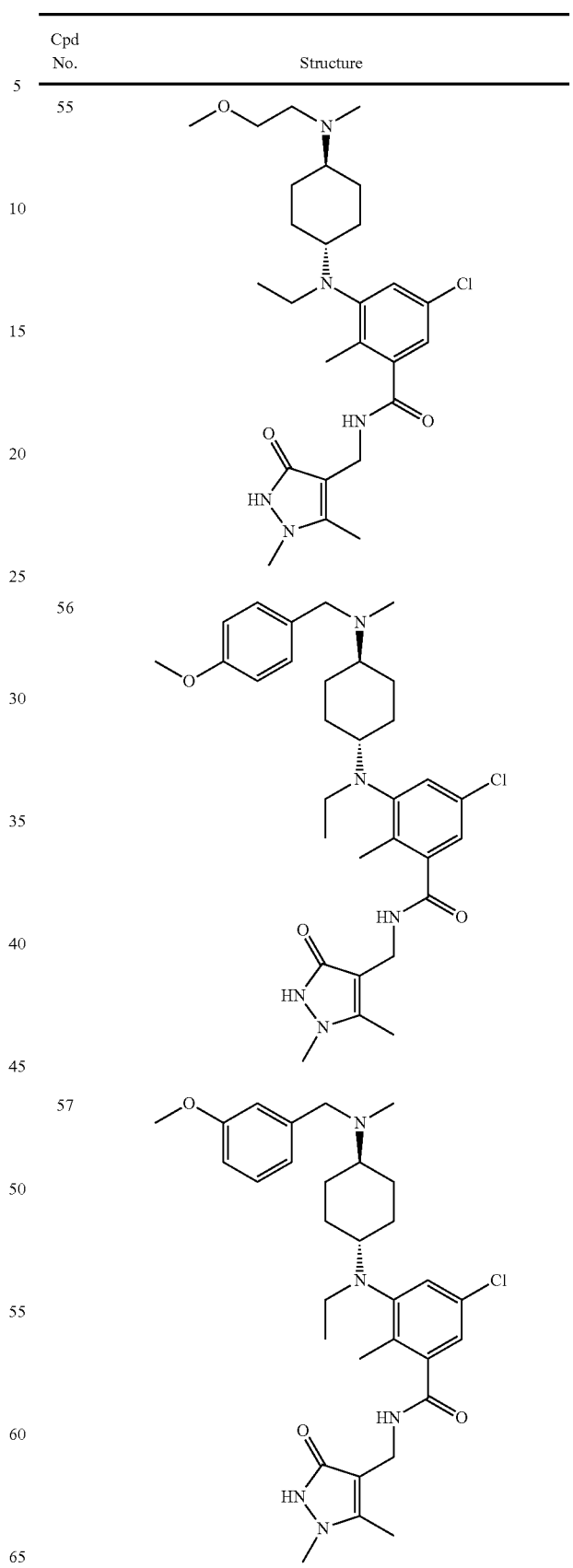

TABLE 2-continued
| Cpd No. | Structure |
|---|---|
| 58 | 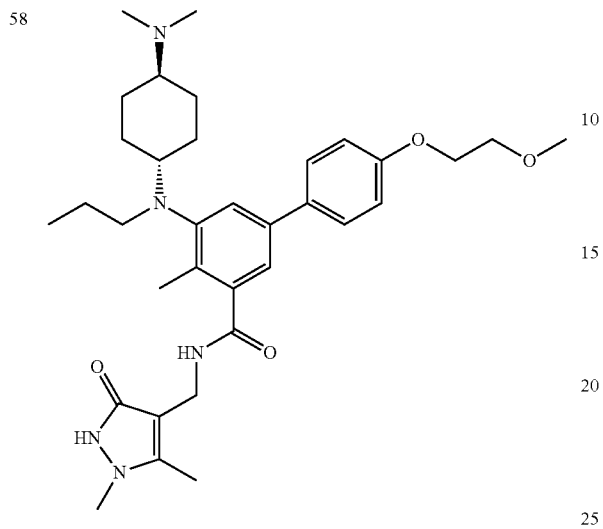 |
| 59 | 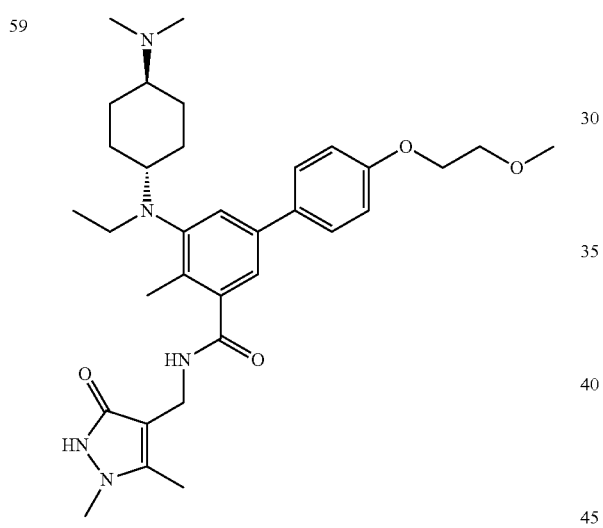 |
| 60 | 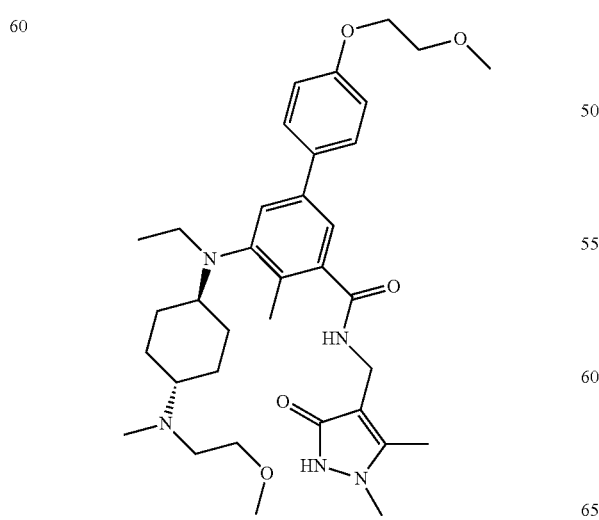 |
TABLE 2-continued
| Cpd No. | Structure |
|---|---|
| 61 | 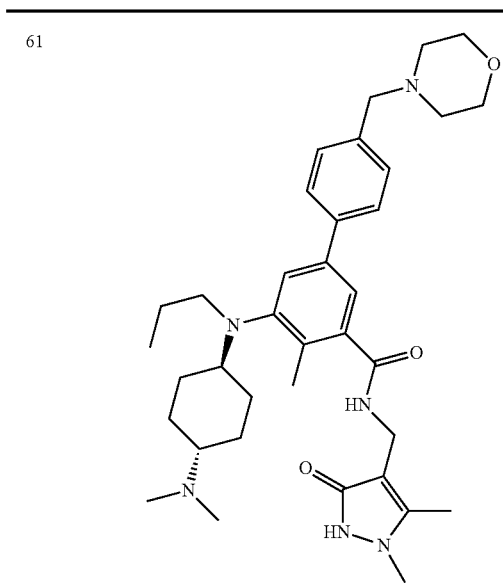 |
| 62 | 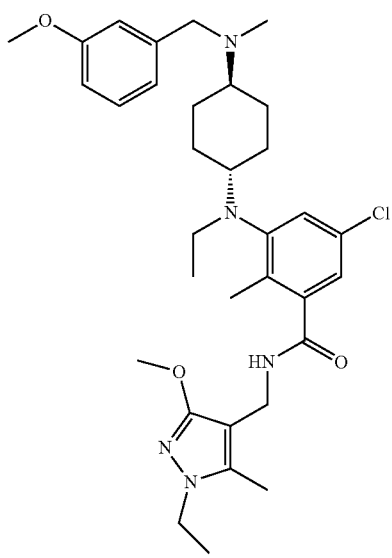 [SMILES: CCn1nc(OC)c(CNC(=O)c2cc(Cl)cc(N(CC)[C@H]3CC[C@H](N(C)Cc4cccc(OC)c4)CC3)c2C)c1C] |

TABLE 2-continued
| Cpd No. | Structure |
|---|---|
| 63 | 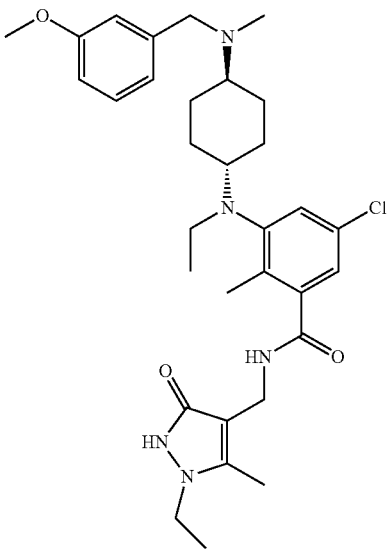 [SMILES: CCn1[nH]c(=O)c(CNC(=O)c2cc(Cl)cc(N(CC)[C@H]3CC[C@H](N(C)Cc4cccc(OC)c4)CC3)c2C)c1C] |
| 64 | 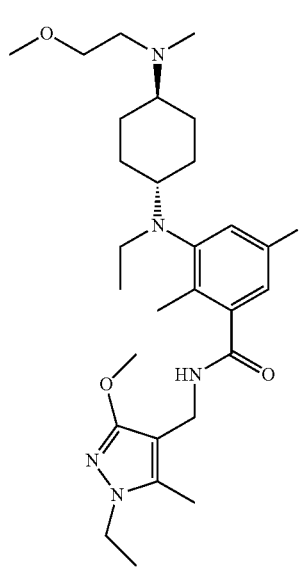 |
TABLE 2-continued
| Cpd No. | Structure |
|---|---|
| 65 | 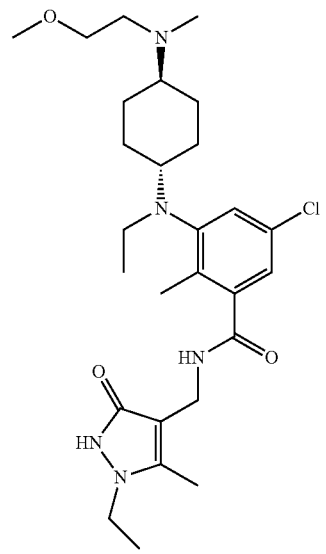 [SMILES: CCn1[nH]c(=O)c(CNC(=O)c2cc(Cl)cc(N(CC)[C@H]3CC[C@H](N(C)CCOC)CC3)c2C)c1C] |
| 66 | 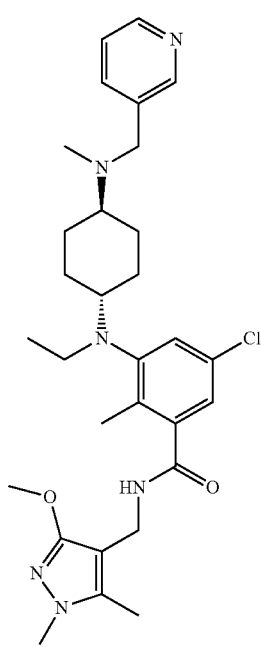 [SMILES: CCN(c1cc(Cl)cc(C(=O)NCc2c(OC)nn(C)c2C)c1C)[C@H]1CC[C@H](N(C)Cc2cccnc2)CC1] |

TABLE 2-continued
| Cpd No. | Structure |
|---|---|
| 67 | 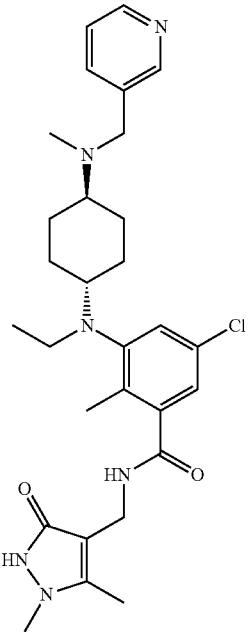 [SMILES: CCN(c1cc(Cl)cc(C(=O)NCc2c(C)n(C)[nH]c2=O)c1C)[C@H]1CC[C@H](N(C)Cc2cccnc2)CC1] |
| 68 | 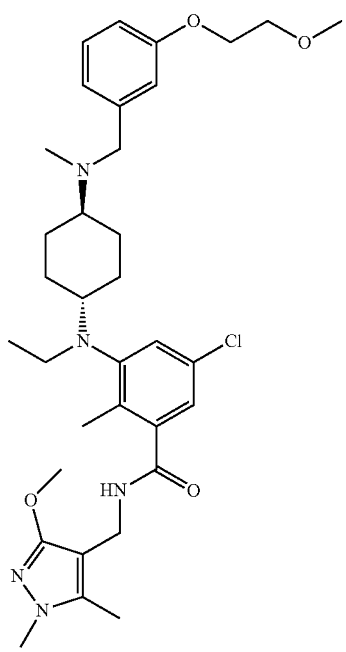 [SMILES: CCN(c1cc(Cl)cc(C(=O)NCc2c(OC)nn(C)c2C)c1C)[C@H]1CC[C@H](N(C)Cc2cccc(OCCOC)c2)CC1] |
TABLE 2-continued
| Cpd No. | Structure |
|---|---|
| 69 | 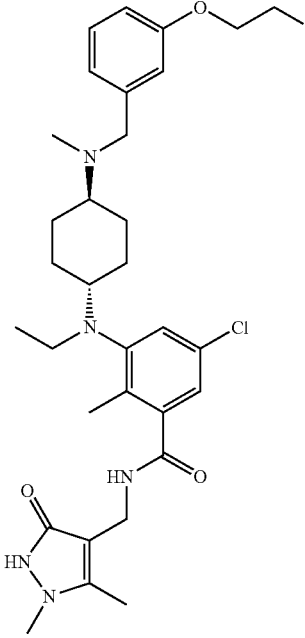 |
| 70 | 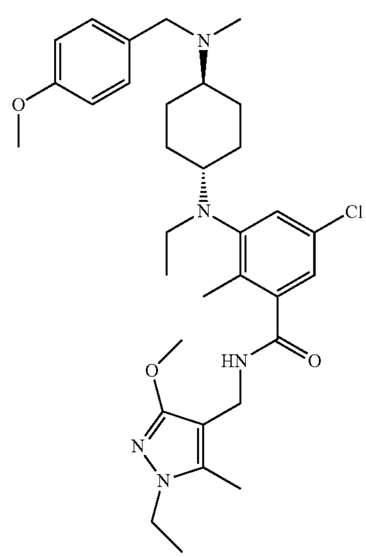 [SMILES: CCn1nc(OC)c(CNC(=O)c2cc(Cl)cc(N(CC)[C@H]3CC[C@H](N(C)Cc4ccc(OC)cc4)CC3)c2C)c1C] |

TABLE 2-continued
| Cpd No. | Structure |
|---|---|
| 71 | 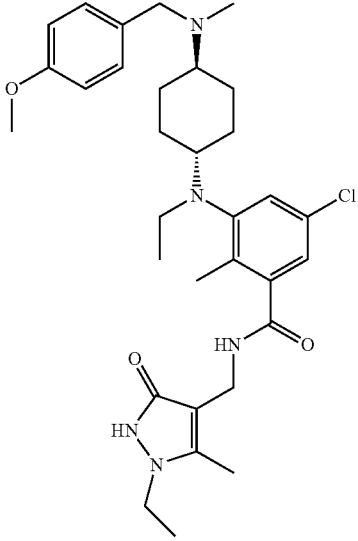 [SMILES: CCn1[nH]c(=O)c(CNC(=O)c2cc(Cl)cc(N(CC)[C@H]3CC[C@H](N(C)Cc4ccc(OC)cc4)CC3)c2C)c1C] |
| 72 | 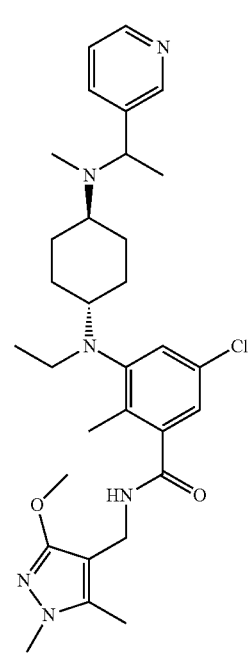 [SMILES: CCN(c1cc(Cl)cc(C(=O)NCc2c(OC)nn(C)c2C)c1C)[C@H]1CC[C@H](N(C)C(C)c2cccnc2)CC1] |
| 73 | 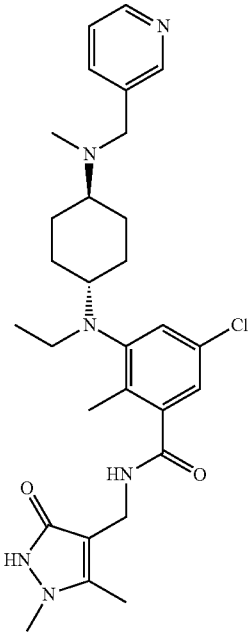 [SMILES: CCN(c1cc(Cl)cc(C(=O)NCc2c(C)n(C)[nH]c2=O)c1C)[C@H]1CC[C@H](N(C)Cc2cccnc2)CC1] |
| 74 | 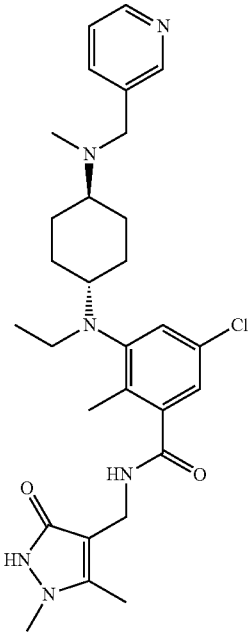 [SMILES: CCN(c1cc(Cl)cc(C(=O)NCc2c(C)n(C)[nH]c2=O)c1C)[C@H]1CC[C@H](N(C)Cc2cccnc2)CC1] |

TABLE 2-continued
| Cpd No. | Structure |
|---|---|
| 75 | 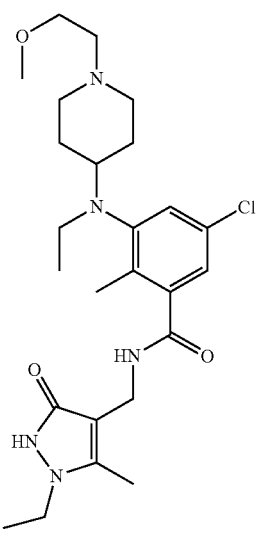 [SMILES: CCN(c1cc(Cl)cc(C(=O)NCc2c(C)n(CC)[nH]c2=O)c1C)C1CCN(CCOC)CC1] |
| 76 | 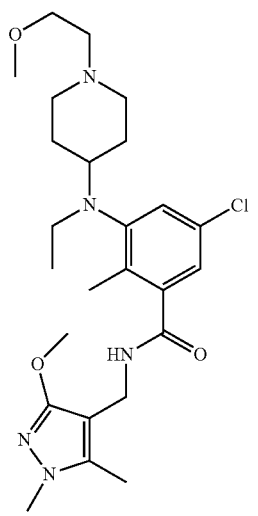 [SMILES: CCN(c1cc(Cl)cc(C(=O)NCc2c(OC)nn(C)c2C)c1C)C1CCN(CCOC)CC1] |
| 77 | 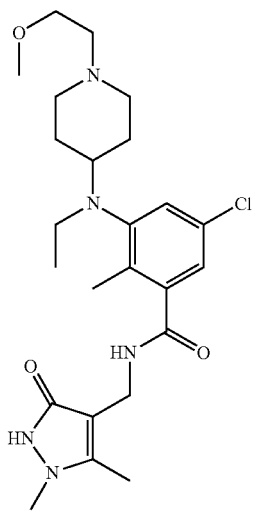 [SMILES: CCN(c1cc(Cl)cc(C(=O)NCc2c(C)n(C)[nH]c2=O)c1C)C1CCN(CCOC)CC1] |
| 78 | 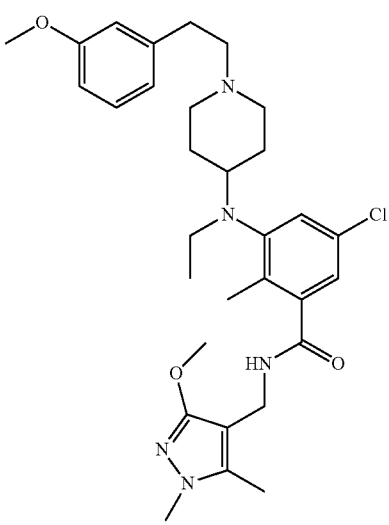 [SMILES: CCN(c1cc(Cl)cc(C(=O)NCc2c(OC)nn(C)c2C)c1C)C1CCN(CCc2cccc(OC)c2)CC1] |
| 79 | 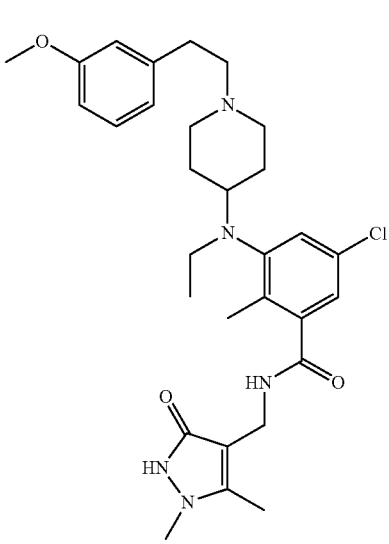 [SMILES: CCN(c1cc(Cl)cc(C(=O)NCc2c(C)n(C)[nH]c2=O)c1C)C1CCN(CCc2cccc(OC)c2)CC1] |
| 80 | 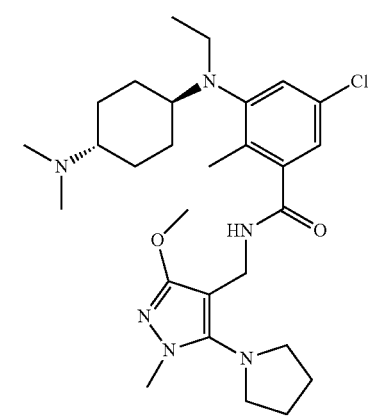 [SMILES: CCN(c1cc(Cl)cc(C(=O)NCc2c(OC)nn(C)c2N2CCCC2)c1C)[C@H]1CC[C@H](N(C)C)CC1] |

TABLE 2-continued
| Cpd No. | Structure |
|---|---|
| 81 | 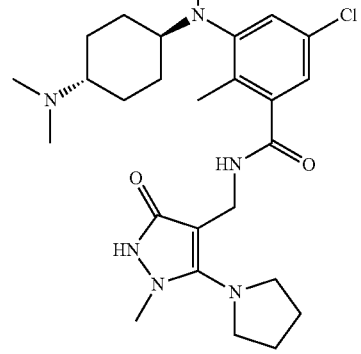 |
| 82 | 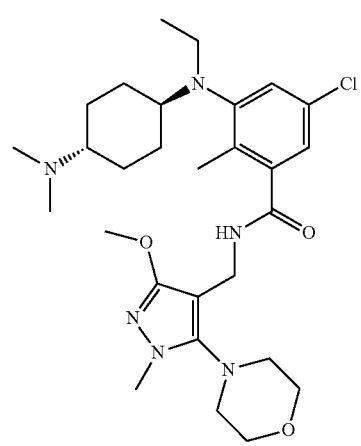 [SMILES: CCN(c1cc(Cl)cc(C(=O)NCc2c(OC)nn(C)c2N2CCOCC2)c1C)[C@H]1CC[C@H](N(C)C)CC1] |
| 83 | 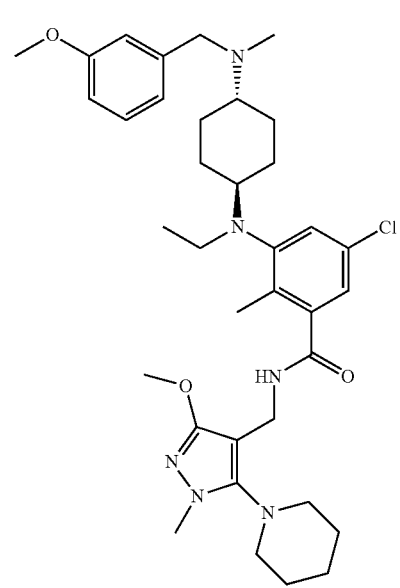 [SMILES: CCN(c1cc(Cl)cc(C(=O)NCc2c(OC)nn(C)c2N2CCCCC2)c1C)[C@H]1CC[C@H](N(C)Cc2cccc(OC)c2)CC1] |
| 84 | 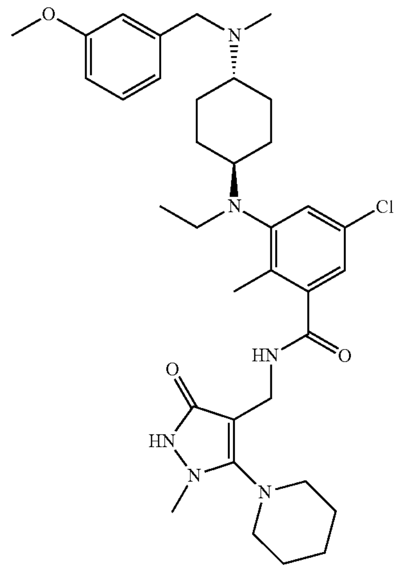 [SMILES: CCN(c1cc(Cl)cc(C(=O)NCc2c(N3CCCCC3)n(C)[nH]c2=O)c1C)[C@H]1CC[C@H](N(C)Cc2cccc(OC)c2)CC1] |
| 85 | 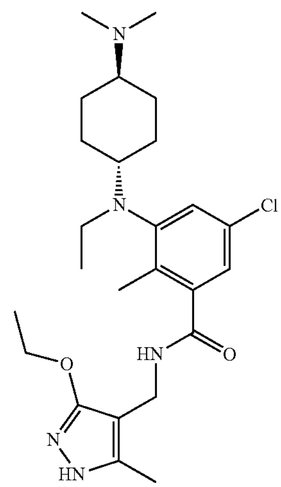 [SMILES: CCOc1n[nH]c(C)c1CNC(=O)c1cc(Cl)cc(N(CC)[C@H]2CC[C@H](N(C)C)CC2)c1C] |
| 86 | 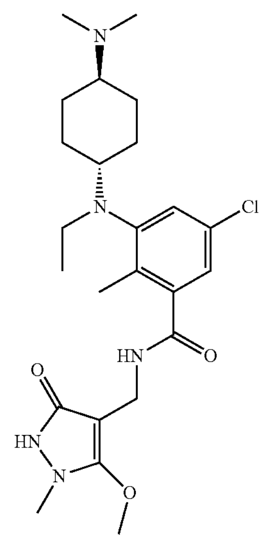 [SMILES: CCN(c1cc(Cl)cc(C(=O)NCc2c(OC)n(C)[nH]c2=O)c1C)[C@H]1CC[C@H](N(C)C)CC1] |

TABLE 2-continued

| Cpd No. | Structure |
|---|---|
| 87 | (chemical structure) |
| 88 | (chemical structure) |
| 89 | (chemical structure) |
| 90 | (chemical structure) |
| 91 | (chemical structure) |
| 92 | (chemical structure) |

TABLE 2-continued
| Cpd No. | Structure |
|---|---|
| 93 | 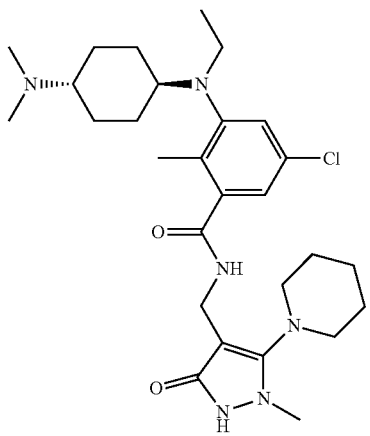 [SMILES: CCN(c1cc(Cl)cc(C(=O)NCc2c(N3CCCCC3)n(C)[nH]c2=O)c1C)[C@H]1CC[C@H](N(C)C)CC1] |
| 94 | 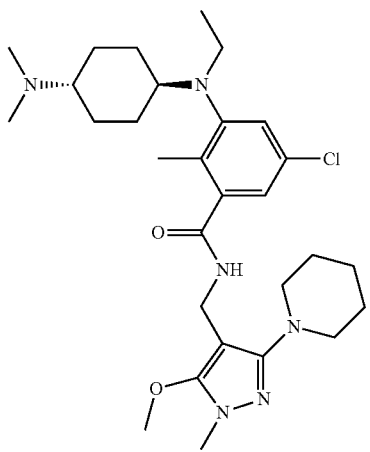 [SMILES: CCN(c1cc(Cl)cc(C(=O)NCc2c(N3CCCCC3)nn(C)c2OC)c1C)[C@H]1CC[C@H](N(C)C)CC1] |
| 95 | 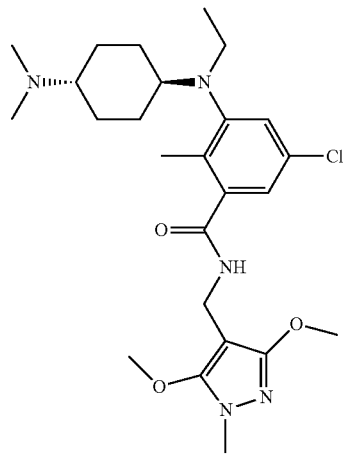 |
TABLE 3
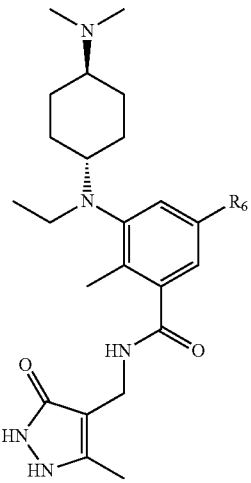
(200)
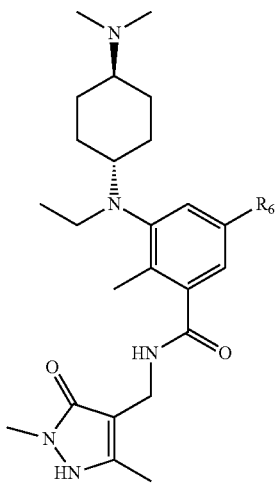
(201)
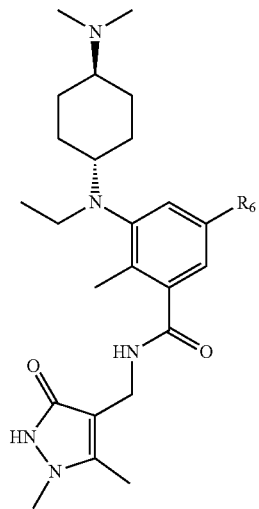
(202)

TABLE 3-continued
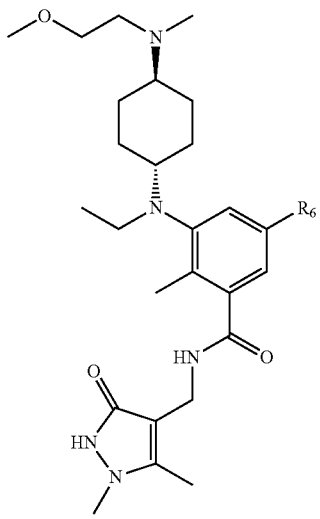
(203)
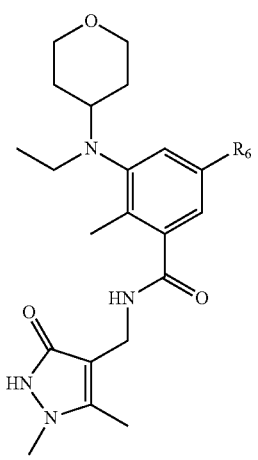
(204)
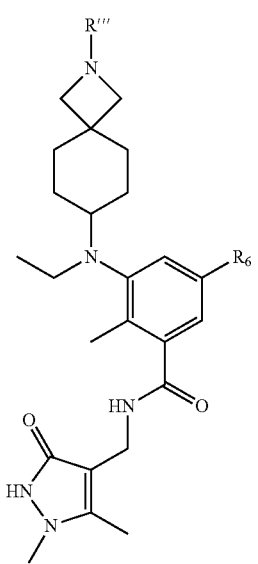
(205)
TABLE 3-continued
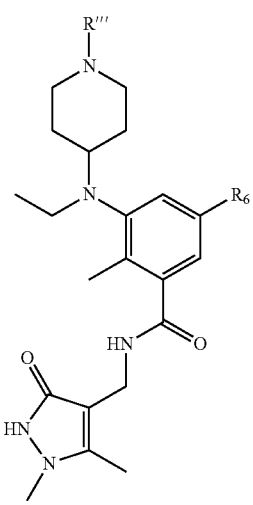
(206)
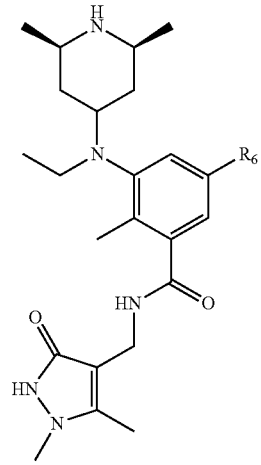
(207)
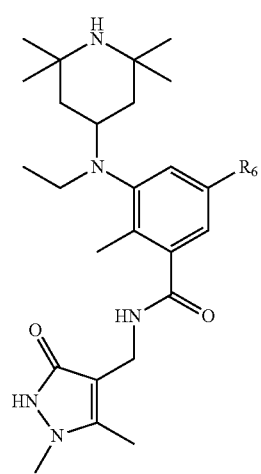
(208)

TABLE 3-continued
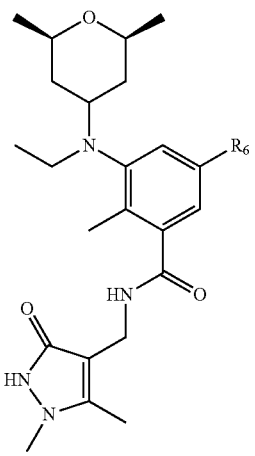
(209)
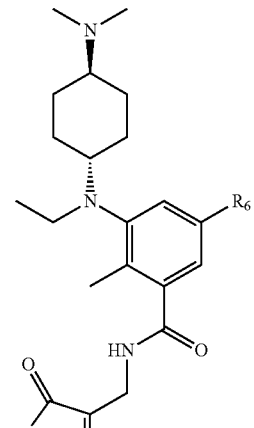
(212)
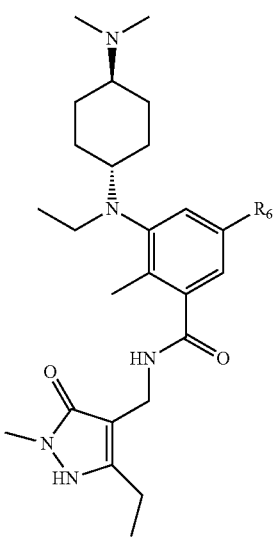
(213)
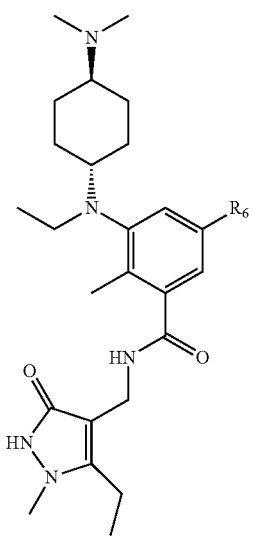
(214)
(210)
(211)

TABLE 3-continued
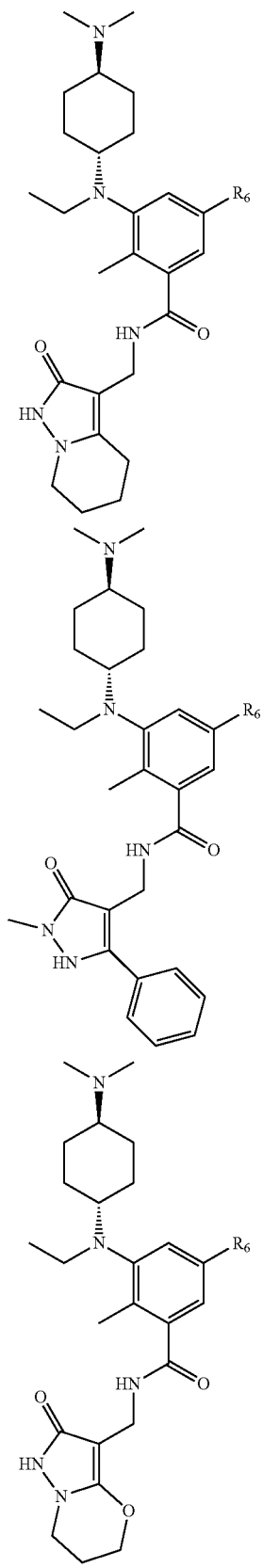
(215)
(216)
(217)
TABLE 3-continued
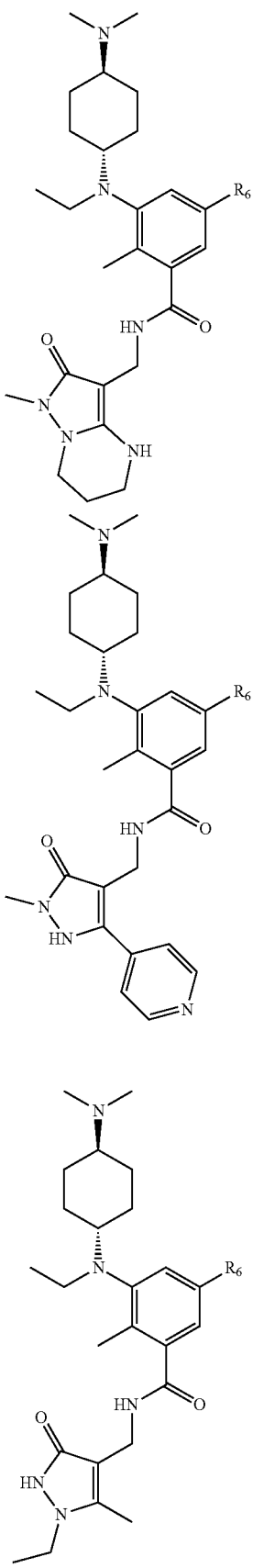
(218)
(219)
(220)

TABLE 3-continued
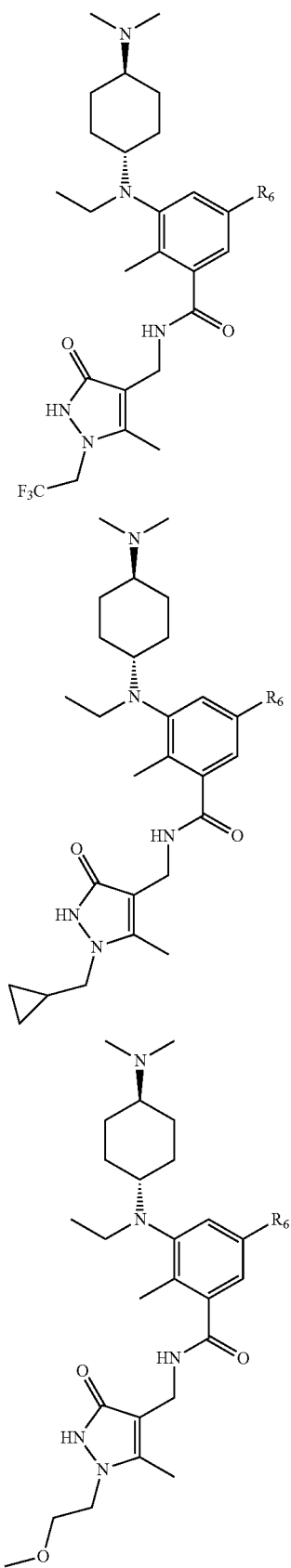
(221)
(222)
(223)
TABLE 3-continued
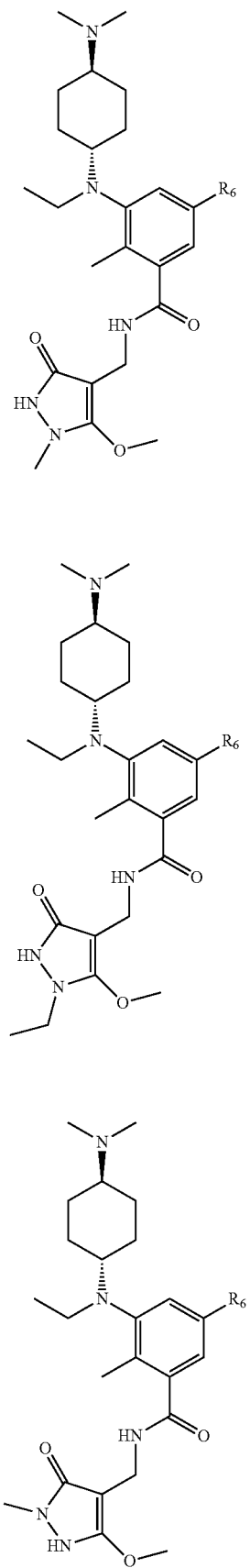
(224)
(225)
(226)

TABLE 3-continued
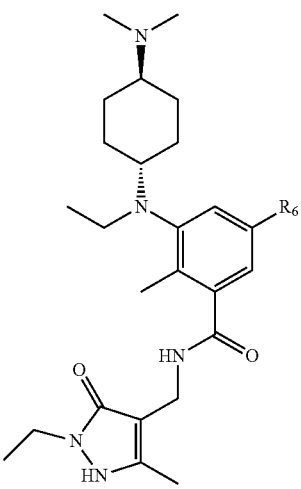
(227)
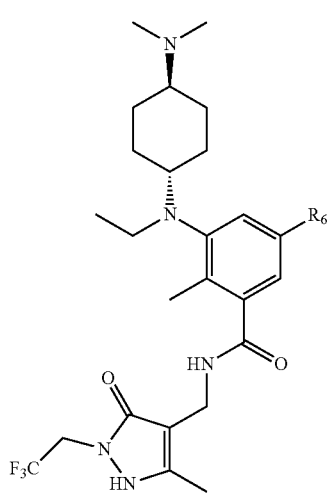
(228)
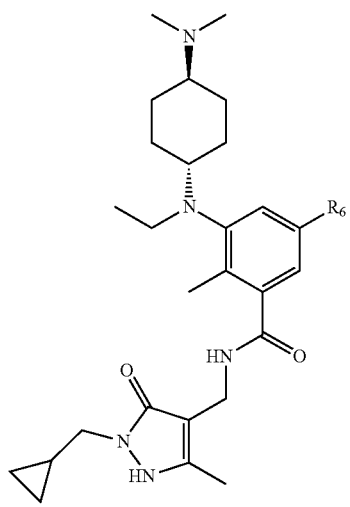
(229)
TABLE 3-continued
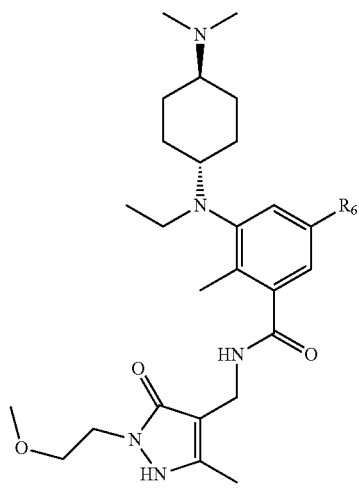
(230)
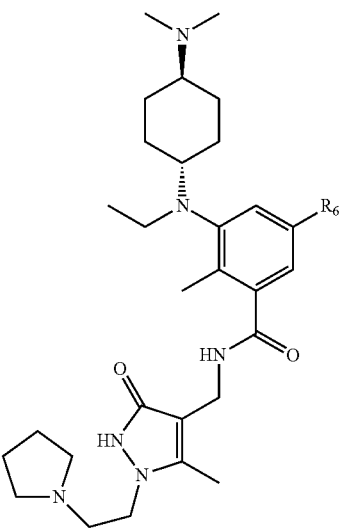
(231)
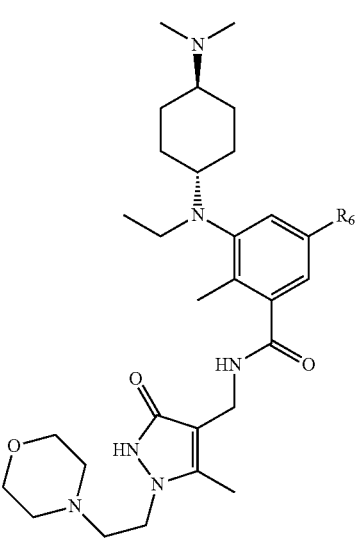
(232)

TABLE 3-continued
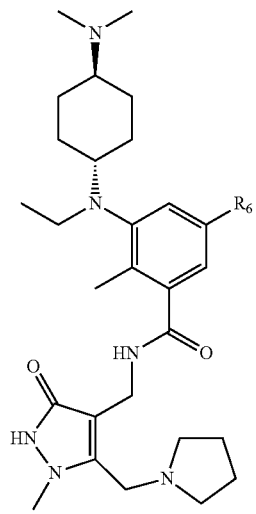
(233)
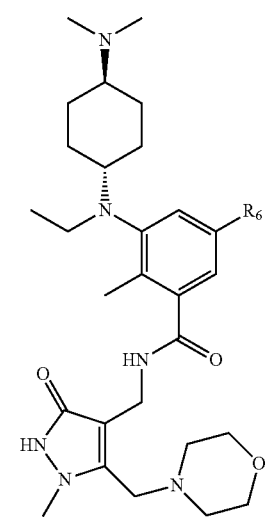
(234)
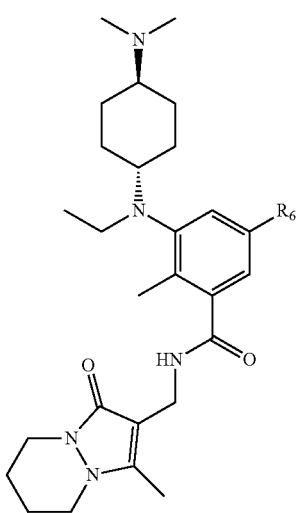
(235)
TABLE 3-continued
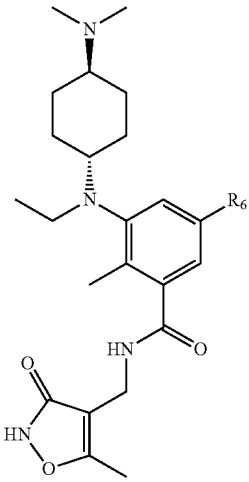
(236)
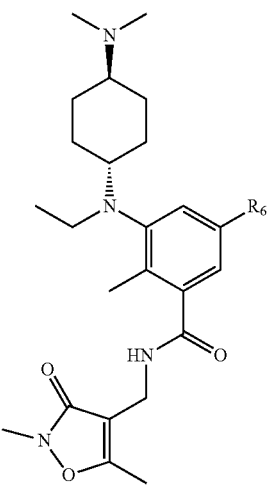
(237)
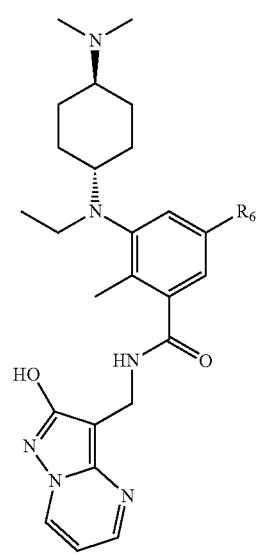
(238)

TABLE 3-continued
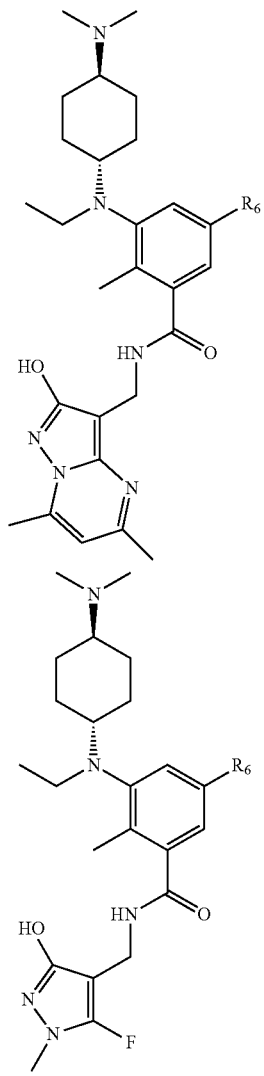
(239)
(240)
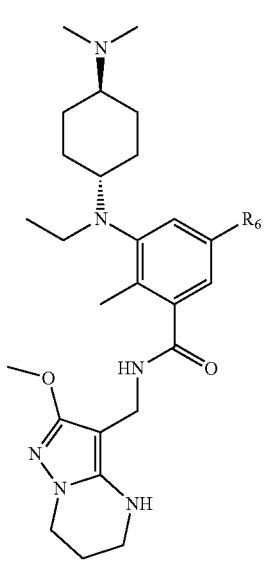
(241)
TABLE 3-continued
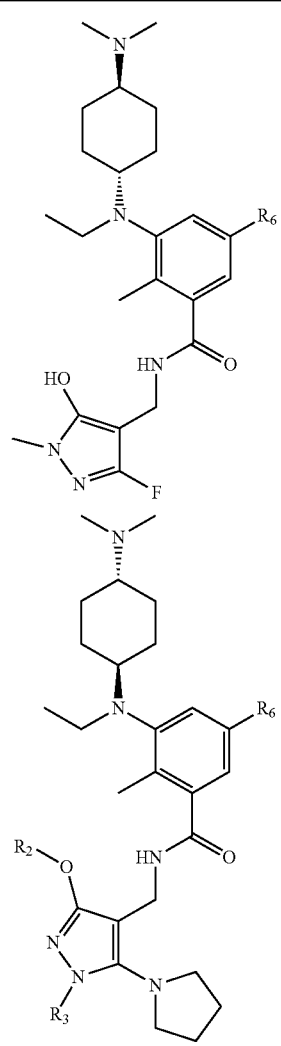
(242)
(243)
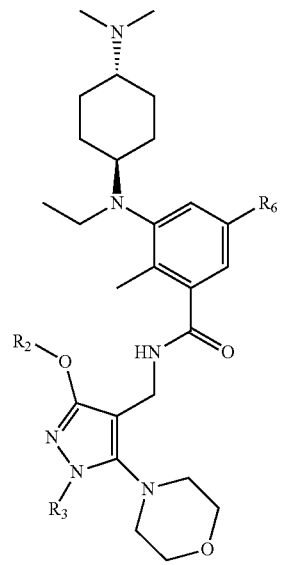
(244)

TABLE 3-continued
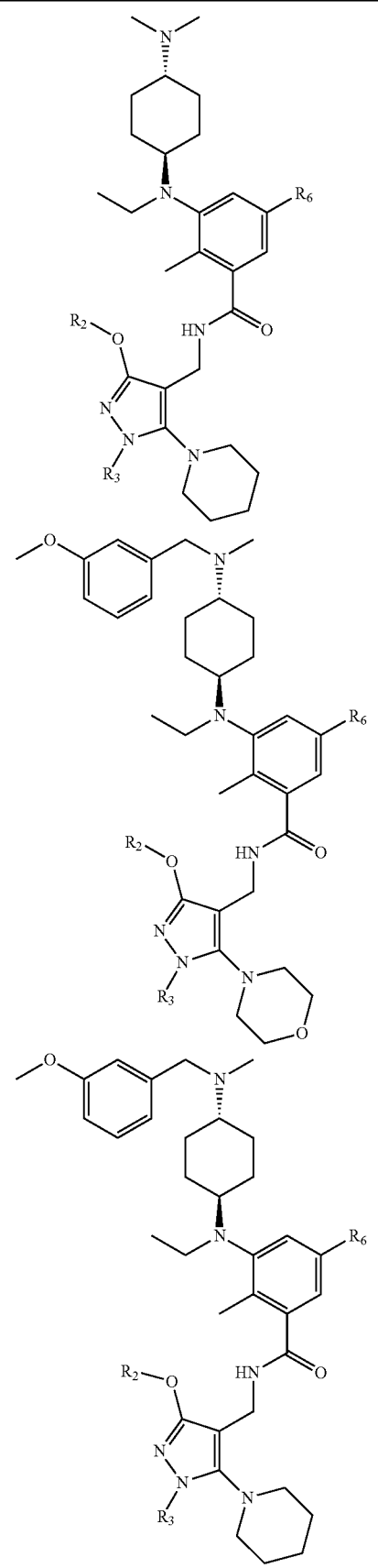
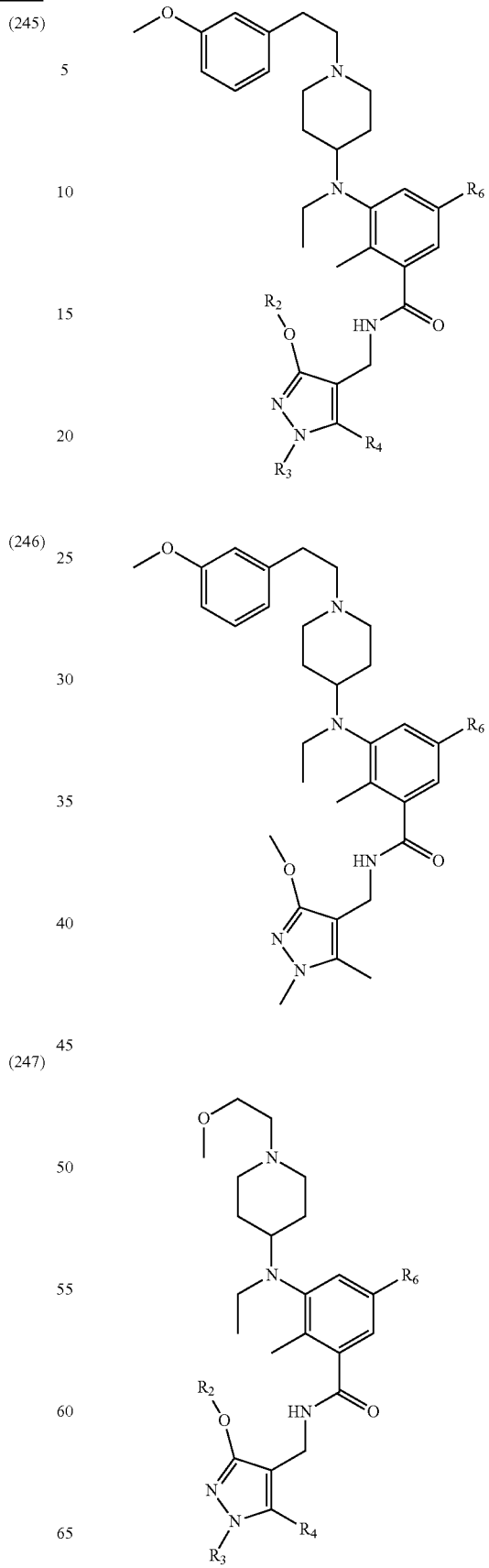

TABLE 3-continued
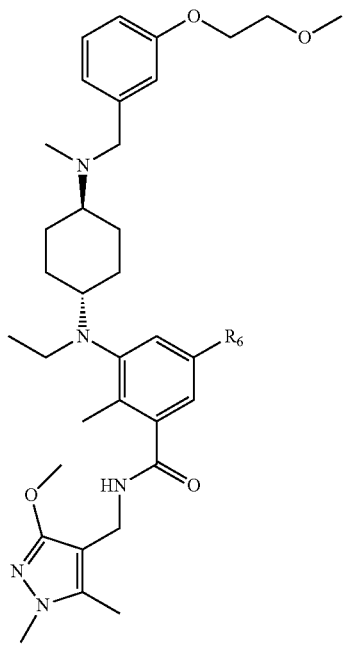
(251)
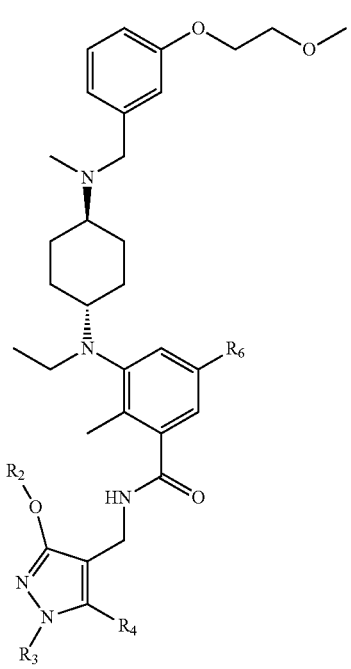
(252)
TABLE 3-continued
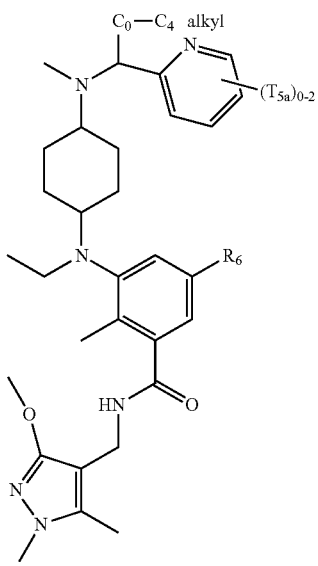
(253)
(254)
(255)
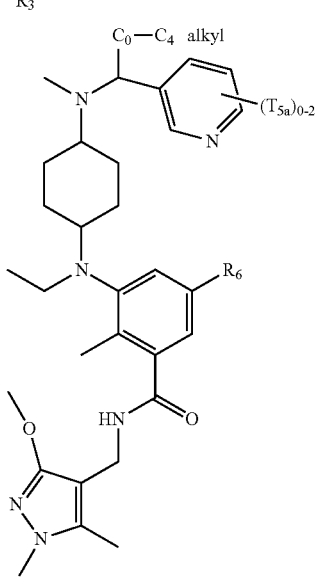

TABLE 3-continued
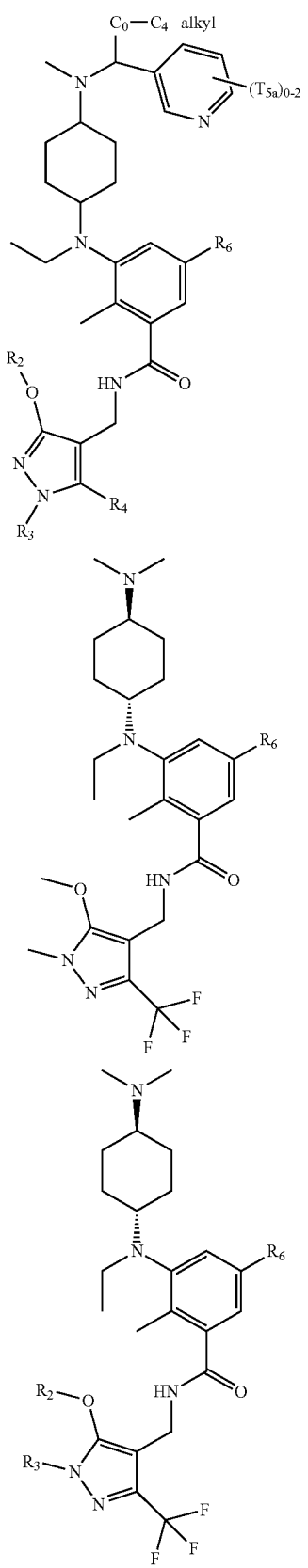
(256)
(257)
(258)
TABLE 4
| Structure of R6 |
|---|
| 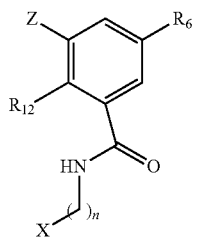 |
| 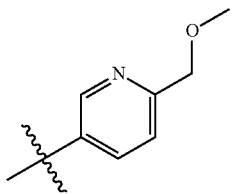 [SMILES: *c1ccc(COC)nc1] |
| 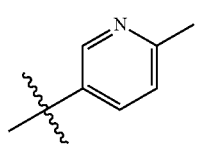 [SMILES: *c1ccc(C)nc1] |
| 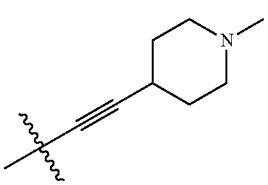 [SMILES: *C#CC1CCN(C)CC1] |
| 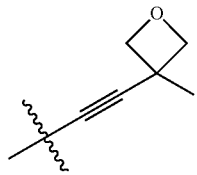 [SMILES: *C#CC1(C)COC1] |
| 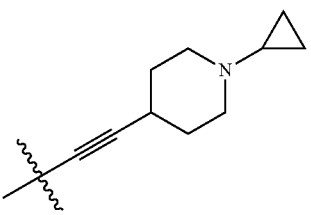 [SMILES: *C#CC1CCN(C2CC2)CC1] |
| 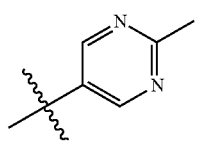 [SMILES: *c1cnc(C)nc1] |
| 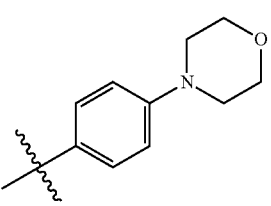 [SMILES: *c1ccc(N2CCOCC2)cc1] |

TABLE 4-continued
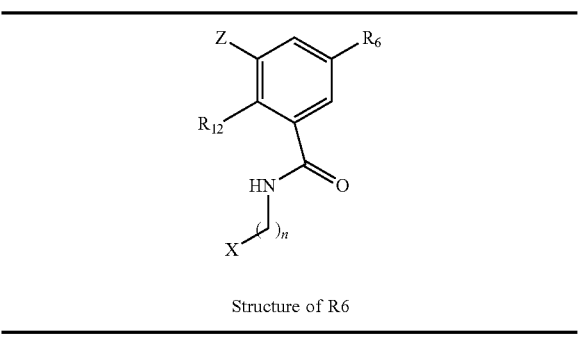
Structure of R6
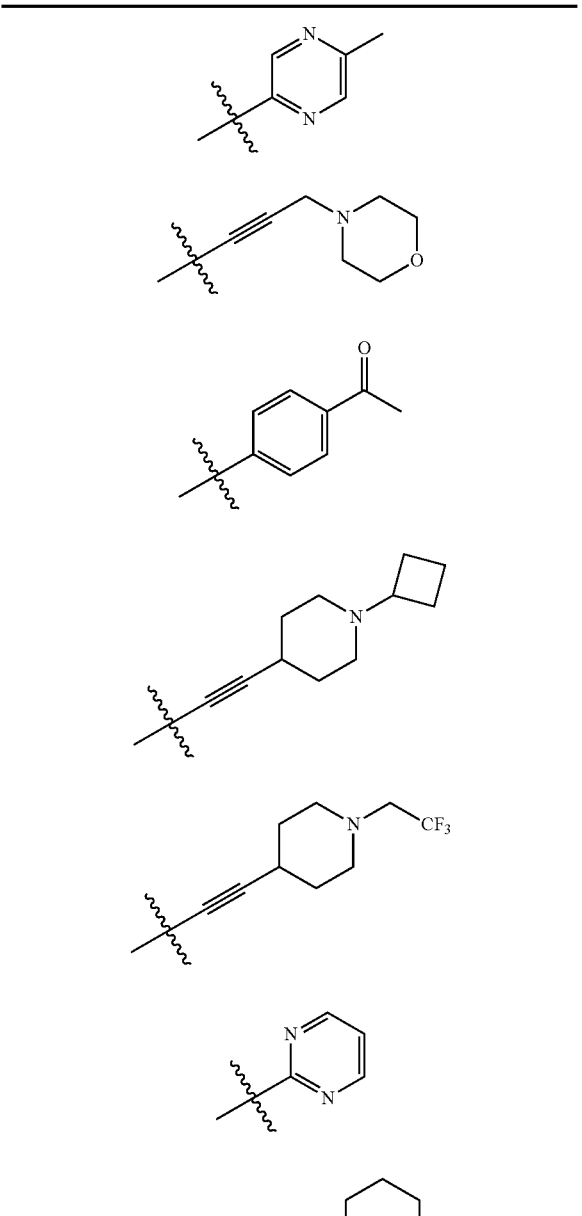
TABLE 4-continued
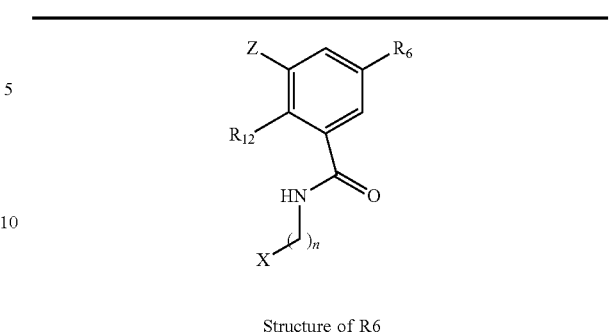
Structure of R6
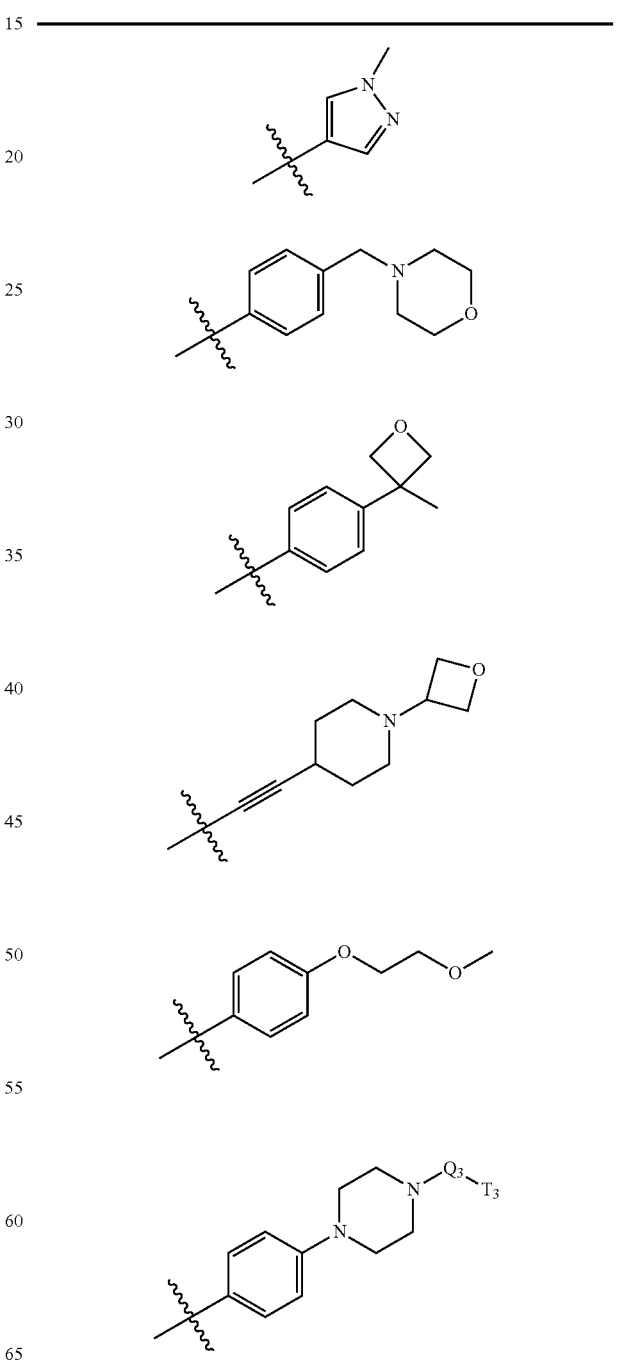

TABLE 4-continued
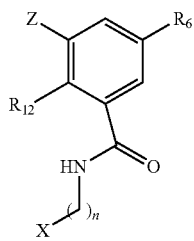
Structure of R6
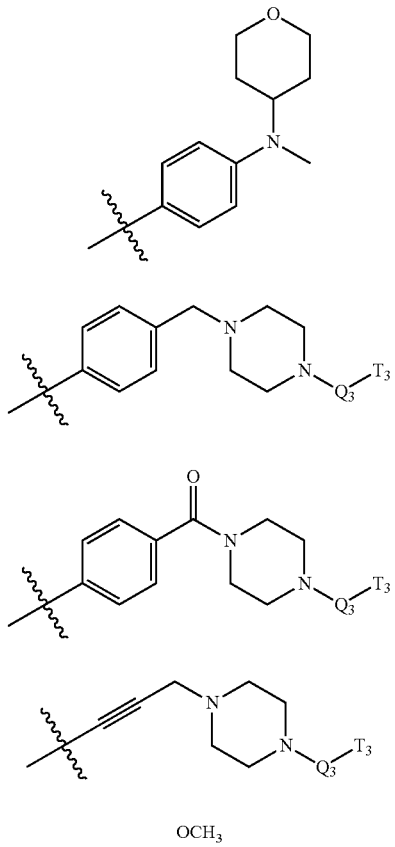
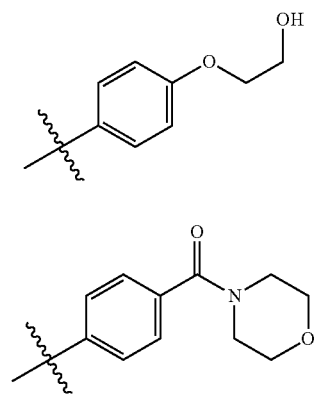
Cl
CH₃
TABLE 4-continued
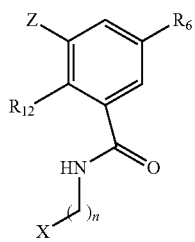
Structure of R6
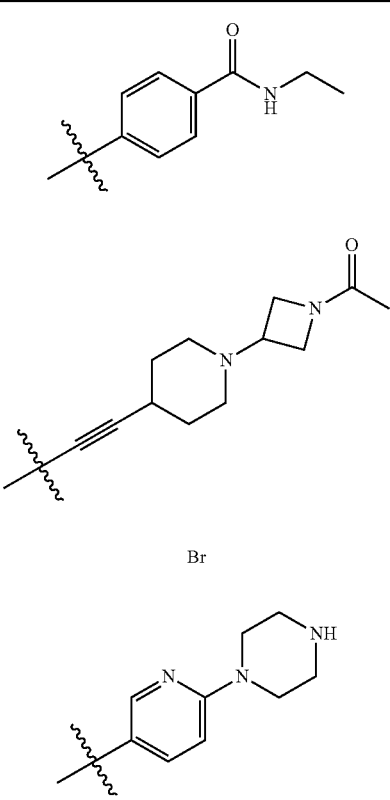
Br
TABLE 5
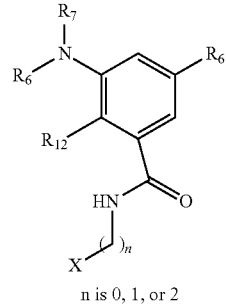
n is 0, 1, or 2
Structure of R7
sec-butyl
cyclopentyl
isopropyl TABLE 5-continued
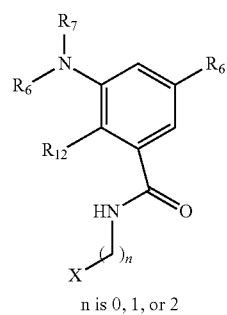
n is 0, 1, or 2
Structure of R7
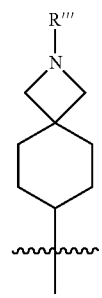
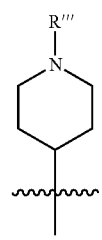
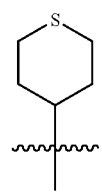 [SMILES: *C1CCSCC1]
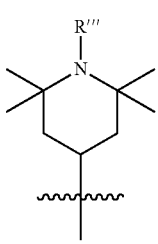
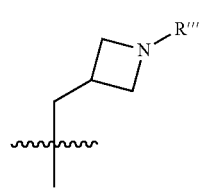
TABLE 5-continued
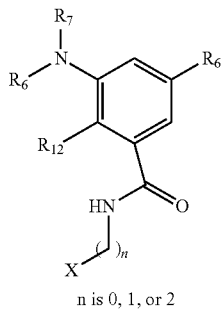
n is 0, 1, or 2
Structure of R7
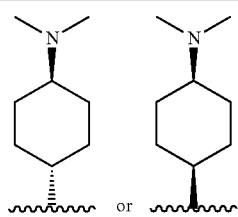
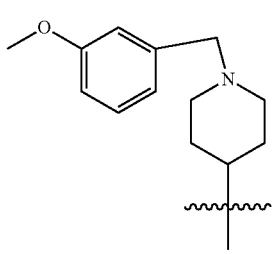 [SMILES: *C1CCN(Cc2cccc(OC)c2)CC1]
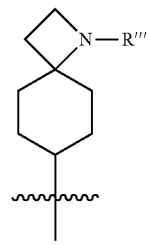
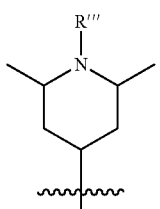
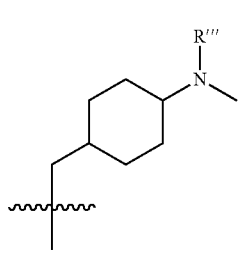

129
TABLE 5-continued
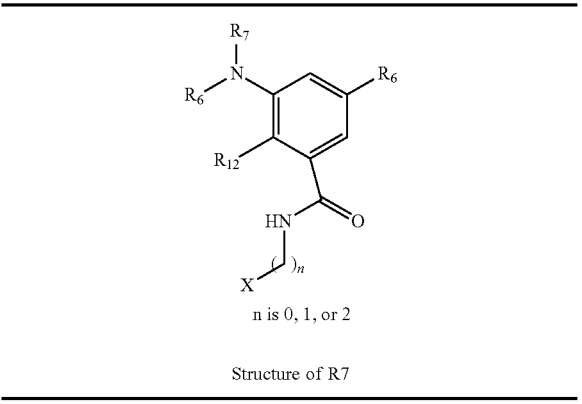
n is 0, 1, or 2
Structure of R7
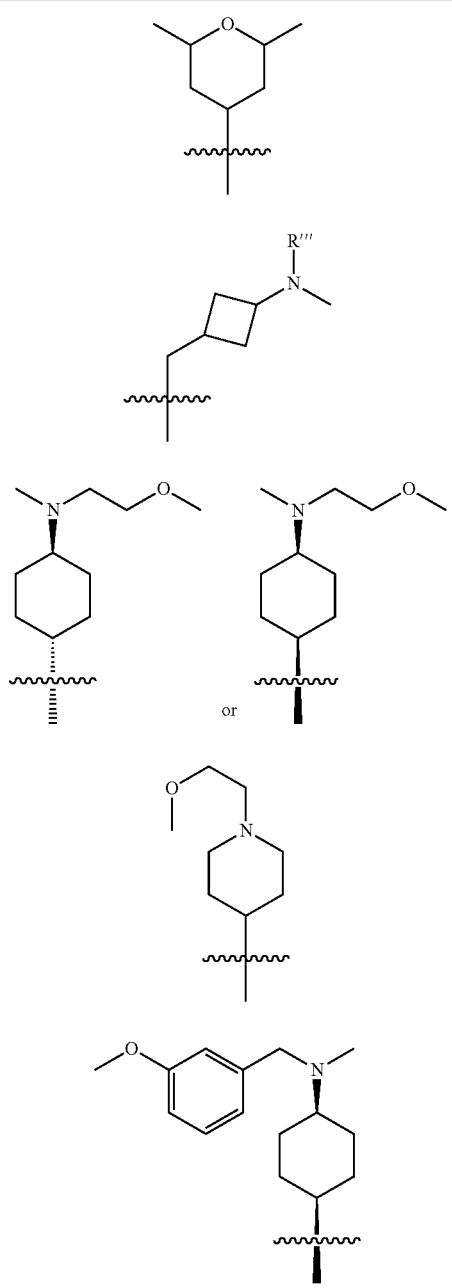
130
TABLE 5-continued
Structure of R7
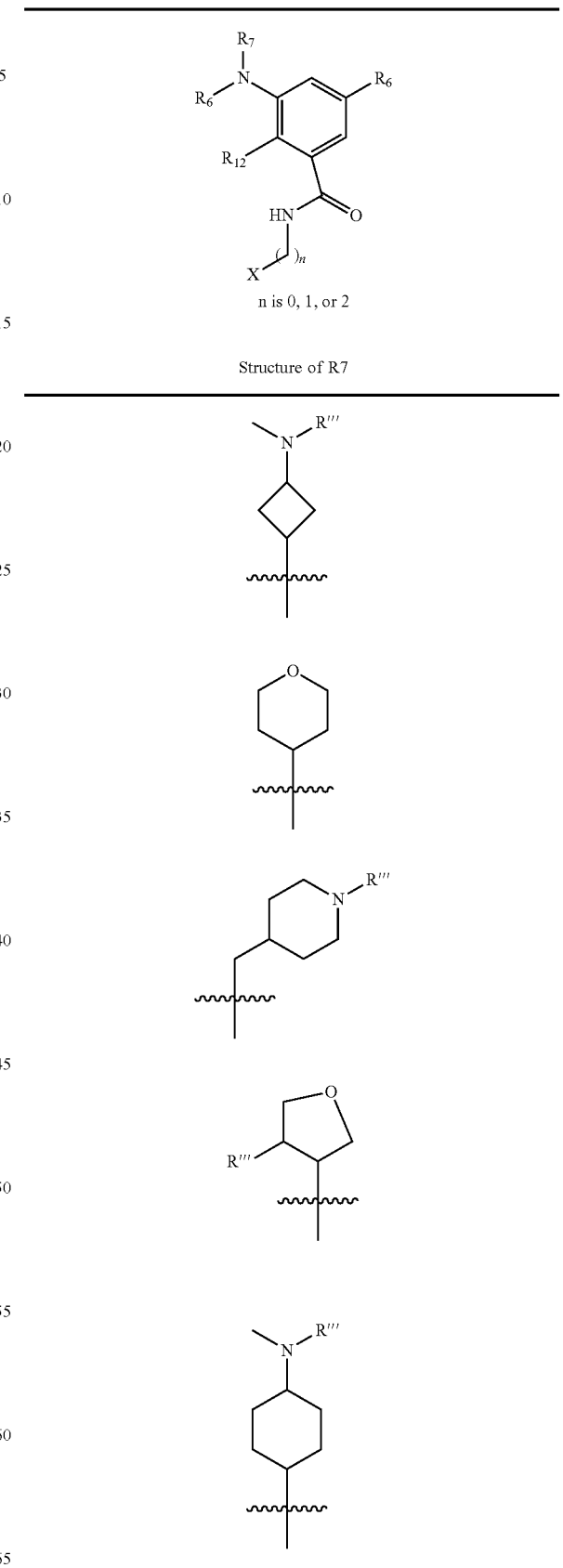

TABLE 5-continued
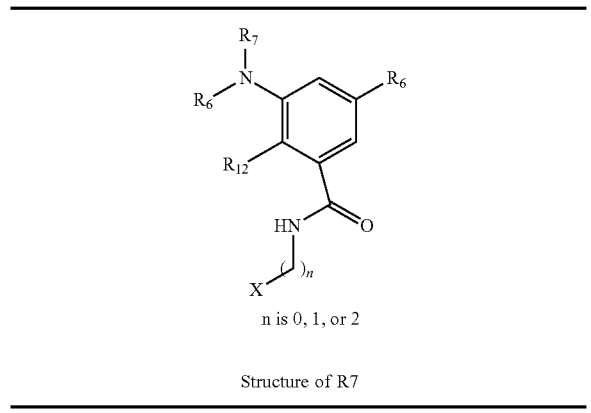
n is 0, 1, or 2
Structure of R7
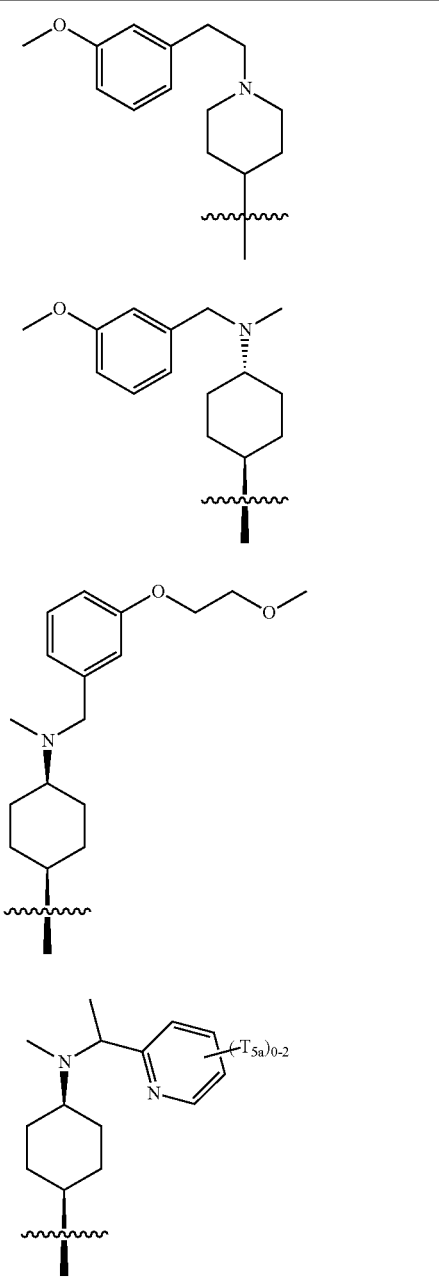
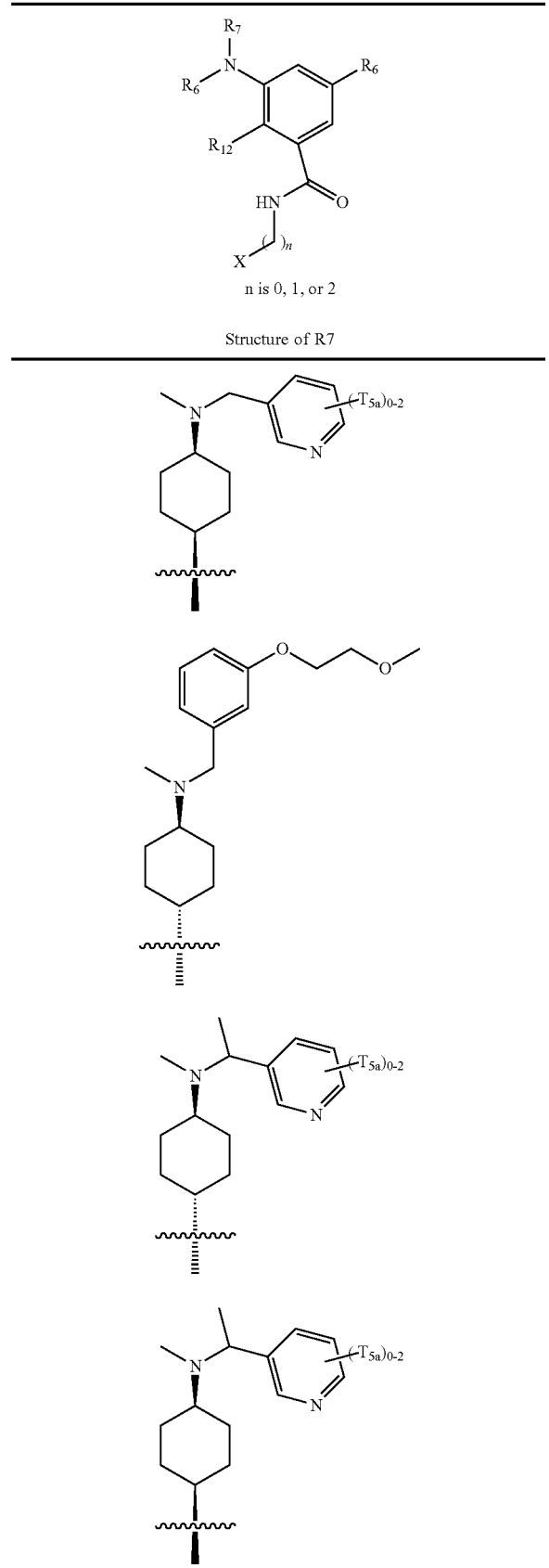

TABLE 5-continued

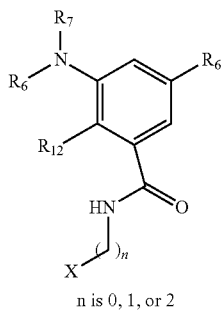

n is 0, 1, or 2

Structure of R7

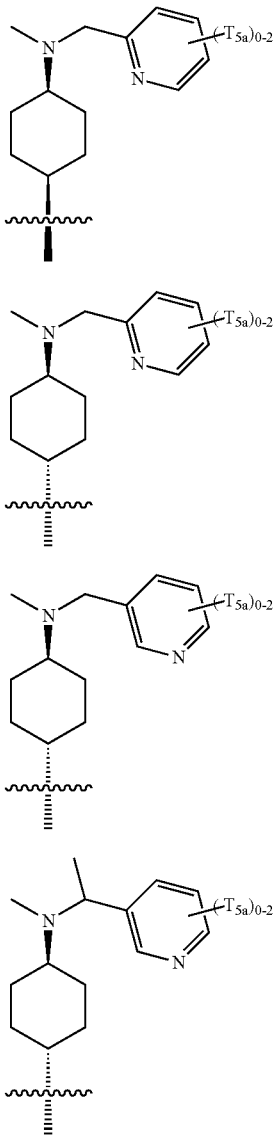

For example, compounds listed in Tables 1-3 can have $R_6$ replaced with those listed in Table 4 and/or have $R_7$ replaced with those listed Table 5.

As used herein, "alkyl", "$C_1$, $C_2$, $C_3$, $C_4$, $C_5$ or $C_6$ alkyl" or "$C_1$-$C_6$ alkyl" is intended to include $C_1$, $C_2$, $C_3$, $C_4$, $C_5$ or $C_6$ straight chain (linear) saturated aliphatic hydrocarbon groups and $C_3$, $C_4$, $C_5$ or $C_6$ branched saturated aliphatic hydrocarbon groups. For example, $C_1$-$C_6$ alkyl is intended to include $C_1$, $C_2$, $C_3$, $C_4$, $C_5$ and $C_6$ alkyl groups. Examples of alkyl include, moieties having from one to six carbon atoms, such as, but not limited to, methyl, ethyl, n-propyl, i-propyl, n-butyl, s-butyl, t-butyl, n-pentyl, s-pentyl or n-hexyl.

In certain embodiments, a straight chain or branched alkyl has six or fewer carbon atoms (e.g., $C_1$-$C_6$ for straight chain, $C_3$-$C_6$ for branched chain), and in another embodiment, a straight chain or branched alkyl has four or fewer carbon atoms.

As used herein, the term "cycloalkyl" refers to a saturated or unsaturated nonaromatic hydrocarbon mono- or multi-ring (e.g., fused, bridged, or spiro rings) system having 3 to 30 carbon atoms (e.g., $C_3$-$C_{10}$). Examples of cycloalkyl include, but are not limited to, cyclopropyl, cyclobutyl, cyclopentyl, cyclohexyl, cycloheptyl, cyclooctyl, cyclopentenyl, cyclohexenyl, cycloheptenyl, and adamantyl. The term "heterocycloalkyl" refers to a saturated or unsaturated nonaromatic 3-8 membered monocyclic, 7-12 membered bicyclic (fused, bridged, or spiro rings), or 11-14 membered tricyclic ring system (fused, bridged, or spiro rings) having one or more heteroatoms (such as O, N, S, or Se), unless specified otherwise. Examples of heterocycloalkyl groups include, but are not limited to, piperidinyl, piperazinyl, pyrrolidinyl, dioxanyl, tetrahydrofuranyl, isoindolinyl, indolinyl, imidazolidinyl, pyrazolidinyl, oxazolidinyl, isoxazolidinyl, triazolidinyl, tetrahyrofuranyl, oxiranyl, azetidinyl, oxetanyl, thietanyl, 1,2,3,6-tetrahydropyridinyl, tetrahydropyranyl, dihydropyranyl, pyranyl, morpholinyl, tetrahydrothiopyranyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, 1,4-dioxa-8-azaspiro[4.5]decanyl, 1,4-dioxaspiro[4.5]decanyl, 1-oxaspiro[4.5]decanyl, 1-azaspiro[4.5]decanyl, 3'H-spiro[cyclohexane-1,1'-isobenzofuran]-yl, 7'H-spiro[cyclohexane-1,5'-furo[3,4-b]pyridin]-yl, 3'H-spiro[cyclohexane-1,1'-furo[3,4-c]pyridin]-yl, and the like.

The term "optionally substituted alkyl" refers to unsubstituted alkyl or alkyl having designated substituents replacing one or more hydrogen atoms on one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

An "arylalkyl" or an "aralkyl" moiety is an alkyl substituted with an aryl (e.g., phenylmethyl (benzyl)). An "alkylaryl" moiety is an aryl substituted with an alkyl (e.g., methylphenyl).

As used herein, "alkyl linker" is intended to include $C_1$, $C_2$, $C_3$, $C_4$, $C_5$ or $C_6$ straight chain (linear) saturated divalent aliphatic hydrocarbon groups and $C_3$, $C_4$, $C_5$ or $C_6$ branched saturated aliphatic hydrocarbon groups. For example, $C_1$-$C_6$ alkyl linker is intended to include $C_1$, $C_2$, $C_3$, $C_4$, $C_5$ and $C_6$ alkyl linker groups. Examples of alkyl linker include, moieties having from one to six carbon atoms, such as, but not limited to, methyl (—$CH_2$—), ethyl (—$CH_2CH_2$—), n-propyl (—$CH_2CH_2CH_2$—), i-propyl (—$CHCH_3CH_2$—), n-butyl (—CH₂CH₂CH₂CH₂—), s-butyl (—CHCH₃CH₂CH₂—), i-butyl (—C(CH₃)₂CH₂—), n-pentyl (—CH₂CH₂CH₂CH₂CH₂—), s-pentyl (—CHCH₃CH₂CH₂CH₂—) or n-hexyl (—CH₂CH₂CH₂CH₂CH₂CH₂—).

"Alkenyl" includes unsaturated aliphatic groups analogous in length and possible substitution to the alkyls described above, but that contain at least one double bond. For example, the term "alkenyl" includes straight chain alkenyl groups (e.g., ethenyl, propenyl, butenyl, pentenyl, hexenyl, heptenyl, octenyl, nonenyl, decenyl), and branched alkenyl groups. In certain embodiments, a straight chain or branched alkenyl group has six or fewer carbon atoms in its backbone (e.g., $C_2$-$C_6$ for straight chain, $C_3$-$C_6$ for branched chain). The term "$C_2$-$C_6$" includes alkenyl groups containing two to six carbon atoms. The term "$C_3$-$C_6$" includes alkenyl groups containing three to six carbon atoms.

The term "optionally substituted alkenyl" refers to unsubstituted alkenyl or alkenyl having designated substituents replacing one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, heterocyclyl, alkylaryl, or an aromatic or heteroaromatic moiety.

"Alkynyl" includes unsaturated aliphatic groups analogous in length and possible substitution to the alkyls described above, but which contain at least one triple bond. For example, "alkynyl" includes straight chain alkynyl groups (e.g., ethynyl, propynyl, butynyl, pentynyl, hexynyl, heptynyl, octynyl, nonynyl, decynyl), and branched alkynyl groups. In certain embodiments, a straight chain or branched alkynyl group has six or fewer carbon atoms in its backbone (e.g., $C_2$-$C_6$ for straight chain, $C_3$-$C_6$ for branched chain). The term "$C_2$-$C_6$" includes alkynyl groups containing two to six carbon atoms. The term "$C_3$-$C_6$" includes alkynyl groups containing three to six carbon atoms.

The term "optionally substituted alkynyl" refers to unsubstituted alkynyl or alkynyl having designated substituents replacing one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

Other optionally substituted moieties (such as optionally substituted cycloalkyl, heterocycloalkyl, aryl, or heteroaryl) include both the unsubstituted moieties and the moieties having one or more of the designated substituents. For example, substituted heterocycloalkyl includes those substituted with one or more alkyl groups, such as 2,2,6,6-tetramethyl-piperidinyl and 2,2,6,6-tetramethyl-1,2,3,6-tetrahydropyridinyl.

"Aryl" includes groups with aromaticity, including "conjugated," or multicyclic systems with at least one aromatic ring and do not contain any heteroatom in the ring structure. Examples include phenyl, benzyl, 1,2,3,4-tetrahydronaphthalenyl, etc.

"Heteroaryl" groups are aryl groups, as defined above, except having from one to four heteroatoms in the ring structure, and may also be referred to as "aryl heterocycles" or "heteroaromatics." As used herein, the term "heteroaryl" is intended to include a stable 5-, 6-, or 7-membered monocyclic or 7-, 8-, 9-, 10-, 11- or 12-membered bicyclic aromatic heterocyclic ring which consists of carbon atoms and one or more heteroatoms, e.g., 1 or 1-2 or 1-3 or 1-4 or 1-5 or 1-6 heteroatoms, or e.g., 1, 2, 3, 4, 5, or 6 heteroatoms, independently selected from the group consisting of nitrogen, oxygen and sulfur. The nitrogen atom may be substituted or unsubstituted (i.e., N or NR wherein R is H or other substituents, as defined). The nitrogen and sulfur heteroatoms may optionally be oxidized (i.e., N→O and S(O)$_p$, where p=1 or 2). It is to be noted that total number of S and O atoms in the aromatic heterocycle is not more than 1.

Examples of heteroaryl groups include pyrrole, furan, thiophene, thiazole, isothiazole, imidazole, triazole, tetrazole, pyrazole, oxazole, isoxazole, pyridine, pyrazine, pyridazine, pyrimidine, and the like.

Furthermore, the terms "aryl" and "heteroaryl" include multicyclic aryl and heteroaryl groups, e.g., tricyclic, bicyclic, e.g., naphthalene, benzoxazole, benzodioxazole, benzothiazole, benzoimidazole, benzothiophene, quinoline, isoquinoline, naphthrydine, indole, benzofuran, purine, benzofuran, deazapurine, indolizine.

In the case of multicyclic aromatic rings, only one of the rings needs to be aromatic (e.g., 2,3-dihydroindole), although all of the rings may be aromatic (e.g., quinoline). The second ring can also be fused or bridged.

The cycloalkyl, heterocycloalkyl, aryl, or heteroaryl ring can be substituted at one or more ring positions (e.g., the ring-forming carbon or heteroatom such as N) with such substituents as described above, for example, alkyl, alkenyl, alkynyl, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl and heteroaryl groups can also be fused or bridged with alicyclic or heterocyclic rings, which are not aromatic so as to form a multicyclic system (e.g., tetralin, methylenedioxyphenyl such as benzo[d][1,3]dioxole-5-yl).

As used herein, "carbocycle" or "carbocyclic ring" is intended to include any stable monocyclic, bicyclic or tricyclic ring having the specified number of carbons, any of which may be saturated, unsaturated, or aromatic. Carbocycle includes cycloalkyl and aryl. For example, a $C_3$-$C_{14}$ carbocycle is intended to include a monocyclic, bicyclic or tricyclic ring having 3, 4, 5, 6, 7, 8, 9, 10, 11, 12, 13 or 14 carbon atoms. Examples of carbocycles include, but are not limited to, cyclopropyl, cyclobutyl, cyclobutenyl, cyclopentyl, cyclopentenyl, cyclohexyl, cyclohexenyl, cycloheptyl, cycloheptenyl, adamantyl, cyclooctyl, cyclooctenyl, cyclooctadienyl, fluorenyl, phenyl, naphthyl, indanyl, adamantyl and tetrahydronaphthyl. Bridged rings are also included in the definition of carbocycle, including, for example, [3.3.0]bicyclooctane, [4.3.0]bicyclononane, and [4.4.0] bicyclodecane and [2.2.2] bicyclooctane. A bridged ring occurs when one or more carbon atoms link two non-adjacent carbon atoms. In one embodiment, bridge rings are one or two carbon atoms. It is noted that a bridge always converts a monocyclic ring into a tricyclic ring. When a ring is bridged, the substituents recited for the ring may also be present on the bridge. Fused (e.g., naphthyl, tetrahydronaphthyl) and spiro rings are also included.

As used herein, "heterocycle" or "heterocyclic group" includes any ring structure (saturated, unsaturated, or aromatic) which contains at least one ring heteroatom (e.g., N, O or S). Heterocycle includes heterocycloalkyl and heteroaryl. Examples of heterocycles include, but are not limited to, morpholine, pyrrolidine, tetrahydrothiophene, piperidine, piperazine, oxetane, pyran, tetrahydropyran, azetidine, and tetrahydrofuran.

Examples of heterocyclic groups include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl (e.g., benzo[d][1,3]dioxole-5-yl), morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2,4-oxadiazol5(4H)-one, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl and xanthenyl.

The term "substituted," as used herein, means that any one or more hydrogen atoms on the designated atom is replaced with a selection from the indicated groups, provided that the designated atom's normal valency is not exceeded, and that the substitution results in a stable compound. When a substituent is oxo or keto (i.e., =O), then 2 hydrogen atoms on the atom are replaced. Keto substituents are not present on aromatic moieties. Ring double bonds, as used herein, are double bonds that are formed between two adjacent ring atoms (e.g., C=C, C=N or N=N). "Stable compound" and "stable structure" are meant to indicate a compound that is sufficiently robust to survive isolation to a useful degree of purity from a reaction mixture, and formulation into an efficacious therapeutic agent.

When a bond to a substituent is shown to cross a bond connecting two atoms in a ring, then such substituent may be bonded to any atom in the ring. When a substituent is listed without indicating the atom via which such substituent is bonded to the rest of the compound of a given formula, then such substituent may be bonded via any atom in such formula. Combinations of substituents and/or variables are permissible, but only if such combinations result in stable compounds.

When any variable (e.g., R) occurs more than one time in any constituent or formula for a compound, its definition at each occurrence is independent of its definition at every other occurrence. Thus, for example, if a group is shown to be substituted with 0-2 R moieties, then the group may optionally be substituted with up to two R moieties and R at each occurrence is selected independently from the definition of R. Also, combinations of substituents and/or variables are permissible, but only if such combinations result in stable compounds.

The term "hydroxy" or "hydroxyl" includes groups with an —OH or —O⁻.

As used herein, "halo" or "halogen" refers to fluoro, chloro, bromo and iodo. The term "perhalogenated" generally refers to a moiety wherein all hydrogen atoms are replaced by halogen atoms. The term "haloalkyl" or "haloalkoxyl" refers to an alkyl or alkoxyl substituted with one or more halogen atoms.

The term "carbonyl" includes compounds and moieties which contain a carbon connected with a double bond to an oxygen atom. Examples of moieties containing a carbonyl include, but are not limited to, aldehydes, ketones, carboxylic acids, amides, esters, anhydrides, etc.

The term "carboxyl" refers to —C(O)OH or its $C_1$-$C_6$ alkyl ester.

"Acyl" includes moieties that contain the acyl radical (R—C(O)—) or a carbonyl group. "Substituted acyl" includes acyl groups where one or more of the hydrogen atoms are replaced by, for example, alkyl groups, alkynyl groups, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

"Aroyl" includes moieties with an aryl or heteroaromatic moiety bound to a carbonyl group. Examples of aroyl groups include phenylcarboxy, naphthyl carboxy, etc.

"Alkoxyalkyl," "alkylaminoalkyl," and "thioalkoxyalkyl" include alkyl groups, as described above, wherein oxygen, nitrogen, or sulfur atoms replace one or more hydrocarbon backbone carbon atoms.

The term "alkoxy" or "alkoxyl" includes substituted and unsubstituted alkyl, alkenyl and alkynyl groups covalently linked to an oxygen atom. Examples of alkoxy groups or alkoxyl radicals include, but are not limited to, methoxy, ethoxy, isopropyloxy, propoxy, butoxy and pentoxy groups. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy and trichloromethoxy.

The term "ether" or "alkoxy" includes compounds or moieties which contain an oxygen bonded to two carbon atoms or heteroatoms. For example, the term includes "alkoxyalkyl," which refers to an alkyl, alkenyl, or alkynyl group covalently bonded to an oxygen atom which is covalently bonded to an alkyl group.

The term "ester" includes compounds or moieties which contain a carbon or a heteroatom bound to an oxygen atom which is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc.

The term "thioalkyl" includes compounds or moieties which contain an alkyl group connected with a sulfur atom. The thioalkyl groups can be substituted with groups such as alkyl, alkenyl, alkynyl, halogen, hydroxyl, alkylcarbonyloxy, arylcarbonyloxy, alkoxycarbonyloxy, aryloxycarbonyloxy, carboxylate, carboxyacid, alkylcarbonyl, arylcarbonyl, alkoxycarbonyl, aminocarbonyl, alkylaminocarbonyl, dialkylaminocarbonyl, alkylthiocarbonyl, alkoxyl, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties.

The term "thiocarbonyl" or "thiocarboxy" includes compounds and moieties which contain a carbon connected with a double bond to a sulfur atom.

The term "thioether" includes moieties which contain a sulfur atom bonded to two carbon atoms or heteroatoms. Examples of thioethers include, but are not limited to alkthioalkyls, alkthioalkenyls, and alkthioalkynyls. The term "alkthioalkyls" include moieties with an alkyl, alkenyl, or alkynyl group bonded to a sulfur atom which is bonded to an alkyl group. Similarly, the term "alkthioalkenyls" refers to moieties wherein an alkyl, alkenyl or alkynyl group is bonded to a sulfur atom which is covalently bonded to an alkenyl group; and alkthioalkynyls" refers to moieties wherein an alkyl, alkenyl or alkynyl group is bonded to a sulfur atom which is covalently bonded to an alkynyl group.

As used herein, "amine" or "amino" refers to —$NH_2$. "Alkylamino" includes groups of compounds wherein the nitrogen of —$NH_2$ is bound to at least one alkyl group. Examples of alkylamino groups include benzylamino, methylamino, ethylamino, phenethylamino, etc. "Dialkylamino" includes groups wherein the nitrogen of —$NH_2$ is bound to two alkyl groups. Examples of dialkylamino groups include, but are not limited to, dimethylamino and diethylamino "Arylamino" and "diarylamino" include groups wherein the nitrogen is bound to at least one or two aryl groups, respectively. "Aminoaryl" and "aminoaryloxy" refer to aryl and aryloxy substituted with amino. "Alkylarylamino," "alkylaminoaryl" or "arylaminoalkyl" refers to an amino group which is bound to at least one alkyl group and at least one aryl group. "Alkaminoalkyl" refers to an alkyl, alkenyl, or alkynyl group bound to a nitrogen atom which is also bound to an alkyl group. "Acylamino" includes groups wherein nitrogen is bound to an acyl group. Examples of acylamino include, but are not limited to, alkylcarbonylamino, arylcarbonylamino, carbamoyl and ureido groups.

The term "amide" or "aminocarboxy" includes compounds or moieties that contain a nitrogen atom that is bound to the carbon of a carbonyl or a thiocarbonyl group. The term includes "alkaminocarboxy" groups that include alkyl, alkenyl or alkynyl groups bound to an amino group which is bound to the carbon of a carbonyl or thiocarbonyl group. It also includes "arylaminocarboxy" groups that include aryl or heteroaryl moieties bound to an amino group that is bound to the carbon of a carbonyl or thiocarbonyl group. The terms "alkylaminocarboxy", "alkenylaminocarboxy", "alkynylaminocarboxy" and "arylaminocarboxy" include moieties wherein alkyl, alkenyl, alkynyl and aryl moieties, respectively, are bound to a nitrogen atom which is in turn bound to the carbon of a carbonyl group. Amides can be substituted with substituents such as straight chain alkyl, branched alkyl, cycloalkyl, aryl, heteroaryl or heterocycle. Substituents on amide groups may be further substituted.

Compounds of the present invention that contain nitrogens can be converted to N-oxides by treatment with an oxidizing agent (e.g., 3-chloroperoxybenzoic acid (mCPBA) and/or hydrogen peroxides) to afford other compounds of the present invention. Thus, all shown and claimed nitrogen-containing compounds are considered, when allowed by valency and structure, to include both the compound as shown and its N-oxide derivative (which can be designated as N→O or $N^+$—$O^-$). Furthermore, in other instances, the nitrogens in the compounds of the present invention can be converted to N-hydroxy or N-alkoxy compounds. For example, N-hydroxy compounds can be prepared by oxidation of the parent amine by an oxidizing agent such as m-CPBA. All shown and claimed nitrogen-containing compounds are also considered, when allowed by valency and structure, to cover both the compound as shown and its N-hydroxy (i.e., N—OH) and N-alkoxy (i.e., N—OR, wherein R is substituted or unsubstituted $C_1$-$C_6$ alkyl, $C_1$-$C_6$ alkenyl, $C_1$-$C_6$ alkynyl, 3-14-membered carbocycle or 3-14-membered heterocycle) derivatives.

In the present specification, the structural formula of the compound represents a certain isomer for convenience in some cases, but the present invention includes all isomers, such as geometrical isomers, optical isomers based on an asymmetrical carbon, stereoisomers, tautomers, and the like, it being understood that not all isomers may have the same level of activity. In addition, a crystal polymorphism may be present for the compounds represented by the formula. It is noted that any crystal form, crystal form mixture, or anhydride or hydrate thereof is included in the scope of the present invention.

"Isomerism" means compounds that have identical molecular formulae but differ in the sequence of bonding of their atoms or in the arrangement of their atoms in space. Isomers that differ in the arrangement of their atoms in space are termed "stereoisomers." Stereoisomers that are not mirror images of one another are termed "diastereoisomers," and stereoisomers that are non-superimposable mirror images of each other are termed "enantiomers" or sometimes optical isomers. A mixture containing equal amounts of individual enantiomeric forms of opposite chirality is termed a "racemic mixture."

A carbon atom bonded to four nonidentical substituents is termed a "chiral center."

"Chiral isomer" means a compound with at least one chiral center. Compounds with more than one chiral center may exist either as an individual diastereomer or as a mixture of diastereomers, termed "diastereomeric mixture." When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the *Sequence Rule* of Cahn, Ingold and Prelog. (Cahn et al., *Angew. Chem. Inter. Edit.* 1966, 5, 385; errata 511; Cahn et al., *Angew. Chem.* 1966, 78, 413; Cahn and Ingold, *J. Chem. Soc.* 1951 (London), 612; Cahn et al., *Experientia* 1956, 12, 81; Cahn, *J. Chem. Educ.* 1964, 41, 116).

"Geometric isomer" means the diastereomers that owe their existence to hindered rotation about double bonds or a cycloalkyl linker (e.g., 1,3-cylcobutyl). These configurations are differentiated in their names by the prefixes cis and trans, or Z and E, which indicate that the groups are on the same or opposite side of the double bond in the molecule according to the Cahn-Ingold-Prelog rules.

It is to be understood that the compounds of the present invention may be depicted as different chiral isomers or geometric isomers. It should also be understood that when compounds have chiral isomeric or geometric isomeric forms, all isomeric forms are intended to be included in the scope of the present invention, and the naming of the compounds does not exclude any isomeric forms, it being understood that not all isomers may have the same level of activity.

Furthermore, the structures and other compounds discussed in this invention include all atropic isomers thereof, it being understood that not all atropic isomers may have the same level of activity. "Atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques, it has been possible to separate mixtures of two atropic isomers in select cases.

"Tautomer" is one of two or more structural isomers that exist in equilibrium and is readily converted from one isomeric form to another. This conversion results in the formal migration of a hydrogen atom accompanied by a switch of adjacent conjugated double bonds. Tautomers exist as a mixture of a tautomeric set in solution. In solutions where tautomerization is possible, a chemical equilibrium of the tautomers will be reached. The exact ratio of the tautomers depends on several factors, including temperature, solvent and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs. Ring-chain tautomerism arises as a result of the aldehyde group (—CHO) in a sugar chain molecule reacting with one of the hydroxy groups (—OH) in the same molecule to give it a cyclic (ring-shaped) form as exhibited by glucose.

Common tautomeric pairs are: ketone-enol, amide-nitrile, lactam-lactim, amide-imidic acid tautomerism in heterocyclic rings (e.g., in nucleobases such as guanine, thymine and cytosine), imine-enamine and enamine-enamine Examples of lactam-lactim tautomerism are as shown below.

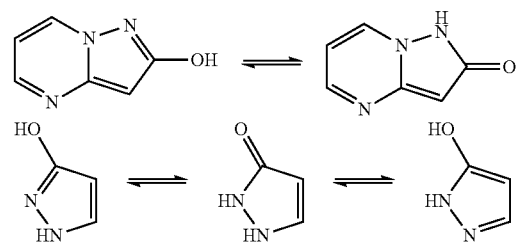

It is to be understood that the compounds of the present invention may be depicted as different tautomers. It should also be understood that when compounds have tautomeric forms, all tautomeric forms are intended to be included in the scope of the present invention, and the naming of the compounds does not exclude any tautomer form. It will be understood that certain tautomers may have a higher level of activity than others.

The term "crystal polymorphs", "polymorphs" or "crystal forms" means crystal structures in which a compound (or a salt or solvate thereof) can crystallize in different crystal packing arrangements, all of which have the same elemental composition. Different crystal forms usually have different X-ray diffraction patterns, infrared spectral, melting points, density hardness, crystal shape, optical and electrical properties, stability and solubility. Recrystallization solvent, rate of crystallization, storage temperature, and other factors may cause one crystal form to dominate. Crystal polymorphs of the compounds can be prepared by crystallization under different conditions.

The compounds of any Formula described herein include the compounds themselves, as well as their salts, and their solvates, if applicable. A salt, for example, can be formed between an anion and a positively charged group (e.g., amino) on a substituted benzene compound. Suitable anions include chloride, bromide, iodide, sulfate, bisulfate, sulfamate, nitrate, phosphate, citrate, methanesulfonate, trifluoroacetate, glutamate, glucuronate, glutarate, malate, maleate, succinate, fumarate, tartrate, tosylate, salicylate, lactate, naphthalenesulfonate, and acetate (e.g., trifluoroacetate). The term "pharmaceutically acceptable anion" refers to an anion suitable for forming a pharmaceutically acceptable salt. Likewise, a salt can also be formed between a cation and a negatively charged group (e.g., carboxylate) on a substituted benzene compound. Suitable cations include sodium ion, potassium ion, magnesium ion, calcium ion, and an ammonium cation such as tetramethylammonium ion. The substituted benzene compounds also include those salts containing quaternary nitrogen atoms.

Additionally, the compounds of the present invention, for example, the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

"Solvate" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate; and if the solvent is alcohol, the solvate formed is an alcoholate. Hydrates are formed by the combination of one or more molecules of water with one molecule of the substance in which the water retains its molecular state as $H_2O$.

As used herein, the term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar or comparable in function and appearance, but not in structure or origin to the reference compound.

As defined herein, the term "derivative" refers to compounds that have a common core structure, and are substituted with various groups as described herein. For example, all of the compounds represented by Formula (I) are substituted benzene compounds, and have Formula (I) as a common core.

The term "bioisostere" refers to a compound resulting from the exchange of an atom or of a group of atoms with another, broadly similar, atom or group of atoms. The objective of a bioisosteric replacement is to create a new compound with similar biological properties to the parent compound. The bioisosteric replacement may be physicochemically or topologically based. Examples of carboxylic acid bioisosteres include, but are not limited to, acyl sulfonimides, tetrazoles, sulfonates and phosphonates. See, e.g., Patani and LaVoie, *Chem. Rev.* 96, 3147-3176, 1996.

The present invention is intended to include all isotopes of atoms occurring in the present compounds. Isotopes include those atoms having the same atomic number but different mass numbers. By way of general example and without limitation, isotopes of hydrogen include tritium and deuterium, and isotopes of carbon include C-13 and C-14.

The present invention provides methods for the synthesis of the compounds of any of the Formulae described herein. The present invention also provides detailed methods for the synthesis of various disclosed compounds of the present invention according to the following schemes as shown in the Examples.

Throughout the description, where compositions are described as having, including, or comprising specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the invention remains operable. Moreover, two or more steps or actions can be conducted simultaneously.

The synthetic processes of the invention can tolerate a wide variety of functional groups, therefore various substituted starting materials can be used. The processes generally provide the desired final compound at or near the end of the overall process, although it may be desirable in certain instances to further convert the compound to a pharmaceutically acceptable salt thereof.

Compounds of the present invention can be prepared in a variety of ways using commercially available starting materials, compounds known in the literature, or from readily prepared intermediates, by employing standard synthetic methods and procedures either known to those skilled in the art, or which will be apparent to the skilled artisan in light of the teachings herein. Standard synthetic methods and procedures for the preparation of organic molecules and functional group transformations and manipulations can be obtained from the relevant scientific literature or from standard textbooks in the field. Although not limited to any one or several sources, classic texts such as Smith, M. B., March, J., *March's Advanced Organic Chemistry: Reactions, Mechanisms, and Structure*, $5^{th}$ edition, John Wiley & Sons: New York, 2001; Greene, T. W., Wuts, P. G. M., *Protective Groups in Organic Synthesis*, $3^{rd}$ edition, John Wiley & Sons: New York, 1999; R. Larock, *Comprehensive Organic Transformations*, VCH Publishers (1989); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), incorporated by reference herein, are useful and recognized reference textbooks of organic synthesis known to those in the art. The following descriptions of synthetic methods are designed to illustrate, but not to limit, general procedures for the preparation of compounds of the present invention.

Compounds of the present invention can be conveniently prepared by a variety of methods familiar to those skilled in the art or those described in WO 2012/142504, WO 2012/142513 and WO 2012/118812, which are incorporated herein by reference. The compounds of this invention having any of the Formulae described herein may be prepared according to the procedures illustrated in Schemes 1-2 below, from commercially available starting materials or starting materials which can be prepared using literature procedures. The R groups (such as $R_6$, $R_7$, $R_8$, and $R_{12}$) in Schemes 1-2 are as defined in any Formula described herein, unless otherwise specified.

One of ordinary skill in the art will note that, during the reaction sequences and synthetic schemes described herein, the order of certain steps may be changed, such as the introduction and removal of protecting groups.

One of ordinary skill in the art will recognize that certain groups may require protection from the reaction conditions via the use of protecting groups. Protecting groups may also be used to differentiate similar functional groups in molecules. A list of protecting groups and how to introduce and remove these groups can be found in Greene, T. W., Wuts, P. G. M., *Protective Groups in Organic Synthesis*, $3^{rd}$ edition, John Wiley & Sons: New York, 1999.

Preferred protecting groups include, but are not limited to:
For a hydroxyl moiety: TBS, benzyl, THP, Ac
For carboxylic acids: benzyl ester, methyl ester, ethyl ester, allyl ester
For amines: Cbz, BOC, DMB
For diols: Ac (×2) TBS (×2), or when taken together acetonides
For thiols: Ac
For benzimidazoles: SEM, benzyl, PMB, DMB
For aldehydes: di-alkyl acetals such as dimethoxy acetal or diethyl acetyl.

In the reaction schemes described herein, multiple stereoisomers may be produced. When no particular stereoisomer is indicated, it is understood to mean all possible stereoisomers that could be produced from the reaction. A person of ordinary skill in the art will recognize that the reactions can be optimized to give one isomer preferentially, or new schemes may be devised to produce a single isomer. If mixtures are produced, techniques such as preparative thin layer chromatography, preparative HPLC, preparative chiral HPLC, or preparative SFC may be used to separate the isomers.

The following abbreviations are used throughout the specification and are defined below:

AA ammonium acetate
ACN acetonitrile
Ac acetyl
AcOH acetic acid
atm atmosphere
aq. Aqueous
BID or b.i.d. bis in die (twice a day)
tBuOK potassium t-butoxide
Bn benzyl
BOC tert-butoxy carbonyl
BOP (benzotriazol-1-yloxy)tris(dimethylamino)-phosphoniumhexafluorophosphate
Cbz benzyloxy carbonyl
$CDCl_3$ deuterated chloroform
$CH_2Cl_2$ dichloromethane
COMU (1-Cyano-2-ethoxy-2-oxoethylidenaminooxy)di-methyl-amino-morpholino-carbenium hexafluorophosphate
d days
DBU 1,8-diazabicyclo[5.4.0]undec-7-ene
DCE 1,2 dichloroethane
DCM dichloromethane
DEAD Diethyl azodicarboxylate
DIAD Diisopropyl azodicarboxylate
DiBAL-H diisobutyl aluminium hydride
DIPEA N,N-diisopropylethylamine (Hunig's base)
DMA Dimethylacetamide
DMAP N, N dimethyl-4-aminopyridine
DMB 2,4 dimethoxy benzyl
DMF N,N-Dimethylformamide
DMF-DMA N,N-Dimethylformamide dimethyl acetal
DMSO Dimethyl sulfoxide
DPPA Diphenylphosphonic azide
EA or EtOAc Ethyl acetate
EDC or EDCI N-(3-Dimethylaminopropyl)-N'-ethylcarbodiimide
$Et_2O$ diethyl ether
ELS Evaporative Light Scattering
ESI– Electrospray negative mode
ESI+ Electrospray positive mode
$Et_3N$ or TEA triethylamine
EtOH ethanol
FA formic acid
FC or FCC Flash chromatogrpahy
h hours
$H_2O$ water
HATU O-(7-Azabenzotriazol-1-yl)-N,N,N',N'-tetramethyluronium hexafluorophosphate
HOAT 1-Hydroxy-7-azabenzotriazole
HOBt 1-Hydroxybenzotriazole
HO-Su N-Hydroxysuccinimide
HCl hydrogen chloride or hydrochloric acid
HPLC High performance liquid chromatography
$K_2CO_3$ potassium carbonate
KHMDs Potassium hexamethyldisilazide
LC/MS or LC-MS Liquid chromatography mass spectrum
LDA Lithium diisopropylamide
LiHMDs Lithium hexamethyldisilazide
LG leaving group
M Molar
m/z mass/charge ratio
m-CPBA meta-chloroperbenzoic acid
MeCN Acetonitrile
MeOD d4-methanol
Met Methyl iodide
MS3 Å 3 Å molecular sieves
$MgSO_4$ Magnesium Sulfate
min minutes
Ms Mesyl
MsCl Mesyl chloride
MsO Mesylate
MS Mass Spectrum
MWI microwave irradiation
$Na_2CO_3$ sodium carbonate
$Na_2SO_4$ sodium sulfate
$NaHCO_3$ sodium bicarbonate
NaHMDs Sodium hexamethyldisilazide
NaOH sodium hydroxide
$NaHCO_3$ sodium bicarbonate
$Na_2SO_4$ sodium sulfate
NIS N-iodosuccinimide
NMR Nuclear Magnetic Resonance
o/n or O/N overnight
Pd/C Palladium on carbon
$Pd(dppf)Cl_2.DCM$ [1,1'-Bis(diphenylphosphino)fenocene] dichloropalladium(II), complex with dichloromethane
PPAA 1-Propanephosphonic acid cyclic anhydride
$Pd(OH)_2$ Palladium dihydroxide
PE Petroleum Ether
PG protecting group
PMB para methoxybenzyl
ppm parts per million
p.o. per os (oral administration)
prep HPLC preparative High Performance Liquid Chromatography
prep TLC preparative thin layer chromatography
p-TsOH para-toluenesulfonic acid
PyBOP (Benzotriazol-1-yloxy)tripyrrolidinophosphonium Hexafluorophosphate
QD or q.d. quaque die (once a day)
RBF round bottom flask
RP-HPLC Reverse phase High Performance liquid chromatography
Rt or RT Room temperature
SEM (Trimethylsilyl)ethoxymethyl
SEMCl (Trimethylsilyl)ethoxymethyl chloride
SFC Super critical chromatography
SGC silica gel chromatography
STAB Sodium triacetoxy borohydride
TBAF tetra-n-butylammonium fluoride
TBME tert-Butyl methyl ether
TEA Triethylamine
TFA trifluoroacetic acid
TfO triflate
THF tetrahydrofuran
THP tetrahydropyran
TID or t.i.d ter in die (three times a day)
TLC thin layer chromatography
TMSCl Trimethylsilyl chloride
Ts tosyl
TsOH tosic acid
UV ultraviolet

Scheme 1

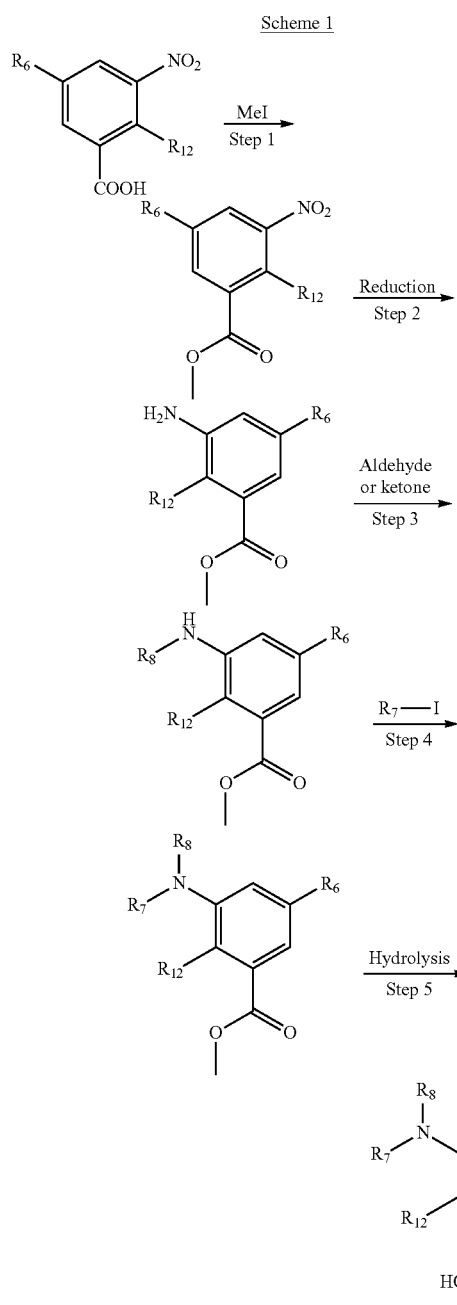

Scheme 1 shows the synthesis of modified aryl analogs following a general route that utilizes well-established chemistry. Substituted nitrobenzoic acids, many of which are commercially available or can be made by nitration of the appropriate substituted benzoic acids or other chemistry known to one skilled in the art, can be converted to their methyl esters by treatment with methyliodide in a polar solvent, such as DMF, in the presence of an appropriate base, such as sodium carbonate, at an appropriate temperature, such as 60° C. (Step 1). The nitro group can be reduced to an amine using an appropriate reducing agent, such as iron, in the presence of an acid, such as ammonium chloride, in a protic solvent, such as ethanol, at an appropriate temperature, such as 80° C. (Step 2). Introduction of the $R_8$ can be done using a reductive amination with an appropriate ketone or aldehyde in the presence of an appropriate reducing agent, such as sodium cyanoborohydride, and catalytic acid, such as acetic acid, in an appropriate solvent, such as methanol. A variety of $R_7$ groups can be introduced by alkylation using $R_7$-LG, where LG is a leaving group, such as iodine, in the presence of a mild base, such as cesium carbonate, in an appropriate polar solvent, such as acetonitrile, at an appropriate temperature, such as 80° C. (Step 4). Alternatively, $R_7$ groups can be introduced by reductive amination with $R_7$-ketone or $R_7$-aldehyde in the presence of an appropriate reducing agent, such as sodium cyanoborohydride, and catalytic acid, such as acetic acid, in an appropriate solvent, such as methanol. The ester moiety can be converted to an amide using a standard two step protocol. The ester can be hydrolyzed to the corresponding acid using a suitable base, such as sodium hydroxide, in a polar solvent, such as ethanol (Step 5).

Scheme 2

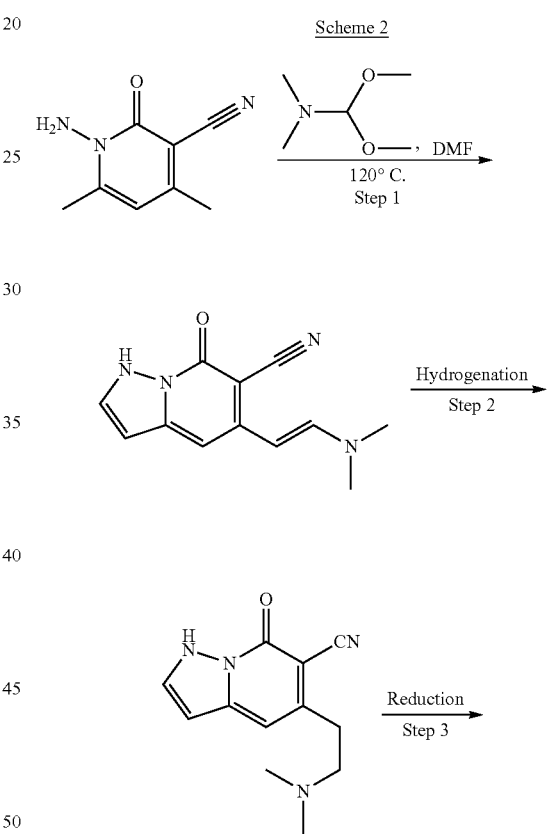

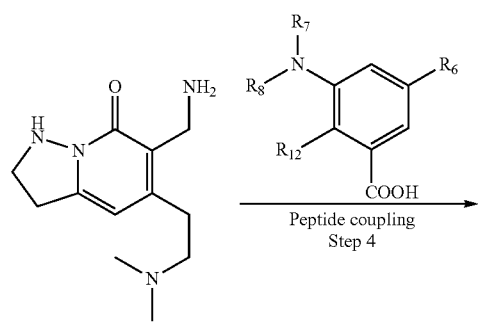

-continued

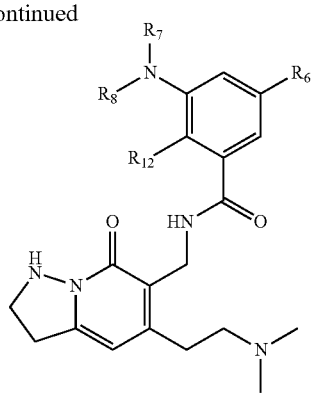

Scheme 2 shows the synthesis of modified tetrahydropyrazolopyridone analogs following a general route that utilizes well-established chemistry. 1-Amino-4,6-dimethyl-2-oxo-1,2-dihydropyridine-3-carbonitrile can be converted to a dihydropyrazolopyridone substituted with a nitrile and an enamine, using DMF-DMA (Step 1) at, e.g., an elevated temperature. The enamine group in the dihydropyrozolopyridone can then be reduced to form an amine via hydrogenation (Step 2). The nitrile group in the dihydropyrozolopyridone can be reduced to an amine using an appropriate reducing agent, such as Raney-Nickel in the presence of hydrogen, in a protic solvent, such as methanol containing ammonia, at an appropriate temperature, such as 22° C. (Step 3). The resulting amine would then be subjected to a standard amide coupling reaction whereupon the appropriate acid (see, e.g., Scheme 1, WO 2012/142504 and WO 2012/142513, which are incorporated herein by reference) would be added along with a suitable amide coupling reagent, such as PyBOP, in a suitable solvent, such as DMSO, to give the desired amide (Step 4). Similarly, other amine compounds (e.g., X—NH$_2$ or X—(CH$_2$)$_2$—NH$_2$), either commercially available or readily synthesized by a skilled chemist, can be coupled with the acid to afford the desired amide having different linkers.

A person of ordinary skill in the art will recognize that in the above schemes the order of many of the steps are interchangeable.

Compounds of the present invention inhibit the histone methyltransferase activity of EZH2 or a mutant thereof and, accordingly, in one aspect of the invention, certain compounds disclosed herein are candidates for treating, or preventing certain conditions and diseases, in which EZH2 plays a role. The present invention provides methods for treating conditions and diseases the course of which can be influenced by modulating the methylation status of histones or other proteins, wherein said methylation status is mediated at least in part by the activity of EZH2. Modulation of the methylation status of histones can in turn influence the level of expression of target genes activated by methylation, and/or target genes suppressed by methylation. The method includes administering to a subject in need of such treatment, a therapeutically effective amount of a compound of the present invention, or a pharmaceutically acceptable salt, polymorph, solvate, or stereoisomeror thereof.

Unless otherwise stated, any description of a method of treatment includes use of the compounds to provide such treatment or prophylaxis as is described herein, as well as use of the compounds to prepare a medicament to treat or prevent such condition. The treatment includes treatment of human or non-human animals including rodents and other disease models.

In still another aspect, this invention relates to a method of modulating the activity of the EZH2, the catalytic subunit of the PRC2 complex which catalyzes the mono- through tri-methylation of lysine 27 on histone H3 (H3-K27) in a subject in need thereof. For example, the method comprises the step of administering to a subject having a cancer expressing a mutant EZH2 a therapeutically effective amount of a compound described herein, wherein the compound(s) inhibits histone methyltransferase activity of EZH2, thereby treating the cancer.

For example, the EZH2-mediated cancer is selected from the group consisting of follicular lymphoma and diffuse large B-cell lymphoma (DLBCL) of germinal center B cell-like (GCB) subtype. For example, the cancer is lymphoma, leukemia or melanoma. Preferably, the lymphoma is non-Hodgkin's lymphoma (NHL), follicular lymphoma or diffuse large B-cell lymphoma. Alternatively, the leukemia is chronic myelogenous leukemia (CML), acute myeloid leukemia, acute lymphocytic leukemia or mixed lineage leukemia.

For example, the EZH2-mediated precancerous condition is myelodysplastic syndromes (MDS, formerly known as preleukemia).

For example, the EZH2-mediated cancer is a hematological cancer.

The compound(s) of the present invention inhibit the histone methyltransferase activity of EZH2 or a mutant thereof and, accordingly, the present invention also provides methods for treating conditions and diseases the course of which can be influenced by modulating the methylation status of histones or other proteins, wherein said methylation status is mediated at least in part by the activity of EZH2. In one aspect of the invention, certain compounds disclosed herein are candidates for treating, or preventing certain conditions and diseases. Modulation of the methylation status of histones can in turn influence the level of expression of target genes activated by methylation, and/or target genes suppressed by methylation. The method includes administering to a subject in need of such treatment, a therapeutically effective amount of a compound of the present invention.

As used herein, a "subject" is interchangeable with a "subject in need thereof", both of which refer to a subject having a disorder in which EZH2-mediated protein methylation plays a part, or a subject having an increased risk of developing such disorder relative to the population at large. A "subject" includes a mammal. The mammal can be e.g., a human or appropriate non-human mammal, such as primate, mouse, rat, dog, cat, cow, horse, goat, camel, sheep or a pig. The subject can also be a bird or fowl. In one embodiment, the mammal is a human. A subject in need thereof can be one who has been previously diagnosed or identified as having cancer or a precancerous condition. A subject in need thereof can also be one who has (e.g., is suffering from) cancer or a precancerous condition. Alternatively, a subject in need thereof can be one who has an increased risk of developing such disorder relative to the population at large (i.e., a subject who is predisposed to developing such disorder relative to the population at large). A subject in need thereof can have a precancerous condition. A subject in need thereof can have refractory or resistant cancer (i.e., cancer that doesn't respond or hasn't yet responded to treatment). The subject may be resistant at start of treatment or may become resistant during treatment. In some embodiments, the subject in need thereof has cancer recurrence following remission on most recent therapy. In some embodiments, the subject in need thereof received and failed all known effective therapies for cancer treatment. In some embodiments, the subject in need thereof received at least one prior therapy. In a preferred embodiment, the subject has cancer or a cancerous condition. For example, the cancer is lymphoma, leukemia, melanoma, or rhabdomyosarcoma. Preferably, the lymphoma is non-Hodgkin's lymphoma, follicular lymphoma or diffuse large B-cell lymphoma. Alternatively, the leukemia is chronic myelogenous leukemia (CML). The precancerous condition is myelodysplastic syndromes (MDS, formerly known as preleukemia).

As used herein, "candidate compound" refers to a compound of the present invention, or a pharmaceutically acceptable salt, polymorph or solvate thereof, that has been or will be tested in one or more in vitro or in vivo biological assays, in order to determine if that compound is likely to elicit a desired biological or medical response in a cell, tissue, system, animal or human that is being sought by a researcher or clinician. A candidate compound is a compound of the present invention, or a pharmaceutically acceptable salt, polymorph or solvate thereof. The biological or medical response can be the treatment of cancer. The biological or medical response can be treatment or prevention of a cell proliferative disorder. The biological response or effect can also include a change in cell proliferation or growth that occurs in vitro or in an animal model, as well as other biological changes that are observable in vitro. In vitro or in vivo biological assays can include, but are not limited to, enzymatic activity assays, electrophoretic mobility shift assays, reporter gene assays, in vitro cell viability assays, and the assays described herein.

For example, an in vitro biological assay that can be used includes the steps of (1) mixing a histone substrate (e.g., an isolated histone sample, an isolated histone peptide representative of human histone H3 residues 21-44 containing either an unmodified lysine 27 (H3K27me0) or dimethylated lysine 27 (H3K27me2), or an isolated oligonucleosome substrate) with recombinant PRC2 enzymes that include a wild type or mutant EZH2 subunit; (2) adding a compound of the invention to this mixture; (3) adding non-radioactive and $^3$H-labeled S-Adenosyl methionine (SAM) to start the reaction; (4) adding excessive amount of non-radioactive SAM to stop the reaction; (4) washing off the free non-incorporated $^3$H-SAM; and (5) detecting the quantity of $^3$H-labeled histone substrate by any methods known in the art (e.g., by a PerkinElmer TopCount platereader).

For example, an in vivo study that can be used includes the steps of (1) administering a compound of the invention into a mouse model (such as WSU-DLCL2 xenograft tumor bearing mouse model or KARPAS-422 human diffused large B-Cell lymphoma mouse xenograft model) at certain level of dosage for certain periods of time, e.g., 7-28 days; (2) sacrificing the mouse and isolating the tumor tissue; (3) measuring the tumor volume and body weight and (4) extracting histone from the tumor tissue for measuring the histone methylation by ELISA.

As used herein, "treating" or "treat" describes the management and care of a patient for the purpose of combating a disease, condition, or disorder and includes the administration of a compound of the present invention, or a pharmaceutically acceptable salt, polymorph or solvate thereof, to alleviate the symptoms or complications of a disease, condition or disorder, or to eliminate the disease, condition or disorder. The term "treat" can also include treatment of a cell in vitro or an animal model.

A compound of the present invention, or a pharmaceutically acceptable salt, polymorph or solvate thereof, can or may also be used to prevent a relevant disease, condition or disorder, or used to identify suitable candidates for such purposes. As used herein, "preventing," "prevent," or "protecting against" describes reducing or eliminating the onset of the symptoms or complications of such disease, condition or disorder.

Point mutations of the EZH2 gene at a single amino acid residue (e.g., Y641, A677, and A687) of EZH2 have been reported to be linked to lymphoma. More examples of EZH2 mutants and methods of treatment are described in U.S. Patent Application Publication No. US 2013-0040906, the entire content of which is incorporated herein by reference in its entirety.

One skilled in the art may refer to general reference texts for detailed descriptions of known techniques discussed herein or equivalent techniques. These texts include Ausubel et al., *Current Protocols in Molecular Biology*, John Wiley and Sons, Inc. (2005); Sambrook et al., *Molecular Cloning, A Laboratory Manual* ($3^{rd}$ edition), Cold Spring Harbor Press, Cold Spring Harbor, N.Y. (2000); Coligan et al., *Current Protocols in Immunology*, John Wiley & Sons, N.Y.; Enna et al., *Current Protocols in Pharmacology*, John Wiley & Sons, N.Y.; Fingl et al., *The Pharmacological Basis of Therapeutics* (1975), Remington's Pharmaceutical Sciences, Mack Publishing Co., Easton, Pa., $18^{th}$ edition (1990). These texts can, of course, also be referred to in making or using an aspect of the invention.

As used herein, "combination therapy" or "co-therapy" includes the administration of a compound of the present invention, or a pharmaceutically acceptable salt, polymorph or solvate thereof, and at least a second agent as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents.

The present invention also provides pharmaceutical compositions comprising a compound of any of the Formulae described herein in combination with at least one pharmaceutically acceptable excipient or carrier.

A "pharmaceutical composition" is a formulation containing the compounds of the present invention in a form suitable for administration to a subject. In one embodiment, the pharmaceutical composition is in bulk or in unit dosage form. The unit dosage form is any of a variety of forms, including, for example, a capsule, an IV bag, a tablet, a single pump on an aerosol inhaler or a vial. The quantity of active ingredient (e.g., a formulation of the disclosed compound or salt, hydrate, solvate or isomer thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this invention include powders, sprays, ointments, pastes, creams, lotions, gels, solutions, patches and inhalants. In one embodiment, the active compound is mixed under sterile conditions with a pharmaceutically acceptable carrier, and with any preservatives, buffers, or propellants that are required.

As used herein, the phrase "pharmaceutically acceptable" refers to those compounds, anions, cations, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

A compound or pharmaceutical composition of the invention can be administered to a subject in many of the well-known methods currently used for chemotherapeutic treatment. For example, for treatment of cancers, a compound of the invention may be injected directly into tumors, injected into the blood stream or body cavities or taken orally or applied through the skin with patches. The dose chosen should be sufficient to constitute effective treatment but not so high as to cause unacceptable side effects. The state of the disease condition (e.g., cancer, precancer, and the like) and the health of the patient should preferably be closely monitored during and for a reasonable period after treatment.

The term "therapeutically effective amount", as used herein, refers to an amount of a pharmaceutical agent to treat, ameliorate, or prevent an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician. In a preferred aspect, the disease or condition to be treated is cancer. In another aspect, the disease or condition to be treated is a cell proliferative disorder.

For any compound, the therapeutically effective amount can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Pharmaceutical compositions that exhibit large therapeutic indices are preferred. The dosage may vary within this range depending upon the dosage form employed, sensitivity of the patient, and the route of administration.

Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

The pharmaceutical compositions containing active compounds of the present invention may be manufactured in a manner that is generally known, e.g., by means of conventional mixing, dissolving, granulating, dragee-making, levigating, emulsifying, encapsulating, entrapping, or lyophilizing processes. Pharmaceutical compositions may be formulated in a conventional manner using one or more pharmaceutically acceptable carriers comprising excipients and/or auxiliaries that facilitate processing of the active compounds into preparations that can be used pharmaceutically. Of course, the appropriate formulation is dependent upon the route of administration chosen.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol and sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible pharmaceutically acceptable carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The active compounds can be prepared with pharmaceutically acceptable carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved.

In therapeutic applications, the dosages of the pharmaceutical compositions used in accordance with the invention vary depending on the agent, the age, weight, and clinical condition of the recipient patient, and the experience and judgment of the clinician or practitioner administering the therapy, among other factors affecting the selected dosage. Generally, the dose should be sufficient to result in slowing, and preferably regressing, the growth of the tumors and also preferably causing complete regression of the cancer. Dosages can range from about 0.01 mg/kg per day to about 5000 mg/kg per day. In preferred aspects, dosages can range from about 1 mg/kg per day to about 1000 mg/kg per day. In an aspect, the dose will be in the range of about 0.1 mg/day to about 50 g/day; about 0.1 mg/day to about 25 g/day; about 0.1 mg/day to about 10 g/day; about 0.1 mg to about 3 g/day; or about 0.1 mg to about 1 g/day, in single, divided, or continuous doses (which dose may be adjusted for the patient's weight in kg, body surface area in $m^2$, and age in years). An effective amount of a pharmaceutical agent is that which provides an objectively identifiable improvement as noted by the clinician or other qualified observer. For example, regression of a tumor in a patient may be measured with reference to the diameter of a tumor. Decrease in the diameter of a tumor indicates regression. Regression is also indicated by failure of tumors to reoccur after treatment has stopped. As used herein, the term "dosage effective manner" refers to amount of an active compound to produce the desired biological effect in a subject or cell.

The pharmaceutical compositions can be included in a container, pack, or dispenser together with instructions for administration.

The compounds of the present invention are capable of further forming salts. All of these forms are also contemplated within the scope of the claimed invention.

As used herein, "pharmaceutically acceptable salts" refer to derivatives of the compounds of the present invention wherein the parent compound is modified by making acid or base salts thereof. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, 1,2-ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, toluene sulfonic, and the commonly occurring amine acids, e.g., glycine, alanine, phenylalanine, arginine, etc.

Other examples of pharmaceutically acceptable salts include hexanoic acid, cyclopentane propionic acid, pyruvic acid, malonic acid, 3-(4-hydroxybenzoyl)benzoic acid, cinnamic acid, 4-chlorobenzenesulfonic acid, 2-naphthalenesulfonic acid, 4-toluenesulfonic acid, camphorsulfonic acid, 4-methylbicyclo-[2.2.2]-oct-2-ene-1-carboxylic acid, 3-phenylpropionic acid, trimethylacetic acid, tertiary butylacetic acid, muconic acid, and the like. The present invention also encompasses salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like. In the salt form, it is understood that the ratio of the compound to the cation or anion of the salt can be 1:1, or any ration other than 1:1, e.g., 3:1, 2:1, 1:2, or 1:3.

It should be understood that all references to pharmaceutically acceptable salts include solvent addition forms (solvates) or crystal forms (polymorphs) as defined herein, of the same salt.

The compounds of the present invention can also be prepared as esters, for example, pharmaceutically acceptable esters. For example, a carboxylic acid function group in a compound can be converted to its corresponding ester, e.g., a methyl, ethyl or other ester. Also, an alcohol group in a compound can be converted to its corresponding ester, e.g., acetate, propionate or other ester.

The compounds, or pharmaceutically acceptable salts thereof, are administered orally, nasally, transdermally, pulmonary, inhalationally, buccally, sublingually, intraperintoneally, subcutaneously, intramuscularly, intravenously, rectally, intrapleurally, intrathecally and parenterally. In one embodiment, the compound is administered orally. One skilled in the art will recognize the advantages of certain routes of administration.

The dosage regimen utilizing the compounds is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Techniques for formulation and administration of the disclosed compounds of the invention can be found in *Remington: the Science and Practice of Pharmacy*, 19$^{th}$ edition, Mack Publishing Co., Easton, Pa. (1995). In an embodiment, the compounds described herein, and the pharmaceutically acceptable salts thereof, are used in pharmaceutical preparations in combination with a pharmaceutically acceptable carrier or diluent. Suitable pharmaceutically acceptable carriers include inert solid fillers or diluents and sterile aqueous or organic solutions. The compounds will be present in such pharmaceutical compositions in amounts sufficient to provide the desired dosage amount in the range described herein.

All percentages and ratios used herein, unless otherwise indicated, are by weight. Other features and advantages of the present invention are apparent from the different examples. The provided examples illustrate different components and methodology useful in practicing the present invention. The examples do not limit the claimed invention. Based on the present disclosure the skilled artisan can identify and employ other components and methodology useful for practicing the present invention.

In the synthetic schemes described herein, compounds may be drawn with one particular configuration for simplicity. Such particular configurations are not to be construed as limiting the invention to one or another isomer, tautomer, regioisomer or stereoisomer, nor does it exclude mixtures of isomers, tautomers, regioisomers or stereoisomers; however, it will be understood that a given isomer, tautomer, regioisomer or stereoisomer may have a higher level of activity than another isomer, tautomer, regioisomer or stereoisomer.

Compounds designed, selected and/or optimized by methods described above, once produced, can be characterized using a variety of assays known to those skilled in the art to determine whether the compounds have biological activity. For example, the molecules can be characterized by conventional assays, including but not limited to those assays described below, to determine whether they have a predicted activity, binding activity and/or binding specificity.

Furthermore, high-throughput screening can be used to speed up analysis using such assays. As a result, it can be possible to rapidly screen the molecules described herein for activity, using techniques known in the art. General methodologies for performing high-throughput screening are described, for example, in Devlin (1998) *High Throughput Screening*, Marcel Dekker; and U.S. Pat. No. 5,763,263. High-throughput assays can use one or more different assay techniques including, but not limited to, those described below.

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow.

Example 1: Syntheses of Certain Compounds in Tables 1 and 2

Compound 1: 5-chloro-3-(((trans)-4-(dimethylamino)cyclohexyl)(ethyl)amino)-N-((5-(2-(dimethylamino)ethyl)-7-oxo-1,2,3,7-tetrahydropyrazolo[1,5-a]pyridin-6-yl)methyl)-2-methylbenzamide

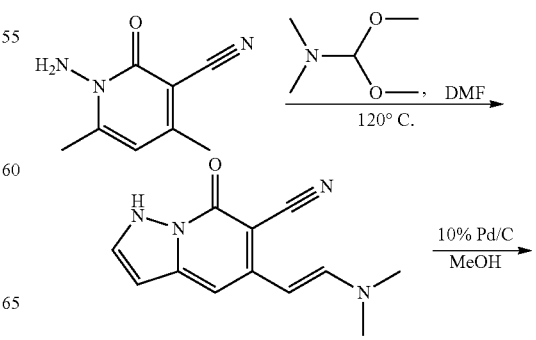

-continued

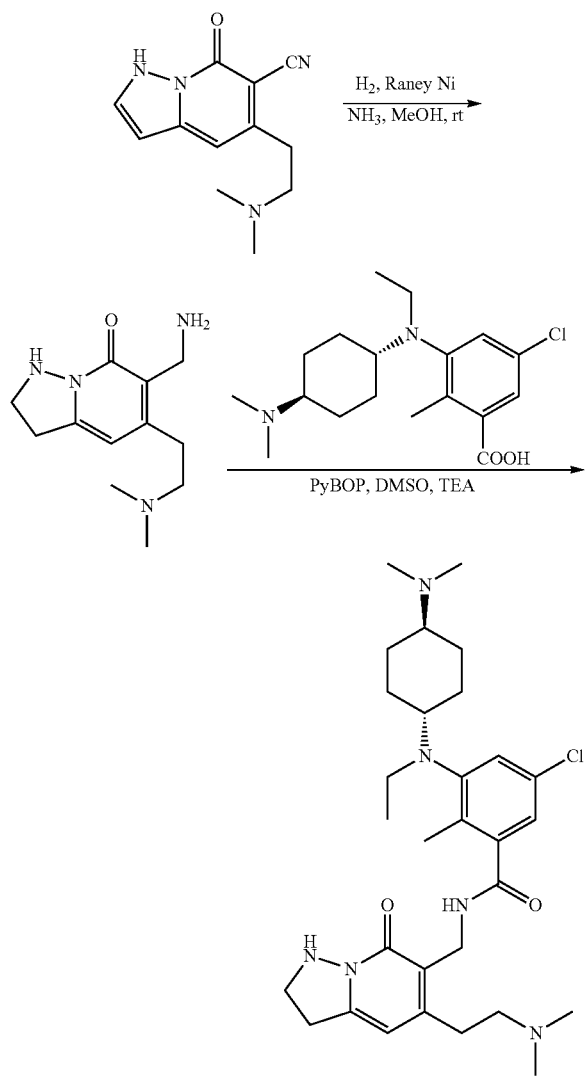

Synthesis of (E)-5-(2-(dimethylamino)vinyl)-7-oxo-1,7-dihydropyrazolo-[1,5-a]-pyridine-6-carbonitrile To a stirred solution of 1-amino-4,6-dimethyl-2-oxo-1,2-dihydropyridine-3-carbonitrile (1 g, 6.09 mmol) in DMF (10 mL), DMF-DMA (7.26 g, 60.97 mmol) was added. The resulting reaction mixture was stirred at 120° C. for 14 h. The progress of the reaction was monitored by TLC. After completion of reaction, the reaction mixture was quenched with water and extracted with 10% MeOH/DCM. The organic layer was separated, washed with brine, dried using $Na_2SO_4$ and concentrated under reduced pressure to give crude compound which was purified by silica gel column chromatography (100-200 mesh) to afford the title compound as light brown solid (0.8 g, 57.6% yield).

$^1$H NMR (DMSO-$d_6$, 400 MHz) δ 7.66 (s, 1H), 7.59-7.50 (m, 2H), 6.41 (s, 1H), 5.14 (d, 1H, J=14 Hz), 4.94 (d, 1H, J=13.6 Hz), 2.93 (s, 6H).

Synthesis of 5-(2-(dimethylamino)ethyl)-7-oxo-1,7-dihydropyrazolo-[1,5-a]-pyridine-6-carbonitrile To a stirred solution of (E)-5-(2-(dimethylamino)vinyl)-7-oxo-1,7-dihydropyrazolo-[1,5-a]-pyridine-6-carbonitrile (0.3 g, 1.31 mmol) in methanol (5 mL), a catalytic amount of 10% Pd/C was added. The reaction mixture was stirred at room temperature under hydrogen (1 atm) for 5 h. On completion of reaction, the reaction mixture was filtered through celite, washed with methanol and the filtrate was concentrated under reduced pressure to afford crude title compound as light yellow thick liquid (0.26 g, 86.1% yield) which was used in the subsequent step without further purification.

Synthesis of 6-(aminomethyl)-5-(2-(dimethylamino)ethyl)-2,3-dihydropyrazolo[1,5-a]pyridin-7(1H)-one To a stirred solution of 5-(2-(dimethylamino)ethyl)-7-oxo-1,7-dihydropyrazolo-[1,5-a]-pyridine-6-carbonitrile (0.26 g, 1.12 mmol) in methanol (5 mL), a catalytic amount of Raney Nickel and ammonia solution (2 mL) were added. The reaction mixture was stirred at room temperature under hydrogen (1 atm) for 12 h. On completion of reaction, the reaction mixture was filtered through celite, washed with methanol and filtrate was concentrated under reduced pressure to afford crude title compound as light yellow thick liquid (0.17 g, 63.9% yield) which was used in the subsequent step without further purification.

Synthesis of 5-chloro-3-(((trans)-4-(dimethylamino)cyclohexyl)(ethyl)amino)-N-((5-(2-(dimethylamino)ethyl)-7-oxo-1,2,3,7-tetrahydropyrazolo[1,5-a]pyridin-6-yl)methyl)-2-methylbenzamide (Compound 1)

To a stirred solution of 6-(aminomethyl)-5-(2-(dimethylamino)ethyl)-2,3-dihydropyrazolo[1,5-a]pyridin-7(1H)-one (0.17 g, 0.720 mmol) and 5-chloro-3-(((trans)-4-(dimethylamino)cyclohexyl)(ethyl)amino)-2-methylbenzoic acid (0.2 g, 0.591 mmol) in DMSO (2 mL), triethyl amine (0.22 g, 2.17 mmol) was added. The reaction mixture was stirred at room temperature for 15 min before PyBOP (0.56 g, 1.07 mmol) was added at 0° C. and stirring was continued for overnight at room temperature. The progress of the reaction was monitored by TLC. After completion of the reaction, reaction mixture was poured on ice cold water and extracted with 10% MeOH/DCM. The organic layer was separated, washed with brine, dried using $Na_2SO_4$ and concentrated under reduced pressure to give crude compound which was purified by prep.HPLC to afford pure title compound as colorless thick liquid (0.04 g, 10% yield).

Analytical Data:

LCMS: 557.45 (M+1)$^+$; HPLC: 98.94% (@ 210 nm-400 nm); $^1$H NMR (DMSO-$d_6$, 400 MHz) δ 7.18-7.14 (m, 2H), 6.98-6.92 (m, 2H), 5.94 (s, 1H), 4.30 (d, 2H, J=4.8 Hz), 3.45 (t, 2H, J=6.8 Hz), 3.03-2.93 (m, 2H), 2.16-2.14 (m, 12H), 2.07 (s, 3H), 1.88-1.77 (m, 6H), 1.38-1.32 (m, 4H), 1.21-1.08 (m, 4H), 0.79 (t, 3H, J=6.8 Hz), 2H merged in solvent peak.

Compound 2: 5-chloro-3-(ethyl((trans)-4-(dimethyl-amino)cyclohexyl)amino)-2-methyl-N-((5-methyl-7-oxo-1H,7H-pyrazolo[1,5-a]pyridin-6-yl)methyl)benzamide

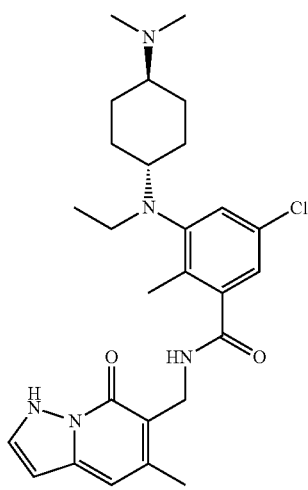

Step 1: Synthesis of (4Z)-5-hydroxy-1,1-dimethoxyhex-4-en-3-one

A 2-neck RBF was charged with dry diethyl ether (20 mL) and treated with the portion wise addition of sodium hydride (60% dispersion in mineral oil, 1.65 g, 41.3 mmol). The resulting suspension was cooled to 5° C. in an ice bath and treated with a mixture of dry propan-2-one (2.53 mL, 34.4 mmol) in diethyl ether (5 mL) over 30 min. The resulting suspension was stirred at 5° C. for 1 h and 10 min and then treated with methyl 3,3-dimethoxypropanoate (4.88 mL, 34.4 mmol) in diethyl ether (10 mL) dropwise over 15 min. Once addition was complete, the reaction mixture was stirred at 5° C. for 25 min and then left to reach room temperature and stirred overnight. The reaction mixture was treated with water (20 mL) and the pH adjusted to pH 6 by the drop wise addition of 2N $H_2SO_4$ (aq. 8 mL). The layers were separated and the aqueous phase was extracted with ether (3×30 mL), the combined ether extracts were dried over $Na_2SO_4$, filtered and concentrated in vacuo. The residue was purified by Kugelrohr distillation (98-160° C.) over 3 h to afford the title compound as a very pale yellow mobile oil (2.16 g, 26% yield), which was used without further purification in the next step. LC-MS showed no ionisation observed under ES+ or ES−. $^1$H NMR (500 MHz, Chloroform-d) δ 15.41 (d, J=7.4 Hz, 1H), 5.53 (s, 1H), 4.77 (t, J=5.7 Hz, 1H), 3.36 (s, 6H), 2.59 (d, J=5.8 Hz, 2H), 2.06 (s, 3H). Contains 72:28 ratio of product to impurity.

Step 2: Synthesis of 1-amino-6-(2,2-dimethoxy-ethyl)-4-methyl-2-oxo-1,2-dihydropyridine-3-carbonitrile A stirred suspension of 2-cyanoacetohydrazide (2.69 g, 27.1 mmol) in EtOH (40 mL), was treated with (4Z)-5-hydroxy-1,1-dimethoxyhex-4-en-3-one (60%, 5.21 g, 18.0 mmol), followed by N-ethylethanamine (2.8 mL, 27.1 mmol). The resulting suspension was heated under reflux for 6 h, after which time, the heat was removed and the reaction mixture was left to reach room temperature and stand at room temperature over the weekend. The solvent was removed in vacuo and the crude semi solid recrystallised from EtOH (20 mL) to afford the title compound as an off white solid (1.75 g, 33% yield). LC-MS 96%, 1.31 min (3 minute LC-MS method), m/z=237.95, $^1$H NMR (500 MHz, DMSO-d6) δ 6.32 (s, 1H), 6.00 (s, 2H), 4.85 (t, J=5.5 Hz, 1H), 3.27 (s, 6H), 3.09 (d, J=5.5 Hz, 2H), 2.33 (s, 3H).

Step 3: Synthesis of 5-methyl-7-oxo-1H,7H-pyrazolo[1,5-a]pyridine-6-carbonitrile hydrochloride 1-amino-6-(2,2-dimethoxyethyl)-4-methyl-2-oxo-1,2-dihydropyridine-3-carbonitrile (1.74 g, 7.33 mmol) was suspended in a mixture of THF (10 mL) and 2M HCl (aq. 5 mL) and the resulting yellow suspension was stirred at room temperature for 18.5 hours. After which time, the solid was collected by filtration and washed with a little of the mother liquor and then dried in vacuo at 40° C. to afford the title compound as a white powder (1.19 g, 77%). LC-MS 99%, 1.26 min (3.5 minute LC-MS method), m/z=173.90, $^1$H NMR (500 MHz, DMSO-d6) δ 8.35 (d, J=3.0 Hz, 1H), 6.61 (d, J=3.0 Hz, 1H), 6.50 (s, 1H), 2.32 (s, 3H).

Step 4: Synthesis of 5-methyl-7-oxo-1-((2-(trimethylsilyl)ethoxy)methyl)-1H,7H-pyrazolo[1,5-a]pyridine-6-carbonitrile To a stirred solution of 5-methyl-7-oxo-1H,7H-pyrazolo[1,5-a]pyridine-6-carbonitrile hydrochloride (500 mg, 2.39 mmol) in DCM (5 mL), was added (2-(chloromethoxy)ethyl)(trimethyl)silane (464 µL, 2.62 mmol), followed by N-ethyl-N-(propan-2-yl)propan-2-amine (623 µL, 3.58 mmol). The resulting solution was flushed with nitrogen, stirred at room temperature over the weekend. The reaction mixture was treated with (2-(chloromethoxy)ethyl)(trimethyl)silane (100 µL, 0.57 mmol) and N-ethyl-N-(propan-2-yl)propan-2-amine (120 µL, 0.69 mmol) and DCM (2 mL) and stirred for a further 3 h at rt, the white suspension was poured into a saturated aqueous solution of $NaHCO_3$ (aq. 30 mL) and extracted with DCM (4×20 mL), the combined organic phases were washed with brine (20 mL), dried over $MgSO_4$, filtered and concentrated in vacuo. The residue was pre-absorbed onto silica and purified by FCC (0-100% EtOAc/heptanes), 25 g SNAP cartridge on the Biotage Isolera, to afford the title compound as an off white solid (755 mg, quant). LC-MS 100%, 2.00 min (3 minute LC-MS method), m/z=303.95, 1H NMR (500 MHz, Methanol-d4) δ 8.29 (d, J=3.5 Hz, 1H), 6.65 (d, J=3.5 Hz, 1H), 6.61 (s, 1H), 6.19 (s, 2H), 3.61-3.45 (m, 2H), 2.52-2.34 (m, 3H), 0.88-0.65 (m, 2H), −0.10 (s, 9H).

Step 5: Synthesis of 6-(aminomethyl)-5-methyl-1-((2-(trimethylsilyl)ethoxy)methyl)-1H,7H-pyrazolo[1,5-a]pyridin-7-one A solution of 5-methyl-7-oxo-1-((2-(trimethylsilyl)ethoxy)methyl)-1H,7H-pyrazolo[1,5-a]pyridine-6-carbonitrile (300 mg, 0.99 mmol) in 2M $NH_3$/MeOH (25 mL), was passed through the H-Cube at 50 bar and 50° C., 1 mL/min using a Raney Nickel cartridge. The resulting solution was concentrated in vacuo to afford the title compound as a yellow glassy solid (277 mg, 38% yield), which was used directly in the next step without any purification. LC-MS 51%, 1.45 min (3 minute LC-MS method), m/z=291.00 (M+H—NH2).

Step 6: Synthesis of 5-chloro-3-(ethyl((trans)-4-(dimethylamino)cyclohexyl)amino)-2-methyl-N-((5-methyl-7-oxo-1-((2-(trimethylsilyl)ethoxy)methyl)-1H,7H-pyrazolo[1,5-a]pyridin-6-yl)methyl)benzamide A stirred solution of 5-chloro-3-(ethyl((trans)-4-(dimethylamino)cyclohexyl)amino)-2-methylbenzoic acid (170 mg, 0.5 mmol) in DMF (2 mL) under a balloon of $N_2$, was treated with HATU (229 mg, 0.6 mmol) and DIPEA (175 µL, 1 mmol), the resulting solution was stirred for 10 min and then added to a pre-cooled flask containing 6-(aminomethyl)-5-methyl-1-((2-(trimethylsilyl)ethoxy)methyl)-1H,7H-pyrazolo[1,5-a]pyridin-7-one (42%, 260 mg, 0.35 mmol) (along with 2 mL of DMF washings). The resulting suspension was stirred at 0° C. for 1 h and 20 min and then at rt overnight. After which time, the reaction mixture was treated with water until a solid precipitated out of solution, the solid was collected by filtration and dried in vacuo. The crude material was purified by FCC (0-100% [90:9:1 DCM:MeOH:$NH_4OH$]/DCM) on the Biotage Isolera, 25 g SNAP cartridge, to afford the title compound as a yellow solid (120 mg, 38% yield). LC-MS 100%, 1.84 min (3 min LC-MS method), m/z=628.15, $^1$H NMR (250 MHz, Methanol-d4) δ 7.97 (d, J=3.7 Hz, 1H), 7.19 (d, J=2.1 Hz, 1H), 7.06 (d, J=2.1 Hz, 1H), 6.57 (s, 1H), 6.51 (d, J=3.7 Hz, 1H), 6.10 (s, 2H), 4.62 (s, 2H), 3.54-3.40 (m, 2H), 3.08 (q, J=7.2 Hz, 2H), 2.86-2.68 (m, 2H), 2.59 (s, 6H), 2.50 (s, 3H), 2.25 (s, 3H), 1.99 (t, J=12.3 Hz, 4H), 1.60-1.26 (m, 4H), 0.85 (t, J=7.0 Hz, 3H), 0.77-0.66 (m, 2H), −0.15 (s, 9H).

Step 7: Synthesis of 5-chloro-3-(ethyl((trans)-4-(dimethylamino)cyclohexyl)amino)-2-methyl-N-((5-methyl-7-oxo-1H,7H-pyrazolo[1,5-a]pyridin-6-yl)methyl)benzamide In a screw top vial was placed 5-chloro-3-(ethyl((trans)-4-(dimethylamino)cyclohexyl) amino)-2-methyl-N-((5-methyl-7-oxo-1-((2-(trimethylsilyl)ethoxy)methyl)-1H,7H-pyrazolo[1,5-a]pyridin-6-yl)methyl)benzamide (25 mg, 0.04 mmol) and methanol (1 mL), followed by pyridinium 4-methylbenzenesulfonate (299 mg, 1.19 mmol). The reaction was stirred at room temperature over 48 h and then treated with a further pyridinium 4-methylbenzenesulfonate (199 mg, 0.8 mmol, 20 equiv.). The reaction mixture was stirred at room temperature for a further 48 h, after which time, the reaction was stopped and the solvent removed under a stream of nitrogen. The crude material was purified by basic preparative HPLC to afford the title compound as a grey solid (5.7 mg, 26%).

Analytical Data:

LC-MS 91%, 1.48 min (3 minute LC-MS method), m/z=499.10, $^1$H NMR (500 MHz, Methanol-d4) δ 7.17 (d, J=2.0 Hz, 1H), 7.07 (d, J=2.0 Hz, 1H), 4.67 (s, 2H), 3.06 (q, J=7.1 Hz, 2H), 2.99 (t, J=11.4 Hz, 1H), 2.79-2.72 (m, 1H), 2.70 (s, 6H), 2.38 (s, 3H), 2.24 (s, 3H), 2.03 (d, J=12.5 Hz, 2H), 1.98-1.88 (m, 2H), 1.45 (tt, J=23.5, 10.8 Hz, 4H), 0.85 (t, J=7.0 Hz, 3H). (Note: 3 aromatic protons missing but they are present in $d_6$-acetone spectrum).

Compound 8: 5-chloro-3-(((trans)-4-(dimethylamino)cyclohexyl)(ethyl)amino)-2-methyl-N-((5-methyl-7-oxo-1,7-dihydropyrazolo[1,5-a]pyrimidin-6-yl)methyl)benzamide

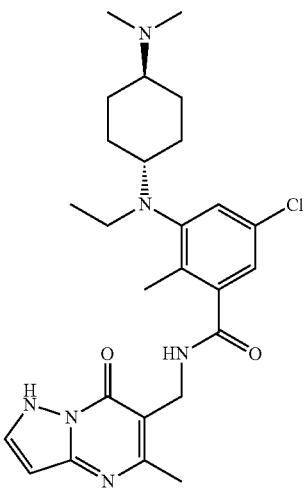 [SMILES: CCN(c1cc(Cl)cc(C(=O)NCc2c(C)nc3cc[nH]n3c2=O)c1C)[C@H]1CC[C@H](N(C)C)CC1]

Step 1: Synthesis of (E)-ethyl 2-cyano-3-ethoxybut-2-enoate

A mixture of ethyl 2-cyanoacetate (10 g, 88.40 mmol) and compound 1 (28.68 g, 176.80 mmol) in acetic acid (2.65 g, 44.20 mmol) was heated at 1300 C for 16 h. After completion of the reaction, reaction mixture was concentrated to dryness to afford crude compound 2 (8 g, 49.47%) which was used as such for next step.

Step 2: Synthesis of 5-methyl-7-oxo-1,7-dihydropyrazolo [1,5-a] pyrimidine-6-carbonitrile A mixture of (E)-ethyl 2-cyano-3-ethoxybut-2-enoate (2 g, 10.92 mmol) and 1H-pyrazol-3-amine (0.907 g, 10.92 mmol) in acetic acid (10 mL) was heated at 80° C. for 16 h. After completion of the reaction, reaction mixture was concentrated to dryness. The residue obtained was diluted with water and extracted with 10% MeOH/DCM. The combined organic layers were dried over anhydrous sodium sulphate and concentrated under reduced pressure to afford compound 3 (1 g, 52.63%).

Step 3: Synthesis of 6-(amino methyl)-5-methyl-pyrazolo [1,5-a] pyrimidin-7(1H)-one To a solution of 5-methyl-7-oxo-1,7-dihydropyrazolo [1,5-a] pyrimidine-6-carbonitrile (0.5 g, 2.87 mmol) in methanol (5 mL), catalytic amount of Raney Nickel and ammonia solution (2 mL) were added. Reaction mass was stirred at room temperature under hydrogen pressure (balloon pressure) for 24 h. On completion of reaction, reaction mass was filtered through celite bed, celite bed washed with methanol and filtrate was concentrated under reduced pressure to afford crude compound 4 (0.3 g) which was used as such for next step without further purification.

Step 4: Synthesis of 5-chloro-3-(((trans)-4-(dimethylamino)cyclohexyl)(ethyl)amino)-2-methyl-N-((5-methyl-7-oxo-1,7-dihydropyrazolo[1,5-a]pyrimidin-6-yl)methyl)benzamide (2646)

To a stirred solution of 5-chloro-3-(ethyl((trans)-4-(dimethylamino)cyclohexyl)amino)-2-methylbenzoic acid (0.25 g, 0.739 mmol) in DMSO (2 mL), 6-(amino methyl)-5-methylpyrazolo [1,5-a] pyrimidin-7(1H)-one (0.263 g, 1.47 mmol) and triethylamine (0.3 mL, 2.21 mmol) were added. The reaction mixture was stirred at room temperature for 15 min before PyBOP (0.576 g, 1.10 mmol) was added to it and stirring was continued for overnight. After completion of the reaction, reaction mass was poured into ice, extracted with 10% MeOH/DCM. Combined organic layers were dried, concentrated to obtain crude; which then purified by prep. HPLC to afford the title compound (0.06 g, 16.3%).

Analytical Data of the TFA Salt:

LCMS: 499.45 (M+1); $^1$H NMR (400 MHz, DMSO-d6) δ 12.34 (s, 1H), 9.47 (s, 1H), 8.36 (t, J=4.8 Hz, 1H), 7.84 (d, J=1.9 Hz, 1H), 7.20 (d, J=2.3 Hz, 1H), 7.00 (d, J=2.1 Hz, 1H), 6.10 (d, J=2.0 Hz, 1H), 4.32 (d, J=4.7 Hz, 2H), 3.11 (s, 1H), 3.02 (q, J=6.9 Hz, 2H), 2.68 (d, J=4.9 Hz, 7H), 2.45 (s, 3H), 2.16 (s, 3H), 1.95 (s, 2H), 1.83 (d, J=7.4 Hz, 2H), 1.42 (t, J=9.6 Hz, 4H), 0.78 (t, J=6.9 Hz, 3H).

Compound 9: 5-chloro-N-((2,7-dimethyl-5-oxo-3,5-dihydro-[1,2,4]triazolo[1,5-a]pyridin-6-yl)methyl)-3-(((trans)-4-(dimethylamino)cyclohexyl)(ethyl)amino)-2-methylbenzamide

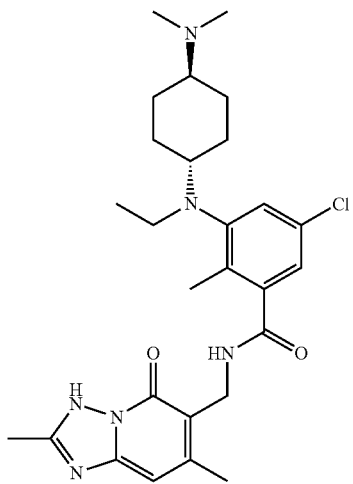 [SMILES: CCN(c1cc(Cl)cc(C(=O)NCc2c(C)cc3nc(C)[nH]n3c2=O)c1C)[C@H]1CC[C@H](N(C)C)CC1]

Step 1: Synthesis of N'-acetyl-2-cyanoacetohydrazide

To a stirred solution of 2-cyanoacetohydrazide (1.2 g, 12.12 mmol) in THF (15 mL), triethylamine (1.7 mL, 12.12 mmol) was added and the solution was stirred at rt for 10 min. Then acetic anhydride (1.24 g, 12.12 mmol) was added and the reaction mixture was stirred at 60° C. for 12 h. After completion of the reaction, the reaction mixture was filtered and solid obtained was washed with diethyl ether; pentane and dried under reduced pressure to afford the title compound (0.6 g, 35.3%).

Step 2: Synthesis of 2,7-dimethyl-5-oxo-3,5-dihydro-[1,2,4]triazolo[1,5-a]pyridine-6-carbonitrile To a stirred solution of N'-acetyl-2-cyanoacetohydrazide (0.6 g, 4.25 mmol) in chlorobenzene (15 mL), (Z)-3-aminobut-2-enenitrile (0.349 g, 4.25 mmol) and acetic anhydride (2 mL) were added and reaction was stirred at 80° C. for 12 h. After completion of the reaction, reaction mixture was filtered and solid obtained was washed with diethyl ether; pentane and dried under reduced pressure to afford the title compound (0.3 g, 37.5%).

Step 3: Synthesis of 6-(aminomethyl)-2,7-dimethyl-[1,2,4]triazolo[1,5-a]pyridin-5(3H)-one To a solution of 2,7-dimethyl-5-oxo-3,5-dihydro-[1,2,4]triazolo[1,5-a]pyridine-6-carbonitrile (0.3 g, 1.59 mmol) in methanol (3 mL), catalytic amount of Raney Nickel and ammonia solution (1 mL) were added. Reaction mass was stirred at room temperature under hydrogen pressure (balloon pressure) for 3 days. On completion of reaction, reaction mass was filtered through celite bed, celite bed washed with methanol and filtrate was concentrated under reduced pressure to afford crude compound 4 (0.1 g) which was used as such for next step without further purification.

Synthesis of 5-chloro-N-((2,7-dimethyl-5-oxo-3,5-dihydro-[1,2,4]triazolo[1,5-a]pyridin-6-yl)methyl)-3-(((trans)-4-(dimethylamino)cyclohexyl)(ethyl)amino)-2-methylbenzamide (2647)

To a stirred solution of 5-chloro-3-(ethyl((trans)-4-(dimethylamino)cyclohexyl)amino)-2-methylbenzoic acid (0.1 g, 0.295 mmol) in DMSO (1 mL), 6-(aminomethyl)-2,7-dimethyl-[1,2,4]triazolo[1,5-a]pyridin-5(3H)-one (0.057 g, 0.295 mmol) and triethylamine (0.12 mL, 0.887 mmol) were added. The reaction mixture was stirred at room temperature for 15 min before PyBOP (0.23 g, 0.443 mmol) was added to it and stirring was continued for overnight. After completion of the reaction, reaction mass was poured into ice, extracted with 10% MeOH/DCM. The combined organic layers were dried, concentrated to obtain crude; which then purified by prep. HPLC to afford the title compound (0.01 g, 6.6%).

Analytical Data of the Formate Salt:

LCMS: 513.50 (M+1); $^1$H NMR (400 MHz, DMSO-d6) δ 8.08 (t, J=4.6 Hz, 1H), 7.15 (d, J=2.2 Hz, 1H), 6.95 (d, J=2.1 Hz, 1H), 5.98 (s, 1H), 4.38 (d, J=4.5 Hz, 2H), 3.01 (q, J=6.9 Hz, 2H), 2.88 (bs, 1H), 2.67 (s, 1H), 2.55 (d, J=18.1 Hz, 6H), 2.28 (d, J=15.9 Hz, 6H), 2.15 (s, 3H), 1.97-1.89 (m, 2H), 1.80 (d, J=10.8 Hz, 2H), 1.38 (q, J=13.2 Hz, 4H), 0.78 (t, J=6.9 Hz, 3H).

Compound 30: 5-(((trans)-4-(dimethylamino)cyclo-hexyl)(ethyl)amino)-4'-(2-methoxyethoxy)-4-methyl-N-((5-methyl-3-oxo-2,3-dihydro-1H-pyrazol-4-yl)methyl)-[1,1'-biphenyl]-3-carboxamide

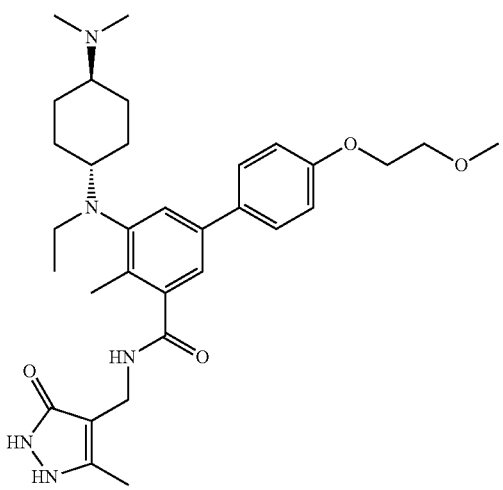 [SMILES: CCN(c1cc(-c2ccc(OCCOC)cc2)cc(C(=O)NCc2c(C)[nH][nH]c2=O)c1C)[C@H]1CC[C@H](N(C)C)CC1]

Step 1: Synthesis of methyl 5-bromo-3-(((trans)-4-((tert-butoxycarbonyl) amino)cyclohexyl)-amino)-2-methylbenzoate To a stirred solution of methyl 3-amino-5-bromo-2-methylbenzoate (860 g, 3.53 mol) and tert-butyl (4-oxocyclohexyl)carbamate (904.6 g, 4.24 mol) in dichloroethane (1 L), acetic acid (1274 g, 21.23 mol) was added and reaction was stirred at room temperature for 30 minutes. Then sodium triacetoxyborohydride (2250 g, 10.61 mol) was added at 0° C. and reaction was stirred at room temperature for 16 hours. On completion (monitored by TLC), reaction was quenched with aqueous sodium bicarbonate, the organic layer was separated and the aqueous layer was extracted with dichloromethane (1.5 L×3). The combined organic layers were dried over anhydrous sodium sulphate and concentrated under reduced pressure. The crude compound was purified by silica gel column chromatography (100-200 mesh size) eluting with 2, 4, 6 & 8% ethyl acetate in hexane to remove maximum cis isomer. This afforded 945 g of mixture of cis and trans isomers (40:60 by HPLC). The trans isomer was purified by repetitive recrystallisation with ethyl acetate: hexane (1:2) to afford 480 g of pure trans isomer as white solid with 99% purity.

Step 2: Synthesis of methyl 5-bromo-3-(((trans)-4-((tert-butoxycarbonyl)amino)cyclohexyl)-(ethyl) amino)-2-methylbenzoate To a stirred solution of methyl 5-bromo-3-(((trans)-4-((tert-butoxycarbonyl) amino)cyclohexyl)-amino)-2-methylbenzoate (240 g, 0.545 mol), acetaldehyde (59.98 g, 1.36 mol) in dichloroethane (1 L) and acetic acid (196.3 g, 3.27 mol) was added and reaction was stirred at room temperature for 30 minutes. Then sodium triacetoxyborohydride (346.8 g, 1.63 mol) was added at 0° C. and reaction was stirred at room temperature for 16 hours. On completion, reaction was quenched with aqueous sodium bicarbonate, the organic layer was separated and the aqueous layer was extracted with dichloromethane (1 L×3). The combined organic layers were dried over anhydrous sodium sulphate and concentrated under reduced pressure. The crude compound was purified by silica gel column chromatography to afford the title compound as white solid (192 g, 75.2%).

Step 3: Synthesis of methyl 5-(((trans)-4-((tert-butoxycarbonyl)-amino)-cyclohexyl)-(ethyl)amino)-4'-hydroxy-4-methyl-[1,1'-biphenyl]-3-carboxylate To a stirred solution of methyl 5-bromo-3-(((trans)-4-((tert-butoxycarbonyl)amino)cyclohexyl)-(ethyl)amino)-2-methylbenzoate (189 g, 0.403 mol) and (4-hydroxyphenyl) boronic acid (66.73 g, 0.484 mol) in dioxane/water mixture (3.5 L+1.26 L), $Na_2CO_3$ (153.7 g, 1.45 mol) was added and solution was purged with argon for 40 min. Then $Pd(PPh_3)_4$ (46.54 g, 0.040 mol) was added and argon was purged again for 30 min. Reaction mass was heated at 100° C. for 5 h. On completion, reaction mixture was diluted with 10% MeOH/DCM (1.5 L) and filtered. The filtrate was concentrated, diluted with water (1 L) and extracted with 10% MeOH in DCM (1 L×3). Combined organic layers were dried over $Na_2SO_4$ and solvent removed under reduced pressure. The crude compound was purified by silica gel column chromatography (100-200 mesh) eluting with 5, 10, 15, 20 & 25% ethyl acetate in hexane to afford desired the title compound as pale yellow solid (179 g, 92.3%).

Step 4: Synthesis of methyl 5-(((trans)-4-((tert-butoxycarbonyl)-amino)-cyclohexyl)-(ethyl)amino)-4'-(2-methoxyethoxy)-4-methyl-[1,1'-biphenyl]-3-carboxylate To stirred solution of methyl 5-(((trans)-4-((tert-butoxycarbonyl)-amino)-cyclohexyl)-(ethyl)amino)-4'-hydroxy-4-methyl-[1,1'-biphenyl]-3-carboxylate (180 g, 0.373 mol) in acetonitrile (2 L), cesium carbonate (364 g, 1.12 mol) and 1-bromo-2-methoxyethane (62.29 g, 0.448 mol) were added. Resulting reaction mass was heated at 80° C. for 12 h. On completion, reaction mixture was filtered and the residue washed well with DCM. The aqueous phase was separated and extracted with DCM. Combined organic layers were dried, concentrated under reduced pressure and purified by column chromatography over silica (100-200 mesh size) eluting with 5, 10, 15, 20 & 25% ethyl acetate in hexane giving the title compound as pale yellow sticky solid (170 g, 84.3%).

Step 5: Synthesis of methyl 5-(((trans)-4-aminocyclohexyl)(ethyl)amino)-4'-(2-methoxyethoxy)-4-methyl-[1,1'-biphenyl]-3-carboxylate To a stirred solution of methyl 5-(((trans)-4-((tert-butoxycarbonyl)-amino)-cyclohexyl)-(ethyl)amino)-4'-(2-methoxyethoxy)-4-methyl-[1,1'-biphenyl]-3-carboxylate (5 g, 9.25 mmol) in DCM (50 mL) at 0° C., TFA (5 mL) was added and reaction was stirred for 2 h at room temperature. After completion, reaction was concentrated to dryness. The residue was then basified with aqueous sat. bicarbonate solution till pH 8 and aqueous layer extracted with 10% methanol in DCM Combined organic layers were dried over $Na_2SO_4$ and concentrated under reduced pressure to afford crude compound (4 g) which was used as such for next reaction without further purification.

Step 6: Synthesis of methyl 5-(((trans)-4-(dimethylamino) cyclohexyl) (ethyl) amino)-4'-(2-methoxyethoxy)-4-methyl-[1,1'-biphenyl]-3-carboxylate To a stirred solution of methyl 5-(((trans)-4-aminocyclohexyl)(ethyl)amino)-4'-(2-methoxyethoxy)-4-methyl-[1,1'-biphenyl]-3-carboxylate (4 g, 9.09 mmol) in dichloromethane (40 mL) at 0° C., aq. 35% formaldehyde solution (0.954 g, 31.84 mmol) was added and solution was stirred for 20 min. Then Na(OAc)₃BH (4.82 g, 22.72 mmol) was added and stirred for 2 h at 0° C. On completion, reaction mixture was diluted with water and extracted with 10% methanol in DCM. Combined organic layers were dried over Na₂SO₄ and concentrated under reduced pressure. The crude compound was purified by column chromatography to afford the title compound (2 g, 47.1%).

Step 7: Synthesis of 5-(((trans)-4-(dimethylamino) cyclohexyl)(ethyl)amino)-4'-(2-methoxyethoxy)-4-methyl-[1,1'-biphenyl]-3-carboxylic Acid To a solution of methyl 5-(((trans)-4-(dimethylamino) cyclohexyl) (ethyl) amino)-4'-(2-methoxyethoxy)-4-methyl-[1,1'-biphenyl]-3-carboxylate (2 g, 4.27 mmol) in EtOH (20 mL), 1N NaOH (8 mL) was added and reaction was stirred at 60° C. for 1 h. After completion of the reaction, ethanol was removed under reduced pressure and acidified using dilute HCl up to pH 6 and pH 4 was adjusted using citric acid. Extraction was carried out using 10% MeOH/DCM. Combined organic layers were dried over Na₂SO₄ and concentrated under reduced pressure to afford crude compound (1.8 g) which was used as such for next reaction without further purification.

Step 8: Synthesis of 5-(((trans)-4-(dimethylamino) cyclohexyl)(ethyl)amino)-4'-(2-methoxyethoxy)-4-methyl-N-((5-methyl-3-oxo-2,3-dihydro-1H-pyrazol-4-yl)methyl)-[1,1'-biphenyl]-3-carboxamide To a stirred solution of 5-(((trans)-4-(dimethylamino) cyclohexyl)(ethyl)amino)-4'-(2-methoxyethoxy)-4-methyl-[1,1'-biphenyl]-3-carboxylic acid (1 g, 2.20 mmol) in DMF (10 mL) at 0° C., 4-(aminomethyl)-3-methyl-1H-pyrazol-5 (4H)-one hydrochloride (0.394 g, 2.42 mmol) and DIPEA (1.14 g, 8.81 mmol) were added. The reaction mixture was stirred at same temperature for 15 min before HATU (0.921 g, 2.42 mmol) was added to it and stirring was continued for overnight at room temperature. After completion of the reaction, reaction mixture was quenched with saturated NaHCO₃ solution and the suspension was stirred for 1 h. The suspension was then extracted with 10% MeOH/DCM. The combined organic layers were dried over Na₂SO₄ and concentrated under reduced pressure. The crude compound was purified by prep. HPLC to afford the desired compound (0.12 g, 9.7%).

Analytical Data:
LCMS: 564 (M+1); ¹H NMR (400 MHz, DMSO-d6) δ 9.34 (s, 1H), 8.63 (t, J=5.2 Hz, 1H), 7.57 (d, J=8.2 Hz, 2H), 7.37 (s, 1H), 7.21 (s, 1H), 7.03 (d, J=8.2 Hz, 2H), 4.16-4.05 (m, 4H), 3.67 (t, J=4.5 Hz, 2H), 3.12-2.98 (m, 5H), 2.80-2.70 (m, 2H), 2.68 (d, J=5.0 Hz, 6H), 2.23 (s, 3H), 2.16 (s, 3H), 1.92 (d, J=16.2 Hz, 4H), 1.44 (t, J=9.5 Hz, 4H), 0.84 (t, J=6.9 Hz, 3H).

Compounds 31a and 31b: 5-chloro-3-(ethyl((trans)-4-(dimethylamino)cyclohexyl]amino)-2-methyl-N-((1-methyl-3-oxo-2,3-dihydro-1H-pyrazol-4-yl) methyl]benzamide formate and 5-chloro-3-{ethyl [(trans)-4-(dimethylamino)cyclohexyl]amino}-2-methyl-N-{[1-methyl-5-(methylsulfanyl)-3-oxo-2,3-dihydro-1H-pyrazol-4-yl]methyl}benzamide Formate

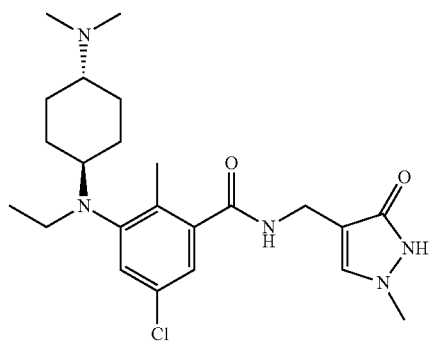

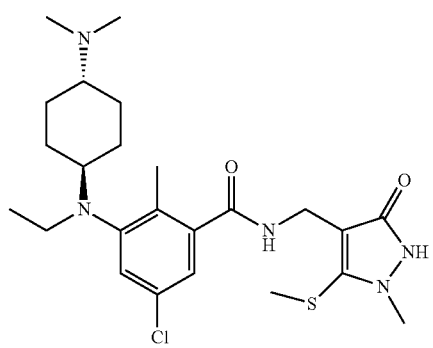

Step 1: Synthesis of 1-methyl-5-(methylsulfanyl)-3-oxo-2,3-dihydro-1H-pyrazole-4-carbonitrile To a stirred solution of ethyl 2-cyano-3,3-bis(methylsulfanyl)prop-2-enoate (11.1 g, 51.1 mmol, 1 equiv.) in MeCN (60 ml) under nitrogen fitted with a bleach trap was added methylhydrazine (2.7 mL, 51.1 mmol, 1 equiv.). The reaction was heated at 50° C. for 3 h after which time the reaction mixture was cooled to room temperature, the title compound was filtered off, washed with TBME and dried on a vac line to afford the title compound (6.87 g, 100% purity, 79% yield). This material was suitable for use without any further purification.

Step 2: Synthesis of 4-(aminomethyl)-1-methyl-2,3-dihydro-1H-pyrazol-3-one and 4-(aminomethyl)-1-methyl-5-(methylsulfanyl)-2,3-dihydro-1H-pyrazol-3-one 1-Methyl-5-(methylsulfanyl)-3-oxo-2,3-dihydro-1H-pyrazole-4-carbonitrile (10 mg, 0.59 mmol) was dissolved in 2M NH₃ in MeOH (12 mL) making a 0.05M solution. This solution was processed using a Thales H-Cube hydrogenator using a Raney Nickel cartridge and 60 Bar H2 pressure and 80° C. chamber temperature. The initial reaction was incomplete and so a second pass was required. The solution was then evaporated to dryness in vacuo, loaded onto a 10 g SCX-2 column using minimal MeOH, washed with MeOH (3×30 ml), eluted with 7M NH₃ in MeOH (2×30 ml) and evaporated to afford the title compounds as a mixture which was used in the next stage without any purification as a white solid (54 mg) which was used in the next stage without any purification.

Step 3: Synthesis of 5-chloro-3-(ethyl((trans)-4-(dimethylamino)cyclohexyl)amino)-2-methyl-N-[(1-methyl-3-oxo-2,3-dihydro-1H-pyrazol-4-yl)methyl] benzamide formate and 5-chloro-3-(ethyl((trans)-4-(dimethylamino)cyclohexyl)amino)-2-methyl-N-((1-methyl-5-(methylsulfanyl)-3-oxo-2,3-dihydro-1H-pyrazol-4-yl)methyl)benzamide Formate To a stirred solution of 5-chloro-3-(ethyl((trans)-4-(dimethylamino)cyclohexyl)amino)-2-methylbenzoic acid hydrochloride (99%, 98 mg, 0.26 mmol) in DMF (2 ml) cooled to 0° C. using an ice batch was added DIPEA (90 µL, 0.52 mmol) and HATU (99 mg, 0.26 mmol), the reaction was stirred for 10 minutes after which time the crude mixture from the previous step (60%, 50 mg, 0.17 mmol) was added and the reaction was then warmed to room temperature and stirred for 20 h. The reaction mixture was then poured onto water (50 mL) and stirred for 20 min after which the solution was extracted with EtOAc (2×50 mL), washed with brine (2×30 mL), dried (Na₂SO₄), filtered and evaporated. The crude product was purified preparative HPLC to afford the title compounds: 5-chloro-3-(ethyl ((trans)-4-(dimethylamino)cyclohexyl]amino)-2-methyl-N-((1-methyl-3-oxo-2,3-dihydro-1H-pyrazol-4-yl)methyl] benzamide formate: 36 mg (41% yield); 5-chloro-3-(ethyl ((trans)-4-(dimethylamino)cyclohexyl)amino)-2-methyl-N-((1-methyl-5-(methylsulfanyl)-3-oxo-2,3-dihydro-1H-pyrazol-4-yl)methyl)benzamide formate: 11 mg (10% yield).

5-chloro-3-(ethyl((trans)-4-(dimethylamino)cyclohexyl] amino)-2-methyl-N-((1-methyl-3-oxo-2,3-dihydro-1H-pyrazol-4-yl)methyl]benzamide formate: LC-MS: 98%, 2.67 min (7 minute LC-MS method), m/z=448.10/450.15, NMR: ¹H NMR (500 MHz, Methanol-d4) δ 8.43 (s, 1H), 7.32 (s, 1H), 7.23 (d, J=2.1 Hz, 1H), 7.08 (d, J=2.1 Hz, 1H), 4.24 (s, 2H), 3.65 (s, 3H), 3.18-3.12 (m, 1H), 3.09 (q, J=7.0 Hz, 2H), 2.83-2.75 (m, 7H), 2.24 (s, 3H), 2.05 (dd, J=32.9, 9.7 Hz, 4H), 1.59-1.44 (m, 4H), 0.87 (t, J=7.0 Hz, 3H).

5-chloro-3-(ethyl((trans)-4-(dimethylamino)cyclohexyl) amino)-2-methyl-N-((1-methyl-5-(methylsulfanyl)-3-oxo-2,3-dihydro-1H-pyrazol-4-yl)methyl)benzamide formate: LC-MS: 90%, 3.04 min (7 minute LC-MS method), m/z=494.10/496.10, NMR: ¹H NMR (500 MHz, Methanol-d4) δ 8.47 (s, 1H), 7.23 (d, J=2.1 Hz, 1H), 7.09 (d, J=2.1 Hz, 1H), 4.36 (s, 2H), 3.78 (s, 3H), 3.16-3.05 (m, 3H), 2.86-2.75 (m, 7H), 2.33 (s, 3H), 2.25 (s, 3H), 2.11-1.95 (m, 4H), 1.61-1.43 (m, 4H), 0.87 (t, J=7.0 Hz, 3H).

Compound 32: 5-chloro-3-(ethyl((trans)-4-(dimethylamino)cyclohexyl)amino)-2-methyl-N-((5-methyl-3-oxo-2,3-dihydro-1H-pyrazol-4-yl)methyl]benzamide Formate

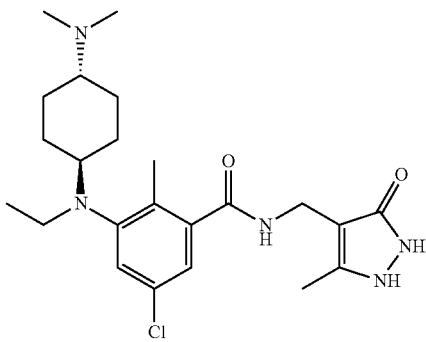 [SMILES: CCN(c1cc(Cl)cc(C(=O)NCc2c(C)[nH][nH]c2=O)c1C)[C@H]1CC[C@H](N(C)C)CC1]

Step 1: Synthesis of 5-chloro-3-(ethyl((trans)-4-(dimethylamino)cyclohexyl)amino)-2-methyl-N-((5-methyl-3-oxo-2,3-dihydro-1H-pyrazol-4-yl)methyl] benzamide Formate To a stirred solution of 5-chloro-3-(ethyl((trans)-4-(dimethylamino)cyclohexyl)amino)-2-methylbenzoic acid hydrochloride (99%, 125 mg, 0.33 mmol) in DMF (1 mL) cooled to 0° C. using an ice batch was added DIPEA (230 µL, 1.32 mmol) and HATU (138 mg, 0.36 mmol), the reaction was stirred for 10 minutes after which time (4-(aminomethyl)-5-methyl-2,3-dihydro-1H-pyrazol-3-one hydrate dihydrochloride (79 mg, 0.36 mmol, ABCR) was added and the reaction was then warmed to room temperature and stirred for 5 h. The reaction mixture was then poured onto satd. NaHCO₃ (30 mL) for 1 h after which the solution was extracted with EtOAc (3×30 ml) followed by 1:1 IPA:CHCl3 (3×30 mL), the combined organics were then washed with brine (30 ml), dried (Na₂SO₄), filtered and evaporated. The crude product was purified using preparative HPLC to afford the title compound (15 mg, 9% yield) as a yellow powder.

Analytical Data:

LC-MS 98%, 2.59 min (7 minute LC-MS method), m/z=210.60 and 420.25/422.15, ¹H NMR (500 MHz, Methanol-d4) δ 8.43 (s, 1H), 7.23 (d, J=2.1 Hz, 1H), 7.07 (d, J=2.1 Hz, 1H), 4.23 (s, 2H), 3.18-3.06 (m, 3H), 2.82-2.80 (m, 6H), 2.79-2.75 (m, 1H), 2.25 (s, 3H), 2.24 (s, 3H), 2.11-2.05 (m, 2H), 2.05-1.98 (m, 2H), 1.52 (q, J=11.4 Hz, 4H), 0.87 (t, J=7.0 Hz, 3H).

Compounds 33a and 33b: 5-chloro-N-((1,5-dimethyl-3-oxo-2,3-dihydro-1H-pyrazol-4-yl)methyl)-3-(ethyl((trans)-4-(dimethylamino)cyclohexyl)amino)-2-methyl benzamide Formate Salt and 5-chloro-3-(ethyl((trans)-4-(dimethylamino)cyclohexyl)amino)-N-((3-methoxy-5-methyl-1H-pyrazol-4-yl)methyl)-2-methylbenzamide Formate Salt

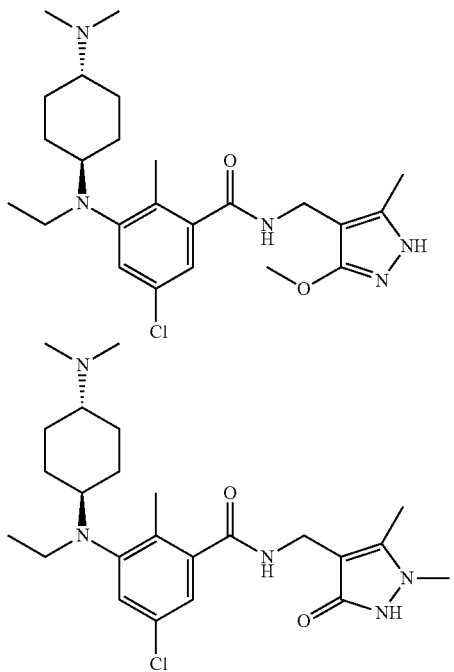

Step 1: Synthesis of tert-butyl N-[(5-methyl-3-oxo-2,3-dihydro-1H-pyrazol-4-yl)methyl]carbamate 4-(Aminomethyl)-5-methyl-2,3-dihydro-1H-pyrazol-3-one hydrate dihydrochloride (1.0 g, 4.59 mmol, 1 equiv. ABCR) was suspended in a mixture of 2:1 DCM:MeOH (7.5 mL) and then DIPEA (2.4 mL, 13.76 mmol, 3 equiv.) was added and the reaction mixture cooled to 0° C. Boc anhydride (2.1 g, 9.63 mmol, 2.1 equiv.) was then added and the reaction mixture was warmed to room temperature and stirred for 3 h after which time the solvent was removed in vacuo. The residue was redissolved in DCM (50 mL), washed with brine (3×30 mL), dried with $Na_2SO_4$, filtered and evaporated. The crude product was purified using a 100 g SNAP KP-Sil column on a Biotage Isolera system eluting with a 0% to 10% MeOH in DCM gradient system to afford the title compound as an off-white solid (596 mg, 36% yield). LC-MS: 100%, 1.92 min, m/z=215.90, 272.00, 328.05, $^1$H NMR (500 MHz, Methanol-d4) δ 3.95 (s, 2H), 2.44 (s, 3H), 1.60 (s, 9H), 1.44 (s, 9H).

Step 2: Synthesis of tert-butyl N-[(5-methyl-3-oxo-2,3-dihydro-1H-pyrazol-4-yl)methyl]carbamate To a stirred solution of tert-butyl N-((5-methyl-3-oxo-2,3-dihydro-1H-pyrazol-4-yl)methyl)carbamate (596 mg, 1.82 mmol, 1 equiv.) in MeOH (20 mL) was added 6M NaOH (6 ml, 20 equiv.) and the reaction mixture was stirred at room temperature for 16 h. The reaction mixture was then neutralized to pH 7 by the addition of 1M HCl, solid NaCl was added to the aqueous solution until saturated and the aqueous was then extracted with EtOAc (6×30 mL), dried with $Na_2SO_4$, filtered and evaporated. The crude product was purified using a 25 g SNAP KP Sil column on a Biotage Isolera system eluting with a 2% to 20% MeOH in DCM gradient system to afford the title compound as an off-white solid (170 mg, 41% yield). LC-MS: 100%, 1.30 min, m/z=228.0, $^1$H NMR (500 MHz, Methanol-d4) δ 3.93 (s, 2H), 2.19 (s, 3H), 1.44 (s, 9H).

Step 3: Synthesis of tert-butyl N-[(1,5-dimethyl-3-oxo-2,3-dihydro-1H-pyrazol-4-yl)methyl]carbamate Tert-butyl N-((5-methyl-3-oxo-2,3-dihydro-1H-pyrazol-4-yl)methyl)carbamate (70 mg, 0.31 mmol, 1.0 eq) was dissolved in anhydrous DMF (1 mL) and cooled to 0° C. in an ice bath. NaH (60% dispersion in oil, 12 mg, 0.31 mmol, 1.0 equiv.) was added and the reaction stirred for 2 minutes followed by the addition of iodomethane (20 µL, 0.32 mmol 1.05 equiv.). The reaction was put under a nitrogen atmosphere and stirred at room temperature for 2 h, after which time water (10 mL) was added and the layers were separated, followed by extraction of the aqueous phase with EtOAc (2×20 mL), the combined organic phases were dried with $Na_2SO_4$, filtered and evaporated. Azeotropic removal of any residual DMF was performed using heptane (2×40 mL). The crude product was purified using a 10 g SNAP HP-Sil column on a Biotage Isolera system eluting with a 1% to 10% MeOH in DCM gradient system to afford the title compounds as a white solid (23 mg, 73% N-methyl isomer and 12% O-methyl isomer). Material was taken through crude to the next stage of the synthesis as a mixture of isomers.

Step 4: Synthesis of 4-(aminomethyl)-1,5-dimethyl-2,3-dihydro-1H-pyrazol-3-one hydrochloride Tert-butyl N-[(1,5-dimethyl-3-oxo-2,3-dihydro-1H-pyrazol-4-yl)methyl]carbamate (73%+12% mixture of isomers, 23 mg, 0.07 mmol) was dissolved in 4M HCl in dioxane (1 mL) and the reaction was stirred for 1 h at room temperature after which the solvent was removed in vacuo, followed by drying in a vacuum oven at 40° C. for 2 h and then room temperature for 16 h to afford the title compound a white solid (18 mg, mixture of N-isomer and O-isomer). Material was taken through crude to the next stage of the synthesis as a mixture of isomers. LC-MS: Product in solvent front, flies as fragmentation of C—NH2 bond—(124.95 (M+H—NH2) and 141.90 (M+H))

Step 5: Synthesis of 5-chloro-N-((1,5-dimethyl-3-oxo-2,3-dihydro-1H-pyrazol-4-yl)methyl)-3-(ethyl((trans)-4-(dimethylamino)cyclohexyl)amino)-2-methyl benzamide Formate Salt and 5-chloro-3-(ethyl((trans)-4-(dimethylamino) cyclohexyl) amino)-N-((3-methoxy-5-methyl-1H-pyrazol-4-yl) methyl)-2-methylbenzamide Formate Salt To a stirred solution of 5-chloro-3-(ethyl((trans)-4-(dimethylamino)cyclohexyl)amino)-2-methylbenzoic acid HCl (99%, 18 mg, 0.09 mmol) in DMF (1 mL) at 0° C. was added DIPEA (48 µL, 0.27 mmol, 3 equiv.) followed by HATU (38 mg, 0.10 mmol, 1.1 equiv.). The reaction was stirred at 0° C. for 5 min after which time 4-(aminomethyl)-1,5-dimethyl-2,3-dihydro-1H-pyrazol-3-one hydrochloride (~90% mixture of N- and O-isomers (35 mg, 0.09 mmol, 1 equiv.) was added and the reaction was stirred at room temperature for 16 h. The reaction mixture was then poured onto saturated NaHCO$_3$ (10 ml) and the suspension was extracted with EtOAc (3×20 mL), the combined organics were washed with brine (30 mL), dried with Na$_2$SO$_4$, filtered and evaporated to give a brown oil. The crude product was purified using preparative HPLC to afford the title compounds: 5-chloro-N-((1,5-dimethyl-3-oxo-2,3-dihydro-1H-pyrazol-4-yl) methyl)-3-(ethyl((trans)-4-(dimethylamino)cyclohexyl) amino)-2-methylbenzamide formate salt, 12 mg (26% yield); 5-chloro-3-(ethyl((trans)-4-(dimethylamino)cyclohexyl)amino)-N-((3-methoxy-5-methyl-1H-pyrazol-4-yl) methyl)-2-methylbenzamide formate salt, 1.9 mg (4% yield).

5-chloro-N-((1,5-dimethyl-3-oxo-2,3-dihydro-1H-pyrazol-4-yl)methyl)-3-(ethyl((trans)-4-(dimethylamino)cyclohexyl)amino)-2-methylbenzamide formate salt: LC-MS: 98%, 2.78 min (7 minute method), m/z=231.60/462.30/464.20, NMR: 1H NMR (500 MHz, Methanol-d4) δ 8.53 (s, 1H), 7.23 (d, J=2.1 Hz, 1H), 7.06 (d, J=2.0 Hz, 1H), 4.22 (s, 2H), 3.56 (s, 3H), 3.21-3.00 (m, 3H), 2.79 (s, 7H), 2.24 (s, 3H), 2.23 (s, 3H), 2.11-1.97 (m, 4H), 1.51 (q, J=11.9 Hz, 4H), 0.86 (t, J=7.0 Hz, 3H).

5-chloro-3-(ethyl((trans)-4-(dimethylamino)cyclohexyl) amino)-N-((3-methoxy-5-methyl-1H-pyrazol-4-yl)methyl)-2-methylbenzamide formate salt: LC-MS: 100%, 2.89 min (7 minute method), m/z=231.55/462.20/464.35, NMR: 1H NMR (500 MHz, Methanol-d4) δ 7.21 (d, J=2.0 Hz, 1H), 7.03 (d, J=2.0 Hz, 1H), 4.26 (s, 2H), 3.87 (s, 3H), 3.16-3.04 (m, 3H), 2.79 (s, 7H), 2.27 (s, 3H), 2.23 (s, 3H), 2.11-1.98 (m, 4H), 1.51 (q, J=12.2 Hz, 4H), 0.87 (t, J=7.0 Hz, 3H).

Compound 34: 5-chloro-N-((2,5-dimethyl-3-oxo-2,3-dihydro-1H-pyrazol-4-yl)methyl)-3-(((trans)-4-(dimethylamino)cyclohexyl)(ethyl)amino)-2-methylbenzamide

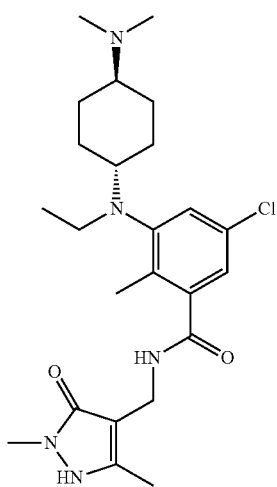 [SMILES: CCN(c1cc(Cl)cc(C(=O)NCc2c(C)[nH]n(C)c2=O)c1C)[C@H]1CC[C@H](N(C)C)CC1]

Step 1: Synthesis of 2,5-dimethyl-1H-pyrazol-3(2H)-one

To a stirred solution ethyl acetoacetate (50 g, 384.61 mmol) in ethanol (200 mL), methyl hydrazine (19.46 g, 423.07 mmol) was added at 0° C. The resulting reaction mixture was heated at 90° C. for 8 h. The progress of the reaction was monitored by TLC. On completion, reaction mixture was concentrated to dryness under reduced pressure and the crude material obtained was purified by column chromatography giving the title compound (32 g, 74.3%).

Step 2: Synthesis of 5-chloro-1,3-dimethyl-1H-pyrazole-4-carbaldehyde

To a mixture of 2,5-dimethyl-1H-pyrazol-3(2H)-one (32 g, 285.71 mmol) and POCl$_3$ (128 mL) at 0° C., DMF (26.35 mL, 342.85 mmol) was added slowly. The resulting reaction mixture was stirred at 100° C. for 7 h. The progress of the reaction was monitored by TLC. On completion, the reaction mixture was concentrated to dryness under reduced pressure. The residue obtained was basified with aqueous sodium bicarbonate solution and extracted with ethyl acetate. The combined organic layers were dried over anhydrous Na$_2$SO$_4$ and concentrated under reduced pressure to afford the crude material which then purified by column chromatography giving the title compound (28 g, 62.0%).

Step 3: Synthesis of 5-chloro-1,3-dimethyl-1H-pyrazole-4-carbonitrile

To a stirred solution of 5-chloro-1,3-dimethyl-1H-pyrazole-4-carbaldehyde (28 g, 177.21 mmol) in methanol (140 mL), hydroxylamine hydrochloride (24.63 g, 354.43 mmol) was added. The resulting reaction mixture was stirred at 70° C. for 3 h. The progress of the reaction was monitored by TLC. On completion, the reaction mixture was concentrated to dryness. The residue obtained was diluted with water and extracted with ethyl acetate. The combined organic layers were dried over Na$_2$SO$_4$ and concentrated under reduced pressure to afford crude oxime compound (28 g) which was used as such for next step.

To above crude oxime compound (14 g, 80.92 mmol), POCl$_3$ (70 mL) was added at 0° C. and the reaction mixture was heated at 65° C. for 12 h. The progress of the reaction was monitored by TLC. On completion, the reaction mixture was concentrated to dryness. The residue obtained was basified with aqueous sodium bicarbonate solution and extracted with ethyl acetate. The combined organic layers were dried over Na$_2$SO$_4$ and concentrated under reduced pressure to afford crude material which then purified by column chromatography giving the title compound (11 g, 87.7%).

Step 4: Synthesis of 5-methoxy-1,3-dimethyl-1H-pyrazole-4-carbonitrile

To a stirred solution of 5-chloro-1,3-dimethyl-1H-pyrazole-4-carbonitrile (8 g, 51.28 mmol) in methanol (80 mL) at 0° C., NaOMe (3.59 g, 66.66 mmol) was added slowly. The resulting reaction mass was heated at 60° C. for 12 h. The progress of the reaction was monitored by TLC. On completion, reaction mixture was concentrated to dryness. The residue obtained was diluted with water and extracted with 10% MeOH/DCM. The combined organic layers were dried over Na$_2$SO$_4$ and concentrated under reduced pressure to afford crude material which then purified by column chromatography giving the title compound (3.5 g, 45.2%).

Step 5: Synthesis of (5-methoxy-1,3-dimethyl-1H-pyrazol-4-yl)methanamine

To a solution of 5-methoxy-1,3-dimethyl-1H-pyrazole-4-carbonitrile (3.5 g, 23.02 mmol) in methanol (40 mL), catalytic amount of Raney Nickel and ammonia solution (10 mL) were added. Reaction mass was stirred at room temperature under hydrogen pressure (balloon pressure) for 12 h. On completion of reaction, reaction mass was filtered through celite bed, celite bed washed with methanol and filtrate was concentrated under reduced pressure to afford crude compound that was used in the next step without further purification (2.9 g, 80.8%).

Step 6: Synthesis of 5-chloro-3-(((trans)-4-(dimethylamino)cyclohexyl)(ethyl)amino)-N-((5-methoxy-1,3-dimethyl-1H-pyrazol-4-yl)methyl)-2-methylbenzamide To a stirred solution of 5-chloro-3-(((trans)-4-(dimethylamino)cyclohexyl)(ethyl)amino)-2-methylbenzoic acid (0.35 g, 1.04 mmol) in DMSO (3 mL) (5-methoxy-1,3-dimethyl-1H-pyrazol-4-yl)methanamine (0.24 g, 1.55 mmol) and triethylamine (0.43 mL, 3.12 mmol) were added. The reaction mixture was stirred at room temperature for 15 min before PyBOP (0.811 g, 1.56 mmol) was added to it and stirring was continued for overnight. The progress of the reaction was monitored by TLC. After completion of the reaction, reaction mass was diluted with ice cold water and extracted with 10% MeOH/DCM. The combined organic layers were dried, concentrated to obtain crude; which then purified by column chromatography to afford the title compound (0.4 g, 81.5%).

Synthesis of 5-chloro-N-((2,5-dimethyl-3-oxo-2,3-dihydro-1H-pyrazol-4-yl)methyl)-3-(((trans)-4-(dimethylamino)cyclohexyl)(ethyl)amino)-2-methylbenzamide To a stirred solution of 5-chloro-3-(((trans)-4-(dimethylamino)cyclohexyl)(ethyl)amino)-N-((5-methoxy-1,3-dimethyl-1H-pyrazol-4-yl)methyl)-2-methylbenzamide (0.2 g, 0.42 mmol) in ACN (2 mL), NaI (0.082 g, 0.546 mmol) was added and the solution was stirred at rt for 10 min. Then TMSCl (0.055 g, 0.504 mmol) was added and the resulting reaction mixture was stirred at 60° C. for 16 h. The progress of the reaction was monitored by TLC. On completion, reaction mass was filtered and filtrate was concentrated under reduced pressure. The crude material obtained was purified by prep. HPLC to afford the title compound (0.05 g, 25.8%).

Analytical Data:
LCMS: 462.40 (M+1); $^1$H NMR (400 MHz, DMSO-d6) δ 8.58 (s, 1H), 7.20 (d, J=2.2 Hz, 1H), 6.99 (d, J=2.1 Hz, 1H), 4.06 (s, 2H), 3.03 (q, J=7.0 Hz, 2H), 2.91-2.81 (m, 1H), 2.16 (s, 3H), 2.05 (s, 3H), 1.91-1.80 (m, 4H), 1.46-1.23 (m, 4H), 0.79 (t, J=6.8 Hz, 3H), 10H merged in solvent peak.

Compound 35: N-((2,5-dimethyl-3-oxo-2,3-dihydro-1H-pyrazol-4-yl)methyl)-5-(((trans)-4-(dimethylamino)cyclohexyl)(ethyl)amino)-4'-(2-methoxyethoxy)-4-methyl-[1,1'-biphenyl]-3-carboxamide

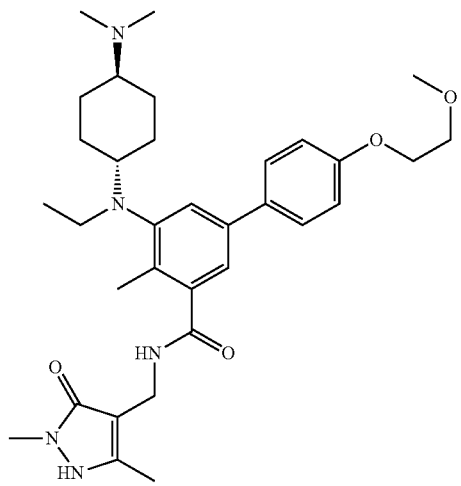 [SMILES: CCN(c1cc(-c2ccc(OCCOC)cc2)cc(C(=O)NCc2c(C)[nH]n(C)c2=O)c1C)[C@H]1CC[C@H](N(C)C)CC1]

Step 1: Synthesis of 5-bromo-3-(((trans)-4-(dimethylamino)cyclohexyl)(ethyl)amino)-N-((5-methoxy-1,3-dimethyl-1H-pyrazol-4-yl) methyl)-2-methylbenzamide To a stirred solution of 5-bromo-3-(((trans)-4-(dimethylamino)cyclohexyl)(ethyl)amino)-2-methylbenzoic acid (0.8 g, 2.09 mmol) in DMSO (6 mL), (5-methoxy-1,3-dimethyl-1H-pyrazol-4-yl)methanamine (0.653 g, 4.19 mmol) and triethylamine (0.9 mL, 6.27 mmol) was added to it. The reaction mixture was stirred at room temperature for 15 min before PyBOP (1.63 g, 3.14 mmol) was added to it at 0° C. and stirring was continued for overnight at room temperature. After completion of the reaction, reaction mixture was diluted with ice cold water and extracted with 10% methanol/DCM. The combined organic layers were dried over Na$_2$SO$_4$ and concentrated under reduced pressure. The crude compound was purified by column chromatography to afford the title compound (0.7 g, 64.2%).

Step 2: Synthesis of 5-bromo-N-((2,5-dimethyl-3-oxo-2,3-dihydro-1H-pyrazol-4-yl)methyl)-3-(((trans)-4-(dimethylamino)cyclohexyl)(ethyl)amino)-2-methylbenzamide To a stirred solution of 5-bromo-3-(((trans)-4-(dimethylamino)cyclohexyl)(ethyl)amino)-N-((5-methoxy-1,3-dimethyl-1H-pyrazol-4-yl) methyl)-2-methylbenzamide (0.7 g, 1.34 mmol), methanolic HCl (10 mL) was added and the solution was stirred at 80° C. for 12 h. The progress of the reaction was monitored by TLC. On completion, reaction mass was concentrated to dryness under reduced pressure to afford the crude material; which then purified by column chromatography afford the title compound (0.3 g, 44.1%).

Step 3: Synthesis of N-((2,5-dimethyl-3-oxo-2,3-dihydro-1H-pyrazol-4-yl)methyl)-5-(((trans)-4-(dimethylamino)cyclohexyl)(ethyl)amino)-4'-(2-methoxyethoxy)-4-methyl-[1,1'-biphenyl]-3-carboxamide To a stirred solution of 5-bromo-N-((2,5-dimethyl-3-oxo-2,3-dihydro-1H-pyrazol-4-yl)methyl)-3-(((trans)-4-(dimethylamino)cyclohexyl)(ethyl)amino)-2-methylbenzamide (0.2 g, 0.39 mmol) and 2-(4-(2-methoxyethoxy)phenyl)-4,4,5,5-tetramethyl-1,3,2-dioxaborolane (0.164 g, 0.59 mmol) in dioxane/water mixture (4 mL+1 mL)), $Na_2CO_3$ (0.148 g, 1.40 mmol) was added and solution was purged with argon for 15 min. Then Pd $(PPh_3)_4$ (0.228 g, 0.197 mmol) was added and argon was purged again for 15 min. Reaction mass was heated at 100° C. for 12 h. The progress of the reaction was monitored by TLC. On completion, reaction mixture was diluted with water and extracted with 10% MeOH/DCM. The combined organic layers were dried over $Na_2SO_4$ and concentrated under reduced pressure. The crude compound was purified by column chromatography afford the title compound (0.03 g, 13.2%).

Analytical Data:

LCMS: 578.55 (M+1); $^1$H NMR (400 MHz, DMSO-d6) δ 8.63 (bs, 1H), 7.53 (d, J=9.2 Hz, 2H), 7.33 (s, 1H), 7.16 (s, 1H), 7.00 (d, J=8.8 Hz, 2H), 4.13-4.08 (m, 4H), 3.67 (t, J=4.8 Hz, 2H), 3.39-3.31 (m, 3H), 3.08 (q, J=7.2 Hz, 2H), 2.67-2.65 (m, 1H), 2.21 (s, 3H), 211 (s, 6H), 2.04 (s, 3H), 1.83-1.75 (m, 4H), 1.38-1.35 (m, 2H), 1.17-1.11 (m, 2H), 0.82 (t, J=6.4 Hz, 3H), 4H merged in solvent peak.

Compound 36: 5-chloro-3-(((trans)-4-(dimethylamino)cyclohexyl)(ethyl)amino)-N-((2-ethyl-5-methyl-3-oxo-2,3-dihydro-1H-pyrazol-4-yl)methyl)-2-methylbenzamide

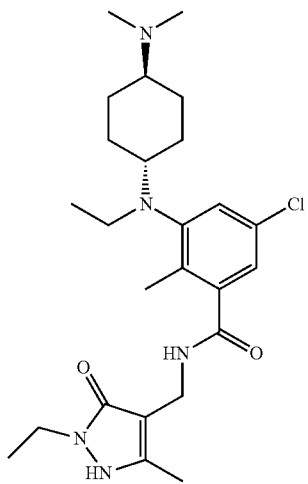 [SMILES: CCn1[nH]c(C)c(CNC(=O)c2cc(Cl)cc(N(CC)[C@H]3CC[C@H](N(C)C)CC3)c2C)c1=O]

Step 1: Synthesis of 5-chloro-3-(((trans)-4-(dimethylamino)cyclohexyl)(ethyl)amino)-N-((1-ethyl-5-methoxy-3-methyl-1H-pyrazol-4-yl)methyl)-2-methylbenzamide To a stirred solution of 5-chloro-3-(((trans)-4-(dimethylamino)cyclohexyl)(ethyl)amino)-2-methylbenzoic acid (0.2 g, 0.591 mmol) in DMSO (3 mL) 1-ethyl-5-methoxy-3-methyl-1H-pyrazol-4-yl)methanamine (Prepared in the same fashion as the methyl analog from the procedure for synthesizing Compound 2, starting from ethylhydrazine, 0.1 g, 0.591 mmol) and triethylamine (0.25 mL, 1.77 mmol) were added. The reaction mixture was stirred at room temperature for 15 min before PyBOP (0.461 g, 0.887 mmol) was added to it and stirring was continued for overnight. After completion of the reaction, reaction mass was poured into ice cold water, extracted with 10% MeOH/DCM. The combined organic layers were dried, concentrated to obtain crude; which then purified by column chromatography to afford the title compound (0.15 g, 51.9%).

Step 2: Synthesis of 5-chloro-3-(((trans)-4-(dimethylamino)cyclohexyl)(ethyl)amino)-N-((2-ethyl-5-methyl-3-oxo-2,3-dihydro-1H-pyrazol-4-yl)methyl)-2-methylbenzamide To a stirring solution of 5-chloro-3-(((trans)-4-(dimethylamino)cyclohexyl)(ethyl)amino)-N-((1-ethyl-5-methoxy-3-methyl-1H-pyrazol-4-yl)methyl)-2-methylbenzamide (0.15 g, 0.306 mmol) in methanolic HCl (prepared by passing HCl gas through MeOH at −10° C. for long time) (3 mL/100 mg), conc. HCl (0.2 mL) was added and the reaction mixture was heated at 80° C. in a sealed tube for 25 h. On completion, solvent was removed under reduced pressure. The crude compound was purified by prep-HPLC to afford the title compound (0.03 g, 20.7%).

Analytical Data of Formate Salt:

LCMS: 476.50 (M+1); $^1$H NMR (DMSO-$d_6$, 400 MHz) δ 8.58 (bs, 1H), 7.16 (d, J=2.0 Hz, 1H), 6.96 (d, J=2.0 Hz, 1H), 4.05 (d, J=5.2 Hz, 2H), 3.73 (q, J=7.2 Hz, 2H), 3.02 (q, J=6.8 Hz, 2H), 2.68-2.66 (m, 1H), 2.33-2.32 (m, 1H), 2.17 (s, 6H), 2.14 (s, 3H), 2.06 (s, 3H), 1.80-1.74 (m, 4H), 1.38-1.35 (m, 2H), 1.19-1.14 (m, 5H), 0.78 (t, J=6.8 Hz, 3H).

Compound 37: 5-chloro-3-(((trans)-4-(dimethylamino) cyclohexyl)(ethyl) amino)-N-((2-isopropyl-5-methyl-3-oxo-2,3-dihydro-1H-pyrazol-4-yl) methyl)-2-methylbenzamide

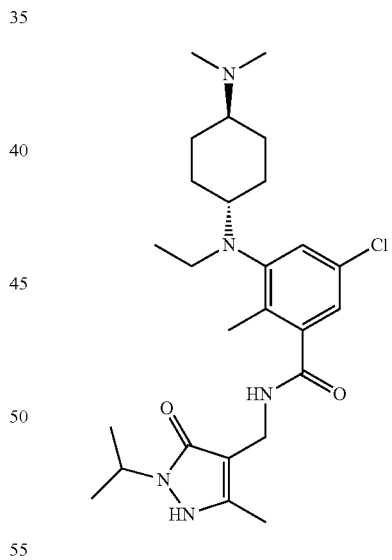

Step 1: Synthesis of 5-chloro-3-(((trans)-4-(dimethylamino) cyclohexyl) (ethyl) amino)-N-((1-isopropyl-5-methoxy-3-methyl-1H-pyrazol-4-yl) methyl)-2-methylbenzamide To a stirred solution of 5-chloro-3-(((trans)-4-(dimethylamino)cyclohexyl)(ethyl)amino)-2-methylbenzoic acid (0.2 g, 0.591 mmol) in DMSO (3 mL) 1-isopropyl-5-methoxy-3-methyl-1H-pyrazol-4-yl)methanamine (Prepared in the same fashion as the methyl analog from the procedure for synthesizing Compound 2, starting from isopropylhydrazine, 0.118 g, 0.65 mmol) and triethylamine (0.25 mL, 1.77 mmol) were added. The reaction mixture was stirred at room temperature for 15 min before PyBOP (0.461 g, 0.887 mmol) was added to it and stirring was continued for overnight. After completion of the reaction, reaction mass was poured into ice cold water, extracted with 10% MeOH/DCM. The combined organic layers were dried, concentrated to obtain crude; which then purified by column chromatography to afford the title compound (0.24 g, 80%).

Step 2: Synthesis of 5-chloro-3-(((trans)-4-(dimethylamino)cyclohexyl)(ethyl)amino)-N-((2-isopropyl-5-methyl-3-oxo-2,3-dihydro-1H-pyrazol-4-yl)methyl)-2-methylbenzamide To a stirring solution of 5-chloro-3-(((trans)-4-(dimethylamino) cyclohexyl) (ethyl) amino)-N-((1-isopropyl-5-methoxy-3-methyl-1H-pyrazol-4-yl) methyl)-2-methylbenzamide (0.225 g, 0.44 mmol) in methanolic HCl (prepared by passing HCl gas through MeOH at −10° C. for long time) (3 mL/100 mg), conc. HCl (0.2 mL) was added and the reaction mixture was heated at 80° C. in a sealed tube for 16 h. On completion, solvent was removed under reduced pressure. The crude compound was purified by prep-HPLC to afford the title compound (0.04 g, 18%).

Analytical Data of the Formate Salt:
LCMS: 490.50 (M+1); $^1$H NMR (400 MHz, DMSO-d6) δ 8.60 (t, J=4.9 Hz, 1H), 7.16 (d, J=2.2 Hz, 1H), 6.96 (d, J=2.1 Hz, 1H), 4.36 (p, J=6.7 Hz, 1H), 4.05 (d, J=5.2 Hz, 2H), 3.02 (q, J=7.0 Hz, 2H), 2.62 (t, J=12.3 Hz, 1H), 2.26 (d, J=12.1 Hz, 1H), 2.20 (s, 6H), 2.14 (s, 3H), 2.06 (s, 3H), 1.84-1.71 (m, 4H), 1.44-1.30 (m, 2H), 1.23 (d, J=6.4 Hz, 6H), 1.19-1.16 (m, 2H), 0.78 (t, J=6.9 Hz, 3H).

Compound 38: 5-chloro-3-(((trans)-4-(dimethylamino)cyclohexyl)(ethyl)amino)-N-((5-ethyl-2-methyl-3-oxo-2,3-dihydro-1H-pyrazol-4-yl)methyl)-2-methylbenzamide

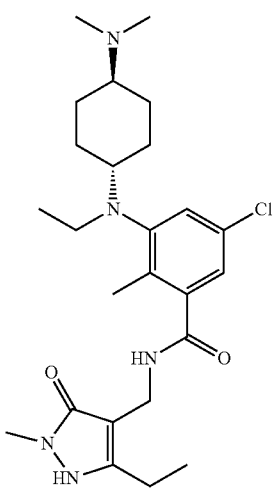 [SMILES: CCc1[nH]n(C)c(=O)c1CNC(=O)c1cc(Cl)cc(N(CC)[C@H]2CC[C@H](N(C)C)CC2)c1C]

Step 1: Synthesis of 5-chloro-3-(((trans)-4-(dimethylamino)cyclohexyl)(ethyl)amino)-N-((3-ethyl-5-methoxy-1-methyl-1H-pyrazol-4-yl)methyl)-2-methylbenzamide To a stirred solution of 5-chloro-3-(((trans)-4-(dimethylamino)cyclohexyl)(ethyl)amino)-2-methylbenzoic acid (0.25 g, 0.739 mmol) in DMSO (3 mL) (3-ethyl-5-methoxy-1-methyl-1H-pyrazol-4-yl)methanamine (Prepared as for the methyl analog in the procedure for synthesizing Compound 2 starting from ethyl 3-oxopentanoate, 0.187 g, 1.10 mmol) and triethylamine (0.3 mL, 2.21 mmol) were added. The reaction mixture was stirred at room temperature for 15 min before PyBOP (0.576 g, 1.10 mmol) was added to it and stirring was continued for overnight. After completion of the reaction, reaction mass was poured into ice cold water, extracted with 10% MeOH/DCM. The combined organic layers were dried, concentrated to obtain crude; which then purified by column chromatography to afford the title compound (0.3 g, 83.1%).

Step 2: Synthesis of 5-chloro-3-(((trans)-4-(dimethylamino)cyclohexyl)(ethyl)amino)-N-((5-ethyl-2-methyl-3-oxo-2,3-dihydro-1H-pyrazol-4-yl)methyl)-2-methylbenzamide To a stirring solution of 5-chloro-3-(((trans)-4-(dimethylamino)cyclohexyl)(ethyl)amino)-N-((3-ethyl-5-methoxy-1-methyl-1H-pyrazol-4-yl)methyl)-2-methylbenzamide (0.3 g, 0.613 mmol) in methanolic HCl (prepared by passing HCl gas through MeOH at −10° C. for long time) (3 mL/100 mg), conc. HCl (0.2 mL) was added and the reaction mixture was heated at 80° C. in a sealed tube for 16 h. On completion, solvent was removed under reduced pressure. The crude compound was purified by prep-HPLC to afford the title compound (0.09 g, 30.9%).

Analytical Data of the Formate Salt:
LCMS: 476.45 (M+1); $^1$H NMR (400 MHz, DMSO-d6) δ 8.61 (t, J=4.8 Hz, 1H), 7.18 (d, J=2.2 Hz, 1H), 6.96 (d, J=2.2 Hz, 1H), 4.07 (d, J=5.1 Hz, 2H), 3.38 (s, 3H), 3.02 (q, J=6.9 Hz, 2H), 2.68-2.53 (m, 2H), 2.49-2.40 (m, 1H), 2.35-2.31 (m, 1H), 2.25 (s, 6H), 2.15 (s, 3H), 1.83-1.76 (m, 4H), 1.40-1.37 (m, 2H), 1.27-1.19 (m, 2H), 1.11 (t, J=7.6 Hz, 3H), 0.78 (t, J=6.9 Hz, 3H).

Compound 39: 5-chloro-3-(((trans)-4-(dimethylamino)cyclohexyl)(ethyl) amino)-N-((5-isopropyl-2-methyl-3-oxo-2,3-dihydro-1H-pyrazol-4-yl)methyl)-2-methylbenzamide

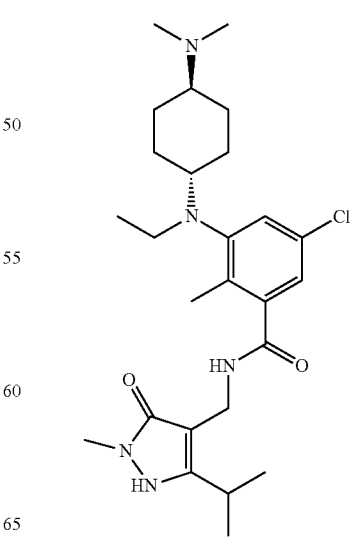

Step 1: Synthesis of 5-chloro-3-(((trans)-4-(dimethylamino)cyclohexyl)(ethyl)amino)-N-((3-isopropyl-5-methoxy-1-methyl-1H-pyrazol-4-yl)methyl)-2-methylbenzamide To a stirred solution of 5-chloro-3-(((trans)-4-(dimethylamino)cyclohexyl)(ethyl)amino)-2-methylbenzoic acid (0.5 g, 1.47 mmol) in DMSO (5 mL) (3-isopropyl-5-methoxy-1-methyl-1H-pyrazol-4-yl)methanamine (Prepared as for the methyl analog in the procedure for synthesizing Compound 2 starting from ethyl 4-methyl-3-oxopentanoate, 0.41 g, 2.21 mmol) and triethylamine (0.6 mL, 4.41 mmol) were added. The reaction mixture was stirred at room temperature for 15 min before PyBOP (1.1 g, 2.21 mmol) was added to it and stirring was continued for overnight. After completion of the reaction, reaction mass was poured into ice cold water, extracted with 10% MeOH/DCM. The combined organic layers were dried, concentrated to obtain crude; which then purified by column chromatography to afford the title compound (0.4 g, 54.1%).

Step 2: Synthesis of 5-chloro-3-(((trans)-4-(dimethylamino)cyclohexyl)(ethyl)amino)-N-((5-isopropyl-2-methyl-3-oxo-2,3-dihydro-1H-pyrazol-4-yl)methyl)-2-methylbenzamide To a stirring solution of 5-chloro-3-(((trans)-4-(dimethylamino)cyclohexyl)(ethyl)amino)-N-((3-isopropyl-5-methoxy-1-methyl-1H-pyrazol-4-yl)methyl)-2-methylbenzamide (0.4 g, 0.79 mmol) in methanolic HCl (prepared by passing HCl gas through MeOH at −10° C. for long time) (3 mL/100 mg), conc. HCl (0.2 mL) was added and the reaction mixture was heated at 80° C. in a sealed tube for 16 h. On completion, solvent was removed under reduced pressure. The crude compound was purified by prep-HPLC to afford the title compound (0.07 g, 18.04%).

Analytical Data:
LCMS: 490.50 (M+1); $^1$H NMR (400 MHz, DMSO-d6) δ 8.64 (s, 1H), 7.17 (d, J=2.2 Hz, 1H), 6.95 (d, J=2.1 Hz, 1H), 4.09 (d, J=5.1 Hz, 2H), 3.37-3.32 (m, 3H), 3.02 (q, J=6.9 Hz, 2H), 2.92-2.90 (m, 1H), 2.61 (t, J=11.1 Hz, 2H), 2.15 (s, 3H), 2.12 (s, 6H), 1.76-1.74 (m, 4H), 1.34 (t, J=12.1 Hz, 2H), 1.15 (d, J=6.9 Hz, 6H), 1.12-1.10 (m, 2H), 0.78 (t, J=6.9 Hz, 3H).

Compound 40: N-((5-butyl-2-methyl-3-oxo-2,3-dihydro-1H-pyrazol-4-yl)methyl)-5-chloro-3-(((trans)-4-(dimethylamino)cyclohexyl)(ethyl)amino)-2-methylbenzamide

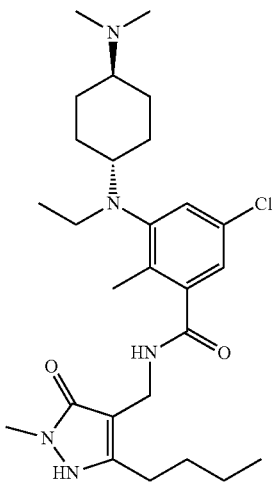 [SMILES: CCCCc1[nH]n(C)c(=O)c1CNC(=O)c1cc(Cl)cc(N(CC)[C@H]2CC[C@H](N(C)C)CC2)c1C]

Step 1: Synthesis of N-((3-butyl-5-methoxy-1-methyl-1H-pyrazol-4-yl)methyl)-5-chloro-3-(((trans)-4-(dimethylamino)cyclohexyl)(ethyl)amino)-2-methylbenzamide To a stirred solution of 5-chloro-3-(((trans)-4-(dimethylamino)cyclohexyl)(ethyl)amino)-2-methylbenzoic acid (0.5 g, 1.47 mmol) in DMSO (5 mL) (3-butyl-5-methoxy-1-methyl-1H-pyrazol-4-yl)methanamine (Prepared as for the methyl analog in the procedure for synthesizing Compound 2 starting from ethyl 3-oxoheptanoate, 0.435 g, 2.21 mmol) and triethylamine (0.6 mL, 4.41 mmol) were added. The reaction mixture was stirred at room temperature for 15 min before PyBOP (1.15 g, 2.21 mmol) was added to it and stirring was continued for overnight. After completion of the reaction, reaction mass was poured into ice cold water, extracted with 10% MeOH/DCM. The combined organic layers were dried, concentrated to obtain crude; which then purified by column chromatography to afford the title compound (0.5 g, 65.4%).

Step 2: Synthesis of N-((5-butyl-2-methyl-3-oxo-2,3-dihydro-1H-pyrazol-4-yl)methyl)-5-chloro-3-(((trans)-4-(dimethylamino)cyclohexyl)(ethyl)amino)-2-methylbenzamide To a stirred solution of N-((3-butyl-5-methoxy-1-methyl-1H-pyrazol-4-yl)methyl)-5-chloro-3-(((trans)-4-(dimethylamino)cyclohexyl)(ethyl)amino)-2-methylbenzamide (0.5 g, 0.97 mmol) in methanolic HCl (prepared by passing HCl gas through MeOH at −10° C. for long time) (3 mL/100 mg), conc. HCl (0.2 mL) was added and the reaction mixture was heated at 80° C. in a sealed tube for 16 h. On completion, solvent was removed under reduced pressure. The crude compound was purified by prep-HPLC to afford the title compound (0.04 g, 8.2%).

Analytical Data of the Formate Salt:
LCMS: 504.50 (M+1); $^1$H NMR (400 MHz, DMSO-d6) δ 8.59 (s, 1H), 7.17 (d, J=2.2 Hz, 1H), 6.95 (d, J=2.1 Hz, 1H), 4.06 (d, J=5.1 Hz, 2H), 3.37 (s, 3H), 3.03-3.01 (m, 3H), 2.61 (t, J=11.6 Hz, 1H), 2.42 (t, J=7.8 Hz, 2H), 2.19 (s, 6H), 2.15 (s, 3H), 1.83-1.71 (m, 4H), 1.53-1.49 (m, 2H), 1.44-1.12 (m, 6H), 0.88 (t, J=7.3 Hz, 3H), 0.78 (t, J=6.9 Hz, 3H).

Compound 41: 5-chloro-N-((2,5-dimethyl-3-oxo-2,3-dihydro-1H-pyrazol-4-yl)methyl)-3-(ethyl((trans)-4-hydroxytetrahydrofuran-3-yl)amino)-2-methylbenzamide

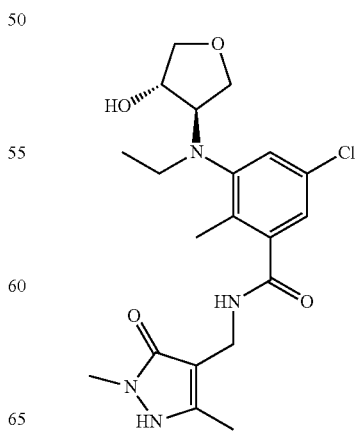

Step 1: Synthesis of methyl 5-chloro-3-(((trans)-4-hydroxytetrahydrofuran-3-yl)amino)-2-methylbenzoate To a stirred solution of methyl 3-amino-5-chloro-2-methylbenzoate (5 g, 25.12 mmol) in ACN (50 mL), (trans)-3,6-dioxabicyclo-[3.1.0]-hexane (2.16 g, 25.12 mmol) and BiCl₃ (11.88 g, 37.68 mmol) were added. The resulting reaction mixture was stirred at 80° C. for 16 h. The progress of the reaction was monitored by TLC. On completion, reaction mixture was filtered and filtrate was concentrated under reduced pressure. The crude material obtained was purified by column chromatography give the title compound (3 g, 41.9%).

Step 2: Synthesis of methyl 5-chloro-3-(ethyl((trans)-4-hydroxytetrahydrofuran-3-yl)amino)-2-methylbenzoate To a stirred solution of 5-chloro-3-(((trans)-4-hydroxytetrahydrofuran-3-yl)amino)-2-methylbenzoate (3 g, 10.52 mmol) and acetaldehyde (2.31 g, 52.63 mmol) in dichloroethane (30 mL), acetic acid (3.78 g, 63.16 mmol) was added and reaction was stirred at room temperature for 20 minutes. Then sodium triacetoxyborohydride (5.56 g, 26.30 mmol) was added at 0° C. and reaction was stirred at room temperature for 16 hours. The progress of the reaction was monitored by TLC. On completion, reaction was quenched with aqueous sodium bicarbonate, the organic layer was separated and the aqueous layer was extracted with dichloromethane. The combined organic layers were dried over anhydrous sodium sulphate and concentrated under reduced pressure. The crude compound was purified by column chromatography to afford the title compound (2.8 g, 85.10%).

Step 3: Synthesis of 5-chloro-3-(ethyl((trans)-4-hydroxytetrahydrofuran-3-yl)amino)-2-methylbenzoic Acid Aqueous NaOH (0.102 g, 2.55 mmol) was added to a solution of methyl 5-chloro-3-(ethyl((trans)-4-hydroxytetrahydrofuran-3-yl)amino)-2-methylbenzoate (0.4 g, 1.27 mmol) in EtOH (4 mL) and stirred at 60° C. for 1 h. After completion of the reaction, ethanol was removed under reduced pressure and acidified using 1N HCl up to pH 6. Extraction was carried out using MeOH: DCM (10:90). Combined organic layers were dried; concentrated afford the title compound (0.5 g, 91.4%).

Step 4: Synthesis of 5-chloro-3-(ethyl((trans)-4-hydroxytetrahydrofuran-3-yl)amino)-N-((5-methoxy-1,3-dimethyl-1H-pyrazol-4-yl)methyl)-2-methylbenzamide To a stirred solution 5-chloro-3-(ethyl((trans)-4-hydroxytetrahydrofuran-3-yl)amino)-2-methylbenzoic acid (0.35 g, 1.16 mmol) in DMSO (3 mL), (5-methoxy-1,3-dimethyl-1H-pyrazol-4-yl)methanamine (0.273 g, 1.750 mmol) and triethyl amine (0.4 mL, 2.91 mmol) were added. The reaction mixture was stirred at room temperature for 15 min before PyBOP (0.904 g, 1.74 mmol) was added to it at 0° C. and stirring was continued for overnight at room temperature. The progress of the reaction was monitored by TLC. After completion, reaction mixture was quenched with ice cold water and extracted with dichloromethane. The combined organic layers were dried over anhydrous sodium sulphate and concentrated under reduced pressure. The crude compound was purified by column chromatography afford the title compound (0.3 g, 59.1%).

Step 5: Synthesis of 5-chloro-N-((2,5-dimethyl-3-oxo-2,3-dihydro-1H-pyrazol-4-yl)methyl)-3-(ethyl((trans)-4-hydroxytetrahydrofuran-3-yl)amino)-2-methylbenzamide To a stirred solution of 5-chloro-3-(ethyl((trans)-4-hydroxytetrahydrofuran-3-yl)amino)-N-((5-methoxy-1,3-dimethyl-1H-pyrazol-4-yl)methyl)-2-methylbenzamide (0.3 g, 0.688 mmol) in ACN (3 mL), NaI (0.134 g, 0.894 mmol) was added and the solution was stirred at rt for 10 min. Then TMSCl (0.090 g, 0.825 mmol) was added and the resulting reaction mixture was stirred at 60° C. for 16 h. The progress of the reaction was monitored by TLC. On completion, reaction mass was quenched with methanol and filtered. Filtrate was concentrated under reduced pressure to afford the crude material; which then purified by prep. HPLC afford the title compound (0.03 g, 10.3%).

Analytical Data:

LCMS: 423.30 (M+1); ¹H NMR (400 MHz, DMSO-d6) δ 8.48 (t, J=4.7 Hz, 1H), 7.29 (d, J=2.2 Hz, 1H), 7.01 (d, J=2.1 Hz, 1H), 5.10 (s, 1H), 4.07 (dd, J=9.8, 4.5 Hz, 3H), 3.80 (td, J=9.0, 5.4 Hz, 2H), 3.56-3.38 (m, 3H), 3.29 (s, 3H), 2.99 (dh, J=13.8, 6.9 Hz, 2H), 2.14 (s, 3H), 2.01 (s, 3H), 0.78 (t, J=7.0 Hz, 3H).

Compound 42: 5-chloro-N-((2,5-dimethyl-3-oxo-2,3-dihydro-1H-pyrazol-4-yl)methyl)-3-(ethyl((trans)-4-methoxytetrahydrofuran-3-yl)amino)-2-methylbenzamide

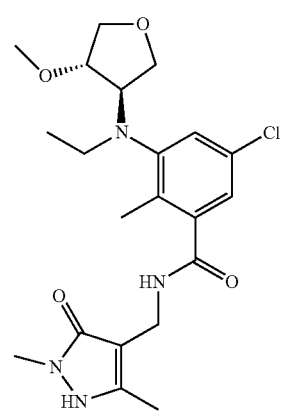 [SMILES: CCN(c1cc(Cl)cc(C(=O)NCc2c(C)[nH]n(C)c2=O)c1C)[C@@H]1COC[C@H]1OC]

Step 1: Synthesis of methyl 5-chloro-3-(ethyl((trans)-4-methoxytetrahydrofuran-3-yl) amino)-2-methylbenzoate To a stirred solution of methyl 5-chloro-3-(ethyl((trans)-4-hydroxytetrahydrofuran-3-yl)amino)-2-methylbenzoate (0.5 g, 1.59 mmol) in DMF (5 mL) at 0° C., NaH (60%, 0.096 g, 2.39 mmol) was added and the solution was stirred at same temperature for 15 min. Then methyl iodide (0.272 g, 1.92 mmol) was added and the resulting reaction mixture was stirred at rt for 2 h. The progress of the reaction was monitored by TLC. On completion, reaction mass was quenched with ice cold water and extracted with ethyl acetate. The combined organic layers were dried over anhydrous sodium sulphate and concentrated under reduced pressure. The crude material obtained was purified by column chromatography afford the title compound (0.3 g, 57.5%).

Step 2: Synthesis of 5-chloro-3-(ethyl((trans)-4-methoxytetrahydrofuran-3-yl)amino)-2-methylbenzoic Acid Aqueous NaOH (0.074 g, 1.83 mmol) was added to the solution of methyl 5-chloro-3-(ethyl((trans)-4-methoxytetrahydrofuran-3-yl)amino)-2-methylbenzoate (0.3 g, 0.917 mmol) in EtOH (3 mL) and stirred at 60° C. for 1 h. After completion of the reaction, ethanol was removed under reduced pressure and the reaction mass was acidified using 1N HCl and extracted with 10% MeOH/DCM. The combined organic layers were dried; concentrated giving the title compound (0.26 g, 90.3%).

Step 3: Synthesis of 5-chloro-3-(ethyl((trans)-4-methoxytetrahydrofuran-3-yl)amino)-N-((5-methoxy-1,3-dimethyl-1H-pyrazol-4-yl)methyl)-2-methylbenzamide To a solution of 5-chloro-3-(ethyl((trans)-4-methoxytetrahydrofuran-3-yl)amino)-2-methylbenzoic acid (0.26 g, 0.828 mmol) in DMSO (3 mL), (5-methoxy-1,3-dimethyl-1H-pyrazol-4-yl)methanamine (0.193 g, 1.24 mmol) and triethylamine (0.28 mL, 2.07 mmol) were added. The reaction mixture was stirred at room temperature for 15 min before PyBOP (0.645 g, 1.24 mmol) was added to it at 0° C. and further stirred for overnight at room temperature. After completion, the reaction mass was diluted with ice water and extracted with 10% MeOH/DCM. The combined organic layers were dried over sodium sulphate and concentrated under reduced pressure. The crude compound was purified by column chromatography to afford the title compound (0.2 g, 53.8%).

Step 4: Synthesis of 5-chloro-N-((2,5-dimethyl-3-oxo-2,3-dihydro-1H-pyrazol-4-yl)methyl)-3-(ethyl((trans)-4-methoxytetrahydrofuran-3-yl)amino)-2-methylbenzamide A mixture of 5-chloro-3-(ethyl((trans)-4-methoxytetrahydrofuran-3-yl)amino)-N-((5-methoxy-1,3-dimethyl-1H-pyrazol-4-yl)methyl)-2-methylbenzamide (0.15 g, 0.33 mmol) and methanolic HCl (3 mL) was heated at 70° C. in a sealed tube for 12 h. On completion, solvent was removed under reduced pressure and the crude compound obtained was purified by prep-HPLC give the title compound (0.014 g, 9.7%).

Analytical Data of Formate Salt:
LCMS: 437.35 (M+1); $^1$H NMR (400 MHz, DMSO-d6) δ 8.54 (t, J=4.7 Hz, 1H), 7.38 (d, J=2.2 Hz, 1H), 7.04 (d, J=2.2 Hz, 1H), 4.06 (d, J=5.1 Hz, 2H), 3.84-3.74 (m, 3H), 3.71-3.59 (m, 2H), 3.46-3.40 (m, 1H), 3.35 (s, 3H), 3.12 (s, 3H), 3.01 (dt, J=8.1, 6.1 Hz, 2H), 2.15 (s, 3H), 2.04 (s, 3H), 0.79 (t, J=7.0 Hz, 3H).

Compound 43: Synthesis of 5-chloro-N-((2,5-dimethyl-3-oxo-2,3-dihydro-1H-pyrazol-4-yl)methyl)-3-(((trans)-4-ethoxytetrahydrofuran-3-yl)(ethyl)amino)-2-methylbenzamide

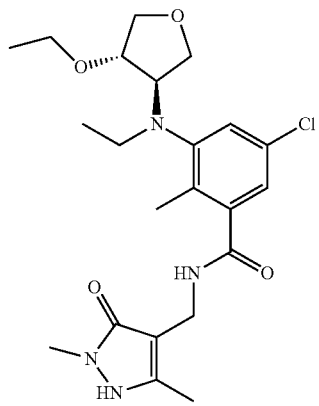 [SMILES: CCO[C@@H]1COC[C@H]1N(CC)c1cc(Cl)cc(C(=O)NCc2c(C)[nH]n(C)c2=O)c1C]

Step 1: Synthesis of 5-chloro-3-(((trans)-4-ethoxytetrahydrofuran-3-yl)(ethyl)amino)-2-methylbenzoic Acid To a stirred solution of methyl 5-chloro-3-(ethyl((trans)-4-hydroxytetrahydrofuran-3-yl)amino)-2-methylbenzoate (0.6 g, 1.91 mmol) in DMF (5 mL) at 0° C., NaH (60%, 0.154 g, 3.83 mmol) was added and the solution was stirred at same temperature for 15 min. Ethyl iodide (0.596 g, 3.83 mmol) was added and the resulting reaction mixture was stirred at rt for 3 h. The progress of the reaction was monitored by TLC. On completion, reaction mass was quenched with ice cold water and extracted with 10% MeOH/DCM. The combined organic layers were dried over anhydrous sodium sulphate and concentrated under reduced pressure to afford crude compound that was used in the next step without further purification (0.3 g, 47.9%).

Step 2: Synthesis of 5-chloro-3-(((trans)-4-ethoxytetrahydrofuran-3-yl)(ethyl)amino)-N-((5-methoxy-1,3-dimethyl-1H-pyrazol-4-yl)methyl)-2-methylbenzamide To a solution of 5-chloro-3-(((trans)-4-ethoxytetrahydrofuran-3-yl)(ethyl)amino)-2-methylbenzoic acid (0.15 g, 0.458 mmol) in DMSO (2 mL), (5-methoxy-1,3-dimethyl-1H-pyrazol-4-yl)methanamine (0.107 g, 0.688 mmol) and triethyl amine (0.19 mL, 1.37 mmol) were added. The reaction mixture was stirred at room temperature for 15 min before PyBOP (0.357 g, 0.688 mmol) was added to it at 0° C. and further stirred for overnight at room temperature. After completion, the reaction mass was diluted with ice water and extracted with 10% MeOH/DCM. The combined organic layers were dried over sodium sulphate and concentrated under reduced pressure. The crude compound obtained was purified by column chromatography to afford the title compound (0.21 g, 98.6%).

Step 3: Synthesis of 5-chloro-N-((2,5-dimethyl-3-oxo-2,3-dihydro-1H-pyrazol-4-yl)methyl)-3-(((trans)-4-ethoxytetrahydrofuran-3-yl)(ethyl)amino)-2-methylbenzamide To a stirring solution of 5-chloro-3-(((trans)-4-ethoxytetrahydrofuran-3-yl)(ethyl)amino)-N-((5-methoxy-1,3-dimethyl-1H-pyrazol-4-yl)methyl)-2-methylbenzamide (0.2 g, 0.43 mmol) in methanolic HCl (prepared by passing HCl gas through MeOH at −10° C. for long time) (3 mL/100 mg), conc. HCl (0.2 mL) was added and the reaction mixture was heated at 80° C. in a sealed tube for 12 h. On completion, solvent was removed under reduced pressure and the crude compound obtained was purified by prep-HPLC afford the title compound (0.05 g, 25.9%).

Analytical Data:

LCMS: 451.35 (M+1); $^1$H NMR (400 MHz, DMSO-d6) δ 10.44 (s, 1H), 8.54 (s, 1H), 7.37 (d, J=2.2 Hz, 1H), 7.04 (d, J=2.1 Hz, 1H), 4.06 (d, J=5.0 Hz, 2H), 3.80 (ddd, J=19.5, 10.7, 5.1 Hz, 3H), 3.67-3.59 (m, 2H), 3.45-3.20 (m, 6H), 2.99 (q, J=7.0 Hz, 2H), 2.15 (s, 3H), 2.04 (s, 3H), 1.03 (t, J=7.0 Hz, 3H), 0.79 (t, J=7.0 Hz, 3H).

Compound 44: 5-chloro-3-(ethyl((trans)-4-(2-methoxyethoxy) tetrahydrofuran-3-yl)amino)-N-((5-methoxy-1,3-dimethyl-1H-pyrazol-4-yl)methyl)-2-methylbenzamide

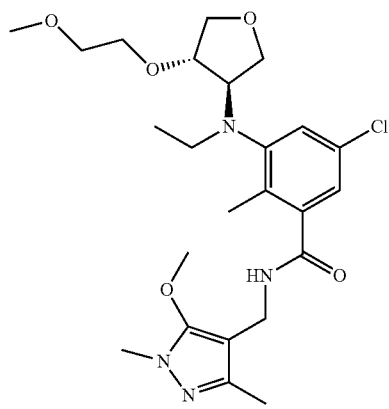 [SMILES: CCN(c1cc(Cl)cc(C(=O)NCc2c(C)nn(C)c2OC)c1C)[C@@H]1COC[C@H]1OCCOC]

Step 2: Synthesis of 5-chloro-3-(ethyl ((trans)-4-(2-methoxyethoxy) tetrahydrofuran-3-yl) amino)-2-methylbenzoic Acid To a stirred solution of methyl 5-chloro-3-(ethyl((trans)-4-hydroxytetrahydrofuran-3-yl)amino)-2-methylbenzoate (0.18 g, 0.602 mmol) in DMF (2 mL) at 0° C., NaH (60%, 0.048 g, 1.20 mmol) was added and the solution was stirred at same temperature for 15 min. Then 1-bromo-2-methoxyethane (0.251 g, 1.81 mmol) was added and the resulting reaction mixture was stirred at rt for 2 h. The progress of the reaction was monitored by TLC. On completion, reaction mass was quenched with ice cold water and extracted with ethyl acetate. The combined organic layers were dried over anhydrous sodium sulphate and concentrated under reduced pressure to afford crude compound that was used in the next reaction without further purification (0.1 g, 46.7%).

Step 2: Synthesis of 5-chloro-3-(ethyl((trans)-4-(2-methoxyethoxy)tetrahydrofuran-3-yl)amino)-N-((5-methoxy-1,3-dimethyl-1H-pyrazol-4-yl)methyl)-2-methylbenzamide To a solution of methyl 5-chloro-3-(ethyl((trans)-4-hydroxytetrahydrofuran-3-yl)amino)-2-methylbenzoate (0.2 g, 0.560 mmol) in DMSO (2 mL), (5-methoxy-1,3-dimethyl-1H-pyrazol-4-yl)methanamine (0.175 g, 1.12 mmol) and triethylamine (0.23 mL, 1.68 mmol) were added. The reaction mixture was stirred at room temperature for 15 min before PyBOP (0.437 g, 0.84 mmol) was added to it at 0° C. and further stirred for overnight at room temperature. After completion, the reaction mass was diluted with ice cold water and extracted with 10% MeOH/DCM. The combined organic layers were dried over sodium sulphate and concentrated under reduced pressure. The crude compound was purified by column chromatography to afford the title compound (0.13 g, 47.1%).

Analytical Data:

LCMS: 495.40 (M+1); $^1$H NMR (400 MHz, DMSO-d6) δ 8.50 (bs, 1H), 7.36 (s, 1H), 7.02 (s, 1H), 4.21-4.14 (m, 4H), 3.93 (s, 3H), 3.80-3.78 (m, 2H), 3.66-3.63 (m, 2H), 3.49-3.40 (m, 4H), 3.17-3.16 (m, 6H), 3.00-2.98 (m, 2H), 2.15 (s, 3H), 2.07 (s, 3H), 0.79 (t, J=7.0 Hz, 3H).

Compound 45: 5-chloro-N-((2,5-dimethyl-3-oxo-2,3-dihydro-1H-pyrazol-4-yl)methyl)-3-(ethyl((trans)-4-(2-methoxyethoxy)tetrahydrofuran-3-yl)amino)-2-methylbenzamide

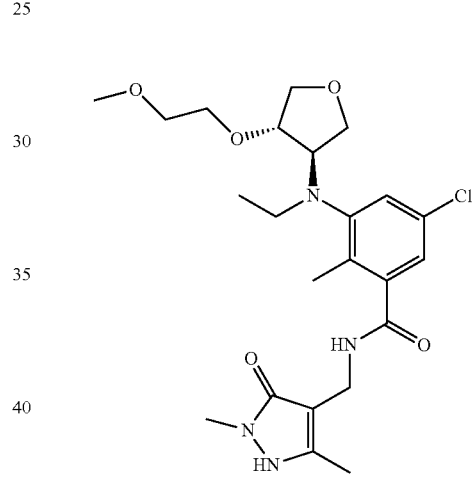

Step 1: Synthesis of 5-chloro-N-((2,5-dimethyl-3-oxo-2,3-dihydro-1H-pyrazol-4-yl)methyl)-3-(ethyl ((trans)-4-(2-methoxyethoxy)tetrahydrofuran-3-yl) amino)-2-methylbenzamide A mixture of 5-chloro-3-(ethyl((trans)-4-(2-methoxyethoxy)tetrahydrofuran-3-yl)amino)-N-((5-methoxy-1,3-dimethyl-1H-pyrazol-4-yl)methyl)-2-methylbenzamide (0.1 g, 0.202 mmol) and methanolic HCl (5 mL) was heated at 80° C. in a sealed tube for 12 h. On completion, solvent was removed under reduced pressure and the crude compound obtained was purified by prep-HPLC to afford the title compound (0.020 g, 20.6%).

Analytical Data of Formate Salt:

LCMS: 481.40 (M+1); $^1$H NMR (400 MHz, DMSO-d6) δ 8.57 (t, J=5.2 Hz, 1H), 7.36 (d, J=2.1 Hz, 1H), 7.04 (d, J=2.2 Hz, 1H), 4.06 (d, J=5.2 Hz, 2H), 3.97-3.89 (m, 2H), 3.85-3.74 (m, 2H), 3.68-3.60 (m, 2H), 3.39-3.34 (m, 8H), 3.19 (s, 3H), 3.00-2.99 (m, 2H), 2.15 (s, 3H), 2.03 (s, 3H), 0.79 (t, J=6.9 Hz, 3H).

Compound 46: Synthesis of N-((2,5-dimethyl-3-oxo-2,3-dihydro-1H-pyrazol-4-yl)methyl)-5-(ethyl(tetrahydro-2H-pyran-4-yl)amino)-4-methyl-4'-(morpholinomethyl)-[1,1'-biphenyl]-3-carboxamide

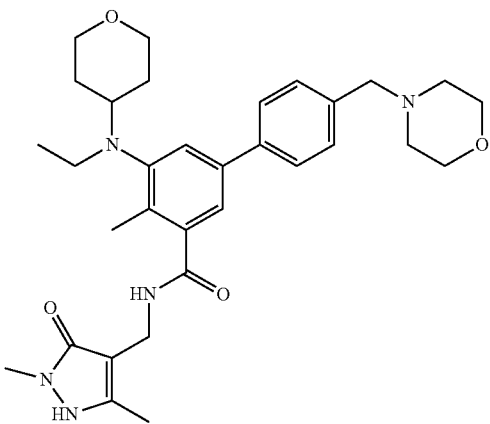 [SMILES: CCN(c1cc(-c2ccc(CN3CCOCC3)cc2)cc(C(=O)NCc2c(C)[nH]n(C)c2=O)c1C)C1CCOCC1]

Step 1: Synthesis of 5-(ethyl(tetrahydro-2H-pyran-4-yl)amino)-N-((5-methoxy-1,3-dimethyl-1H-pyrazol-4-yl)methyl)-4-methyl-4'-(morpholinomethyl)-[1,1'-biphenyl]-3-carboxamide To a stirred solution 5-(ethyl(tetrahydro-2H-pyran-4-yl)amino)-4-methyl-4'-(morpholinomethyl)-[1,1'-biphenyl]-3-carboxylic acid (0.2 g, 0.456 mmol) in DMSO (3 mL), (5-methoxy-1,3-dimethyl-1H-pyrazol-4-yl)methanamine (0.107 g, 0.684 mmol) and triethylamine (0.2 mL, 1.36 mmol) were added. The reaction mixture was stirred at room temperature for 15 min before PyBOP (0.356 g, 0.684 mmol) was added to it at 0° C. and stirring was continued for overnight at room temperature. After completion of the reaction, reaction mixture was poured on ice; extracted with dichloromethane. The combined organic layers were dried over anhydrous sodium sulphate and concentrated under reduced pressure. The crude compound was purified by column chromatography to afford the title compound (0.24 g, 91.6%).

Step 2: Synthesis of N-((2,5-dimethyl-3-oxo-2,3-dihydro-1H-pyrazol-4-yl)methyl)-5-(ethyl(tetrahydro-2H-pyran-4-yl)amino)-4-methyl-4'-(morpholinomethyl)-[1,1'-biphenyl]-3-carboxamide To a stirred solution of 5-(ethyl(tetrahydro-2H-pyran-4-yl)amino)-N-((5-methoxy-1,3-dimethyl-1H-pyrazol-4-yl)methyl)-4-methyl-4'-(morpholinomethyl)-[1,1'-biphenyl]-3-carboxamide (0.24 g, 0.42 mmol) in ACN (3 mL), NaI (0.082 g, 0.542 mmol) was added and the solution was stirred at rt for 10 min. Then TMSCl (0.055 g, 0.504 mmol) was added and the resulting reaction mixture was stirred at 60° C. for 16 h. The progress of the reaction was monitored by TLC. On completion, reaction mass was quenched with methanol and solvent was removed under reduced pressure. The residue obtained was basified with sodium bicarbonate solution and extracted with 10% methanol/DCM. The combined organic layers were dried over anhydrous $Na_2SO_4$ and concentrated under reduced pressure. The crude compound was purified by column chromatography afford the title compound (0.06 g, 25.6%).

Analytical Data:
LCMS: 562.30 (M+1); $^1$H NMR (400 MHz, DMSO-d6) δ 8.63 (s, 1H), 7.57 (d, J=7.9 Hz, 2H), 7.45-7.34 (m, 3H), 7.24 (d, J=1.8 Hz, 1H), 4.09 (d, J=5.2 Hz, 2H), 3.87-3.79 (m, 2H), 3.57 (t, J=4.6 Hz, 4H), 3.48 (s, 2H), 3.24 (d, J=12.3 Hz, 2H), 3.19-2.96 (m, 3H), 2.36 (t, J=4.5 Hz, 4H), 2.25 (s, 3H), 2.05 (s, 3H), 1.71-1.62 (m, 2H), 1.53 (qd, J=11.7, 4.3 Hz, 2H), 0.83 (t, J=6.9 Hz, 3H), 3H merged in solvent peak.

Compound 47: Synthesis of N-((2,5-dimethyl-3-oxo-2,3-dihydro-1H-pyrazol-4-yl)methyl)-3-(ethyl(tetrahydro-2H-pyran-4-yl)amino)-2-methyl-5-(6-(piperazin-1-yl)pyridin-3-yl)benzamide

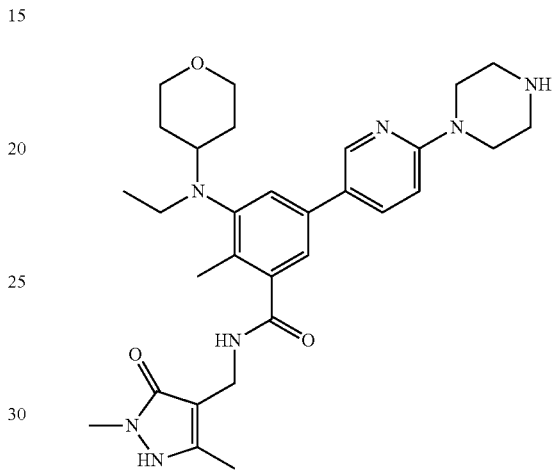

Step 1: Synthesis of tert-butyl 4-(5-(3-(ethyl(tetrahydro-2H-pyran-4-yl)amino)-5-(((5-methoxy-1,3-dimethyl-1H-pyrazol-4-yl)methyl)carbamoyl)-4-methylphenyl)pyridin-2-yl) piperazine-1-carboxylate To a stirred solution 5-(6-(4-(tert-butoxycarbonyl)piperazin-1-yl)pyridin-3-yl)-3-(ethyl(tetrahydro-2H-pyran-4-yl)amino)-2-methylbenzoic acid (0.4 g, 0.76 mmol) in DMSO (3 mL), (5-methoxy-1,3-dimethyl-1H-pyrazol-4-yl)methanamine (0.179 g, 1.14 mmol) and triethyl amine (0.32 mL, 2.29 mmol) were added. The reaction mixture was stirred at room temperature for 15 min before PyBOP (0.592 g, 1.14 mmol) was added to it at 0° C. and stirring was continued for overnight at room temperature. After completion of the reaction, reaction mixture was diluted with ice cold water and extracted with 10% MeOH/DCM. The combined organic layers were dried over anhydrous $Na_2SO_4$ and concentrated under reduced pressure. The crude compound was purified by column chromatography to the title compound (0.24 g, 47.6%).

Step 2: Synthesis of N-((2,5-dimethyl-3-oxo-2,3-dihydro-1H-pyrazol-4-yl)methyl)-3-(ethyl(tetrahydro-2H-pyran-4-yl)amino)-2-methyl-5-(6-(piperazin-1-yl)pyridin-3-yl)benzamide To a stirred solution of tert-butyl 4-(5-(3-(ethyl(tetrahydro-2H-pyran-4-yl)amino)-5-(((5-methoxy-1,3-dimethyl-1H-pyrazol-4-yl)methyl)carbamoyl)-4-methylphenyl)pyridin-2-yl)piperazine-1-carboxylate (0.24 g, 0.36 mmol) in ACN (3 mL), NaI (0.071 g, 0.47 mmol) was added and the solution was stirred at rt for 10 min. Then TMSCl (0.047 g, 0.43 mmol) was added and the resulting reaction mixture was stirred at 60° C. for 16 h. The progress of the reaction was monitored by TLC. On completion, reaction mass was quenched with methanol and concentrated under reduced pressure. The residue obtained was basified with sodium bicarbonate solution and extracted with 10% methanol/DCM. The combined organic layers were dried over anhydrous sodium sulphate and concentrated under reduced pressure. The crude compound was purified by column chromatography to afford the title compound (0.026 g, 13.1%).

Analytical Data:
LCMS: 548.55 (M+1); $^1$H NMR (400 MHz, DMSO-d6) δ 8.63 (bs, 1H), 8.39 (bs, 1H), 7.80-7.78 (m, 1H), 7.38 (s, 1H), 7.19 (s, 1H), 6.85 (d, J=8.4 Hz, 1H), 4.07 (d, J=4.4 Hz, 2H), 3.82 (d, J=10 Hz, 2H), 3.43-3.42 (m, 4H), 3.28-3.22 (m, 3H), 3.12-3.05 (m, 3H), 2.93-2.78 (m, 4H), 2.23 (s, 3H), 2.05 (s, 3H), 1.67-1.64 (m, 2H), 1.52-1.50 (m, 2H), 0.82 (t, J=6.8 Hz, 3H), 2H merged in solvent peak.

Compound 48: 5-chloro-3-(((trans)-4-(dimethylamino)cyclohexyl)(ethyl) amino)-N-((2-methoxy-5,7-dimethylpyrazolo[1,5-a]pyrimidin-3-yl)methyl)-2-methylbenzamide

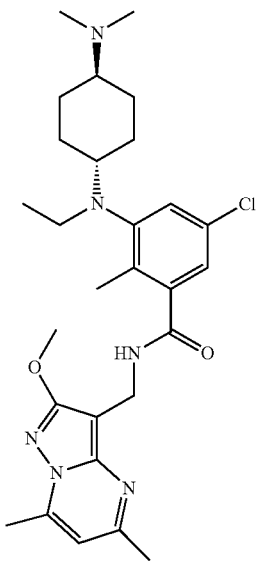 [SMILES: CCN(c1cc(Cl)cc(C(=O)NCc2c(OC)nn3c(C)cc(C)nc23)c1C)[C@H]1CC[C@H](N(C)C)CC1]

Step 1: Synthesis of 2-methoxy-5,7-dimethylpyrazolo [1,5-a]pyrimidine-3-carbonitrile To a stirred solution of 2-(dimethoxymethylene)malononitrile (1 g, 7.24 mmol) in methanol (10 mL) hydrazine hydrate (0.4 g, 7.97 mmol) was added and the solution was stirred at 80° C. for 4 h. The progress of the reaction was monitored by TLC. On completion, ethanol was added to reaction mixture followed by addition of pentane-2,4-dione (1.08 g, 10.86 mmol) and diethylamine (1.58 g, 21.74 mmol). The resulting reaction mixture was stirred at 80° C. for 2 h. The progress of the reaction was monitored by TLC. On completion, reaction mixture was concentrated to dryness and the crude material obtained was purified by column chromatography to afford the title compound (0.9 g, 61.6%).

Step 2: Synthesis of (2-methoxy-5,7-dimethylpyrazolo[1,5-a]pyrimidin-3-yl)methanamine To a solution of 2-methoxy-5,7-dimethylpyrazolo [1,5-a] pyrimidine-3-carbonitrile (0.9 g, 4.45 mmol) in methanol (10 mL), catalytic amount of Raney Nickel and ammonia solution (4 mL) were added. Reaction mass was stirred at room temperature under hydrogen pressure (balloon pressure) for 16 h. On completion of reaction, reaction mass was filtered through celite bed, celite bed washed with methanol and filtrate was concentrated under reduced pressure to afford crude compound that was used in the next reaction without further purification (0.7 g, 76.3%).

Step 3: Synthesis of 5-chloro-3-(((trans)-4-(dimethylamino)cyclohexyl)(ethyl)amino)-N-((2-methoxy-5,7-dimethylpyrazolo[1,5-a]pyrimidin-3-yl)methyl)-2-methylbenzamide To a solution of 5-(6-(4-(tert-butoxycarbonyl)piperazin-1-yl)pyridin-3-yl)-3-(ethyl(tetrahydro-2H-pyran-4-yl)amino)-2-methylbenzoic acid (0.4 g, 1.18 mmol) in DMSO (2 mL), (2-methoxy-5,7-dimethylpyrazolo[1,5-a]pyrimidin-3-yl)methanamine (0.365 g, 1.77 mmol) and triethylamine (0.5 mL, 3.56 mmol) were added. The reaction mixture was stirred at room temperature for 15 min before PyBOP (0.920 g, 1.77 mmol) was added to it at 0° C. and further stirred for overnight at room temperature. After completion, the reaction mass was poured into ice water and extraction was carried out using 10% MeOH/DCM. The combined organic layers were dried over sodium sulphate and concentrated under reduced pressure. The crude compound was purified by column chromatography to afford the title compound (0.34 g, 54.7%).

Analytical Data of Formate Salt:
LCMS: 527.50 (M+1); $^1$H NMR (400 MHz, Methanol-d4) δ 7.20 (s, 1H), 7.12 (s, 1H), 6.64 (s, 1H), 4.61 (s, 2H), 4.09 (s, 3H), 3.13-3.11 (m, 2H), 3.08 (q, J=6.8 Hz, 2H), 2.77 (s, 6H), 2.65 (s, 3H), 2.52 (s, 3H), 2.27 (s, 3H), 2.12-2.00 (m, 4H), 1.54-1.47 (m, 4H), 0.86 (t, J=7.0 Hz, 3H).

Compound 49: 5-chloro-N-((5,7-dimethyl-2-oxo-1,2-dihydropyrazolo[1,5-a]pyrimidin-3-yl)methyl)-3-(((trans)-4-(dimethylamino)cyclohexyl)(ethyl)amino)-2-methylbenzamide

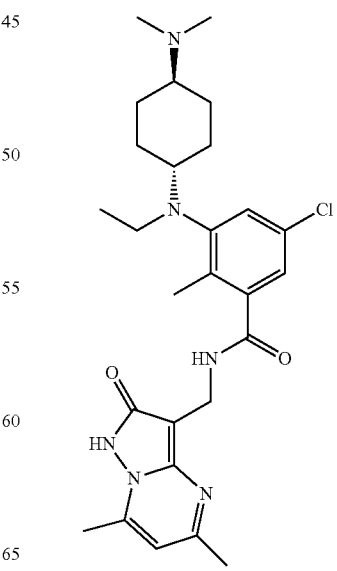

Step 1: Synthesis of 5-chloro-N-((5,7-dimethyl-2-oxo-1,2-dihydropyrazolo[1,5-a]pyrimidin-3-yl)methyl)-3-(((trans)-4-(dimethylamino)cyclohexyl)(ethyl)amino)-2-methylbenzamide To a stirred solution of 5-chloro-3-(((trans)-4-(dimethylamino)cyclohexyl)(ethyl)amino)-N-((2-methoxy-5,7-dimethylpyrazolo[1,5-a]pyrimidin-3-yl)methyl)-2-methylbenzamide (0.2 g, 0.379 mmol), BBr$_3$ (15 mL, 1M in DCM) was added 0° C. The resulting reaction mixture was stirred at room temperature for overnight. After completion, the reaction mass was quenched with ice cold water and concentrated under reduced pressure. The crude compound was purified by prep.HPLC to afford the title compound (0.025 g, 12.9%).

Analytical Data of the TFA Salt:

LCMS: 513.40 (M+1); $^1$H NMR (400 MHz, DMSO-d6) δ 9.33 (s, 1H), 8.65 (t, J=5.1 Hz, 1H), 7.20 (d, J=2.2 Hz, 1H), 7.09 (d, J=2.1 Hz, 1H), 6.67 (s, 1H), 4.40 (d, J=5.0 Hz, 2H), 3.10 (s, 1H), 3.02 (q, J=6.9 Hz, 2H), 2.76-2.74 (m, 1H), 2.67 (d, J=5.0 Hz, 6H), 2.53 (s, 3H), 2.43 (s, 3H), 2.18 (s, 3H), 1.94 (d, J=5.7 Hz, 2H), 1.83 (s, 2H), 1.42 (t, J=9.5 Hz, 4H), 0.78 (t, J=6.8 Hz, 3H).

Compound 50: 5-chloro-3-(((trans)-4(dimethylamino)cyclohexyl)(ethyl)amino)-N-((2-methoxypyrazolo[1,5-a]pyrimidin-3-yl)methyl)-2-methylbenzamide

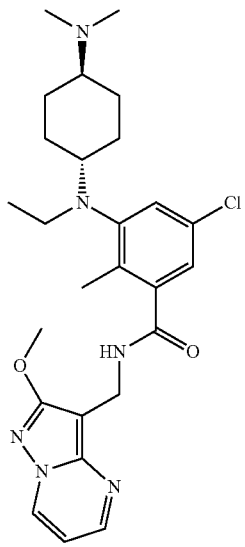 [SMILES: CCN(c1cc(Cl)cc(C(=O)NCc2c(OC)nn3cccnc23)c1C)[C@H]1CC[C@H](N(C)C)CC1]

Step 1: Synthesis of 2-methoxypyrazolo-[1,5-a]-pyrimidine-3-carbonitrile

To a mixture of 3-amino-5-methoxy-1H-pyrazole-4-carbonitrile (0.5 g, 3.62 mmol) and 1,1,3,3-tetramethoxypropane (0.891 g, 5.43 mmol) in ethanol (10 mL), TFA (2 mL) was added. The resulting reaction mixture was stirred at 80° C. for 5 h. The progress of the reaction was monitored by TLC. On completion, reaction mixture was concentrated to dryness under reduced pressure to afford the crude material; which then purified by column chromatography give the title compound (0.45 g, 71.4%).

Step 2: Synthesis of (2-methoxypyrazolo-[1,5-a]-pyrimidin-3-yl)methanamine

To a solution of 2-methoxypyrazolo-[1,5-a]-pyrimidine-3-carbonitrile (0.45 g, 2.58 mmol) in methanol (5 mL), catalytic amount of Raney Nickel and ammonia solution (2 mL) were added. Reaction mass was stirred at room temperature under hydrogen pressure (balloon pressure) for 18 h. On completion of reaction, reaction mass was filtered through celite bed, celite bed washed with methanol and filtrate was concentrated under reduced pressure to afford the title compound (0.4 g, 87.0%).

Step 3: Synthesis of 5-chloro-3-(((trans)-4-(dimethylamino)cyclohexyl)(ethyl)amino)-N-((2-methoxypyrazolo[1,5-a]pyrimidin-3-yl)methyl)-2-methylbenzamide To a solution of 5-(6-(4-(tert-butoxycarbonyl)piperazin-1-yl)pyridin-3-yl)-3-(ethyl(tetrahydro-2H-pyran-4-yl)amino)-2-methylbenzoic acid (0.3 g, 0.887 mmol) in DMSO (2 mL), (2-methoxypyrazolo[1,5-a] pyrimidin-3-yl)methanamine (0.315 g, 1.77 mmol) and triethyl amine (0.268 g, 2.66 mmol) were added. The reaction mixture was stirred at room temperature for 15 min before PyBOP (0.692 g, 1.33 mmol) was added to it at 0° C. and further stirred for overnight at room temperature. After completion, the reaction mass was diluted with ice cold water and extracted with 10% MeOH/DCM. The combined organic layers were dried over sodium sulphate and concentrated under reduced pressure. The crude compound was purified by column chromatography to afford the title compound (0.25 g, 56.6%).

Analytical Data of the TFA Salt:

LCMS: 499.40 (M+1); $^1$H NMR (400 MHz, Methanol-d4) δ 8.69 (dd, J=6.9, 1.8 Hz, 1H), 8.41 (dd, J=4.2, 1.8 Hz, 1H), 7.22 (d, J=2.2 Hz, 1H), 7.11 (t, J=2.9 Hz, 1H), 6.83 (dd, J=6.9, 4.2 Hz, 1H), 4.63 (s, 2H), 4.08 (s, 3H), 3.37-3.25 (m, 1H), 3.22-3.05 (m, 3H), 2.81 (s, 6H), 2.27 (s, 3H), 2.12-1.98 (m, 4H), 1.61-1.42 (m, 4H), 0.86 (t, J=6.9 Hz, 3H).

Compound 51: 5-chloro-3-(((trans)-4-(dimethylamino)cyclohexyl)(ethyl) amino)-2-methyl-N-((2-oxo-1,2-dihydropyrazolo-[1,5-a]-pyrimidin-3-yl)methyl)benzamide

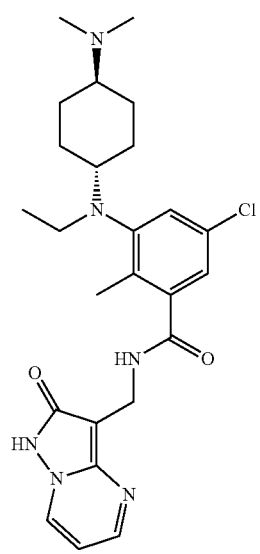 [SMILES: CCN(c1cc(Cl)cc(C(=O)NCc2c(=O)[nH]n3cccnc23)c1C)[C@H]1CC[C@H](N(C)C)CC1]

Step 1: Synthesis of 5-chloro-3-(((trans)-4-(dimethylamino)cyclohexyl)(ethyl)amino)-2-methyl-N-((2-oxo-1,2-dihydropyrazolo-[1,5-a]-pyrimidin-3-yl)methyl)benzamide To a stirred solution of 5-chloro-3-(((trans)-4-(dimethylamino)cyclohexyl)(ethyl)amino)-N-((2-methoxypyrazolo-[1,5-a]-pyrimidin-3-yl)methyl)-2-methylbenzamide (0.2 g, 0.401 mmol), BBr$_3$ (15 mL, 1M in DCM) was added 0° C. The resulting reaction mixture was stirred at room temperature for overnight. After completion, the reaction mass was quenched with ice cold water and concentrated under reduced pressure. The crude compound was purified by prep. HPLC to afford the title compound (0.018 g, 9.3%).

Analytical Data of the TFA Salt:

LCMS: 485.35 (M+1); $^1$H NMR (400 MHz, Methanol-d4) δ 8.59 (dd, J=6.9, 1.8 Hz, 1H), 8.53 (s, 1H), 8.36 (dd, J=4.2, 1.8 Hz, 1H), 7.22 (d, J=2.2 Hz, 1H), 7.13 (d, J=2.0 Hz, 1H), 6.80-6.76 (m, 1H), 4.79 (s, 2H), 3.26-2.80 (m, 3H), 2.78-2.72 (m, 1H), 2.70 (s, 6H), 2.21 (s, 3H), 2.08-1.94 (m, 4H), 1.56-1.31 (m, 4H), 0.85 (t, J=6.8 Hz, 3H).

Compound 52: 5-chloro-3-(((trans)-4-(dimethylamino)cyclohexyl)(ethyl) amino)-N-((1-ethyl-5-methyl-3-oxo-2,3-dihydro-1H-pyrazol-4-yl)methyl)-2-methylbenzamide

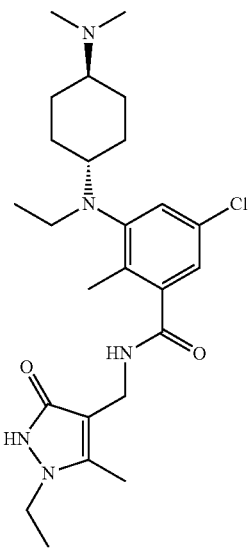 [SMILES: CCn1[nH]c(=O)c(CNC(=O)c2cc(Cl)cc(N(CC)[C@H]3CC[C@H](N(C)C)CC3)c2C)c1C]

Step 1: Synthesis of 5-chloro-3-(((trans)-4-(dimethylamino)cyclohexyl)(ethyl)amino)-N-((1-ethyl-3-methoxy-5-methyl-1H-pyrazol-4-yl)methyl)-2-methylbenzamide To a stirred solution of 5-chloro-3-(((trans)-4-(dimethylamino)cyclohexyl)(ethyl)amino)-2-methylbenzoic acid (0.36 g, 1.06 mmol) in DMSO (3 mL), (1-ethyl-3-methoxy-5-methyl-1H-pyrazol-4-yl)methanamine (Prepared as for Compound 21 using ethyl iodide in Step 4, 0.36 g, 2.13 mmol) and triethyl amine (0.44 mL, 3.18 mmol) were added. The reaction mixture was stirred at rt for 15 min before PyBOP (0.83 g, 1.59 mmol) was added to it and stirring was continued at rt for 16 h. The progress of the reaction was monitored by TLC. Upon completion the reaction mixture was diluted with water and extracted with 10% MeOH/DCM. The combined organic layers were dried over Na$_2$SO$_4$ and concentrated under reduced pressure. The crude compound was purified by column chromatography to afford the title compound (0.38 g, 73%).

Step 2: Synthesis of 5-chloro-3-(((trans)-4-(dimethylamino)cyclohexyl)(ethyl)amino)-N-((1-ethyl-5-methyl-3-oxo-2,3-dihydro-1H-pyrazol-4-yl)methyl)-2-methylbenzamide A mixture of 5-chloro-3-(((trans)-4-(dimethylamino)cyclohexyl)(ethyl)amino)-N-((1-ethyl-3-methoxy-5-methyl-1H-pyrazol-4-yl)methyl)-2-methylbenzamide (0.3 g, 0.613 mmol) and BBr$_3$ (1M in DCM, 3 mL, 3.04 mmol) was stirred at rt for 16 h. The progress of the reaction was monitored by TLC. Upon completion the reaction mixture was basified with aqueous sodium bicarbonate solution and extracted with 10% MeOH/DCM. The combined organic layers were dried over Na$_2$SO$_4$ and concentrated under reduced pressure. The crude compound was purified by prep HPLC to afford the title compound (0.1 g, 34%).

Analytical Data of the TFA Salt:

LCMS: 476.40 (M+1); $^1$H NMR (400 MHz, DMSO-d6) δ 9.39 (s, 1H), 8.53 (t, J=5.3 Hz, 1H), 7.21 (d, J=2.3 Hz, 1H), 6.99 (d, J=2.1 Hz, 1H), 4.07 (d, J=5.2 Hz, 2H), 3.82 (q, J=7.1 Hz, 2H), 3.11 (s, 1H), 3.03 (q, J=6.9 Hz, 2H), 2.68 (d, J=5.0 Hz, 7H), 2.16 (d, J=3.3 Hz, 6H), 1.94-1.83 (m, 4H), 1.45-1.40 (m, 4H), 1.20 (t, J=7.1 Hz, 3H), 0.79 (t, J=6.9 Hz, 3H).

Compound 53: 5-(((trans)-4-(dimethylamino) cyclohexyl) (ethyl) amino)-N-((3-methoxy-1,5-dimethyl-1H-pyrazol-4-yl) methyl)-4-methyl-4'-(morpholinomethyl)-[1,1'-biphenyl]-3-carboxamide

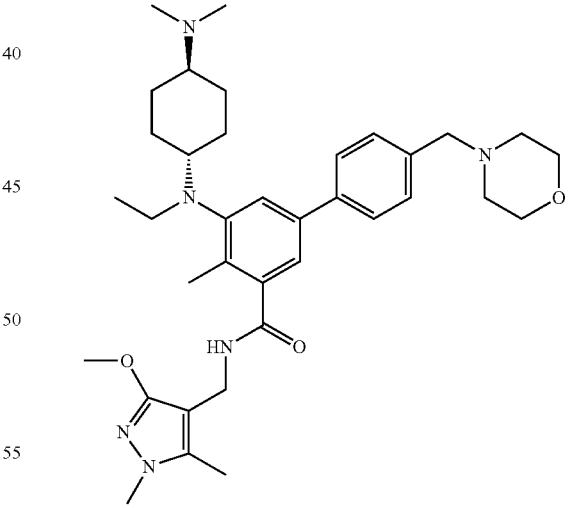

Step 1: Synthesis of 5-(((trans)-4-(dimethylamino) cyclohexyl) (ethyl) amino)-N-((3-methoxy-1,5-dimethyl-1H-pyrazol-4-yl) methyl)-4-methyl-4'-(morpholinomethyl)-[1,1'-biphenyl]-3-carboxamide To a stirred solution of 5-(((trans)-4-(dimethylamino) cyclohexyl) (ethyl)amino)-4-methyl-4'-(morpholinomethyl)-[1,1'-biphenyl]-3-carboxylic acid (0.3 g, 0.63 mmol)

in DMSO (3 mL), (3-methoxy-1,5-dimethyl-1H-pyrazol-4-yl)methanamine (0.12 g, 0.75 mmol) and triethyl amine (0.26 mL, 1.88 mmol) were added. The reaction mixture was stirred at rt for 15 min before PyBOP (0.489 g, 0.94 mmol) was added to it at 0° C. and stirring was continued at rt for 12 h. The progress of the reaction was monitored by TLC. Upon completion the reaction mixture was diluted with water and extracted with 10% methanol/DCM. The combined organic layers were dried over $Na_2SO_4$ and concentrated under reduced pressure. The crude compound was purified by prep. HPLC to afford the title compound (0.28 g, 72%).

Analytical Data of the Formate Salt:

LCMS: 617.65 (M+1); $^1$H NMR (400 MHz, DMSO-d6) δ 8.50 (t, 1H), 7.61-7.55 (m, 2H), 7.43-7.34 (m, 3H), 7.18 (s, 1H), 4.24 (d, J=5.2 Hz, 2H), 3.96 (s, 3H), 3.58-3.49 (m, 9H), 3.09 (q, J=6.4 Hz, 2H), 2.72-2.67 (m, 1H), 2.47-2.33 (m, 5H), 2.28 (s, 6H), 2.24 (s, 3H), 2.09 (s, 3H), 1.86-1.83 (m, 4H), 1.42-1.36 (m, 2H), 1.27-1.21 (m, 2H), 0.83 (t, J=7.0 Hz, 3H).

Compound 54: N-((1,5-dimethyl-3-oxo-2,3-dihydro-1H-pyrazol-4-yl)methyl)-5-(((trans)-4-(dimethylamino)cyclohexyl)(ethyl)amino)-4-methyl-4'-(morpholinomethyl)-[1,1'-biphenyl]-3-carboxamide

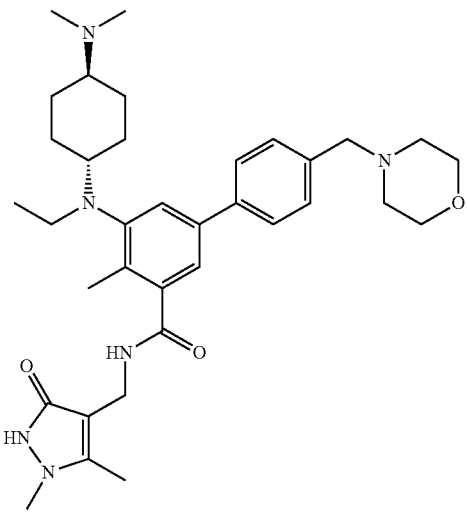 [SMILES: CCN(c1cc(-c2ccc(CN3CCOCC3)cc2)cc(C(=O)NCc2c(C)n(C)[nH]c2=O)c1C)[C@H]1CC[C@H](N(C)C)CC1]

Step 1: Synthesis of N-((1,5-dimethyl-3-oxo-2,3-dihydro-1H-pyrazol-4-yl)methyl)-5-(((trans)-4-(dimethylamino)cyclohexyl)(ethyl)amino)-4-methyl-4'-(morpholinomethyl)-[1,1'-biphenyl]-3-carboxamide To a stirred solution of 5-(((trans)-4-(dimethylamino)cyclohexyl)(ethyl)amino)-N-((3-methoxy-1,5-dimethyl-1H-pyrazol-4-yl)methyl)-4-methyl-4'-(morpholinomethyl)-[1,1'-biphenyl]-3-carboxamide (0.18 g, 0.29 mmol), $BBr_3$ (1M in DCM, 0.36 g, 1.46 mmol) was added at 0° C. The resulting reaction mixture was stirred at rt for 12 h. The progress of the reaction was monitored by TLC. Upon completion the reaction mixture was concentrated to dryness. The residue obtained was basified with aqueous sodium bicarbonate solution and extracted with 10% MeOH/DCM. The combined organic layers were dried over anhydrous $Na_2SO_4$ and concentrated under reduced pressure. The crude compound obtained was purified by prep. HPLC to afford the title compound (0.003 g, 1.7%).

Analytical Data of the Formate Salt:

LCMS: 603.60 (M+1); $^1$H NMR (400 MHz, Methanol-d4) δ 7.55 (d, J=8.0 Hz, 2H), 7.45-7.41 (m, 3H), 7.32 (s, 1H), 4.23 (s, 2H), 3.70 (t, J=4.7 Hz, 4H), 3.57 (s, 2H), 3.44 (s, 3H), 3.24-3.03 (m, 3H), 2.85-2.80 (m, 1H), 2.76 (s, 6H), 2.49 (t, J=4.6 Hz, 4H), 2.29 (s, 3H), 2.21 (s, 3H), 2.10-2.05 (m, 4H), 1.51-1.35 (m, 4H), 0.91 (t, J=6.9 Hz, 3H).

Compound 55: 5-chloro-N-((1,5-dimethyl-3-oxo-2,3-dihydro-1H-pyrazol-4-yl)methyl)-3-(ethyl((trans)-4-((2-methoxyethyl)(methyl)amino)cyclohexyl)amino)-2-methylbenzamide

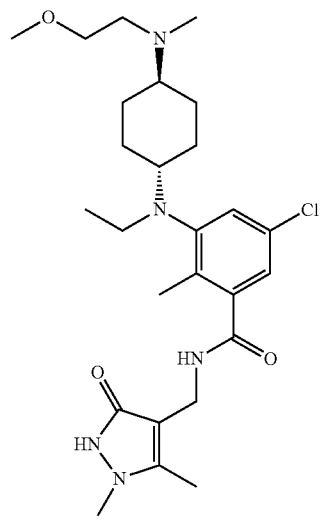 [SMILES: CCN(c1cc(Cl)cc(C(=O)NCc2c(C)n(C)[nH]c2=O)c1C)[C@H]1CC[C@H](N(C)CCOC)CC1]

Step 1: Synthesis of 5-chloro-N-((1,5-dimethyl-3-oxo-2,3-dihydro-1H-pyrazol-4-yl)methyl)-3-(ethyl((trans)-4-((2-methoxyethyl)(methyl)amino)cyclohexyl)amino)-2-methylbenzamide To a stirred solution of 5-chloro-3-(ethyl ((trans)-4-((2-methoxyethyl)-(methyl)-amino)-cyclohexyl) amino)-2-methylbenzoic acid (0.3 g, 0.785 mmol) in DCM: DMF (10 mL+2 mL), TBTU (0.328 g, 1.02 mmol) and DIPEA (0.303 g, 2.35 mmol) were added and the solution was stirred at rt for 30 min. Then 4-(aminomethyl)-1,5-dimethyl-1H-pyrazol-3(2H)-one (0.22 g, 1.57 mmol) was added and the reaction mixture was stirred at 50° C. for 5 h. The progress of the reaction was monitored by TLC. Upon completion the reaction mixture was diluted with water and extracted with 10% MeOH/DCM. Combined organic layers were washed with water, dried, concentrated under reduced pressure. The crude compound was purified by column chromatography over basic alumina to afford the title compound (0.045 g, 11%).

Analytical Data:

LCMS: 506.45 (M+1); $^1$H NMR (400 MHz, DMSO-d6) δ 10.50 (bs, 1H), 8.60 (bs, 1H), 7.17 (s, 1H), 6.97 (s, 1H), 4.06 (s, 2H), 3.43-3.32 (m, 5H), 3.24 (s, 3H), 3.01 (q, J=6.8 Hz, 2H), 2.80-2.74 (m, 2H), 2.67-2.61 (m, 2H), 2.33 (s, 3H), 2.15 (s, 3H), 2.10 (s, 3H), 1.78-1.75 (m, 4H), 1.42-1.23 (m, 4H), 0.78 (t, J=6.8 Hz, 3H).

Compound 56: 5-chloro-N-((1,5-dimethyl-3-oxo-2,3-dihydro-1H-pyrazol-4-yl)methyl)-3-(ethyl((trans)-4-((4-methoxybenzyl)(methyl)amino)cyclohexyl)amino)-2-methylbenzamide

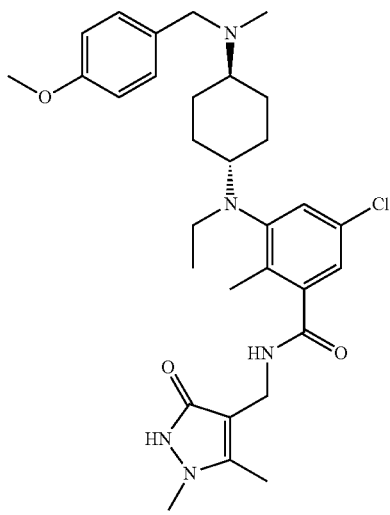 [SMILES: CCN(c1cc(Cl)cc(C(=O)NCc2c(C)n(C)[nH]c2=O)c1C)[C@H]1CC[C@H](N(C)Cc2ccc(OC)cc2)CC1]

Step 1: Synthesis of 4-(aminomethyl)-1,5-dimethyl-1H-pyrazol-3(2H)-one

To a stirred solution of (3-methoxy-1,5-dimethyl-1H-pyrazol-4-yl)methanamine (2 g, 12.90 mmol) in methanolic HCl (20 mL) at 0° C., Conc. HCl (0.5 mL) was added. The reaction mixture was heated at 80° C. for 12 h. The progress of the reaction was monitored by TLC. Upon completion the reaction mass was concentrated to dryness and azeotroped with toluene, pentane and dried under reduced pressure to afford the title compound as HCl salt (4.5 g, 98%)

Step 2: Synthesis of methyl 5-chloro-3-(ethyl((trans)-4-((4-methoxybenzyl)-(methyl)-amino)-cyclohexyl) amino)-2-methylbenzoate To a stirred solution of methyl 5-chloro-3-(ethyl((trans)-4-(methylamino)-cyclohexyl)-amino)-2-methylbenzoate (1 g, 2.96 mmol) and 4-methoxybenzaldehyde (0.482 g, 3.55 mmol) in dichloroethane (10 mL), titanium isopropoxide (1.68 g, 5.91 mmol) was added and the solution was stirred at rt for 10 min. Then sodium cyanoborohydride (0.372 g, 5.91 mmol) was added and the reaction was stirred at rt for 16 h. The progress of the reaction was monitored by TLC. Upon completion the reaction was quenched with water and filtered through a bed of celite. The filtrate was diluted with 10% MeOH/DCM. The organic layer was separated; aqueous layer was extracted with 10% MeOH/DCM. The combined organic layers were dried over anhydrous $Na_2SO_4$ and concentrated under reduced pressure. The crude compound was purified by column chromatography to afford the title compound (0.5 g, 37%).

Step 3: Synthesis of 5-chloro-3-(ethyl((trans)-4-((4-methoxybenzyl)-(methyl)-amino)-cyclohexyl)amino)-2-methylbenzoic Acid To a stirred solution of methyl 5-chloro-3-(ethyl((trans)-4-((4-methoxybenzyl)-(methyl)-amino)cyclohexyl)amino)-2-methylbenzoate (1 g, 2.18 mmol) in EtOH (10 mL), aq. NaOH (0.13 g, 3.26 mmol) was added and the reaction was stirred at 60° C. for 1 h. The progress of the reaction was monitored by TLC. Upon completion; ethanol was removed under reduced pressure and the reaction mass was acidified using dil. HCl up to pH 6 and extracted with 10% MeOH/DCM. The combined organic layers were dried, concentrated giving the respective acid (0.6 g) which was used in the subsequent step without further purification.

Step 4: Synthesis of 5-chloro-N-((1,5-dimethyl-3-oxo-2,3-dihydro-1H-pyrazol-4-yl)methyl)-3-(ethyl((trans)-4-((4-methoxybenzyl)(methyl)amino)cyclohexyl)amino)-2-methylbenzamide To a stirred solution of 5-chloro-3-(ethyl((trans)-4-((4-methoxybenzyl)-(methyl)-amino)-cyclohexyl)amino)-2-methylbenzoic acid (0.3 g, 0.675 mmol) in DCM:DMF (10 mL+2 mL), TBTU (0.282 g, 0.877 mmol) and DIPEA (0.261 g, 2.03 mmol) were added and the solution was stirred at rt for 30 min. Then 4-(aminomethyl)-1,5-dimethyl-1H-pyrazol-3(2H)-one (0.19 g, 1.35 mmol) was added and the reaction mixture was stirred at 50° C. for 5 h. The progress of the reaction was monitored by TLC. Upon completion the reaction mixture was diluted with water and extracted with 10% MeOH/DCM. Combined organic layers were washed with water, dried, concentrated under reduced pressure. The crude compound was purified by column chromatography over basic alumina to afford the title compound (0.055 g, 14%).

Analytical Data:
LCMS: 568.45 (M+1); $^1$H NMR (400 MHz, DMSO-d6) δ 8.50 (bs, 1H), 7.20-7.14 (m, 3H), 6.90 (s, 1H), 6.85-6.84 (m, 2H), 4.06 (s, 2H), 3.72 (s, 3H), 3.42 (s, 2H), 3.02 (q, J=6.8 Hz, 2H), 2.67-2.60 (m, 1H), 2.38-2.33 (m, 1H), 2.15 (s, 3H), 2.04 (s, 3H), 2.02 (s, 3H), 1.79-1.76 (m, 4H), 1.40-1.24 (m, 4H), 0.78 (t, J=6.8 Hz, 3H), 3H merged in solvent peak.

Compound 57: 5-chloro-N-((1,5-dimethyl-3-oxo-2,3-dihydro-1H-pyrazol-4-yl)methyl)-3-(ethyl((trans)-4-((3-methoxybenzyl)(methyl)amino)cyclohexyl)amino)-2-methylbenzamide

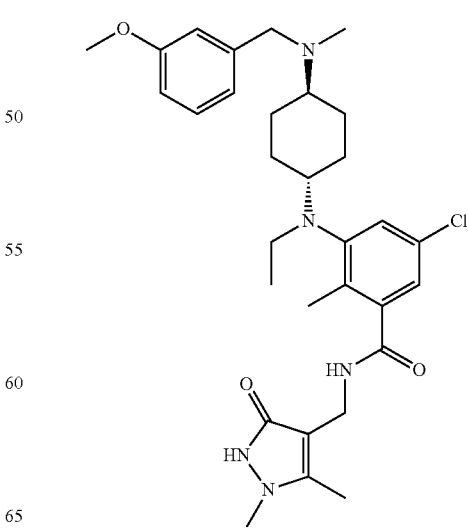

Step 1: Synthesis of methyl 5-chloro-3-(ethyl ((trans)-4-((3-methoxybenzyl)-(methyl)-amino)-cyclohexyl) amino)-2-methylbenzoate To a stirred solution of methyl 5-chloro-3-(ethyl((trans)-4-(methylamino)-cyclohexyl)-amino)-2-methylbenzoate (1 g, 2.96 mmol) and 3-methoxybenzaldehyde (0.482 g, 3.55 mmol) in dichloroethane (10 mL), titanium isopropoxide (1.68 g, 5.91 mmol) was added and the solution was stirred at rt for 10 min. Then sodium cyanoborohydride (0.372 g, 5.91 mmol) was added and the reaction was stirred at rt for 16 h. The progress of the reaction was monitored by TLC. Upon completion the reaction was quenched with water and filtered through a bed of celite. The filtrate was diluted with 10% MeOH/DCM. The organic layer was separated; aqueous layer was extracted with 10% MeOH/DCM. The combined organic layers were dried over anhydrous sodium sulphate and concentrated under reduced pressure. The crude compound was purified by column chromatography to afford the title compound (1 g, 74%).

Step 2: Synthesis of 5-chloro-3-(ethyl ((trans)-4-((3-methoxybenzyl)-(methyl)-amino)-cyclohexyl)-amino)-2-methylbenzoic Acid To a stirred solution of methyl 5-chloro-3-(ethyl((trans)-4-((3-methoxybenzyl)-(methyl)-amino)cyclohexyl)amino)-2-methylbenzoate (1 g, 2.18 mmol) in EtOH (10 mL), aq. NaOH (0.13 g, 3.26 mmol) was added and the reaction was stirred at 60° C. for 1 h. The progress of the reaction was monitored by TLC. Upon completion ethanol was removed under reduced pressure and the reaction mass was acidified using dil. HCl up to pH 6 and extracted with 10% MeOH/DCM. The combined organic layers were dried, concentrated giving respective acid (0.6 g) which was used in the subsequent step without further purification.

Step 3: Synthesis of 5-chloro-N-((1,5-dimethyl-3-oxo-2,3-dihydro-1H-pyrazol-4-yl)methyl)-3-(ethyl ((trans)-4-((3-methoxybenzyl)(methyl)amino)cyclohexyl)amino)-2-methylbenzamide To a stirred solution of 5-chloro-3-(ethyl((trans)-4-((3-methoxybenzyl)-(methyl)-amino)-cyclohexyl)amino)-2-methylbenzoic acid (0.25 g, 0.563 mmol) in DCM: DMF (10 mL+2 mL), TBTU (0.234 g, 0.732 mmol) and DIPEA (0.218 g, 1.69 mmol) were added and the solution was stirred at rt for 30 min. Then 4-(aminomethyl)-1,5-dimethyl-1H-pyrazol-3(2H)-one (0.159 g, 1.13 mmol) was added and the reaction mixture was stirred at 50° C. for 5 h. The progress of the reaction was monitored by TLC. Upon completion the reaction mixture was diluted with water and extracted with 10% MeOH/DCM. The combined organic layers were washed with water, dried, concentrated under reduced pressure. The crude compound was purified by column chromatography over basic alumina to afford the title compound (0.045 g, 14%).

Analytical Data:

LCMS: 568.45 (M+1); $^1$H NMR (400 MHz, DMSO-d6) δ 10.39 (bs, 1H), 8.61 (bs, 1H), 7.21-7.17 (m, 2H), 6.89 (s, 1H), 6.88-6.74 (m, 3H), 4.06 (s, 2H), 3.72 (s, 3H), 3.47 (s, 2H), 3.33 (s, 3H), 3.02 (q, J=6.8 Hz, 2H), 2.67-2.60 (m, 1H), 2.38-2.33 (m, 1H), 2.15 (s, 3H), 2.06 (s, 6H), 1.78-1.77 (m, 4H), 1.39-1.23 (m, 4H), 0.78 (t, J=6.8 Hz, 3H).

Compound 58: N-((1,5-dimethyl-3-oxo-2,3-dihydro-1H-pyrazol-4-yl)methyl)-5-(((trans)-4-(dimethyl-amino)cyclohexyl)(propyl)amino)-4'-(2-methoxy-ethoxy)-4-methyl-[1,1'-biphenyl]-3-carboxamide

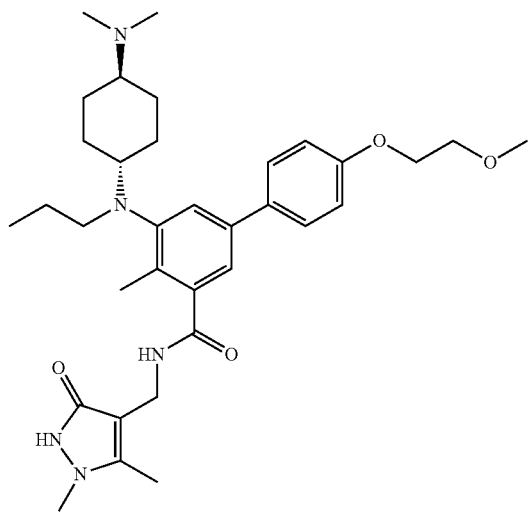 [SMILES: CCCN(c1cc(-c2ccc(OCCOC)cc2)cc(C(=O)NCc2c(C)n(C)[nH]c2=O)c1C)[C@H]1CC[C@H](N(C)C)CC1]

Step 1: Synthesis of methyl 5-bromo-3-(((trans)-4-((tert-butoxycarbonyl)-amino)-cyclohexyl)-(propyl)-amino)-2-methylbenzoate To a stirred solution of methyl 5-bromo-3-(((trans)-4-((tert-butoxycarbonyl)-amino)cyclohexyl)amino)-2-methyl-benzoate (8 g, 18.18 mmol) and propionaldehyde (5.28 g, 90.90 mmol) in dichloroethane (80 mL), acetic acid (6.54 g, 109.08 mmol) was added and the reaction was stirred at rt for 30 min. Then sodium triacetoxyborohydride (11.56 g, 54.54 mmol) was added at 0° C. and the resulting reaction was stirred at rt for 16 h. The progress of the reaction was monitored by TLC. Upon completion the reaction mass was quenched with aqueous sodium bicarbonate, the organic layer was separated and the aqueous layer was extracted with dichloromethane. The combined organic layers were dried over anhydrous Na$_2$SO$_4$ and concentrated under reduced pressure. The crude compound was purified by column chromatography to afford the title compound (6.5 g, 74%).

Step 2: Synthesis of methyl 5-bromo-3-(((trans)-4-(dimethylamino)-cyclohexyl)-(propyl)-amino)-2-methylbenzoate To a stirred solution of methyl 5-bromo-3-(((trans)-4-((tert-butoxycarbonyl)amino) cyclohexyl)(propyl)amino)-2-methylbenzoate (1.1 g, 2.28 mmol) in DCM (15 mL) at 0° C., TFA (3 mL) was added and the reaction was stirred at rt for 2 h. The progress of the reaction was monitored by TLC. Upon completion the reaction mixture was concentrated to dryness. The residue obtained was basified with aqueous sat. bicarbonate solution till pH 8 and extracted with 10% MeOH/DCM. The combined organic layers were dried over Na$_2$SO$_4$ and concentrated under reduced pressure to afford the crude amine (0.8 g) which was used in the subsequent step without further purification.

To a stirred solution of above crude amine (0.8 g, 2.09 mmol) in dichloromethane (8 mL) at 0° C., aq. 35% formaldehyde solution (0.22 g, 7.33 mmol) was added and the solution was stirred for 20 min. Then sodium triacetoxyborohydride (1.11 g, 5.24 mmol) was added and the reaction mixture was stirred at 0° C. for 2 h. The progress of the reaction was monitored by TLC. Upon completion the reaction mass was diluted with water and extracted with 10% MeOH/DCM. The combined organic layers were dried over $Na_2SO_4$ and concentrated under reduced pressure. The crude compound was purified by column chromatography to afford the title compound (0.5 g, 58%).

Step 3: Synthesis of methyl 5-(((trans)-4-(dimethylamino) cyclohexyl) (propyl) amino)-4'-(2-methoxyethoxy)-4-methyl-[1,1'-biphenyl]-3-carboxylate To a stirred solution of methyl 5-bromo-3-(((trans)-4-(dimethylamino)-cyclohexyl)-(propyl)-amino)-2-methylbenzoate (0.5 g, 1.22 mmol) and 2-(4-(2-methoxyethoxy)phenyl)-4,4,5,5-tetramethyl-1,3,2-dioxaborolane (0.405 g, 1.46 mmol) in dioxane/water mixture (10 mL+2.5 mL), $Na_2CO_3$ (0.464 g, 4.38 mmol) was added and the solution was purged with argon for 20 min. Then Pd $(PPh_3)_4$ (0.14 g, 0.121 mmol) was added and argon was purged again for 20 min. The reaction mixture was heated at 90° C. for 5 h. The progress of the reaction was monitored by TLC. Upon completion the reaction mixture was diluted with water and extracted with 10% MeOH/DCM. The combined organic layers were dried over $Na_2SO_4$ and concentrated under reduced pressure. The crude compound was purified by column chromatography to afford the title compound (0.5 g, 85%).

Step 4: Synthesis of 5-(((trans)-4-(dimethylamino) cyclohexyl) (propyl) amino)-4'-(2-methoxyethoxy)-4-methyl-[1,1'-biphenyl]-3-carboxylic Acid To a stirred solution of methyl 5-(((trans)-4-(dimethylamino) cyclohexyl) (propyl) amino)-4'-(2-methoxyethoxy)-4-methyl-[1,1'-biphenyl]-3-carboxylate (0.5 g, 1.03 mmol) in EtOH (5 mL), aq. NaOH (0.062 g, 1.55 mmol) was added and the reaction was stirred at 60° C. for 1 h. The progress of the reaction was monitored by TLC. Upon completion ethanol was removed under reduced pressure and the reaction mass was acidified with 1N HCl and extracted with 10% MeOH/DCM. The combined organic layers were dried over anhydrous $Na_2SO_4$ and concentrated under reduced pressure to afford the title compound (0.45 g, 93%).

Step 5: Synthesis of N-((1,5-dimethyl-3-oxo-2,3-dihydro-1H-pyrazol-4-yl)methyl)-5-(((trans)-4-(dimethylamino)cyclohexyl)(propyl)amino)-4'-(2-methoxyethoxy)-4-methyl-[1,1'-biphenyl]-3-carboxamide To a stirred solution of 5-(((trans)-4-(dimethylamino) cyclohexyl) (propyl) amino)-4'-(2-methoxyethoxy)-4-methyl-[1,1'-biphenyl]-3-carboxylic acid (0.25 g, 0.53 mmol), in DCM:DMF (4 mL: 1 mL), TBTU (0.223 g, 0.694 mmol) and DIPEA (0.205 g, 1.59 mmol) were added. The solution was stirred at rt for 20 min. Then 4-(aminomethyl)-1,5-dimethyl-1H-pyrazol-3(2H)-one hydrochloride (0.189 g, 1.06 mmol) was added and the reaction mixture was stirred at rt for 16 h. The progress of the reaction was monitored by TLC. Upon completion the reaction mixture was diluted with water and extracted with 10% methanol/DCM. The combined organic layers were dried over $Na_2SO_4$ and concentrated under reduced pressure. The crude compound was purified by column chromatography over basic alumina to afford the title compound (0.017 g, 5%).

Analytical Data:

LCMS: 592.55 (M+1); $^1$H NMR (DMSO-$d_6$, 400 MHz) δ 8.60 (bs, 1H), 7.53 (d, J=8.8 Hz, 2H), 7.34 (s, 1H), 7.15 (s, 1H), 7.01 (d, J=9.2 Hz, 2H), 4.13-4.07 (m, 4H), 3.67 (t, J=4.4 Hz, 2H), 3.42-3.35 (m, 2H), 3.15-2.98 (m, 3H), 2.67-2.61 (m, 1H), 2.22 (s, 3H), 2.13 (s, 6H), 2.05 (s, 3H), 1.82-1.75 (m, 4H), 1.44-1.41 (m, 2H), 1.23-1.12 (m, 4H), 0.76 (t, J=7.2 Hz, 3H), 4H merged in solvent peak.

Compound 59: N-((1,5-dimethyl-3-oxo-2,3-dihydro-1H-pyrazol-4-yl)methyl)-5-(((trans)-4-(dimethylamino)cyclohexyl)(ethyl)amino)-4'-(2-methoxyethoxy)-4-methyl-[1,1'-biphenyl]-3-carboxamide

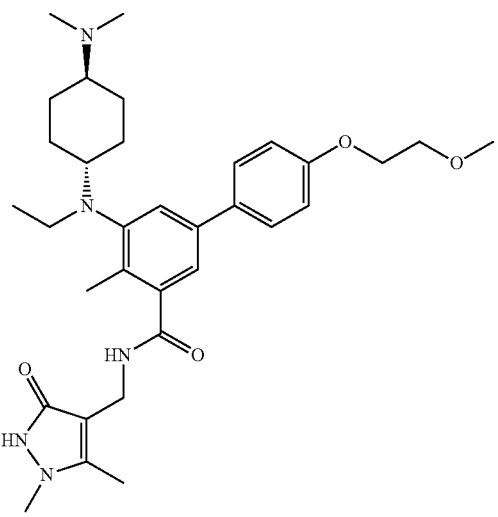 [SMILES: CCN(c1cc(-c2ccc(OCCOC)cc2)cc(C(=O)NCc2c(C)n(C)[nH]c2=O)c1C)[C@H]1CC[C@H](N(C)C)CC1]

Step 1: Synthesis of N-((1,5-dimethyl-3-oxo-2,3-dihydro-1H-pyrazol-4-yl)methyl)-5-(((trans)-4-(dimethylamino)cyclohexyl)(ethyl)amino)-4'-(2-methoxyethoxy)-4-methyl-[1,1'-biphenyl]-3-carboxamide To a stirred solution of 5-(((trans)-4-(dimethylamino) cyclohexyl)(ethyl)amino)-4'-(2-methoxyethoxy)-4-methyl-[1,1'-biphenyl]-3-carboxylic acid (0.3 g, 0.66 mmol), in DCM:DMF (4 mL:1 mL), TBTU (0.276 g, 0.859 mmol) and DIPEA (0.255 g, 1.98 mmol) were added. The solution was stirred at rt for 20 min. Then 4-(aminomethyl)-1,5-dimethyl-1H-pyrazol-3(2H)-one hydrochloride (0.233 g, 1.32 mmol) was added and the reaction mixture was stirred at rt for 16 h. The progress of the reaction was monitored by TLC. Upon completion the reaction mixture was diluted with water and extracted with 10% methanol/DCM. The combined organic layers were dried over $Na_2SO_4$ and concentrated under reduced pressure. The crude compound was purified by column chromatography over basic alumina to afford the title compound (0.008 g, 2%).

Analytical Data:

LCMS: 578.55 (M+1); $^1$H NMR (DMSO-$d_6$, 400 MHz) δ 8.62 (bs, 1H), 7.54 (d, J=8.4 Hz, 2H), 7.34 (s, 1H), 7.17 (s, 1H), 7.01 (d, J=8.8 Hz, 2H), 4.13-4.07 (m, 4H), 3.67 (t, J=4.4 Hz, 2H), 3.14-2.98 (m, 3H), 2.65-2.51 (m, 1H), 2.22 (s, 3H), 2.12 (s, 6H), 2.05 (s, 3H), 1.89-1.75 (m, 4H), 1.41-1.12 (m, 4H), 0.83 (t, J=6.8 Hz, 3H), 6H merged in solvent peak.

Compound 60: N-((1,5-dimethyl-3-oxo-2,3-dihydro-1H-pyrazol-4-yl)methyl)-5-(ethyl((trans)-4-((2-methoxyethyl)(methyl)amino)cyclohexyl)amino)-4'-(2-methoxyethoxy)-4-methyl-[1,1'-biphenyl]-3-carboxamide

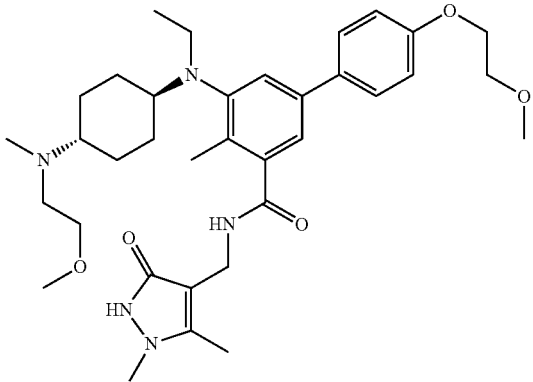

Step 1: Synthesis of methyl 5-bromo-3-(((trans)-4-((tert-butoxycarbonyl) amino) cyclohexyl)-amino)-2-methylbenzoate To a stirred solution of methyl 3-amino-5-bromo-2-methylbenzoate (860 g, 3524 mmol) and tert-butyl (4-oxocyclohexyl) carbamate (904.6 g, 4246 mmol) in dichloroethane (1 L), acetic acid (1274 g, 21233 mmol) was added and the reaction was stirred at rt for 30 min. Then sodium triacetoxyborohydride (2250 g, 10613 mmol) was added at 0° C. and the reaction was stirred at rt for 16 h. The progress of the reaction was monitored by TLC. Upon completion the reaction mass was quenched with aqueous sodium bicarbonate, the organic layer was separated and the aqueous layer was extracted with dichloromethane. The combined organic layers were dried over anhydrous Na$_2$SO$_4$ and concentrated under reduced pressure. The crude compound was purified by silica gel column chromatography (100-200 mesh size) eluting with 2, 4, 6 & 8% ethyl acetate in hexane to remove maximum cis isomer. This afforded 945 g of mixture of cis and trans isomers (40:60 by HPLC). The trans isomer was purified by repetitive recrystallisation with ethyl acetate:hexane (1:2) to afford 480 g of pure trans isomer as white solid with 99% purity.

Step 2: Synthesis of methyl 5-bromo-3-(((trans)-4-((tert-butoxycarbonyl) amino) cyclohexyl)-(ethyl) amino)-2-methylbenzoate To a stirred solution of methyl 5-bromo-3-(((trans)-4-((tert-butoxycarbonyl)-amino)-cyclohexyl)amino)-2-methylbenzoate (240 g, 545 mmol) and acetaldehyde (59.98 g, 1363 mmol) in dichloroethane (1 L), acetic acid (196.3 g, 3271 mmol) was added and the reaction was stirred at rt for 30 min. Then sodium triacetoxyborohydride (346.8 g, 1635 mmol) was added at 0° C. and the reaction mixture was stirred at rt for 16 h. The progress of the reaction was monitored by TLC. Upon completion the reaction mixture was quenched with aqueous sodium bicarbonate, the organic layer was separated and the aqueous layer was extracted with dichloromethane. The combined organic layers were dried over anhydrous Na$_2$SO$_4$ and concentrated under reduced pressure. The crude compound was purified by column chromatography to afford the title compound (192 g, 75%).

Step 3: Synthesis of methyl 5-(((trans)-4-((tert-butoxycarbonyl)-amino)-cyclohexyl)-(ethyl) amino)-4'-hydroxy-4-methyl-[1,1'-biphenyl]-3-carboxylate To a stirred solution of methyl 5-bromo-3-(((trans)-4-((tert-butoxycarbonyl)-amino)-cyclohexyl)-(ethyl)-amino)-2-methylbenzoate (189 g, 402 mmol) and (4-hydroxyphenyl) boronic acid (66.73 g, 484 mmol) in dioxane/water mixture (3.5 L+1.26 L), Na$_2$CO$_3$ (153.7 g, 1450 mmol) was added and the solution was purged with argon for 40 min. Then Pd(PPh$_3$)$_4$ (46.54 g, 40.29 mmol) was added and argon was purged again for 30 min. The reaction mass was heated at 100° C. for 5 h. The progress of the reaction was monitored by TLC. Upon completion the reaction mixture was diluted with 10% MeOH/DCM and filtered. The filtrate was concentrated, diluted with water and extracted with 10% MeOH/DCM. The combined organic layers were dried over Na$_2$SO$_4$ and concentrated under reduced pressure. The crude compound was purified by column chromatography to afford the title compound (179 g, 92%).

Step 4: Synthesis of methyl 5-(((trans)-4-((tert-butoxycarbonyl)-amino)-cyclohexyl)-(ethyl) amino)-4'-(2-methoxyethoxy)-4-methyl-[1,1'-biphenyl]-3-carboxylate To a stirred solution of methyl 5-(((trans)-4-((tert-butoxycarbonyl)-amino)-cyclohexyl)-(ethyl)amino)-4'-hydroxy-4-methyl-[1,1'-biphenyl]-3-carboxylate (180 g, 373 mmol) in acetonitrile (2 L), cesium carbonate (364 g, 1120 mmol) and 1-bromo-2-methoxyethane (62.29 g, 448 mmol) were added. The reaction mass was heated at 80° C. for 12 h. The progress of the reaction was monitored by TLC. Upon completion the reaction mixture diluted with water and extracted with 10% MeOH/DCM. The combined organic layers were dried over Na$_2$SO$_4$ and concentrated under reduced pressure. The crude compound was purified by column chromatography to afford the title compound (170 g, 84%).

Step 5: Synthesis of methyl 5-(((trans)-4-((tert-butoxycarbonyl)-(methyl)-amino)-cyclohexyl)-(ethyl) amino)-4'-(2-methoxyethoxy)-4-methyl-[1,1'-biphenyl]-3-carboxylate To a stirred solution of methyl 5-(((trans)-4-((tert-butoxycarbonyl)-amino)-cyclohexyl)-(ethyl) amino)-4'-(2-methoxyethoxy)-4-methyl-[1,1'-biphenyl]-3-carboxylate (1.5 g, 2.77 mmol) in dry DMF (15 mL) at 0° C., NaH (60%, 0.277 g, 6.94 mmol) was added and the solution was stirred at 0° C. for 20 min. Then methyl iodide (2.36 g, 16.62 mmol) was added at 0° C. and the reaction was stirred at rt for 16 h. The progress of the reaction was monitored by TLC. Upon completion the reaction was quenched with water and extracted with DCM. The combined organic layers were washed with water, dried over $Na_2SO_4$ and concentrated under reduced pressure. The crude compound was purified by column chromatography to afford the title compound (1.5 g, 98%).

Step 6: Synthesis of methyl 5-(ethyl((trans)-4-(methylamino)cyclohexyl)amino)-4'-(2-methoxyethoxy)-4-methyl-[1,1'-biphenyl]-3-carboxylate To a stirred solution of methyl 5-(((trans)-4-((tert-butoxycarbonyl)-(methyl)-amino)-cyclohexyl)-(ethyl) amino)-4'-(2-methoxyethoxy)-4-methyl-[1,1'-biphenyl]-3-carboxylate (1.5 g, 2.70 mmol) in DCM (20 mL) at 0° C., TFA (4 mL) was added and the reaction was stirred at rt for 2 h. The progress of the reaction was monitored by TLC. Upon completion the reaction mass was concentrated to dryness. The residue obtained was basified with sat. sodium bicarbonate solution till pH 8 and aqueous layer extracted with 10% MeOH/DCM. The combined organic layers were dried over $Na_2SO_4$ and concentrated under reduced pressure to afford the title compound (1.2 g) which was used in the subsequent step without further purification.

Step 7: Synthesis of methyl 5-(ethyl((trans)-4-((2-methoxyethyl)-(methyl)-amino)-cyclohexyl)-amino)-4'-(2-methoxyethoxy)-4-methyl-[1,1'-biphenyl]-3-carboxylate To a stirred solution of methyl 5-(ethyl((trans)-4-(methylamino)cyclohexyl)amino)-4'-(2-methoxyethoxy)-4-methyl-[1,1'-biphenyl]-3-carboxylate (1.6 g, 3.52 mmol) and 1-bromo-2-methoxyethane (0.978 g, 7.04 mmol) in ACN (20 mL), $K_2CO_3$ (0.973 g, 7.04 mmol) and KI (0.35 g, 2.11 mmol) were added. The reaction mixture was stirred at 60° C. for 16 h. The progress of the reaction was monitored by TLC. Upon completion the reaction mass was diluted with water and extracted with 10% MeOH/DCM. The combined organic layers were dried over anhydrous sodium sulphate and concentrated under reduced pressure. The crude compound was purified by column chromatography to afford the title compound (1.62 g, 90%).

Step 8: Synthesis of N-((1,5-dimethyl-3-oxo-2,3-dihydro-1H-pyrazol-4-yl)methyl)-5-(ethyl((trans)-4-((2-methoxyethyl)(methyl)amino)cyclohexyl)amino)-4'-(2-methoxyethoxy)-4-methyl-[1,1'-biphenyl]-3-carboxamide To a stirred solution of methyl 5-(ethyl((trans)-4-((2-methoxyethyl)-(methyl)-amino)-cyclohexyl)-amino)-4'-(2-methoxyethoxy)-4-methyl-[1,1'-biphenyl]-3-carboxylate (1.6 g, 3.12 mmol) in EtOH (20 mL), aq. NaOH (0.188 g, 4.68 mmol) was added and the reaction was stirred at 60° C. for 1 h. The progress of the reaction was monitored by TLC. Upon completion ethanol was removed under reduced pressure and the reaction mass was acidified using dil. HCl up to pH 6 and extracted with 10% MeOH/DCM. The combined organic layers were dried, concentrated giving the respective acid (1.45 g) which was used in the subsequent step without further purification.

To a stirred solution of the above acid (0.3 g, 0.602 mmol) in DCM: DMF (5 mL+1 mL), TBTU (0.251 g, 0.783 mmol) and DIPEA (0.465 g, 3.61 mmol) were added and the solution was stirred at rt for 20 min. Then 4-(amino methyl)-1,5-dimethyl-1H-pyrazol-3(2H)-one hydrochloride (0.106 g, 0.602 mmol) was added and the reaction mixture was stirred at rt for 16 h. The progress of the reaction was monitored by TLC. Upon completion the reaction mixture was diluted with sat. $NaHCO_3$ solution and extracted with 10% MeOH/DCM. The combined organic layers were washed with water, dried over $Na_2SO_4$ and concentrated under reduced pressure. The crude compound was purified by column chromatography to afford the title compound (0.010 g, 2.6%).

Analytical Data:

LCMS: 622.65 (M+1); $^1H$ NMR (400 MHz, DMSO-$d_6$) δ 10.50 (bs, 1H), 8.60 (bs, 1H), 7.54 (d, J=8.4 Hz, 2H), 7.35 (s, 1H), 7.17 (s, 1H), 7.02 (d, J=8.4 Hz, 2H), 4.12-4.08 (m, 4H), 3.68-3.67 (m, 2H), 3.20 (s, 3H), 3.10-3.07 (m, 4H), 2.68-2.65 (m, 1H), 2.33-2.29 (m, 1H), 2.22 (s, 6H), 2.14 (s, 3H), 1.83-1.68 (m, 4H), 1.39-1.18 (m, 4H), 0.82 (t, J=6.4 Hz, 3H), 8H merged in solvent peak.

Compound 61: N-((1,5-dimethyl-3-oxo-2,3-dihydro-1H-pyrazol-4-yl)methyl)-5-(((trans)-4-(dimethylamino)cyclohexyl)(propyl)amino)-4-methyl-4'-(morpholinomethyl)-[1,1'-biphenyl]-3-carboxamide

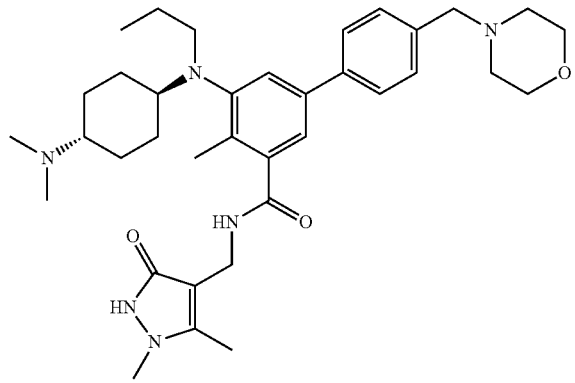 [SMILES: CCCN(c1cc(-c2ccc(CN3CCOCC3)cc2)cc(C(=O)NCc2c(C)n(C)[nH]c2=O)c1C)[C@H]1CC[C@H](N(C)C)CC1]

Step 1: Synthesis of methyl 5-bromo-3-(((trans)-4-((tert-butoxycarbonyl) amino)cyclohexyl)-amino)-2-methylbenzoate To a stirred solution of methyl 3-amino-5-bromo-2-methylbenzoate (860 g, 3.53 mol) and tert-butyl (4-oxocyclohexyl)carbamate (904.6 g, 4.24 mol) in dichloroethane (1 L), acetic acid (1274 g, 21.23 mol) was added and reaction was stirred at rt for 30 minutes. Then sodium triacetoxyborohydride (2250 g, 10.61 mol) was added at 0° C. and the reaction was stirred at rt for 16 hours. Upon completion (monitored by TLC), the reaction was quenched with aqueous sodium bicarbonate, the organic layer was separated and the aqueous layer was extracted with dichloromethane (1.5 L×3). The combined organic layers were dried over anhydrous sodium sulphate and concentrated under reduced pressure. The crude compound was purified by silica gel column chromatography (100-200 mesh size) eluting with 2, 4, 6 & 8% ethyl acetate in hexane to remove maximum cis isomer. This afforded 945 g of mixture of cis and trans isomers (40:60 by HPLC). The trans isomer was purified by repetitive recrystallisation with ethyl acetate:hexane (1:2) to afford 480 g of pure trans isomer as white solid with 99% purity.

Step 2: Synthesis of methyl 5-bromo-3-(((trans)-4-((tertbutoxycarbonyl)amino) cyclohexyl)(propyl) amino)-2-methylbenzoate To a stirred solution of methyl 5-bromo-3-(((trans)-4-((tert-butoxycarbonyl)amino) cyclohexyl)amino)-2-methylbenzoate (3 g, 6.81 mmol), propionaldehyde (1.97 g, 34.08 mmol) in dichloroethane (30 mL) and acetic acid (2.45 g, 40.89 mmol) was added and the reaction was stirred at rt for 20 minutes. Then sodium triacetoxyborohydride (4.33 g, 20.44 mmol) was added at 0° C. and the reaction was stirred at rt for 16 h. The progress of the reaction was monitored by TLC. Upon completion the reaction was quenched with aqueous sodium bicarbonate, the organic layer was separated and the aqueous layer was extracted with dichloromethane. The combined organic layers were dried over anhydrous $Na_2SO_4$ and concentrated under reduced pressure. The crude compound was purified by column chromatography to afford compound (1.5 g, 45%).

Step 3: Synthesis of methyl 5-(((trans)-4-((tertbutoxycarbonyl)amino)cyclohexyl)(propyl) amino)-4-methyl-4'-(morpholinomethyl)-[1,1'-biphenyl]-3-carboxylate To a stirred solution of methyl 5-bromo-3-(((trans)-4-((tert-butoxycarbonyl)amino)cyclohexyl)(propyl)amino)-2-methylbenzoate (1.5 g, 3.11 mmol) and 4-(4-(4,4,5,5-tetramethyl-1,3,2-dioxaborolan-2-yl)benzyl)morpholine (1.13 g, 3.73 mmol) in dioxane/water mixture (15 mL+2 mL), $Na_2CO_3$ (1.18 g, 11.19 mmol) was added and the solution was purged with argon for 20 min. Then $Pd(PPh_3)_4$ (0.36 g, 0.311 mmol) was added and argon was purged again for 20 min. The reaction mass was heated at 100° C. for 3 h. The progress of the reaction was monitored by TLC. Upon completion the reaction mixture diluted with water and extracted with 10% MeOH/DCM. The combined organic layers were dried over $Na_2SO_4$ and concentrated under reduced pressure. The crude compound was purified by column chromatography to afford the title compound (1.1 g, 61%).

Step 4: Synthesis of methyl 5-(((trans)-4-(dimethylamino)cyclohexyl)(propyl)amino)-4-methyl-4'-(morpholinomethyl)-[1,1'-biphenyl]-3-carboxylate To a stirred solution of methyl 5-(((trans)-4-((tert-butoxycarbonyl)amino)cyclohexyl) (propyl)amino)-4-methyl-4'-(morpholinomethyl)-[1,1'-biphenyl]-3-carboxylate (1.1 g, 1.89 mmol) in DCM (10 mL) at 0° C., TFA (2 mL) was added and the reaction was stirred at rt for 2 h. The progress of the reaction was monitored by TLC. Upon completion the reaction was concentrated to dryness. The residue was then basified with aqueous saturated sodium bicarbonate solution up to pH 8 and aqueous layer extracted with 20% MeOH/DCM. The combined organic layer were dried over $Na_2SO_4$ and concentrated under reduced pressure to afford the title compound (0.8 g) which was used in the next step without further purification.

To a stirred solution of above crude amine (0.8 g, 1.67 mmol) in dichloromethane (8 mL) was added aq. 35% formaldehyde solution (0.175 g, 5.84 mmol) at 0° C. and stirred for 20 min. Then $Na(OAc)_3BH$ (0.885 g, 4.17 mmol) was added and stirred at rt for 2 h. The progress of the reaction was monitored by TLC. Upon completion the reaction mixture was diluted water and extracted with 10% MeOH/DCM. The combined organic layers were dried over $Na_2SO_4$ and concentrated under reduced pressure. The crude compound was purified by column chromatography to afford the title compound (0.65 g, 76%).

Step 5: Synthesis of 5-(((trans)-4-(dimethylamino) cyclohexyl)(propyl)amino)-4-methyl-4'-(morpholinomethyl)-[1,1'-biphenyl]-3-carboxylic Acid Aqueous NaOH (0.102 g, 2.56 mmol) was added to a solution of methyl 5-(((trans)-4-(dimethylamino)cyclohexyl)(propyl)amino)-4-methyl-4'-(morpholinomethyl)-[1,1'-biphenyl]-3-carboxylate (0.65 g, 1.28 mmol) in EtOH (6 mL) and stirred at 60° C. for 1 h. The progress of the reaction was monitored by TLC. Upon completion the ethanol was removed under reduced pressure and acidified using dilute HCl up to pH 6 and pH 4 was adjusted using citric acid. Extraction was carried out using 10% MeOH/DCM. The combined organic layers were dried over $Na_2SO_4$ and concentrated giving respective acid (0.45 g) which was used in the next step without further purification.

Step 6: Synthesis of N-((1,5-dimethyl-3-oxo-2,3-dihydro-1H-pyrazol-4-yl)methyl)-5-(((trans)-4-(dimethylamino)cyclohexyl)(propyl)amino)-4-methyl-4'-(morpholinomethyl)-[1,1'-biphenyl]-3-carboxamide To a stirred solution of 5-(((trans)-4-(dimethylamino) cyclohexyl)(propyl)amino)-4-methyl-4'-(morpholinomethyl)-[1,1'-biphenyl]-3-carboxylic acid (0.2 g, 0.406 mmol) in DCM: DMF (3 mL+1 mL), TBTU (0.170 g, 0.528 mmol) and DIPEA (0.157 g, 1.21 mmol) were added and the solution was stirred at rt for 20 min. Then 4-(amino methyl)-1,5-dimethyl-1H-pyrazol-3(2H)-one hydrochloride (0.143 g, 0.812 mmol) was added and the reaction mixture was stirred at rt for 16 h. The progress of the reaction was monitored by TLC. Upon completion the reaction mixture was diluted with aqueous saturated sodium bicarbonate solution and extracted with 10% MeOH/DCM. The combined organic layers were washed with water, dried over sodium sulphate and concentrated under reduced pressure. The crude compound was purified by column chromatography to afford the title compound (0.01 g, 4%).

Analytical Data:

LCMS: 617.85 (M+1); $^1$H NMR (400 MHz, DMSO-d6) δ 8.65 (bs, 1H), 7.56 (d, J=8.0 Hz, 2H), 7.39-7.37 (m, 3H), 7.19 (s, 1H), 4.08 (d, 2H), 3.58 (t, 4H), 3.48 (s, 2H), 3.43-3.40 (m, 1H), 3.06-3.01 (m, 2H), 2.67-2.63 (m, 1H), 2.38-2.34 (m, 3H), 2.23 (s, 3H), 2.18 (s, 6H), 2.06 (s, 3H), 1.80-1.76 (m, 4H), 1.45-1.35 (m, 4H), 0.88-0.83 (m, 2H), 0.77 (t, J=7.2 Hz, 3H), 4H merged in solvent peak.

213

Compound 62: 5-chloro-3-(ethyl((trans)-4-((3-methoxybenzyl)-(methyl)-amino)-cyclohexyl)-amino)-N-((1-ethyl-3-methoxy-5-methyl-1H-pyrazol-4-yl)methyl)-2-methylbenzamide

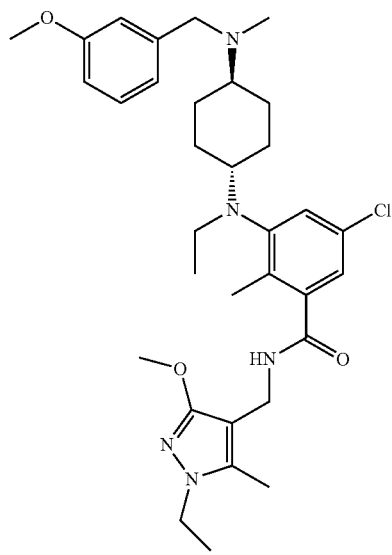 [SMILES: CCn1nc(OC)c(CNC(=O)c2cc(Cl)cc(N(CC)[C@H]3CC[C@H](N(C)Cc4cccc(OC)c4)CC3)c2C)c1C]

Step 1: Synthesis of 5-chloro-3-(ethyl((trans)-4-((3-methoxybenzyl)-(methyl)-amino)-cyclohexyl)-amino)-N-((1-ethyl-3-methoxy-5-methyl-1H-pyrazol-4-yl)methyl)-2-methylbenzamide To a stirred solution of 5-chloro-3-(ethyl((trans)-4-((3-methoxybenzyl)-(methyl)-amino)cyclohexyl)amino)-2-methylbenzoic acid (0.3 g, 0.675 mmol) in DCM: DMF (5 mL+1 mL), TBTU (0.281 g, 0.877 mmol) and DIPEA (0.261 g, 2.02 mmol) were added and the solution was stirred at rt for 30 min. Then (1-ethyl-3-methoxy-5-methyl-1H-pyrazol-4-yl)methanamine (0.228 g, 1.35 mmol) was added and the reaction mixture was stirred at rt for 16 h. The progress of the reaction was monitored by TLC. Upon completion the reaction mixture was diluted with sat. sodium bicarbonate solution and extracted with 10% MeOH/DCM. The combined organic layers were washed with water, dried over $Na_2SO_4$ and concentrated under reduced pressure. The crude compound was purified by column chromatography to afford the title compound (0.17 g, 42%).

Analytical Data:

LCMS: 596.55 (M+1); $^1$H NMR (400 MHz, DMSO-d6) δ 8.50 (t, J=4.8 Hz, 1H), 7.20-7.15 (m, 2H), 6.98-6.94 (m, 2H), 6.90-6.80 (m, 2H), 4.21 (d, J=5.2 Hz, 2H), 3.95 (s, 3H), 3.82 (q, J=7.2 Hz, 2H), 3.76-3.72 (m, 3H), 3.52-3.45 (m, 1H), 3.02 (q, J=6.8 Hz, 2H), 2.69-2.67 (m, 1H), 2.17 (s, 3H), 2.09 (s, 3H), 1.85-1.80 (m, 4H), 1.41-1.29 (m, 4H), 1.23 (t, J=7.2 Hz, 3H), 0.79 (t, J=6.8 Hz, 3H), 5H merged in solvent peak.

214

Compound 63: 5-chloro-3-(ethyl ((trans)-4-((3-methoxybenzyl)-(methyl)-amino)-cyclohexyl) amino)-N-((1-ethyl-5-methyl-3-oxo-2,3-dihydro-1H-pyrazol-4-yl)methyl)-2-methylbenzamide

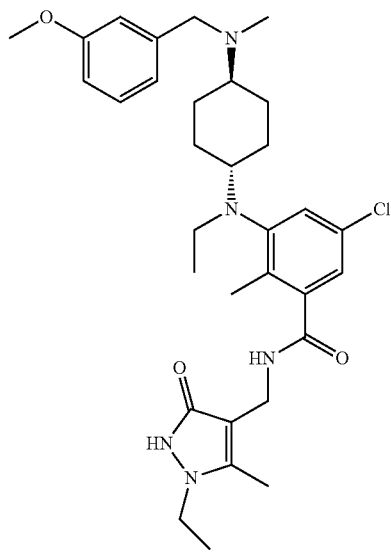 [SMILES: CCn1[nH]c(=O)c(CNC(=O)c2cc(Cl)cc(N(CC)[C@H]3CC[C@H](N(C)Cc4cccc(OC)c4)CC3)c2C)c1C]

Step 1: Synthesis of 5-chloro-3-(ethyl ((trans)-4-((3-methoxybenzyl)-(methyl)-amino)-cyclohexyl) amino)-N-((1-ethyl-5-methyl-3-oxo-2,3-dihydro-1H-pyrazol-4-yl)methyl)-2-methylbenzamide To a stirred solution of 5-chloro-3-(ethyl((trans)-4-((3-methoxybenzyl)-(methyl)-amino)-cyclohexyl)-amino)-N-((1-ethyl-3-methoxy-5-methyl-1H-pyrazol-4-yl)methyl)-2-methylbenzamide (0.15 g, 0.252 mmol) in methanolic HCl (2 mL), conc. HCl (2-3 drops) was added and the reaction mixture was stirred at 80° C. for 12 h. The progress of the reaction was monitored by TLC. Upon completion the reaction mixture was concentrated to dryness under reduced pressure. The residue obtained was basified with aqueous sodium bicarbonate solution and extracted with 10% MeOH\DCM. The combined organic layers were dried over $Na_2SO_4$ and concentrated under reduced pressure to afford the crude material; which was purified by column chromatography to afford the title compound (0.055 g, 37%).

Analytical Data:

LCMS: 582.55 (M+1); $^1$H NMR (400 MHz, $CD_3OD$-d4) δ 7.34 (t, 1H), 7.20 (d, J=2.0 Hz, 1H), 7.06 (d, J=2.0 Hz, 1H), 7.01-6.96 (m, 3H), 4.20 (s, 2H), 4.02 (s, 2H), 3.84 (q, J=6.8 Hz, 2H), 3.82 (s, 3H), 3.08 (q, J=7.2 Hz, 2H), 3.01-2.97 (m, 1H), 2.83-2.75 (m, 1H), 2.51 (s, 3H), 2.27 (s, 3H), 2.24 (s, 3H), 2.10-1.98 (m, 4H), 1.54-1.50 (m, 4H), 1.28 (t, J=7.2 Hz, 3H), 0.86 (t, J=7.2 Hz, 3H).

Compound 64: Synthesis of 5-chloro-3-(ethyl ((trans)-4-((2-methoxyethyl)-(methyl)-amino)-cyclohexyl) amino)-N-((1-ethyl-3-methoxy-5-methyl-1H-pyrazol-4-yl) methyl)-2-methylbenzamide

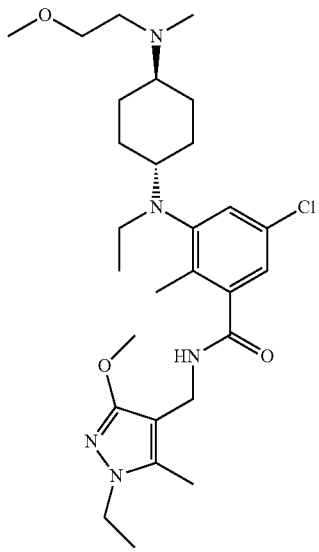 [SMILES: CCn1nc(OC)c(CNC(=O)c2cc(Cl)cc(N(CC)[C@H]3CC[C@H](N(C)CCOC)CC3)c2C)c1C]

Step 1: Synthesis of 5-chloro-3-(ethyl ((trans)-4-((2-methoxyethyl)-(methyl)-amino)-cyclohexyl) amino)-N-((1-ethyl-3-methoxy-5-methyl-1H-pyrazol-4-yl)methyl)-2-methylbenzamide To a stirred solution of 5-chloro-3-(ethyl((trans)-4-((2-methoxyethyl)-(methyl)-amino)-cyclohexyl)amino)-2-methylbenzoic acid (0.35 g, 0.913 mmol) in DCM: DMF (10 mL+2 mL), TBTU (0.381 g, 1.19 mmol) and DIPEA (0.353 g, 2.73 mmol) were added and the solution was stirred at rt for 20 min. Then (1-ethyl-3-methoxy-5-methyl-1H-pyrazol-4-yl) methanamine (0.31 g, 1.83 mmol) was added and the reaction mixture was stirred at rt for 12 h. The progress of the reaction was monitored by TLC. Upon completion the reaction mixture was diluted with sat. sodium bicarbonate solution and extracted with 10% MeOH/DCM. The combined organic layers were washed with water, dried over sodium sulphate and concentrated under reduced pressure. The crude compound was purified by column chromatography to afford the title compound (0.3 g, 61%).

Analytical Data:

LCMS: 534.60 (M+1); $^1$H NMR (400 MHz, DMSO-d6) δ 8.52 (t, 1H), 7.19 (s, 1H), 6.96 (s, 1H), 4.21 (d, J=5.2 Hz, 2H), 3.95 (s, 3H), 3.82 (q, J=6.8 Hz, 2H), 3.65-3.55 (m, 2H), 3.32-3.25 (m, 3H), 3.04-3.02 (m, 3H), 2.67-2.65 (m, 3H), 2.16 (s, 3H), 2.09 (s, 3H), 1.90-1.79 (m, 4H), 1.45-1.35 (m, 4H), 1.23 (t, J=7.2 Hz, 3H), 0.79 (t, J=6.8 Hz, 3H), 3H merged in solvent peak.

Compound 65: 5-chloro-3-(ethyl((trans)-4-((2-methoxyethyl)-(methyl)-amino)-cyclohexyl)-amino)-N-((1-ethyl-5-methyl-3-oxo-2,3-dihydro-1H-pyrazol-4-yl)methyl)-2-methylbenzamide

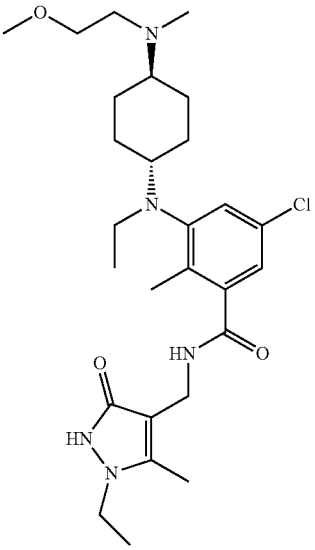 [SMILES: CCn1[nH]c(=O)c(CNC(=O)c2cc(Cl)cc(N(CC)[C@H]3CC[C@H](N(C)CCOC)CC3)c2C)c1C]

Step 1: Synthesis of 5-chloro-3-(ethyl((trans)-4-((2-methoxyethyl)-(methyl)-amino)-cyclohexyl)-amino)-N-((1-ethyl-5-methyl-3-oxo-2,3-dihydro-1H-pyrazol-4-yl)methyl)-2-methylbenzamide To a stirred solution of 5-chloro-3-(ethyl((trans)-4-((2-methoxyethyl)-(methyl)-amino)-cyclohexyl)amino)-N-((1-ethyl-3-methoxy-5-methyl-1H-pyrazol-4-yl)methyl)-2-methylbenzamide (0.3 g, 0.561 mmol) in methanolic HCl (10 mL), conc. HCl (0.2 mL) was added and the reaction mixture was stirred at 80° C. for 16 h. The progress of the reaction was monitored by TLC. Upon completion the reaction mixture was concentrated to dryness under reduced pressure. The residue obtained was basified with aqueous sodium bicarbonate solution and extracted with 10% MeOH\DCM. The combined organic layers were dried over Na$_2$SO$_4$ and concentrated under reduced pressure to afford crude material; which was purified by column chromatography to afford the title compound (0.05 g, 17%).

Analytical Data:

LCMS: 520.50 (M+1); $^1$H NMR (400 MHz, MeOD) δ 7.21 (s, 1H), 7.09 (s, 1H), 4.20 (s, 2H), 3.84 (q, J=7.2 Hz, 2H), 3.54 (t, J=5.2 Hz, 2H), 3.35 (s, 3H), 3.09 (q, J=6.8 Hz, 2H), 2.87-2.82 (m, 2H), 2.72-2.67 (m, 2H), 2.44 (s, 3H), 2.22 (s, 3H), 2.20 (s, 3H), 1.94-1.92 (m, 4H), 1.51-1.22 (m, 7H), 0.86 (t, J=6.8 Hz, 3H).

Compound 66: 5-chloro-3-(ethyl((trans)-4-(methyl (pyridin-3-ylmethyl)amino)cyclohexyl)amino)-N-((3-methoxy-1,5-dimethyl-1H-pyrazol-4-yl)methyl)-2-methylbenzamide

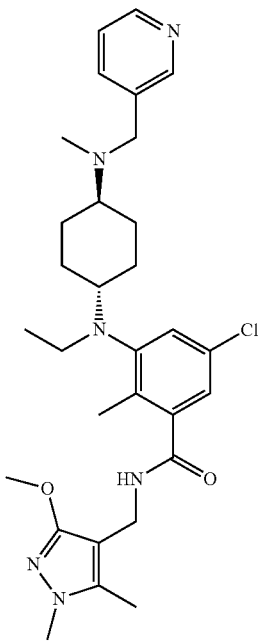 [SMILES: CCN(c1cc(Cl)cc(C(=O)NCc2c(OC)nn(C)c2C)c1C)[C@H]1CC[C@H](N(C)Cc2cccnc2)CC1]

Step 1: Synthesis of methyl 3-(((trans)-4-((tert-butoxycarbonyl) amino) cyclohexyl) amino)-5-chloro-2-methylbenzoate To a stirred solution of methyl 3-amino-5-chloro-2-methylbenzoate (100 g, 502 mmol) and tert-butyl (4-oxocyclohexyl) carbamate (160.5 g, 753 mmol) in dichloroethane (1 L), acetic acid (180.9 g, 3015 mmol) was added and the reaction was stirred at rt for 30 min. Then sodium triacetoxyborohydride (319.5 g, 1507 mmol) was added at 0° C. and the reaction was stirred at rt for 16 h. The progress of the reaction was monitored by TLC. Upon completion; the reaction was quenched with aqueous sodium bicarbonate, the organic layer was separated and the aqueous layer was extracted with dichloromethane. The combined organic layers were dried over anhydrous sodium sulphate and concentrated under reduced pressure. The crude compound was purified by silica gel column chromatography (100-200 mesh size) eluting with 2, 4, 6 & 8% ethyl acetate in hexane to remove maximum cis isomer. This afforded 120 g of mixture of cis and trans isomers (40:60 by HPLC). The trans isomer was purified by repetitive recrystallisation with ethyl acetate:hexane (1:2) to afford 65 g of pure trans isomer (65 g, 33%).

Step 2: Synthesis of methyl 3-(((trans)-4-((tert-butoxycarbonyl) amino) cyclohexyl) (ethyl) amino)-5-chloro-2-methylbenzoate To a stirred solution of methyl 3-(((trans)-4-((tert-butoxycarbonyl) amino) cyclohexyl) amino)-5-chloro-2-methylbenzoate (60 g, 151 mmol) and acetaldehyde (16.6 g, 379 mmol) in dichloroethane (500 mL), acetic acid (54.54 g, 909 mmol) was added and the reaction was stirred at rt for 20 min. Then sodium triacetoxyborohydride (96 g, 453 mmol) was added and the reaction was stirred at rt for 12 h. The progress of the reaction was monitored by TLC. Upon completion; the reaction was quenched with aqueous sodium bicarbonate, the organic layer was separated and the aqueous layer was extracted with dichloromethane. The combined organic layers were dried over anhydrous sodium sulphate and concentrated under reduced pressure. The crude compound was purified by silica gel column chromatography to afford the title compound (55 g, 86%).

Step 3: Synthesis of methyl 3-(((trans)-4-((tert-butoxycarbonyl)-(methyl)-amino)-cyclohexyl)(ethyl) amino)-5-chloro-2-methylbenzoate To a stirred solution of methyl 3-(((trans)-4-((tert-butoxycarbonyl) amino) cyclohexyl) (ethyl) amino)-5-chloro-2-methylbenzoate (10 g, 23.58 mmol) in dry DMF (100 mL) at 0° C., NaH (60%, 2.35 g, 58.95 mmol) was added and the solution was stirred at 0° C. for 20 min. Then methyl iodide (20 g, 141.5 mmol) was added at 0° C. and the reaction was stirred at rt for 16 h. The progress of the reaction was monitored by TLC. Upon completion the reaction was quenched with water and extracted with DCM. The combined organic layers were washed with water, dried and concentrated under reduced pressure. The crude compound was purified by column chromatography to afford the title compound (9.1 g, 88%).

Step 4: Synthesis of tert-butyl ((trans)-4-((5-chloro-3-(((3-methoxy-1,5-dimethyl-1H-pyrazol-4-yl) methyl)carbamoyl)-2-methylphenyl)(ethyl)amino) cyclohexyl)(methyl)carbamate To a stirred solution of methyl 3-(((trans)-4-((tert-butoxycarbonyl)-(methyl)-amino)-cyclohexyl)(ethyl)amino)-5-chloro-2-methylbenzoate (9.1 g, 20.77 mmol) in EtOH (90 mL), aq.NaOH (1.25 g, 31.16 mmol) was added and the reaction was stirred at 60° C. for 1 h. The progress of the reaction was monitored by TLC. Upon completion the ethanol was removed under reduced pressure and the reaction mass was acidified using dil.HCl up to pH 6 and extracted with 10% MeOH/DCM. The combined organic layers were dried; concentrated giving respective acid (7 g) which was used in the subsequent step without further purification.

To a stirred solution of above acid (2 g, 4.71 mmol) in DCM:DMF (20 mL+4 mL), TBTU (1.97 g, 6.12 mmol) and DIPEA (1.82 g, 14.13 mmol) were added and the solution was stirred at rt for 20 min. Then (3-methoxy-1,5-dimethyl-1H-pyrazol-4-yl)methanamine (1.46 g, 9.43 mmol) was added and the reaction mixture was stirred at rt for 16 h. The progress of the reaction was monitored by TLC. Upon completion the reaction mass was diluted with water and extracted with 10% MeOH/DCM. The combined organic layers were dried over sodium sulphate and concentrated under reduced pressure. The crude compound was purified by column chromatography to afford the title compound (2 g, 75%).

Step 5: Synthesis of 5-chloro-3-(ethyl((trans)-4-(methylamino) cyclohexyl) amino)-N-((3-methoxy-1,5-dimethyl-1H-pyrazol-4-yl)methyl)-2-methylbenzamide To a stirred solution of tert-butyl ((trans)-4-((5-chloro-3-(((3-methoxy-1,5-dimethyl-1H-pyrazol-4-yl)methyl)carbamoyl)-2-methylphenyl)(ethyl)amino)cyclohexyl)(methyl) carbamate (2 g, 3.56 mmol) in DCM (20 mL) at 0° C., TFA (5 mL) was added and the reaction was stirred at rt for 2 h.

The progress of the reaction was monitored by TLC. Upon completion the reaction mass was concentrated to dryness. The residue obtained was basified with aqueous saturated bicarbonate solution up to pH 8 and aqueous layer extracted with 10% MeOH/DCM. The combined organic layers were dried over $Na_2SO_4$ and concentrated under reduced pressure to afford the title compound (1.8 g) which was used in the subsequent step without further purification.

Step 6: Synthesis of 5-chloro-3-(ethyl((trans)-4-(methyl(pyridin-3-ylmethyl)amino)cyclohexyl) amino)-N-((3-methoxy-1,5-dimethyl-1H-pyrazol-4-yl)methyl)-2-methylbenzamide To a stirred solution of 5-chloro-3-(ethyl((trans)-4-(methylamino)cyclohexyl)amino)-N-((3-methoxy-1,5-dimethyl-1H-pyrazol-4-yl)methyl)-2-methylbenzamide (0.4 g, 0.86 mmol) and nicotinaldehyde (0.139 g, 1.30 mmol) in dichloroethane (10 mL), titanium isopropoxide (0.493 g, 1.74 mmol) was added and the solution stirred at rt for 10 min. Then sodium cyanoborohydride (0.109 g, 1.74 mmol) was added and the reaction stirred at rt for 12 h. The progress of the reaction was monitored by TLC. Upon completion the reaction was quenched with water and filtered through a bed of celite. The filtrate was diluted with 10% MeOH/DCM. The organic layer was separated and the aqueous layer was extracted with 10% MeOH/DCM. The combined organic layers were dried over anhydrous sodium sulphate and concentrated under reduced pressure. The crude compound was purified by column chromatography to afford the title compound (0.11 g, 23%).

Analytical Data:
LCMS: 553.45 (M+1); $^1$H NMR (400 MHz, DMSO-d6) 8.51 (t, J=5.2 Hz, 1H), 8.50-8.42 (m, 2H), 7.65 (s, 1H), 7.33 (s, 1H), 7.17 (s, 1H), 6.94 (s, 1H), 4.20 (d, J=5.2 Hz, 2H), 3.94 (s, 3H), 3.53-3.51 (m, 2H), 3.49 (s, 3H), 3.02 (q, J=6.8 Hz, 2H), 2.70-2.64 (m, 1H), 2.40-2.37 (m, 1H), 2.16 (s, 3H), 2.08-2.06 (m, 6H), 1.82-1.77 (m, 4H), 1.41-1.24 (m, 4H), 0.79 (t, J=5.2 Hz, 3H).

Compound 67: 5-chloro-N-((1,5-dimethyl-3-oxo-2,3-dihydro-1H-pyrazol-4-yl)methyl)-3-(ethyl((trans)-4-(methyl(pyridin-3-ylmethyl)amino)cyclohexyl) amino)-2-methylbenzamide

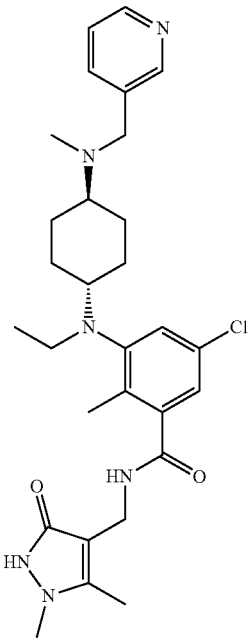

Step 1: Synthesis of 5-chloro-N-((1,5-dimethyl-3-oxo-2,3-dihydro-1H-pyrazol-4-yl)methyl)-3-(ethyl((trans)-4-(methyl(pyridin-3-ylmethyl)amino)cyclohexyl)amino)-2-methylbenzamide To a stirred solution of 5-chloro-3-(ethyl((trans)-4-(methyl(pyridin-3-ylmethyl)amino)cyclohexyl)amino)-N-((3-methoxy-1,5-dimethyl-1H-pyrazol-4-yl)methyl)-2-methylbenzamide (0.09 g, 0.163 mmol) in methanolic HCl (5 mL), conc. HCl (0.2 mL) was added and the reaction mixture was stirred at 80° C. for 12 h. The progress of the reaction was monitored by TLC. Upon completion the reaction mixture was concentrated to dryness under reduced pressure. The residue obtained was basified with aqueous saturated sodium bicarbonate solution and extracted with 10% MeOH\DCM. The combined organic layers were dried over $Na_2SO_4$ and concentrated under reduced pressure to afford the crude material, which was purified by column chromatography to afford the title compound (0.04 g, 45%).

Analytical Data:
LCMS: 539.40 (M+1); $^1$H NMR (400 MHz, Methanol-d4) δ 8.51-8.40 (m, 2H), 7.82 (d, J=7.6 Hz, 1H), 7.41 (dd, J=7.2, 5.2 Hz, 1H), 7.18 (d, J=2.2 Hz, 1H), 7.03 (d, J=2.2 Hz, 1H), 4.19 (s, 2H), 3.67 (s, 2H), 3.43 (s, 3H), 3.08 (q, J=6.9 Hz, 2H), 2.74-2.71 (m, 1H), 2.56-2.44 (m, 1H), 2.25 (s, 3H), 2.23 (s, 3H), 2.21 (s, 3H), 1.97-1.91 (m, 4H), 1.47-1.29 (m, 4H), 0.85 (t, J=6.8 Hz, 3H).

Compound 68: 5-chloro-3-(ethyl((trans)-4-((3-(2-methoxyethoxy)benzyl)(methyl)amino)cyclohexyl) amino)-N-((3-methoxy-1,5-dimethyl-1H-pyrazol-4-yl)methyl)-2-methylbenzamide

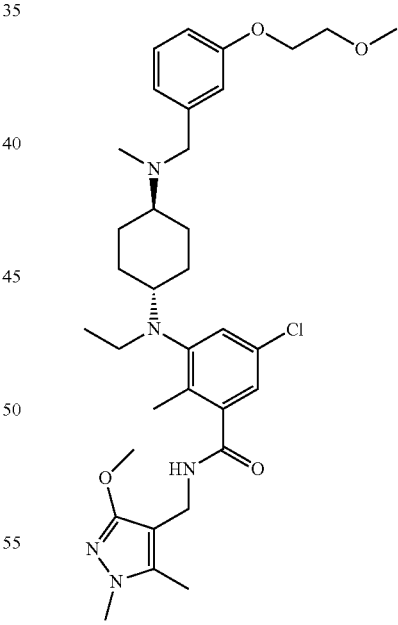

Step 1: Synthesis of 5-chloro-3-(ethyl((trans)-4-((3-(2-methoxyethoxy)benzyl)(methyl)amino)cyclohexyl)amino)-N-((3-methoxy-1,5-dimethyl-1H-pyrazol-4-yl)methyl)-2-methylbenzamide To a stirred solution of 5-chloro-3-(ethyl((trans)-4-(methylamino)cyclohexyl)amino)-N-((3-methoxy-1,5-dimethyl- 1H-pyrazol-4-yl)methyl)-2-methylbenzamide (0.4 g, 0.86 mmol) and 3-(2-methoxyethoxy)benzaldehyde (0.31 g, 1.72 mmol) in dichloroethane (10 mL), titanium isopropoxide (0.493 g, 1.74 mmol) was added and the solution stirred at rt for 10 min. Then sodium cyanoborohydride (0.109 g, 1.74 mmol) was added and the reaction stirred at rt for 12 h. The progress of the reaction was monitored by TLC. Upon completion the reaction was quenched with water and filtered through a bed of celite. The filtrate was diluted with 10% MeOH/DCM. The organic layer was separated; aqueous layer was extracted with 10% MeOH/DCM. The combined organic layers were dried over anhydrous sodium sulphate and concentrated under reduced pressure. The crude compound was purified by column chromatography to afford the title compound (0.12 g, 22%).

Analytical Data:

LCMS: 626.55 (M+1); $^1$H NMR (400 MHz, MeOD-d4) 7.35 (t, 1H), 7.21 (d, J=1.6 Hz, 1H), 7.03-7.00 (m, 4H), 4.37 (s, 2H), 4.14 (t, J=4.8 Hz, 2H), 4.03 (s, 3H), 3.75 (t, J=4.8 Hz, 2H), 3.58 (s, 3H), 3.42 (s, 3H), 3.08 (q, J=6.8 Hz, 2H), 3.05-2.99 (m, 1H), 2.85-2.80 (m, 1H), 2.55 (s, 3H), 2.25 (s, 3H), 2.20 (s, 3H), 2.08-1.99 (m, 4H), 1.55-1.51 (m, 4H), 0.86 (t, J=6.8 Hz, 3H), 2H merged in solvent peak.

Compound 69: 5-chloro-N-((1,5-dimethyl-3-oxo-2,3-dihydro-1H-pyrazol-4-yl)methyl)-3-(ethyl((trans)-4-((3-(2-methoxyethoxy)benzyl)(methyl)amino)cyclohexyl)amino)-2-methylbenzamide

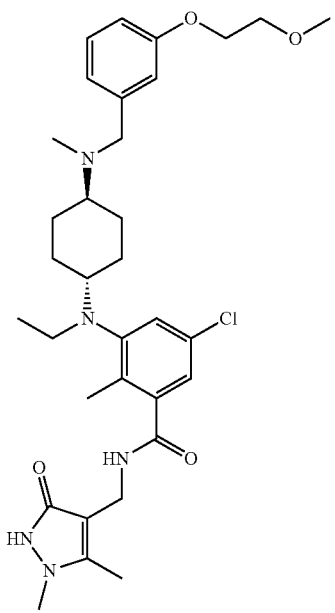 [SMILES: CCN(c1cc(Cl)cc(C(=O)NCc2c(C)n(C)[nH]c2=O)c1C)[C@H]1CC[C@H](N(C)Cc2cccc(OCCOC)c2)CC1]

Step 1: Synthesis of 5-chloro-N-((1,5-dimethyl-3-oxo-2,3-dihydro-1H-pyrazol-4-yl)methyl)-3-(ethyl((trans)-4-((3-(2-methoxyethoxy)benzyl)(methyl)amino)cyclohexyl)amino)-2-methylbenzamide To a stirred solution of 5-chloro-3-(ethyl((trans)-4-((3-(2-methoxyethoxy)benzyl)(methyl)amino)cyclohexyl)amino)-N-((3-methoxy-1,5-dimethyl-1H-pyrazol-4-yl)methyl)-2-methylbenzamide (0.1 g, 0.16 mmol) in methanolic HCl (5 mL), conc. HCl (0.3 mL) was added and the reaction mixture was stirred at 80° C. for 12 h. The progress of the reaction was monitored by TLC. Upon completion the reaction mixture was concentrated to dryness under reduced pressure. The residue obtained was basified with aqueous sat. sodium bicarbonate solution and extracted with 10% MeOH\DCM. The combined organic layers were dried over Na$_2$SO$_4$ and concentrated under reduced pressure to afford the crude material, which was purified by column chromatography to afford the title compound (0.045 g, 46%).

Analytical Data:

LCMS: 612.45 (M+1); $^1$H NMR (400 MHz, DMSO-d6) δ 10.39 (s, 1H), 8.65 (s, 1H), 7.21-7.17 (m, 2H), 6.96 (s, 1H), 6.84 (s, 2H), 6.78 (d, J=7.2 Hz, 1H), 4.08-4.03 (m, 3H), 3.64 (t, J=4.8 Hz, 2H), 3.46-3.42 (m, 4H), 3.30 (s, 3H), 3.02 (q, J=6.4 Hz, 2H), 2.67-2.60 (m, 1H), 2.37-2.33 (m, 1H), 2.15 (s, 3H), 2.06-2.02 (m, 6H), 1.80-1.77 (m, 4H), 1.39-1.23 (m, 4H), 0.78 (t, J=6.8 Hz, 3H), 2H merged in solvent peak.

Compound 70: 5-chloro-3-(ethyl((trans)-4-((4-methoxybenzyl)-(methyl)-amino)-cyclohexyl)-amino)-N-((1-ethyl-3-methoxy-5-methyl-1H-pyrazol-4-yl)methyl)-2-methylbenzamide

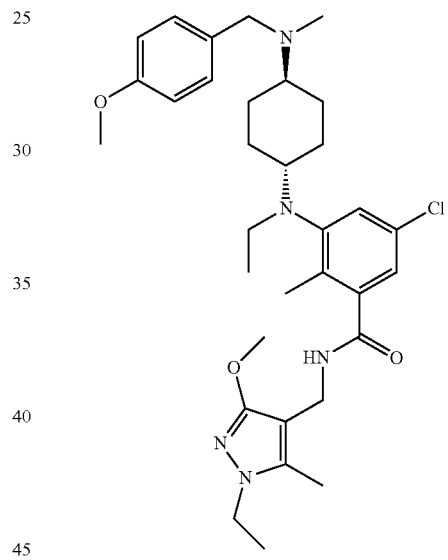

Step 1: Synthesis of 5-chloro-3-(ethyl((trans)-4-((4-methoxybenzyl)-(methyl)-amino)-cyclohexyl)-amino)-N-((1-ethyl-3-methoxy-5-methyl-1H-pyrazol-4-yl)methyl)-2-methylbenzamide To a stirred solution of 5-chloro-3-(ethyl((trans)-4-((4-methoxybenzyl)-(methyl)-amino)cyclohexyl)amino)-2-methylbenzoic acid (0.35 g, 0.788 mmol) in DCM: DMF (10 mL+2 mL), TBTU (0.328 g, 1.02 mmol) and DIPEA (0.305 g, 2.36 mmol) were added and the solution was stirred at rt for 20 min. Then (1-ethyl-3-methoxy-5-methyl-1H-pyrazol-4-yl) methanamine (0.266 g, 1.58 mmol) was added and the reaction mixture was stirred at rt for 12 h. The progress of the reaction was monitored by TLC. Upon completion the reaction mixture was diluted with sat. sodium bicarbonate solution and extracted with 10% MeOH/DCM. The combined organic layers were washed with water, dried over sodium sulphate and concentrated under reduced pressure. The crude compound was purified by column chromatography to afford the title compound (0.2 g, 43%).

Analytical Data:

LCMS: 596.60 (M+1); $^1$H NMR (400 MHz, DMSO-d6) δ 8.51 (t, J=5.2 Hz, 1H), 7.17-7.15 (m, 3H), 6.94 (d, J=2.1 Hz, 1H), 6.84 (d, J=8.4 Hz, 2H), 4.22 (d, J=5.2 Hz, 2H), 3.95 (s, 3H), 3.83 (q, J=7.2 Hz, 2H), 3.72 (s, 3H), 3.42 (s, 2H), 3.02 (q, J=7.0 Hz, 2H), 2.69-2.67 (m, 1H), 2.36-2.33 (m, 1H), 2.16 (s, 3H), 2.09 (s, 3H), 2.02 (s, 3H), 1.79-1.76 (m, 4H), 1.40-1.29 (m, 4H), 1.23 (t, J=7.2 Hz, 3H), 0.78 (t, J=6.8 Hz, 3H).

Compound 71: 5-chloro-3-(ethyl((trans)-4-((4-methoxybenzyl)-(methyl)-amino)-cyclohexyl)-amino)-N-((1-ethyl-5-methyl-3-oxo-2,3-dihydro-1H-pyrazol-4-yl)methyl)-2-methylbenzamide

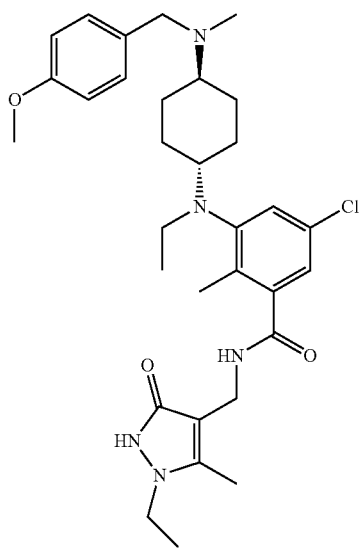 [SMILES: CCn1[nH]c(=O)c(CNC(=O)c2cc(Cl)cc(N(CC)[C@H]3CC[C@H](N(C)Cc4ccc(OC)cc4)CC3)c2C)c1C]

Step 1: Synthesis of 5-chloro-3-(ethyl((trans)-4-((4-methoxybenzyl)-(methyl)-amino)-cyclohexyl)-amino)-N-((1-ethyl-5-methyl-3-oxo-2,3-dihydro-1H-pyrazol-4-yl)methyl)-2-methylbenzamide To a stirred solution of 5-chloro-3-(ethyl((trans)-4-((4-methoxybenzyl)-(methyl)-amino)-cyclohexyl)-amino)-N-((1-ethyl-3-methoxy-5-methyl-1H-pyrazol-4-yl)methyl)-2-methylbenzamide (0.2 g, 0.33 mmol) in methanolic HCl (10 mL), conc. HCl (0.5 mL) was added and the reaction mixture was stirred at 80° C. for 16 h. The progress of the reaction was monitored by TLC. Upon completion the reaction mixture was concentrated to dryness under reduced pressure. The residue obtained was basified with aqueous sodium bicarbonate solution and extracted with 10% MeOH\DCM. The combined organic layers were dried over Na$_2$SO$_4$ and concentrated under reduced pressure to afford crude material; which was purified by column chromatography to afford the title compound (0.11 g, 56%).

Analytical Data:

LCMS: 582.55 (M+1); $^1$H NMR (400 MHz, MeOD-d4) δ 7.34 (d, J=8.4 Hz, 2H), 7.21 (d, J=1.6 Hz, 1H), 7.06 (d, J=2.4 Hz, 1H), 6.97 (d, J=8.0 Hz, 2H), 4.20 (s, 2H), 4.00 (s, 2H), 3.86 (q, J=7.2 Hz, 2H), 3.81 (s, 3H), 3.06 (q, J=6.8 Hz, 2H), 3.05-2.95 (m, 1H), 2.80-2.75 (m, 1H), 2.51 (s, 3H), 2.26 (s, 3H), 2.24 (s, 3H), 2.11-1.98 (m, 4H), 1.57-1.47 (m, 4H), 1.28 (t, J=7.6 Hz, 3H), 0.86 (t, J=6.8 Hz, 3H).

Compound 72: 5-chloro-3-(ethyl((trans)-4-(methyl(1-(pyridin-3-yl)ethyl)amino)cyclohexyl)amino)-N-((3-methoxy-1,5-dimethyl-1H-pyrazol-4-yl)methyl)-2-methylbenzamide

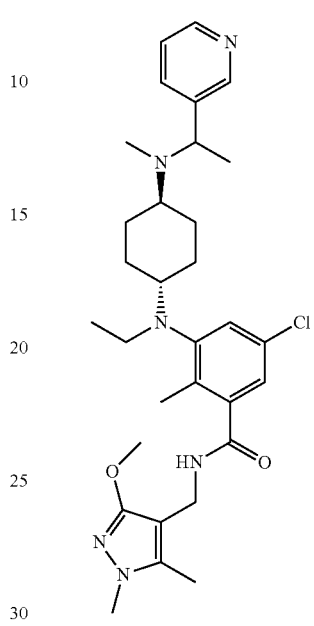

Step 1: Synthesis of methyl 3-(((trans)-4-((tert-butoxycarbonyl)amino)cyclohexyl)amino)-5-chloro-2-methylbenzoate To a stirred solution of methyl 3-amino-5-chloro-2-methylbenzoate (100 g, 502 mmol) and tert-butyl (4-oxocyclohexyl)carbamate (160.5 g, 753 mmol) in dichloroethane (1 L), acetic acid (180.9 g, 3015 mmol) was added and the reaction was stirred at rt for 30 min. Then sodium triacetoxyborohydride (319.5 g, 1507 mmol) was added at 0° C. and the reaction was stirred at rt for 16 h. The progress of the reaction was monitored by TLC. Upon completion the reaction was quenched with aqueous sodium bicarbonate, the organic layer was separated and the aqueous layer was extracted with dichloromethane. The combined organic layers were dried over anhydrous sodium sulphate and concentrated under reduced pressure. The crude compound was purified by silica gel column chromatography (100-200 mesh size) eluting with 2, 4, 6 & 8% ethyl acetate in hexane to remove maximum cis isomer. This afforded 120 g of mixture of cis and trans isomers (40:60 by HPLC). The trans isomer was purified by repetitive recrystallization with ethyl acetate:hexane (1:2) to afford 65 g of pure trans isomer (65 g, 33%).

Step 2: Synthesis of methyl 3-(((trans)-4-((tert-butoxycarbonyl)amino)cyclohexyl) (ethyl)amino)-5-chloro-2-methylbenzoate To a stirred solution of methyl 3-(((trans)-4-((tert-butoxycarbonyl)amino) cyclohexyl)amino)-5-chloro-2-methylbenzoate (60 g, 151 mmol) and acetaldehyde (16.6 g, 379 mmol) in dichloroethane (500 mL), acetic acid (54.54 g, 909 mmol) was added and the reaction was stirred at rt for 20 min. Then sodium triacetoxyborohydride (96 g, 453 mmol)

was added and the reaction was stirred at rt for 12 h. The progress of the reaction was monitored by TLC. Upon completion the reaction was quenched with aqueous sodium bicarbonate, the organic layer was separated and the aqueous layer was extracted with dichloromethane. The combined organic layers were dried over anhydrous sodium sulphate and concentrated under reduced pressure. The crude compound was purified by silica gel column chromatography to afford the title compound (55 g, 86%).

Step 3: Synthesis of methyl 3-(((trans)-4-aminocyclohexyl)(ethyl)amino)-5-chloro-2-methylbenzoate To a stirred solution of methyl 3-(((trans)-4-((tert-butoxycarbonyl)amino)cyclohexyl)(ethyl)amino)-5-chloro-2-methylbenzoate (1 g, 2.36 mmol) in DCM (10 mL) at 0° C., TFA (2 mL) was added and the reaction was stirred at rt for 2 h. The progress of the reaction was monitored by TLC. Upon completion the reaction mass was concentrated to dryness. The residue obtained was basified with aqueous saturated sodium bicarbonate solution up to pH 8 and aqueous layer was extracted with 10% MeOH/DCM. The combined organic layers were dried over $Na_2SO_4$ and concentrated under reduced pressure to afford the title compound (0.6 g) which was used in the subsequent step without further purification.

Step 4: Synthesis of methyl 5-chloro-3-(ethyl ((trans)-4-((1-(pyridin-3-yl)ethyl)amino)cyclohexyl) amino)-2-methylbenzoate To a stirred solution of methyl 3-(((trans)-4-aminocyclohexyl)(ethyl)amino)-5-chloro-2-methylbenzoate (2.5 g, 7.69 mmol) and 1-(pyridin-3-yl)ethanone (1.13 g, 9.23 mmol) in dichloroethane (25 mL), titanium isopropoxide (4.37 g, 15.38 mmol) was added and the solution was stirred at rt for 20 min. Then sodium cyanoborohydride (0.969 g, 15.38 mmol) was added and the reaction was stirred at rt for 12 h. The progress of the reaction was monitored by TLC. Upon completion the reaction was quenched with water and filtered through a bed of celite. The filtrate was diluted with 10% MeOH/DCM. The organic layer was separated; aqueous layer was extracted with 10% MeOH/DCM. The combined organic layers were dried over anhydrous $Na_2SO_4$ and concentrated under reduced pressure. The crude compound was purified by column chromatography over basic alumina to afford the title compound (2.5 g, 75%).

Step 5: Synthesis of methyl 5-chloro-3-(ethyl ((trans)-4-(methyl(1-(pyridin-3-yl)ethyl)amino)cyclohexyl)amino)-2-methylbenzoate To a stirred solution of methyl 5-chloro-3-(ethyl((trans)-4-((1-(pyridin-3-yl)ethyl)amino)cyclohexyl)amino)-2-methylbenzoate (2.5 g, 5.81 mmol) in dichloromethane (25 mL) at 0° C., aq. 35% formaldehyde solution (0.61 g, 20.34 mmol) was added and the solution was stirred for 20 min. Then $Na(OAc)_3BH$ (3.09 g, 14.53 mmol) was added and the reaction mixture was stirred at 0° C. for 5 h. The progress of the reaction was monitored by TLC. Upon completion the reaction mixture was diluted with water and extracted with 10% MeOH/DCM. The combined organic layers were dried over $Na_2SO_4$ and concentrated under reduced pressure. The crude material obtained was purified by column chromatography to afford the title compound (2.3 g, 89%).

Step 6: Synthesis of 5-chloro-3-(ethyl((trans)-4-(methyl(1-(pyridin-3-yl)ethyl)amino)cyclohexyl) amino)-2-methylbenzoic Acid To a stirred solution of methyl 5-chloro-3-(ethyl((trans)-4-(methyl(1-(pyridin-3-yl)ethyl)amino)cyclohexyl)amino)-2-methylbenzoate (2.3 g, 5.18 mmol) in EtOH (25 mL), aq. NaOH (0.31 g, 7.77 mmol) was added and the reaction mixture was stirred at 60° C. for 1 h. The progress of the reaction was monitored by TLC. Upon completion the ethanol was removed under reduced pressure and the reaction mass was acidified using dil. HCl and extracted with 10% MeOH/DCM. The combined organic layers were dried over $Na_2SO_4$ and concentrated under reduced pressure to afford the title compound (1.7 g) which was used in the subsequent step without further purification.

Step 7: Synthesis of 5-chloro-3-(ethyl((trans)-4-(methyl(1-(pyridin-3-yl)ethyl)amino)cyclohexyl) amino)-N-((3-methoxy-1,5-dimethyl-1H-pyrazol-4-yl)methyl)-2-methylbenzamide To a stirred solution of 5-chloro-3-(ethyl((trans)-4-(methyl(1-(pyridin-3-yl)ethyl)amino)cyclohexyl)amino)-2-methylbenzoic acid (0.6 g, 1.39 mmol) in DCM:DMF (10 mL+2 mL), TBTU (0.58 g, 1.81 mmol) and DIPEA (0.541 g, 4.19 mmol) were added and the solution was stirred at rt for 20 min. Then (3-methoxy-1,5-dimethyl-1H-pyrazol-4-yl)methanamine (0.432 g, 2.78 mmol) was added and the reaction mixture was stirred at rt for 16 h. The progress of the reaction was monitored by TLC. Upon completion the reaction mass was diluted with water and extracted with 10% MeOH/DCM. The combined organic layers were dried over sodium sulphate and concentrated under reduced pressure. The crude compound was purified by column chromatography to afford the title compound (0.35 g, 44%).

Analytical Data:

LCMS: 567.40 (M+1); $^1$H NMR (400 MHz, MeOD-d4) δ 8.53 (s, 1H), 8.44 (d, J=4.0 Hz, 1H), 7.87 (d, J=7.6 Hz, 1H), 7.44-7.41 (m, 1H), 7.15 (s, 1H), 6.99 (d, J=2.0 Hz, 1H), 4.37 (s, 2H), 4.03 (s, 3H), 4.01-3.95 (m, 1H), 3.58 (s, 3H), 3.03 (q, J=6.8 Hz, 2H), 2.70-2.55 (m, 2H), 2.22-2.19 (m, 9H), 1.87-1.79 (m, 4H), 1.42-1.29 (m, 7H), 0.83 (t, J=6.8 Hz, 3H).

227

Compound 73: 5-chloro-N-((1,5-dimethyl-3-oxo-2,3-dihydro-1H-pyrazol-4-yl)methyl)-3-(ethyl((trans)-4-(methyl(1-(pyridin-3-yl)ethyl)amino)cyclohexyl)amino)-2-methylbenzamide

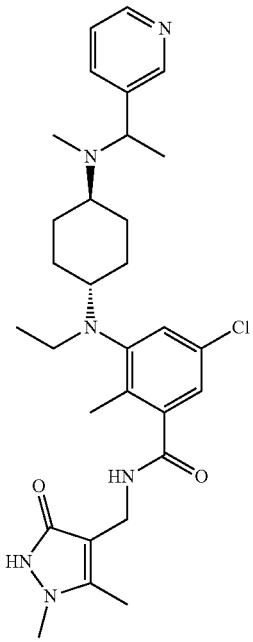 [SMILES: CCN(c1cc(Cl)cc(C(=O)NCc2c(C)n(C)[nH]c2=O)c1C)[C@H]1CC[C@H](N(C)C(C)c2cccnc2)CC1]

Synthesis of 5-chloro-N-((1,5-dimethyl-3-oxo-2,3-dihydro-1H-pyrazol-4-yl)methyl)-3-(ethyl((trans)-4-(methyl(1-(pyridin-3-yl)ethyl)amino)cyclohexyl)amino)-2-methylbenzamide To a stirred solution of 5-chloro-3-(ethyl((trans)-4-(methyl(1-(pyridin-3-yl)ethyl)amino)cyclohexyl)amino)-N-((3-methoxy-1,5-dimethyl-1H-pyrazol-4-yl)methyl)-2-methylbenzamide (0.35 g, 0.617 mmol) in methanolic HCl (15 mL), conc. HCl (0.2 mL) was added and the reaction mixture was stirred at 90° C. for 12 h. The progress of the reaction was monitored by TLC. Upon completion the reaction mixture was concentrated to dryness under reduced pressure. The residue obtained was basified with aqueous sat. sodium bicarbonate solution and extracted with 10% MeOH\DCM. The combined organic layers were dried over Na2SO4 and concentrated under reduced pressure to afford the crude material, which was purified by column chromatography to afford the title compound (0.025 g, 7%).

Analytical Data:

LCMS: 553.55 (M+1); $^1$H NMR (400 MHz, MeOD-d4) δ 8.53 (s, 1H), 8.44 (d, J=4.0 Hz, 1H), 7.88 (d, J=7.6 Hz, 1H), 7.44-7.41 (m, 1H), 7.16 (s, 1H), 7.03 (s, 1H), 4.19 (s, 2H), 4.00-3.99 (m, 1H), 3.43 (s, 3H), 3.03 (q, J=6.8 Hz, 2H), 2.73-2.56 (m, 2H), 2.25 (s, 3H), 2.24 (s, 3H), 2.21 (s, 3H), 1.87-1.79 (m, 4H), 1.43-1.29 (m, 7H), 0.83 (t, J=6.4 Hz, 3H).

228

Compound 74: 5-chloro-N-((4,6-dimethyl-2-oxo-1,2-dihydropyridin-3-yl)methyl)-3-(ethyl(1-(2-methoxyethyl)piperidin-4-yl)amino)-2-methylbenzamide

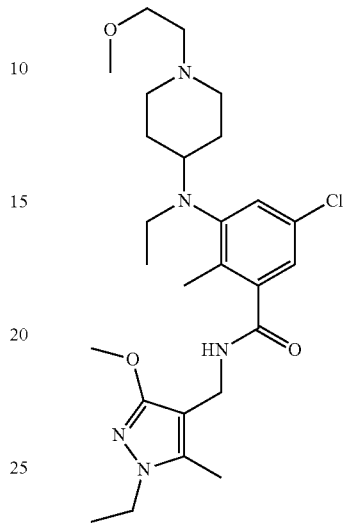

Step 1: Synthesis of tert-butyl 4-((5-chloro-3-(methoxycarbonyl)-2-methylphenyl)-amino)-piperidine-1-carboxylate To a stirred solution of methyl 3-amino-5-chloro-2-methylbenzoate (10 g, 50.25 mmol) and tert-butyl 4-oxopiperidine-1-carboxylate (19.9 g, 100.5 mmol) in dichloroethane (100 mL), acetic acid (18.09 g, 301.5 mmol) was added and the reaction was stirred at rt for 20 min. Then sodium triacetoxyborohydride (31.95 g, 150.7 mmol) was added at 0° C. and the reaction was stirred at rt for 16 h. The progress of the reaction was monitored by TLC. Upon completion the reaction was quenched with aqueous sodium bicarbonate solution, the organic layer was separated and the aqueous layer was extracted with dichloromethane. The combined organic layers were dried over anhydrous sodium sulphate and concentrated under reduced pressure. The crude compound was purified by column chromatography to afford the title compound (12.5 g, 65%).

Step 2: Synthesis of tert-butyl 4-((5-chloro-3-(methoxycarbonyl)-2-methylphenyl)-(ethyl)-amino)piperidine-1-carboxylate To a stirred solution of tert-butyl 4-((5-chloro-3-(methoxycarbonyl)-2-methylphenyl)-amino)-piperidine-1-carboxylate (12 g, 31.41 mmol) and acetaldehyde (3.46 g, 78.53 mmol) in dichloroethane (150 mL), acetic acid (11.30 g, 188.4 mmol) was added and the reaction was stirred at rt for 20 min. Then sodium triacetoxyborohydride (19.9 g, 93.86 mmol) was added and the reaction was stirred at rt for 12 h. The progress of the reaction was monitored by TLC. Upon completion the reaction was quenched with aqueous sodium bicarbonate solution, the organic layer was separated and the aqueous layer was extracted with dichloromethane. The combined organic layers were dried over anhydrous Na2SO4 and concentrated under reduced pressure. The crude compound was purified by column chromatography to afford the title compound (10.2 g, 79%).

Step 3: Synthesis of methyl 5-chloro-3-(ethyl(piperidin-4-yl)amino)-2-methylbenzoate To a stirred solution of tert-butyl 4-((5-chloro-3-(methoxycarbonyl)-2-methylphenyl)-(ethyl)-amino)-piperidine-1-carboxylate (10.2 g, 24.87 mmol) in DCM (100 mL) at 0° C., TFA (10 mL) was added and the reaction was stirred at rt for 2 h. The progress of the reaction was monitored by TLC. Upon completion the reaction mass was concentrated to dryness. The residue obtained was basified with sat. sodium bicarbonate solution till pH 8 and aqueous layer extracted with 10% MeOH/DCM. The combined organic layers were dried over Na$_2$SO$_4$ and concentrated under reduced pressure to afford the title compound (7.5 g) which was used in the subsequent step without further purification.

Step 4: Synthesis of methyl 5-chloro-3-(ethyl(1-(2-methoxyethyl)piperidin-4-yl)amino)-2-methylbenzoate To a stirred solution of methyl 5-chloro-3-(ethyl(piperidin-4-yl)amino)-2-methylbenzoate (4 g, 12.90 mmol) and 1-bromo-2-methoxyethane (2.69 g, 19.35 mmol) in ACN (40 mL), K$_2$CO$_3$ (3.56 g, 25.8 mmol) and KI (1.28 g, 7.71 mmol) were added. The reaction mixture was stirred at 60° C. for 16 h. The progress of the reaction was monitored by TLC. Upon completion the reaction mass was diluted with water and extracted with 10% MeOH/DCM. The combined organic layers were dried over anhydrous Na$_2$SO$_4$ and concentrated under reduced pressure. The crude compound was purified by column chromatography to afford the title compound (3 g, 63%).

Step 5: Synthesis of 5-chloro-3-(ethyl(1-(2-methoxyethyl)piperidin-4-yl)amino)-2-methylbenzoic Acid To a stirred solution of methyl 5-chloro-3-(ethyl(1-(2-methoxyethyl)piperidin-4-yl)amino)-2-methylbenzoate (3 g, 8.15 mmol) in EtOH (30 mL), aq. NaOH (0.489 g, 12.22 mmol) was added and the reaction was stirred at 60° C. for 1 h. The progress of the reaction was monitored by TLC. Upon completion ethanol was removed under reduced pressure and the reaction mass was acidified using dil. HCl up to pH 6 and extracted with 10% MeOH/DCM. The combined organic layers were dried over anhydrous Na$_2$SO$_4$ and concentrated giving the respective acid (2.5 g) which was used in the subsequent step without further purification.

Step 6: Synthesis of 5-chloro-3-(ethyl(1-(2-methoxyethyl) piperidin-4-yl) amino)-N-((1-ethyl-3-methoxy-5-methyl-1H-pyrazol-4-yl)methyl)-2-methylbenzamide To a stirred solution of 5-chloro-3-(ethyl(1-(2-methoxyethyl)piperidin-4-yl)amino)-2-methylbenzoic acid (0.35 g, 0.98 mmol) in DCM: DMF (5 mL+1 mL), TBTU (0.413 g, 1.28 mmol) and DIPEA (0.382 g, 2.96 mmol) were added and the solution was stirred at rt for 20 min. Then (1-ethyl-3-methoxy-5-methyl-1H-pyrazol-4-yl) methanamine (0.334 g, 1.97 mmol) was added and the reaction mixture was stirred at rt for 16 h. The progress of the reaction was monitored by TLC. Upon completion the reaction mixture was diluted with sat. sodium bicarbonate solution and extracted with 10% MeOH/DCM. The combined organic layers were washed with water, dried over Na$_2$SO$_4$ and concentrated under reduced pressure. The crude compound was purified by column chromatography to afford the title compound (0.2 g, 40%).

Analytical Data:

LCMS: 506.50 (M+1); $^1$H NMR (400 MHz, DMSO-d6) δ 8.51 (t, J=5.2 Hz, 1H), 7.22 (s, 1H), 6.98 (s, 1H), 4.21 (d, J=5.2 Hz, 2H), 3.95 (s, 3H), 3.82 (q, J=7.2 Hz, 2H), 3.50-3.44 (m, 2H), 3.24 (s, 3H), 3.03-3.01 (m, 3H), 2.88-2.67 (m, 2H), 2.17 (s, 3H), 2.09 (s, 3H), 1.80-1.65 (m, 4H), 1.23 (t, J=7.2 Hz, 3H), 0.79 (t, J=6.8 Hz, 3H), 4H merged in solvent peak.

Compound 75: 5-chloro-3-(ethyl(1-(2-methoxyethyl)piperidin-4-yl)amino)-N-((1-ethyl-5-methyl-3-oxo-2,3-dihydro-1H-pyrazol-4-yl)methyl)-2-methylbenzamide

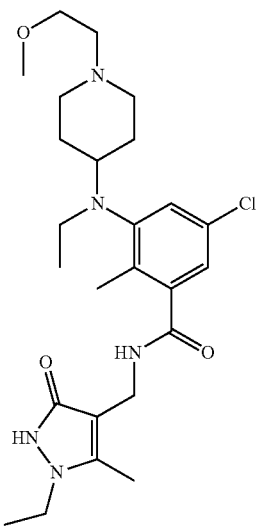 [SMILES: CCN(c1cc(Cl)cc(C(=O)NCc2c(C)n(CC)[nH]c2=O)c1C)C1CCN(CCOC)CC1]

Step 1: Synthesis of 5-chloro-3-(ethyl(1-(2-methoxyethyl)piperidin-4-yl)amino)-N-((1-ethyl-5-methyl-3-oxo-2,3-dihydro-1H-pyrazol-4-yl)methyl)-2-methylbenzamide To a stirred solution of 5-chloro-3-(ethyl(1-(2-methoxyethyl)piperidin-4-yl)amino)-N-((1-ethyl-3-methoxy-5-methyl-1H-pyrazol-4-yl)methyl)-2-methylbenzamide (0.18 g, 0.35 mmol) in methanolic HCl (2 mL), conc. HCl (2-3 drops) was added and the reaction mixture was stirred at 80° C. for 12 h. The progress of the reaction was monitored by TLC. Upon completion the reaction mixture was concentrated to dryness under reduced pressure. The residue obtained was basified with aqueous sodium bicarbonate solution and extracted with 10% MeOH\DCM. The combined organic layers were dried over Na$_2$SO$_4$ and concentrated under reduced pressure to afford the crude material; which was purified by column chromatography over basic alumina to afford the title compound (0.025 g, 14%).

Analytical Data:

LCMS: 492.45 (M+1); $^1$H NMR (400 MHz, MeOD) δ 7.21 (d, J=2.0 Hz, 1H), 7.06 (d, J=2.0 Hz, 1H), 4.20 (s, 2H), 3.85 (q, J=7.2 Hz, 2H), 3.53 (t, J=5.6 Hz, 2H), 3.33 (s, 3H), 3.11-3.02 (m, 4H), 2.89-2.85 (m, 1H), 2.66 (t, J=5.6 Hz, 2H), 2.25-2.17 (m, 8H), 1.80-1.69 (m, 4H), 1.27 (t, J=6.8 Hz, 3H), 0.86 (t, J=7.2 Hz, 3H).

Compound 76: 5-chloro-3-(ethyl(1-(2-methoxyethyl)piperidin-4-yl)amino)-N-((3-methoxy-1,5-dimethyl-1H-pyrazol-4-yl)methyl)-2-methylbenzamide

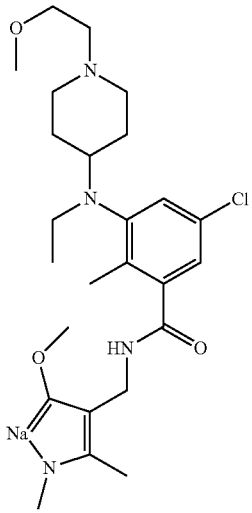

Step 1: Synthesis of 5-chloro-3-(ethyl(1-(2-methoxyethyl)piperidin-4-yl)amino)-N-((3-methoxy-1,5-dimethyl-1H-pyrazol-4-yl)methyl)-2-methylbenzamide To a stirred solution of 5-chloro-3-(ethyl(1-(2-methoxyethyl)piperidin-4-yl)amino)-2-methylbenzoic acid (0.3 g, 0.84 mmol) in DCM: DMF (3 mL+1 mL), TBTU (0.353 g, 1.10 mmol) and DIPEA (0.325 g, 2.52 mmol) were added and the solution was stirred at rt for 20 min. Then (3-methoxy-1,5-dimethyl-1H-pyrazol-4-yl)methanamine (0.26 g, 1.68 mmol) was added and the reaction mixture was stirred at rt for 16 h. The progress of the reaction was monitored by TLC. Upon completion the reaction mixture was diluted with water and extracted with 10% MeOH/DCM. The combined organic layers were washed with water, dried over $Na_2SO_4$ and concentrated under reduced pressure. The crude compound was purified by column chromatography to afford the title compound (0.23 g, 55%).

Analytical Data:

LCMS: 492.50 (M+1); $^1$H NMR (400 MHz, DMSO-d6) δ 8.49 (t, J=5.2 Hz, 1H), 7.21 (d, J=2.0 Hz, 1H), 6.98 (d, J=2.0 Hz, 1H), 4.21 (d, J=5.2 Hz, 2H), 3.94 (s, 3H), 3.49 (s, 3H), 3.48-3.45 (m, 2H), 3.23 (s, 3H), 3.02 (q, J=6.8 Hz, 2H), 2.17 (s, 3H), 2.08 (s, 3H), 1.67 (s, 1H), 1.57 (s, 1H), 0.79 (t, J=6.8 Hz, 3H), 7H merged in solvent peak.

Compound 77: 5-chloro-N-((1,5-dimethyl-3-oxo-2,3-dihydro-1H-pyrazol-4-yl)methyl)-3-(ethyl(1-(2-methoxyethyl)piperidin-4-yl)amino)-2-methylbenzamide

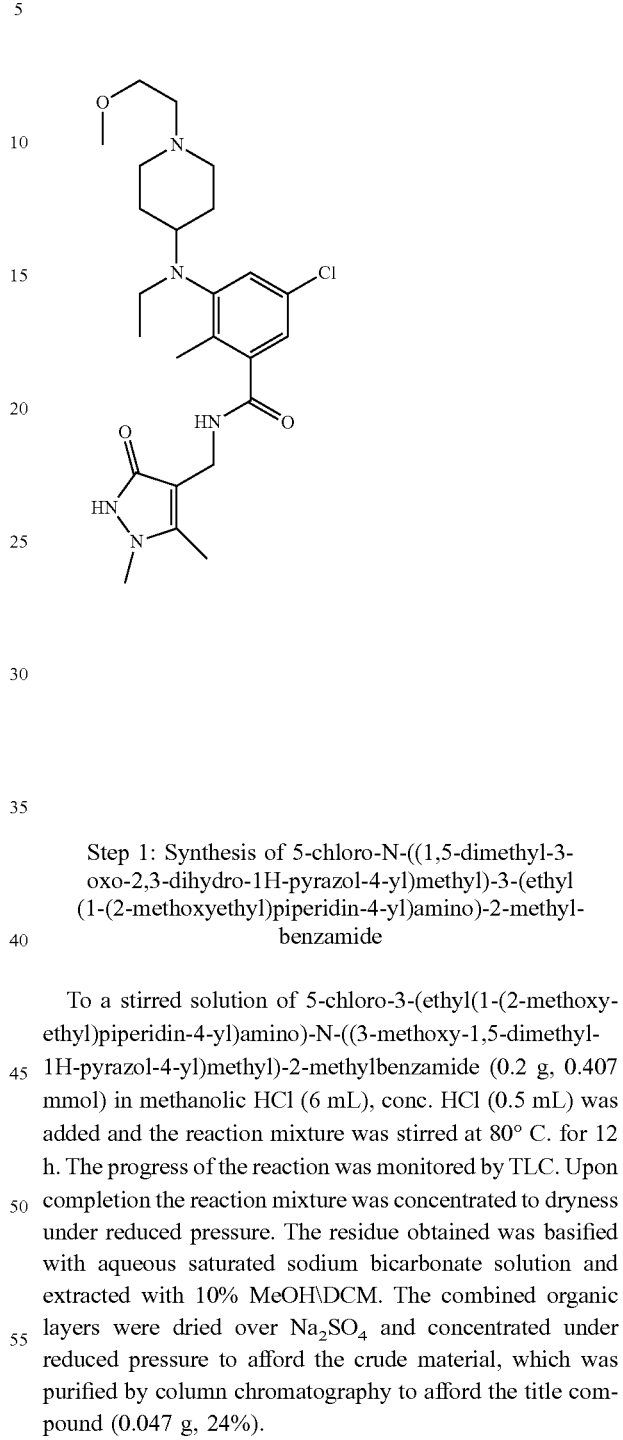

Step 1: Synthesis of 5-chloro-N-((1,5-dimethyl-3-oxo-2,3-dihydro-1H-pyrazol-4-yl)methyl)-3-(ethyl(1-(2-methoxyethyl)piperidin-4-yl)amino)-2-methylbenzamide To a stirred solution of 5-chloro-3-(ethyl(1-(2-methoxyethyl)piperidin-4-yl)amino)-N-((3-methoxy-1,5-dimethyl-1H-pyrazol-4-yl)methyl)-2-methylbenzamide (0.2 g, 0.407 mmol) in methanolic HCl (6 mL), conc. HCl (0.5 mL) was added and the reaction mixture was stirred at 80° C. for 12 h. The progress of the reaction was monitored by TLC. Upon completion the reaction mixture was concentrated to dryness under reduced pressure. The residue obtained was basified with aqueous saturated sodium bicarbonate solution and extracted with 10% MeOH\DCM. The combined organic layers were dried over $Na_2SO_4$ and concentrated under reduced pressure to afford the crude material, which was purified by column chromatography to afford the title compound (0.047 g, 24%).

Analytical Data:

LCMS: 478.45 (M+1); $^1$H NMR (400 MHz, DMSO-d6) δ 11.00-10.50 (bs, 1H), 8.59-8.53 (m, 1H), 7.19 (d, J=2.0 Hz, 1H), 6.98 (d, J=2.0 Hz, 1H), 4.06 (d, J=3.6 Hz, 2H), 3.37 (t, J=5.6 Hz, 2H), 3.20 (s, 3H), 3.01 (q, J=6.8 Hz, 2H), 2.84-2.81 (m, 2H), 2.70-2.65 (m, 1H), 2.40 (t, J=5.6 Hz, 2H), 2.15 (s, 3H), 2.04 (s, 3H), 1.93-1.87 (m, 2H), 1.62-1.46 (m, 4H), 0.780 (t, J=6.8 Hz, 3H), 3H merged in solvent peak.

Compound 78: 5-chloro-3-(ethyl(1-(3-methoxyphenethyl)piperidin-4-yl)amino)-N-((3-methoxy-1,5-dimethyl-1H-pyrazol-4-yl)methyl)-2-methylbenzamide

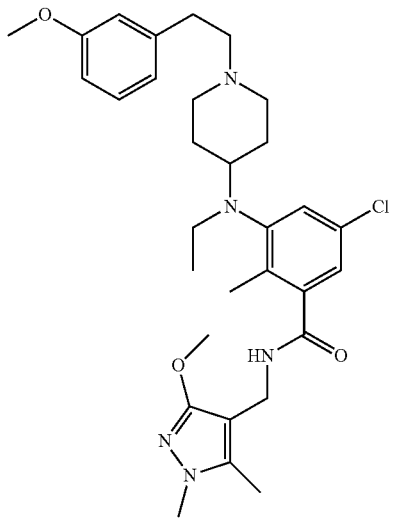 [SMILES: CCN(c1cc(Cl)cc(C(=O)NCc2c(OC)nn(C)c2C)c1C)C1CCN(CCc2cccc(OC)c2)CC1]

Step 1: Synthesis of 2-(3-methoxyphenyl)ethan-1-ol

To a stirred solution of methyl 2-(3-methoxyphenyl)acetate (5 g, 27.77 mmol) in dry THF (50 mL) at 0° C., LAH 1M in THF (42 mL, 41.66 mmol) was added and the reaction was stirred at 0° C. for 1 h. The progress of the reaction was monitored by TLC. Upon completion the reaction mass was quenched with aqueous saturated aqueous sodium sulphate solution and filtered. The filtrate was concentrated to dryness under reduced pressure. The residue obtained was diluted with water and extracted with DCM. The combined organic layers were dried over $Na_2SO_4$ and concentrated under reduced pressure. The crude compound was purified by column chromatography to afford the title compound (3.4 g, 80%).

Step 2: Synthesis of 1-(2-bromoethyl)-3-methoxybenzene

To a stirred solution of 2-(3-methoxyphenyl)ethan-1-ol (0.6 g, 3.94 mmol) in DCM, PPh3 (1.6 g, 5.92 mmol) was added and the solution was stirred at rt for 10 min. Then $CBr_4$ (2.6 g, 7.88 mmol) was added at 0° C. The resulting reaction mixture was stirred at rt for 2 h. The progress of the reaction was monitored by TLC. Upon completion the reaction mass was diluted with water and extracted with DCM. The combined organic layers were dried over $Na_2SO_4$ and concentrated under reduced pressure. The crude compound was purified by column chromatography to afford the title compound (0.725 g, 85%).

Step 3: Synthesis of methyl 5-chloro-3-(ethyl(1-(3-methoxyphenethyl)piperidin-4-yl)amino)-2-methylbenzoate To a stirred solution of methyl 5-chloro-3-(ethyl(piperidin-4-yl)amino)-2-methylbenzoate (0.7 g, 2.26 mmol) and 1-(2-bromoethyl)-3-methoxybenzene (0.725 g, 3.38 mmol) in ACN (10 mL), $K_2CO_3$ (0.623 g, 4.51 mmol) and KI (0.225 g, 1.36 mmol) were added. The reaction mixture was stirred at 60° C. for 16 h. The progress of the reaction was monitored by TLC. Upon completion the reaction mass was diluted with water and extracted with 10% MeOH/DCM. The combined organic layers were dried over anhydrous sodium sulphate and concentrated under reduced pressure. The crude compound was purified by column chromatography to afford the title compound (0.5 g, 50%).

Step 4: Synthesis of 5-chloro-3-(ethyl(1-(3-methoxyphenethyl)piperidin-4-yl)amino)-2-methylbenzoic Acid To a stirred solution of methyl 5-chloro-3-(ethyl(1-(3-methoxyphenethyl)piperidin-4-yl)amino)-2-methylbenzoate (0.5 g, 1.13 mmol) in EtOH (10 mL), aq. NaOH (0.068 g, 1.69 mmol) was added and the reaction was stirred at 60° C. for 1 h. The progress of the reaction was monitored by TLC. Upon completion the ethanol was removed under reduced pressure and the reaction mass was acidified using dil. HCl up to pH 6 and extracted with 10% MeOH/DCM. The combined organic layers were dried over anhydrous sodium sulphate and concentrated under reduced pressure to afford the title compound (0.41 g) which was used in the subsequent step without further purification.

Step 5: Synthesis of 5-chloro-3-(ethyl(1-(3-methoxyphenethyl)piperidin-4-yl)amino)-N-((3-methoxy-1,5-dimethyl-1H-pyrazol-4-yl)methyl)-2-methylbenzamide To a stirred solution of 5-chloro-3-(ethyl(1-(3-methoxyphenethyl)piperidin-4-yl)amino)-2-methylbenzoic acid (0.2 g, 0.406 mmol) in DCM: DMF (3 mL+1 mL), TBTU (0.194 g, 0.604 mmol) and DIPEA (0.180 g, 1.40 mmol) were added and the solution was stirred at rt for 20 min. Then (3-methoxy-1,5-dimethyl-1H-pyrazol-4-yl)methanamine (0.125 g, 0.812 mmol) was added and the reaction mixture was stirred at rt for 16 h. The progress of the reaction was monitored by TLC. Upon completion the reaction mixture was diluted with aqueous saturated aqueous sodium bicarbonate solution and extracted with 10% MeOH/DCM. The combined organic layers were washed with water, dried over sodium sulphate and concentrated under reduced pressure. The crude compound was purified by column chromatography to afford the title compound (0.16 g, 60%).

Analytical Data:

LCMS: 568.45 (M+1); $^1$H NMR (400 MHz, DMSO-d6) δ 8.52 (t, J=4.8 Hz, 1H), 7.25-7.20 (m, 2H), 7.00 (s, 1H), 6.85-6.78 (m, 3H), 4.21 (d, J=5.2 Hz, 2H), 3.94 (s, 3H), 3.73 (s, 3H), 3.49 (s, 3H), 3.48-3.45 (m, 1H), 3.04-3.02 (m, 3H), 2.94-2.89 (m, 2H), 2.18 (s, 3H), 2.08 (s, 3H), 1.92-1.67 (m, 4H), 0.80 (t, J=6.8 Hz, 3H), 5H merged in solvent peak.

235

Compound 79: 5-chloro-N-((1,5-dimethyl-3-oxo-2,3-dihydro-1H-pyrazol-4-yl)methyl)-3-(ethyl(1-(3-methoxyphenethyl)piperidin-4-yl)amino)-2-methyl-benzamide

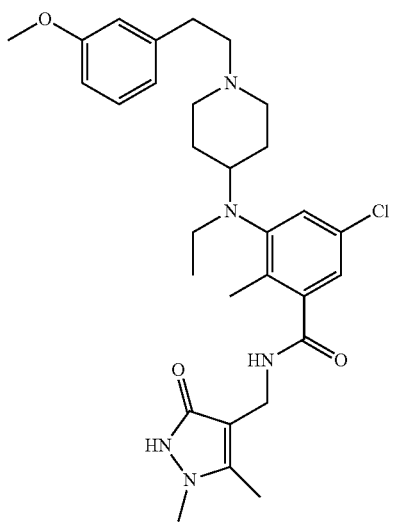 [SMILES: CCN(c1cc(Cl)cc(C(=O)NCc2c(C)n(C)[nH]c2=O)c1C)C1CCN(CCc2cccc(OC)c2)CC1]

Step 1: Synthesis of 5-chloro-N-((1,5-dimethyl-3-oxo-2,3-dihydro-1H-pyrazol-4-yl)methyl)-3-(ethyl(1-(3-methoxyphenethyl)piperidin-4-yl)amino)-2-methylbenzamide To a stirred solution of 5-chloro-3-(ethyl(1-(3-methoxyphenethyl)piperidin-4-yl)amino)-N-((3-methoxy-1,5-dimethyl-1H-pyrazol-4-yl)methyl)-2-methylbenzamide (0.11 g, 0.194 mmol) in methanolic HCl (2 mL), conc. HCl (2-3 drops) was added and the reaction mixture was stirred at 80° C. for 12 h. The progress of the reaction was monitored by TLC. Upon completion the reaction mixture was concentrated to dryness under reduced pressure. The residue obtained was basified with aqueous saturated aqueous sodium bicarbonate solution and extracted with 10% MeOH\DCM. The combined organic layers were dried over Na$_2$SO$_4$ and concentrated under reduced pressure to afford the crude material, which was purified by column chromatography to afford the title compound (0.07 g, 65%).

Analytical Data:

LCMS: 554 (M+1); $^1$H NMR (400 MHz, DMSO-d6) δ 8.54 (bs, 1H), 7.20-7.14 (m, 2H), 6.99 (s, 1H), 6.77-6.72 (m, 3H), 4.05 (d, J=4.0 Hz, 2H), 3.72 (s, 3H), 3.35-3.31 (s, 3H), 3.02 (q, J=7.2 Hz, 2H), 2.90-2.88 (m, 2H), 2.71-2.64 (m, 3H), 2.47-2.43 (m, 2H), 2.16 (s, 3H), 2.05 (s, 3H), 1.91 (t, J=10.8 Hz, 2H), 1.66-1.63 (m, 2H), 1.53-1.50 (m, 2H), 0.79 (t, J=6.8 Hz, 3H).

236

Compound 80: 5-chloro-3-(((trans)-4-(dimethyl-amino)cyclohexyl)(ethyl)amino)-N-((3-methoxy-1-methyl-5-(pyrrolidin-1-yl)-1H-pyrazol-4-yl)methyl)-2-methylbenzamide

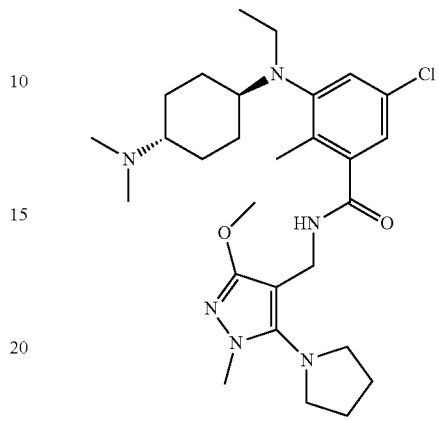

Step 1: Synthesis of (Z)-ethyl 2-cyano-3-(methyl-thio)-3-(pyrrolidin-1-yl)acrylate To a stirred solution of ethyl 2-cyano-3,3-bis(methylthio)acrylate (10 g, 46.02 mmol) in ACN (100 mL), pyrrolidine (3.77 mL, 46.02 mmol) was added. The resulting reaction mixture was heated at 50° C. for 2 h. The progress of the reaction was monitored by TLC. Upon completion the reaction was cooled to rt and diluted with ethyl acetate. The organic layer was washed with brine, dried over Na2SO4, filtered and evaporated to afford the title compound (10.2 g, 92%).

Step 2: Synthesis of 1-methyl-3-oxo-5-(pyrrolidin-1-yl)-2,3-dihydro-1H-pyrazole-4-carbonitrile To a stirred solution of (Z)-ethyl 2-cyano-3-(methylthio)-3-(pyrrolidin-1-yl)acrylate (10 g, 41.6 mmol) in ACN (100 mL), DBU (12.4 mL, 83.3 mmol) and methyl hydrazine (2.4 mL, 45.76 mmol) were added. The resulting reaction mixture was heated at 60° C. for 12 h. The progress of the reaction was monitored by TLC. Upon completion the reaction mixture was concentrated to dryness under reduced pressure. The residue obtained was diluted with water and extracted with ethyl acetate. The combined organic layers were washed with water, dried over Na$_2$SO$_4$ and concentrated under reduced pressure. The crude compound was purified by column chromatography to afford the title compound (2 g, 25%).

Step 3: Synthesis of 3-methoxy-1-methyl-5-(pyrrolidin-1-yl)-1H-pyrazole-4-carbonitrile To a stirred solution of 1-methyl-3-oxo-5-(pyrrolidin-1-yl)-2,3-dihydro-1H-pyrazole-4-carbonitrile (1.5 g, 7.80 mmol) in dry THF (15 mL) at 0° C., dry MeOH (0.375 g, 11.71 mmol), PPh$_3$ (3.07 g, 11.71 mmol) and DIAD (2.36 g, 11.71 mmol) were added. The reaction mixture was stirred at rt for 16 h. The progress of the reaction was monitored by TLC. Upon completion the reaction mixture was diluted with water and extracted with ethyl acetate. The combined organic layers were washed with water, dried over Na$_2$SO$_4$ and concentrated under reduced pressure. The crude compound was purified by column chromatography to afford the title compound (1 g, 62%).

Step 4: Synthesis of (3-methoxy-1-methyl-5-(pyrrolidin-1-yl)-1H-pyrazol-4-yl)methanamine To a stirred solution of 3-methoxy-1-methyl-5-(pyrrolidin-1-yl)-1H-pyrazole-4-carbonitrile (1 g, 4.85 mmol) in methanol (10 mL), catalytic amount of Raney Nickel and ammonia solution (2 mL) were added. The reaction mass was stirred at rt under hydrogen pressure (balloon pressure) for 12 h. The progress of the reaction was monitored by TLC. Upon completion the reaction mass was filtered through a bed of celite and washed with methanol. The filtrate was concentrated under reduced pressure to afford the title compound (0.7 g) which was used in the subsequent step without further purification.

Step 5: Synthesis of 5-chloro-3-(((trans)-4-(dimethylamino)cyclohexyl)(ethyl)amino)-N-((3-methoxy-1-methyl-5-(pyrrolidin-1-yl)-1H-pyrazol-4-yl)methyl)-2-methylbenzamide To a stirred solution of 5-chloro-3-(((trans)-4-(dimethylamino)cyclohexyl)(ethyl)amino)-2-methylbenzoic acid (0.44 g, 1.30 mmol) in DCM:DMF (5 mL+1 mL), TBTU (0.54 g, 1.69 mmol) and DIPEA (0.671 g, 5.20 mmol) were added and the solution was stirred at rt for 20 min. Then (3-methoxy-1-methyl-5-(pyrrolidin-1-yl)-1H-pyrazol-4-yl)methanamine (0.3 g, 1.43 mmol) was added and the reaction mixture was stirred at rt for 16 h. The progress of the reaction was monitored by TLC. Upon completion the reaction mixture was diluted with aqueous sat. sodium bicarbonate solution and extracted with 10% MeOH/DCM. The combined organic layers were washed with water, dried over $Na_2SO_4$ and concentrated under reduced pressure. The crude compound was purified by column chromatography to afford the title compound (0.1 g, 14%).

Analytical Data:
LCMS: 531.40 (M+1); $^1$H NMR (400 MHz, DMSO-d6) δ 8.29 (t, 1H), 7.18 (s, 1H), 6.93 (s, 1H), 4.14 (d, J=4.4 Hz, 2H), 3.74 (s, 3H), 3.47 (s, 3H), 3.41-3.38 (m, 1H), 3.24-3.19 (m, 4H), 3.01 (q, J=6.8 Hz, 2H), 2.68-2.64 (m, 1H), 2.16 (s, 3H), 1.88-1.80 (m, 8H), 1.41-1.25 (m, 4H), 0.79 (t, J=6.8 Hz, 3H), 6H merged in solvent peak.

Compound 81: 5-chloro-3-(((trans)-4-(dimethylamino)cyclohexyl) (ethyl)amino)-2-methyl-N-((1-methyl-3-oxo-5-(pyrrolidin-1-yl)-2,3-dihydro-1H-pyrazol-4-yl)methyl)benzamide

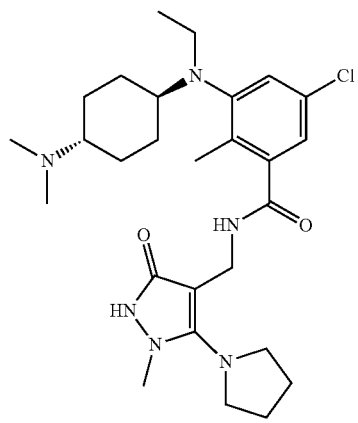 [SMILES: CCN(c1cc(Cl)cc(C(=O)NCc2c(N3CCCC3)n(C)[nH]c2=O)c1C)[C@H]1CC[C@H](N(C)C)CC1]

Step 1: Synthesis of 5-chloro-3-(((trans)-4-(dimethylamino)cyclohexyl)(ethyl)amino)-N-((3-hydroxy-1-methyl-5-(pyrrolidin-1-yl)-1H-pyrazol-4-yl)methyl)-2-methylbenzamide To a stirred solution of 5-chloro-3-(((trans)-4-(dimethylamino)cyclohexyl)(ethyl)amino)-N-((3-methoxy-1-methyl-5-(pyrrolidin-1-yl)-1H-pyrazol-4-yl)methyl)-2-methylbenzamide (0.24 g, 0.45 mmol), $BBr_3$ (1M in DCM, 0.36 g, 1.46 mmol) was added at 0° C. The resulting reaction mixture was stirred at rt for 12 h. The progress of the reaction was monitored by TLC. Upon completion; the reaction mixture was concentrated to dryness. The residue obtained was basified with aqueous sodium bicarbonate solution and extracted with 10% MeOH/DCM. The combined organic layers were dried over anhydrous $Na_2SO_4$ and concentrated under reduced pressure. The crude compound obtained was purified by silica gel (100-200) column chromatography to afford the title compound (0.075 g, 32.2%).

Analytical Data:
LCMS: 517.40 (M+1); $^1$H NMR (400 MHz, Methanol-d4) δ 7.19 (d, J=2.3 Hz, 1H), 7.03 (d, J=2.1 Hz, 1H), 4.30 (s, 2H), 3.55-3.50 (m, 4H), 3.18 (s, 3H), 3.09 (q, J=7.0 Hz, 2H), 2.75-2.70 (m, 1H), 2.39 (s, 7H), 2.25 (s, 3H), 2.03-1.88 (m, 8H), 1.53-1.39 (m, 2H), 1.38-1.14 (m, 2H), 0.87 (q, J=8.4, 7.0 Hz, 3H).

Compound 82: 5-chloro-3-(((trans)-4-(dimethylamino)cyclohexyl) (ethyl)amino)-N-((3-methoxy-1-methyl-5-morpholino-1H-pyrazol-4-yl)methyl)-2-methylbenzamide

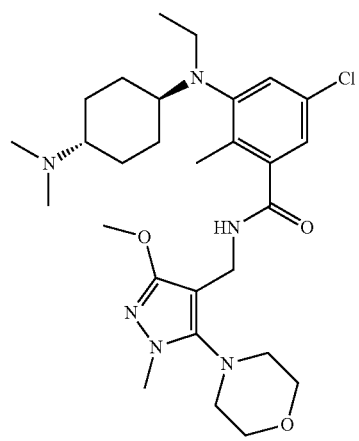 [SMILES: CCN(c1cc(Cl)cc(C(=O)NCc2c(OC)nn(C)c2N2CCOCC2)c1C)[C@H]1CC[C@H](N(C)C)CC1]

Synthesis of 5-chloro-3-(((trans)-4-(dimethylamino)cyclohexyl)(ethyl)amino)-N-((3-methoxy-1-methyl-5-morpholino-1H-pyrazol-4-yl)methyl)-2-methylbenzamide To a stirred solution of 5-chloro-3-(((trans)-4-(dimethylamino)cyclohexyl)(ethyl)amino)-2-methylbenzoic acid (0.4 g, 1.18 mmol) in DCM: DMF (5 mL+1 mL), TBTU (0.493 g, 1.53 mmol) and DIPEA (0.61 g, 4.73 mmol) were added and the solution was stirred at rt for 20 min. Then (3-methoxy-1-methyl-5-morpholino-1H-pyrazol-4-yl)methanamine (0.32 g, 1.42 mmol) was added and the reaction mixture was stirred at rt for 16 h. The progress of the reaction was monitored by TLC. Upon completion the reaction mixture was diluted with aqueous saturated sodium bicarbonate solution and extracted with 10% MeOH/DCM. The combined organic layers were washed with water, dried over Na$_2$SO$_4$ and concentrated under reduced pressure. The crude compound was purified by column chromatography to afford the title compound (0.17 g, 26%).

Analytical Data:

LCMS: 547.40 (M+1); $^1$H NMR (400 MHz, MeOD-d4) δ 7.21 (s, 1H), 7.10 (s, 1H), 4.37 (s, 2H), 3.85 (s, 3H), 3.80 (t, J=4.4 Hz, 4H), 3.59 (s, 3H), 3.16-3.07 (m, 8H), 2.78 (s, 6H), 2.27 (s, 3H), 2.09-2.00 (m, 4H), 1.55-1.47 (m, 4H), 0.87 (t, J=6.8 Hz, 3H).

Compound 83: 5-chloro-3-(ethyl((trans)-4-((3-methoxybenzyl)(methyl)amino) cyclohexyl)amino)-N-((3-methoxy-1-methyl-5-(piperidin-1-yl)-1H-pyrazol-4-yl)methyl)-2-methylbenzamide

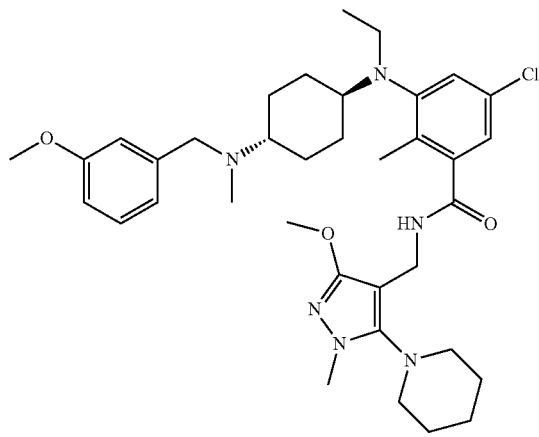 [SMILES: CCN(c1cc(Cl)cc(C(=O)NCc2c(OC)nn(C)c2N2CCCCC2)c1C)[C@H]1CC[C@H](N(C)Cc2cccc(OC)c2)CC1]

Step 1: Synthesis of 5-chloro-3-(ethyl((trans)-4-((3-methoxybenzyl)(methyl)amino)cyclohexyl)amino)-N-((3-methoxy-1-methyl-5-(piperidin-1-yl)-1H-pyrazol-4-yl)methyl)-2-methylbenzamide To a stirred solution of 5-chloro-3-(ethyl((trans)-4-((3-methoxybenzyl)(methyl)amino)cyclohexyl)amino)-2-methylbenzoic acid (1 g, 2.25 mmol) in DCM:DMF (10 mL+2 mL), TBTU (0.94 g, 2.93 mmol) and DIPEA (0.87 g, 6.75 mmol) were added and the solution was stirred at rt for 20 min. Then (3-methoxy-1-methyl-5-(piperidin-1-yl)-1H-pyrazol-4-yl)methanamine (0.761 g, 3.37 mmol) was added and the reaction mixture was stirred at rt for 16 h. The progress of the reaction was monitored by TLC. Upon completion the reaction mixture was diluted with aqueous saturated sodium bicarbonate solution and extracted with 10% MeOH/DCM. The combined organic layers were washed with water, dried over Na2SO4 and concentrated under reduced pressure. The crude compound was purified by column chromatography to afford the title compound (0.2 g, 14%).

Analytical Data:

LCMS: 651.55 (M+1); $^1$H NMR (400 MHz, DMSO-d6) δ 8.29 (t, 1H), 7.20-7.15 (m, 2H), 6.94-6.85 (m, 4H), 4.17 (d, J=4.0 Hz, 2H), 3.74 (s, 5H), 3.47 (s, 3H), 3.06-2.98 (m, 6H), 2.17 (s, 3H), 2.15-2.10 (m, 2H), 1.84-1.78 (m, 4H), 1.59-1.52 (m, 6H), 1.50-1.25 (m, 4H), 0.79 (t, J=6.8 Hz, 3H), 6H merged in solvent peak.

Compound 84: 5-chloro-3-(ethyl((trans)-4-((4-methoxybenzyl)(methyl)amino) cyclohexyl)amino)-2-methyl-N-((1-methyl-3-oxo-5-(piperidin-1-yl)-2,3-dihydro-1H-pyrazol-4-yl)methyl)benzamide

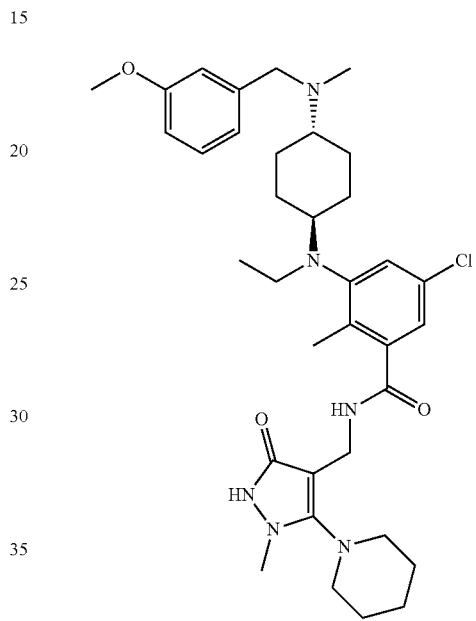

Step 1: Synthesis of 5-chloro-3-(ethyl((trans)-4-((3-methoxybenzyl)(methyl) amino)cyclohexyl)amino)-N-((3-hydroxy-1-methyl-5-(piperidin-1-yl)-1H-pyrazol-4-yl)methyl)-2-methylbenzamide To a stirring solution of compound 5-chloro-3-(ethyl((trans)-4-((3-methoxybenzyl)(methyl)amino)cyclohexyl)amino)-N-((3-methoxy-1-methyl-5-(piperidin-1-yl)-1H-pyrazol-4-yl)methyl)-2-methylbenzamide (0.05 g, 0.077 mmol) in methanolic HCl (prepared by passing HCl gas through MeOH at −10° C. for 4 h) (3 mL/100 mg), conc. HCl (0.5 mL) was added and the reaction mixture was stirred at rt for 20 h. On completion, the solvent was removed under reduced pressure. The crude compound was purified by prep-HPLC to afford the title compound (0.01 g, 20.4%).

Analytical Data of Formate Salt:

LCMS: 637.50 (M+1); $^1$H NMR (400 MHz, Methanol-d4) δ 7.28-7.18 (m, 2H), 7.03-7.00 (m, 1H), 6.91-6.80 (m, 3H), 4.35 (s, 3H), 3.84 (s, 3H), 3.55 (s, 2H), 3.12-3.07 (m, 4H), 2.82-2.78 (m, 2H), 2.59-2.49 (m, 3H), 2.38-2.28 (m, 1H), 2.26 (s, 3H), 2.10-1.95 (m, 4H), 1.68-1.61 (m, 4H), 1.50-1.02 (m, 8H), 1.00-0.94 (m, 5H).

Compound 85: 5-chloro-3-(((trans)-4-(dimethyl-amino)cyclohexyl)(ethyl) amino)-N-((3-ethoxy-5-methyl-1H-pyrazol-4-yl)methyl)-2-methylbenzamide

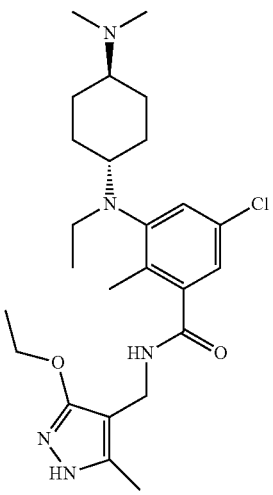 [SMILES: CCOc1n[nH]c(C)c1CNC(=O)c1cc(Cl)cc(N(CC)[C@H]2CC[C@H](N(C)C)CC2)c1C]

Step 1: Synthesis of ethyl 2-[(1,3-dioxo-2,3-di-hydro-1H-isoindol-2-yl)methyl]-3-oxobutanoate To a stirred mixture of ethyl 3-oxobutanoate (2.5 g, 19.21 mmol) and 2-(hydroxymethyl)-2,3-dihydro-1H-isoindole-1,3-dione (3.4 g, 19.21 mmol) in a flask cooled to 0° C. was added BF3 etherate (4.7 ml, 38.42 mmol) drop wise keeping the internal temperature <10° C. The reaction mixture was then allowed to warm to room temperature, after 30 min diethyl ether (~7 mL) was added since the reaction mixture had become very viscous. After stirring for 5 h the reaction mixture was poured onto 30 mL of saturated NaHCO₃, washed with DCM (2×50 mL), dried (MgSO₄) filtered and evaporated. Compound purified using a 100 g SNAP Biotage column on an Isolera system eluting with 5-60% EtOAc in heptane to afford the title compound as a white solid (832 mg, 87% purity by NMR, 15% yield). LC-MS 93%, 1.81 min (3.5 minute LC-MS method), m/z=289.90, 311.85 (M+Na), ¹H NMR (500 MHz, Chloroform-d) δ 7.84 (dd, J=5.4, 3.1 Hz, 2H), 7.72 (dd, J=5.5, 3.0 Hz, 2H), 4.25-4.12 (m, 4H), 4.03 (dd, J=8.1, 6.9 Hz, 1H), 2.30 (s, 3H), 1.23 (t, J=7.1 Hz, 3H).

Step 2: Synthesis of 2-[(3-ethoxy-5-methyl-1H-pyrazol-4-yl)methyl]-2,3-dihydro-1H-isoindole-1,3-dione To a stirred solution of ethyl 2-[(1,3-dioxo-2,3-dihydro-1H-isoindol-2-yl)methyl]-3-oxobutanoate (87% purity, 730 mg, 2.2 mmol) in EtOH (15 mL) was added drop wise a solution of hydrazine monohydrate (107 μL, 2.2 mmol, neutralised with 1M HCl). The reaction as stirred at 80° C. for 2 h and then cooled to room temperature and stirred for 16 h. A further 0.25 equiv. hydrazine hydrate was added (27 μL) and the reaction stirred at 80° C. for 3 h after which time the reaction mixture was evaporated to dryness and purified over a 50 g SNAP column on a Biotage Isolera system eluting with 1-10% MeOH in DCM to afford the title compound as an off-white powder (138 mg, 22% yield). LC-MS 100%, 1.65 min (3.5 minute LC-MS method), m/z=286.00, ¹H NMR (500 MHz, Methanol-d4) δ 7.84 (dd, J=5.4, 3.1 Hz, 2H), 7.79 (dd, J=5.5, 3.0 Hz, 2H), 4.59 (s, 2H), 4.04 (q, J=7.0 Hz, 2H), 2.30 (s, 3H), 1.17 (t, J=7.0 Hz, 3H).

From the purification the reaction also yielded 2-[(5-methyl-3-oxo-2,3-dihydro-1H-pyrazol-4-yl)methyl]-2,3-dihydro-1H-isoindole-1,3-dione (205 mg, 36%). LC-MS 99%, 1.35 min (3.5 minute LC-MS method), m/z=257.95, 1H NMR (500 MHz, Methanol-d4) δ 7.86 (dd, J=5.4, 3.1 Hz, 2H), 7.80 (dd, J=5.5, 3.0 Hz, 2H), 4.61 (s, 2H), 2.32 (s, 3H).

Step 3: Synthesis of (3-ethoxy-5-methyl-1H-pyrazol-4-yl)methanamine

To a stirred solution of 2-[(3-ethoxy-5-methyl-1H-pyrazol-4-yl)methyl]-2,3-dihydro-1H-isoindole-1,3-dione (120 mg, 0.42 mmol) in EtOH (5 mL) was added hydrazine hydrate (103 μL, 2.1 mmol) and the reaction was stirred at room temperature for 18 h. The reaction was evaporated to dryness in vacuo, dissolved in 5 mL of MeOH passed over a 10 g SCX-2 column, washed with MeOH (~50 mL), eluted with 7M NH3 in MeOH (~50 mL) and evaporated to dryness to give 68 mg of product that was taken on to the next stage without any further purification.

To a stirred solution of 3-((3-(((tert-butoxy)carbonyl)amino)cyclobutyl)(ethyl)amino]-5-chloro-2-methylbenzoic acid (99%, 153 mg, 0.40 mmol) in DMF (2 mL) cooled to 0° C. using an ice bath was added DIPEA (211 μL, 1.21 mmol) and HATU (169 mg, 0.4 mmol), the reaction was stirred for 10 minutes after which time (3-ethoxy-5-methyl-1H-pyrazol-4-yl)methanamine (95%, 66 mg, 0.4 mmol) was added and the reaction was then warmed to room temperature and stirred for 16 h. The reaction mixture was then poured onto satd. NaHCO₃ (10 mL) then the product was extracted into EtOAc (3×30 mL), the combined organics were washed with brine (20 mL), dried with Na₂SO₄, filtered and evaporated. The crude product was purified using acid preparative HPLC (low pH method) to afford the title compound as a white solid (48 mg, 23% yield). LC-MS: 100%, 2.95 min (7 minute method), m/z=238.55 and 476/478. ¹H NMR (500 MHz, Methanol-d4) δ 8.40 (s, 1H), 7.21 (d, J=2.1 Hz, 1H), 7.05 (d, J=2.1 Hz, 1H), 4.27 (s, 2H), 4.19 (q, J=7.1 Hz, 2H), 3.18-3.13 (m, 1H), 3.09 (q, J=7.0 Hz, 2H), 2.80 (s, 7H), 2.27 (s, 3H), 2.24 (s, 3H), 2.08 (d, J=9.6 Hz, 2H), 2.01 (d, J=10.4 Hz, 2H), 1.51 (q, J=11.4 Hz, 4H), 1.37 (t, J=7.1 Hz, 3H), 0.87 (t, J=7.0 Hz, 3H).

Step 4: Synthesis of 5-chloro-3-(ethyl((trans)-4-((4-methoxybenzyl)(methyl)amino) cyclohexyl)amino)-2-methyl-N-((1-methyl-3-oxo-5-(piperidin-1-yl)-2,3-dihydro-1H-pyrazol-4-yl)methyl)benzamide To a stirred solution of 5-chloro-3-(ethyl((trans)-4-(dimethylamino)cyclohexyl)amino)-2-methylbenzoic acid HCl (99% purity, 116 mg, 0.31 mmol) in DMF (2 mL) at 0° C. was added DIPEA (160 μL, 0.916 mmol, 3 equiv.) followed by HATU (128 mg, 0.336 mmol, 1.1 equiv.). The reaction was stirred at 0° C. for 5 min after which time (3-ethoxy-5-methyl-1H-pyrazol-4-yl)methanamine hydrochloride (90%, 65 mg, 0.31 mmol) was added and the reaction was stirred at room temperature for 16 h. The reaction mixture was then poured onto water (10 mL) and the suspension stirred for 20 min. The suspension was then extracted with EtOAc (3×20 mL) the combined organics were washed with brine (2×30 mL), dried with Na₂SO₄, filtered and evaporated to give a brown oil. The crude product was purified using preparative HPLC to afford the title compound B (12 mg, 7% yield):

Analytical Data:

LC-MS 95%, 2.97 min (7 minute LC-MS method), m/z=239.05 and 476.20/478.15, $^1$H NMR (500 MHz, Methanol-d4) δ 8.45 (s, 1H), 7.21 (d, J=2.1 Hz, 1H), 7.04 (d, J=2.1 Hz, 1H), 4.27 (s, 2H), 4.19 (q, J=7.0 Hz, 2H), 3.17-3.12 (m, 1H), 3.09 (q, J=7.0 Hz, 2H), 2.84-2.75 (m, 7H), 2.27 (s, 3H), 2.24 (s, 3H), 2.11-1.97 (m, 4H), 1.51 (q, J=11.6 Hz, 4H), 1.37 (t, J=7.0 Hz, 3H), 0.87 (t, J=7.0 Hz, 3H).

Compound 86: 5-chloro-3-(ethyl((trans)-4-(dimethylamino)cyclohexyl]amino)-N-((5-methoxy-1-methyl-3-oxo-2,3-dihydro-1H-pyrazol-4-yl)methyl)-2-methylbenzamide

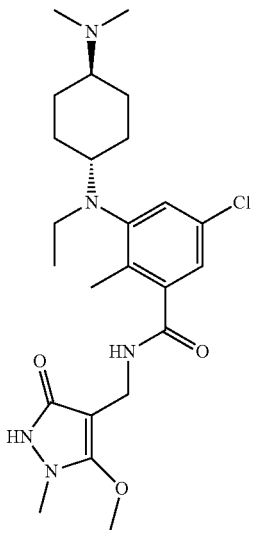

Step 1: Synthesis of 3-(benzyloxy)-1-methyl-5-(methylsulfanyl)-1H-pyrazole-4-carbonitrile To a stirred solution of 1-methyl-5-(methylsulfanyl)-3-oxo-2,3-dihydro-1H-pyrazole-4-carbonitrile (500 mg, 2.96 mmol) in anhydrous THF (15 mL) was added benzyl alcohol (461 μL, 4.43 mmol), PPh3 (1.16 g, 4.43 mmol) followed by DIAD (873 μL, 4.43 mmol) and the reaction was stirred at room temperature for 4 h under a nitrogen atmosphere. The crude reaction mixture was then evaporated to dryness in vacuo and purified on a 50 g KP-SIL column on a Biotage Horizon system eluting with a gradient of 12% to 75% EtOAc in heptane mixture to afford the title compound as a yellow oil (625 mg, 95% purity based on NMR, 78% yield). LC-MS 79%, 1.41 min (2 minute LC-MS method), m/z=260.00, $^1$H NMR (500 MHz, Chloroform-d) δ 7.48-7.27 (m, 5H), 5.26 (s, 2H), 3.76 (s, 3H), 2.58 (s, 3H).

Step 2: Synthesis of 3-(benzyloxy)-5-methanesulfonyl-1-methyl-1H-pyrazole-4-carbonitrile To a solution of 3-(benzyloxy)-1-methyl-5-(methylsulfanyl)-1H-pyrazole-4-carbonitrile (95%, 625 mg, 2.29 mmol) in acetic acid (5 mL) was added hydrogen peroxide (30% aq. solution, 779 μl, 6.87 mmol) followed by disodium tungstate dihydrate (151 mg, 0.46 mmol) and the reaction was stirred at room temperature for 2 h after which water was added (20 mL) and the product extracted with EtOAc (3×30 mL), the combined organic phases were washed with sat. NaHCO$_3$ (2×30 mL), dried (Na$_2$SO$_4$) filtered and evaporated to afford the title compound (564 mg, 85% purity by LC-MS, 72% yield) as a white crystalline solid which was pure enough to used in subsequent chemistry without purification. LC-MS 85%, 1.32 min (2 minute LC-MS method), m/z=291.90, $^1$H NMR (500 MHz, Chloroform-d) δ 7.46-7.43 (m, 2H), 7.42-7.35 (m, 3H), 5.32 (s, 2H), 4.07 (s, 3H), 3.29 (s, 3H).

Step 3: Synthesis of 3-(benzyloxy)-5-methoxy-1-methyl-1H-pyrazole-4-carbonitrile To a stirred solution of 3-(benzyloxy)-5-methanesulfonyl-1-methyl-1H-pyrazole-4-carbonitrile (85%, 564 mg, 1.65 mmol) in anhydrous MeOH was added NaOMe (0.5M solution in MeOH, 4.61 ml, 2.30 mmol) and the reaction was stirred at 55° C. for 1.5 h after which the reaction was cooled to room temperature, water (200 μL) was added and the mixture was evaporated to dryness in vacuo. The crude product was purified on a Biotage Isolera system using a 25 g KP-SIL columns eluting with a 12% to 100% EtOAc in heptane gradient to afford the title compound (262 mg, 61% yield) as a white solid. LC-MS 93%, 1.32 min (2 minute LC-MS method), m/z=243.95, $^1$H NMR (500 MHz, Chloroform-d) δ 7.46-7.41 (m, 2H), 7.40-7.35 (m, 2H), 7.35-7.30 (m, 1H), 5.23 (s, 2H), 4.24 (s, 3H), 3.48 (s, 3H).

Step 4: Synthesis of (3-(benzyloxy)-5-methoxy-1-methyl-1H-pyrazol-4-yl)methanamine 3-(Benzyloxy)-5-methoxy-1-methyl-1H-pyrazole-4-carbonitrile (260 mg, 0.99 mmol) was dissolved in 2M NH$_3$ in MeOH (20 mL) making a 0.03M solution. This solution was processed using a Thales H-Cube hydrogenator using a Raney nickel cartridge and 50 Bar H$_2$ pressure and 80° C. chamber temperature. The initial reaction was incomplete and so a second pass was required at 60 Bar H$_2$ pressure and 80° C. chamber temperature. The solution was then evaporated to dryness in vacuo, loaded onto a 10 g SCX-2 column using minimal MeOH, washed with MeOH (3×30 mL), eluted with 7M NH$_3$ in MeOH (2×35 mL) and evaporated to afford the title compound (160 mg, ~90% purity based on NMR) which was used in the next stage without any further purification. $^1$H NMR (500 MHz, Chloroform-d) δ 7.43 (d, J=7.3 Hz, 2H), 7.37 (t, J=7.4 Hz, 2H), 7.31 (dd, J=8.4, 6.1 Hz, 1H), 5.20 (s, 2H), 3.99 (s, 3H), 3.64 (s, 2H), 3.53 (s, 3H).

Step 5: Synthesis of tert-butyl N-((3-(benzyloxy)-5-methoxy-1-methyl-1H-pyrazol-4-yl)methyl)carbamate To a suspension of (3-(benzyloxy)-5-methoxy-1-methyl-1H-pyrazol-4-yl)methanamine (90%, 160 mg, 0.58 mmol) in MeOH (10 mL) was added Boc anhydride (133 mg, 0.61 mmol) and the reaction was stirred at room temperature under a nitrogen atmosphere for 3 days. The reaction mixture was then evaporated to dryness in vacuo and the crude product purified using a 10 g KP-SIL column on a Biotage Isolera system eluting with a 12% to 100% gradient to afford the title compound as a colourless oil (152 mg, 71% yield). LC-MS 95%, 1.44 min (2 minute LC-MS method), m/z=348.95, $^1$H NMR (500 MHz, Chloroform-d) δ 7.43 (d, J=7.2 Hz, 2H), 7.37 (t, J=7.4 Hz, 2H), 7.34-7.27 (m, 1H), 5.20 (s, 2H), 4.70 (s, 1H), 4.13 (d, J=4.8 Hz, 2H), 4.00 (s, 3H), 3.52 (s, 3H), 1.43 (s, 9H).

Step 6: Synthesis of tert-butyl N-((5-methoxy-1-methyl-3-oxo-2,3-dihydro-1H-pyrazol-4-yl)methyl)carbamate Tert-butyl N-((3-(benzyloxy)-5-methoxy-1-methyl-1H-pyrazol-4-yl)methyl)carbamate (150 mg, 0.41 mmol) was dissolved in MeOH (10 mL) making a 0.04M solution. This solution was processed using a Thales H-Cube hydrogenator using a 10% Pd/C cartridge under 10 Bar $H_2$ pressure and 70° C. chamber temperature. The initial reaction was incomplete and so a second pass at 30 Bar $H_2$ pressure and 70° C. chamber temperature was required to complete the reaction. The solution was then evaporated to dryness in vacuo, to afford the title compound (91 mg, >95% purity based on NMR, 82% yield) which was used in the next stage without any further purification. $^1$H NMR (500 MHz, Methanol-d4) δ 4.00 (s, 3H), 3.97 (s, 2H), 3.38 (s, 3H), 1.44 (s, 9H).

Step 7: Synthesis of 4-(aminomethyl)-5-methoxy-1-methyl-2,3-dihydro-1H-pyrazol-3-one hydrochloride Tert-butyl N-((5-methoxy-1-methyl-3-oxo-2,3-dihydro-1H-pyrazol-4-yl)methyl)carbamate (73%, 90 mg, 0.26 mmol) was dissolved in 4M HCl in dioxane (2 mL) and the reaction was stirred for 1 h at room temperature after which the solvent was removed in vacuo to afford the title compound as a white solid (74 mg) which was taken through to the next stage of the synthesis without purification.

Step 8: Synthesis of 5-chloro-3-(ethyl((trans)-4-(dimethylamino)cyclohexyl]amino)-N-((5-methoxy-1-methyl-3-oxo-2,3-dihydro-1H-pyrazol-4-yl)methyl)-2-methylbenzamide To a stirred solution of 5-chloro-3-(ethyl((trans)-4-(dimethylamino)cyclohexyl)amino)-2-methylbenzoic acid hydrochloride (99%, 206 mg, 0.55 mmol) in DMF (2 mL) cooled to 0° C. using an ice batch was added DIPEA (253 μL, 1.45 mmol) and HATU (207 mg, 0.55 mmol), the reaction was stirred for 10 minutes after which time the amine from the previous step (95% purity, 74 mg, 0.36 mmol) was added and the reaction was then warmed to room temperature and stirred for 20 h. The reaction mixture was then poured onto water (50 mL) and stirred for 10 min after which the solution was extracted with EtOAc (3×30 mL), washed with brine (3×20 mL), dried ($Na_2SO_4$), filtered and evaporated. The crude product was purified preparative HPLC to afford the title compound as an off-white solid (20 mg, 11% yield) LC-MS 99%, 2.76 min (7 min LC-MS method), m/z=478.05/480.15, $^1$H NMR (500 MHz, Methanol-d4) δ 8.46 (s, 1H), 7.24 (d, J=2.1 Hz, 1H), 7.09 (d, J=2.1 Hz, 1H), 4.29 (s, 2H), 4.07 (s, 3H), 3.41 (s, 3H), 3.19-3.02 (m, 3H), 2.88-2.73 (m, 7H), 2.25 (s, 3H), 2.12-1.93 (m, 4H), 1.61-1.41 (m, 4H), 0.87 (t, J=7.0 Hz, 3H).

Compound 87: 5-chloro-3-(ethyl((trans)-4-(dimethylamino)cyclohexyl)amino)-2-methyl-N-((1,2,5-trimethyl-3-oxo-2,3-dihydro-1H-pyrazol-4-yl)methyl)benzamide

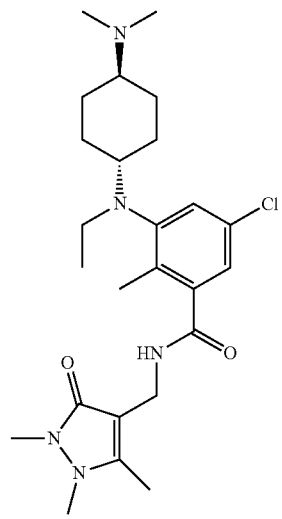 [SMILES: CCN(c1cc(Cl)cc(C(=O)NCc2c(C)n(C)n(C)c2=O)c1C)[C@H]1CC[C@H](N(C)C)CC1]

Step 1: Synthesis of 1,2,5-trimethyl-2,3-dihydro-1H-pyrazol-3-one

A suspension of 1,2-dimethylhydrazine dihydrochloride (2.04 g, 15.4 mmol) in acetic acid (20 ml) was treated with ethyl 3-oxobutanoate (1.95 mL, 15.4 mmol). The mixture was stirred at room temperature for 45 min, at 50° C. for 40 min and then at 80° C. overnight. After which time, the reaction mixture was left to reach room temperature and then concentrated in vacuo. The residue was partitioned between EtOAc (10 mL) and a saturated solution of sodium hydrogen carbonate (aq. 50 mL) was added until pH 8 was achieved, the layers were separated and the aqueous phase extracted with EtOAc (1×10 mL), DCM (2×10 mL) and 1:1 IPA/CHCl$_3$ (2×10 mL). The combined organic phases were dried over MgSO$_4$ to afford the title compound as a brown mobile oil (225 mg, 11% yield), which was used without purification in the next step. LC-MS (ELS detection) 100%, 0.16 min (2 minute LC-MS method), m/z=126.95, $^1$H NMR (500 MHz, Methanol-d4) δ 5.21 (s, 1H), 3.45 (s, 3H), 3.41 (s, 3H), 2.21 (s, 3H), $^{13}$C NMR (63 MHz, Methanol-d4) δ 166.27 (C), 150.66 (C), 94.17 (CH), 32.66 (CH3), 28.87 (CH3), 11.94 (CH3).

Step 2: Synthesis of 1,2,5-trimethyl-3-oxo-2,3-dihydro-1H-pyrazole-4-carbaldehyde To a solution of DMF (272 μL, 3.51 mmol) in a screw top vial at 0° C., was added POCl$_3$ (246 μL, 2.64 mmol). The resulting solution was stirred at 0° C. for 40 min and then transferred to a flask containing 1,2,5-trimethyl-2,3-dihydro-1H-pyrazol-3-one (222 mg, 1.76 mmol). The resulting brown solution was stirred at 84° C. for 23 h, after which time, the reaction was allowed to reach room temperature and once at rt, the reaction mixture was treated with ice and the ice was allowed to melt. The pH was adjusted to ~11 with 1M NaOH (4.5 mL). The aqueous phase was extracted with DCM (2×10 mL) and a mixture of 1:1 IPA/CHCl$_3$ (2×10 mL). The aqueous was re-basified to pH 11 with 1M NaOH (1 mL) and re-extracted with a mixture of 1:1 IPA/CHCl₃ (1×15 mL). The organic extracts were combined and were found to contain the demethylated product. After standing overnight, the aqueous phase was re-extracted with a mixture of 1:1 IPA/CHCl₃ (3×15 mL). The combined organic extracts were dried over MgSO₄, filtered and concentrated in vacuo to afford the title compound as a yellow solid (53 mg, 18% yield) which was used without purification in the next step. LC-MS (ELS) 98%, 0.24 min (3 minute LC-MS method), m/z=154.90 (M+H), 172.90 (hydrate)], $^1$H NMR (500 MHz, Methanol-d4) δ 9.69 (s, 1H), 3.64 (s, 3H), 3.47 (s, 3H), 2.55 (s, 3H).

Step 3: Synthesis of 1,2,5-trimethyl-3-oxo-2,3-dihydro-1H-pyrazole-4-carbonitrile To a stirred solution of 1,2,5-trimethyl-3-oxo-2,3-dihydro-1H-pyrazole-4-carbaldehyde (90%, 47 mg, 0.28 mmol) in DMSO (3 mL), was added hydroxylamine hydrochloride (21 mg, 0.3 mmol), the resulting mixture was stirred at 90° C. for 6 h and then allowed to cool. The reaction mixture was diluted with water (10 mL) and extracted with DCM (3×15 mL). The combined extracts were dried over MgSO₄, filtered and concentrated in vacuo to afford the title compound as a light yellow solid (22 mg, 51% yield), which was used in the next step without purification. LC-MS (ELS) 69% and 15%, 0.25 and 0.43 min (3 minute LC-MS method), m/z=151.90, $^1$H NMR (500 MHz, methanol-d4) δ 3.63 (s, 3H), 3.45 (s, 3H), 2.38 (s, 3H), $^{13}$C NMR (126 MHz, Methanol-d4) δ 163.57 (C), 151.85 (C), 114.54 (C), 79.75 (C), 33.01 (CH3), 28.98 (CH3), 11.44 (CH3). IR=2208 cm-1 (CN).

Step 4: Synthesis of 4-(aminomethyl)-1,2,5-trimethyl-2,3-dihydro-1H-pyrazol-3-one A solution of 1,2,5-trimethyl-3-oxo-2,3-dihydro-1H-pyrazole-4-carbonitrile (22 mg, 0.15 mmol) in 2M NH₃/MeOH (3 ml), was passed through the H-Cube at 50 bar and 80° C. at 1 ml/min using a Raney Nickel cartridge. The resulting solution was concentrated in vacuo to afford the title compound as a white solid (25 mg, 77% yield), which was used in the next step without purification. LC-MS (ELS) 19% and 80%, 0.22 and 0.31 min (3 minute LC-MS method), m/z=155.90, $^1$H NMR (500 MHz, Methanol-d4) δ 3.66 (s, 2H), 3.49 (s, 3H), 3.44 (s, 3H), 3.35 (s, 2H), 2.25 (s, 3H).

Step 5: Synthesis of 5-chloro-3-(ethyl((trans)-4-(dimethylamino)cyclohexyl)amino)-2-methyl-N-((1,2,5-trimethyl-3-oxo-2,3-dihydro-1H-pyrazol-4-yl)methyl)benzamide A stirred solution of 5-chloro-3-(ethyl((trans)-4-(dimethylamino)cyclohexyl)amino)-2-methylbenzoic acid (55 mg, 0.16 mmol) in DMF (1 mL) under a balloon of N₂ at 0° C., was treated with HATU (74 mg, 0.19 mmol) and DIPEA (57 µL, 0.32 mmol). The resulting solution was stirred for 10 min and then treated with a solution of 4-(aminomethyl)-1,2,5-trimethyl-2,3-dihydro-1H-pyrazol-3-one (70%, 25 mg, 0.11 mmol) in DMF (1 mL) and the resulting suspension was stirred at 0° C. for 30 min and then at room temperature over the weekend. Water (2 mL) was added to the reaction mixture, which was then extracted with DCM (3×10 mL) and the combined extracts were dried over MgSO₄, filtered and concentrated in vacuo. The aqueous phase was re-extracted with a mixture of 1:1 IPA/CHCl₃ (4×10 mL). The combined extracts were dried over MgSO₄, filtered and concentrated in vacuo. The combined batches were purified by preparative HPLC (high pH method) to afford the title compound as an off white glassy solid (13 mg, 17% yield).

Analytical Data:
LC-MS: 99%, 2.67 min (7 minute LC-MS method), m/z=476.20, 478.15, $^1$H NMR (500 MHz, Methanol-d4) δ 7.18 (d, J=2.1 Hz, 1H), 7.03 (d, J=2.1 Hz, 1H), 4.21 (s, 2H), 3.48 (s, 3H), 3.44 (s, 3H), 3.08 (q, J=7.0 Hz, 2H), 2.70 (tt, J=11.6, 3.4 Hz, 1H), 2.34 (s, 3H), 2.27 (s, 6H), 2.23 (s, 4H), 1.92 (dd, J=27.0, 12.5 Hz, 4H), 1.45 (q, J=11.8, 11.1 Hz, 2H), 1.22 (q, J=11.2, 10.3 Hz, 2H), 0.85 (t, J=7.0 Hz, 3H).

Compound 88: 5-chloro-3-(ethyl((trans)-4-(dimethylamino)cyclohexyl)amino)-N-((5-methoxy-1-methyl-3-(trifluoromethyl)-1H-pyrazol-4-yl)methyl)-2-methylbenzamide

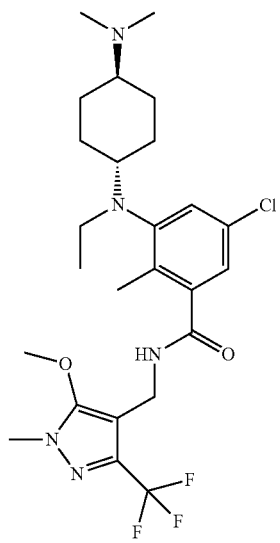 [SMILES: CCN(c1cc(Cl)cc(C(=O)NCc2c(C(F)(F)F)nn(C)c2OC)c1C)[C@H]1CC[C@H](N(C)C)CC1]

Step 1; Synthesis of [5-methoxy-1-methyl-3-(trifluoromethyl)-1H-pyrazol-4-yl]methanamine A solution of 5-methoxy-1-methyl-3-(trifluoromethyl)-1H-pyrazole-4-carbonitrile (50 mg, 0.24 mmol) in 2M NH₃ in MeOH (5.0 mL), was passed through the H-Cube at 50 bar and 80° C. at 1 ml/min using a Raney Nickel cartridge. The resulting solution was concentrated in vacuo, and further dried in vacuo at 40° C. to afford the title compound as a white solid (49 mg, 97% yield) which was used directly in the next step without purification. LC-MS 100%, 1.09 min (2.5 min basic LC-MS method), m/z=210.2, $^1$H NMR (500 MHz, Methanol-d4) δ 4.06 (s, 3H), 3.71 (s, 5H).

Step 2: Synthesis of 5-chloro-3-(ethyl((trans)-4-(dimethylamino)cyclohexyl)amino)-N-((5-methoxy-1-methyl-3-(trifluoromethyl)-1H-pyrazol-4-yl)methyl)-2-methylbenzamide In a vial was placed a stirred solution of 5-chloro-3-(ethyl((trans)-4-(dimethylamino)cyclohexyl)amino)-2-methylbenzoic acid (80 mg, 0.24 mmol) in DMF (2 mL) under a balloon of N₂ at 0° C. (ice/salt) and treated with HATU (108 mg, 0.28 mmol) and DIPEA (82 µL, 0.47 mmol). The resulting solution was stirred for 10 min and transferred into a pre-cooled RBF (ice/water) containing [5-methoxy-1-methyl-3-(trifluoromethyl)-1H-pyrazol-4-yl]methanamine (49 mg, 0.24 mmol). The resulting suspension was stirred at 0° C. for 1 hour and then at room temperature overnight. The reaction mixture was added dropwise to water (5 mL) and then extracted with DCM (4×10 mL), followed by a mixture of 1:1 IPA:CHCl$_3$ (4×10 ml). The combined extracts were dried over MgSO$_4$, filtered and concentrated in vacuo. The crude material was purified by FCC (0-100% [90:9:1 DCM/MeOH/NH$_4$OH]/DCM) 10 g SNAP cartridge on the Biotage Isolera to afford the title compound as an off-white solid (75 mg, 57% yield).

Analytical Data:

LC-MS 95%, 3.23 min (7 minute LC-MS method), m/z=530.10, 532.15, $^1$H NMR (500 MHz, Methanol-d4) δ 7.21 (d, J=2.1 Hz, 1H), 7.02 (d, J=2.1 Hz, 1H), 4.47 (s, 2H), 4.10 (s, 3H), 3.73 (s, 3H), 3.09 (q, J=7.1 Hz, 2H), 2.74 (tt, J=11.4, 3.3 Hz, 1H), 2.59 (t, J=12.3 Hz, 1H), 2.49 (s, 6H), 2.25 (s, 3H), 1.97 (dd, J=27.4, 12.4 Hz, 4H), 1.54-1.42 (m, 2H), 1.33 (tt, J=13.3, 7.5 Hz, 2H), 0.86 (t, J=7.0 Hz, 3H).

Compound 89: 5-chloro-3-(ethyl((trans)-4-(dimethylamino)cyclohexyl)amino)-2-methyl-N-((2-methyl-3-oxo-5-(trifluoromethyl)-2,3-dihydro-1H-pyrazol-4-yl)methyl)benzamide

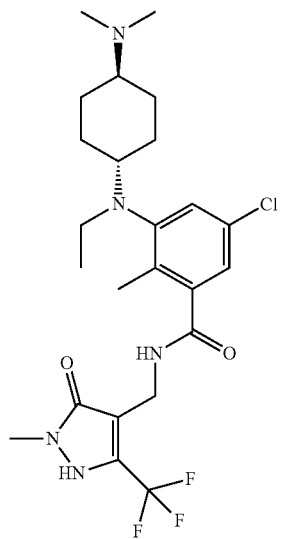 [SMILES: CCN(c1cc(Cl)cc(C(=O)NCc2c(C(F)(F)F)[nH]n(C)c2=O)c1C)[C@H]1CC[C@H](N(C)C)CC1]

Step 1: Synthesis of 5-chloro-3-(ethyl((trans)-4-(dimethylamino)cyclohexyl)amino)-2-methyl-N-((2-methyl-3-oxo-5-(trifluoromethyl)-2,3-dihydro-1H-pyrazol-4-yl)methyl)benzamide In a sealed tube, was placed 5-chloro-3-(ethyl((trans)-4-(dimethylamino)cyclohexyl) amino)-N-((5-methoxy-1-methyl-3-(trifluoromethyl)-1H-pyrazol-4-yl)methyl)-2-methylbenzamide (55 mg, 0.10 mmol) and DCM (4 mL). The resulting solution was treated with a 1M solution of BBr$_3$ in DCM (2.57 mL) at room temperature. The top was sealed and the reaction mixture was placed on a heating block set at 40° C. for 69 h. The reaction mixture was cooled in an ice bath and carefully quenched by the drop wise addition of MeOH (10 mL), the resulting yellow solution was concentrated in vacuo and the resulting residue purified by preparative HPLC (high pH method) to afford the title compound as a beige solid (18 mg, 34% yield).

Analytical Data:

LC-MS 99%, 3.29 min (7 minute LC-MS method), m/z=516.10, 517.15, 518.15, 519.15, $^1$H NMR (500 MHz, Methanol-d4) δ 7.19 (d, J=2.1 Hz, 1H), 7.07 (d, J=2.1 Hz, 1H), 4.34 (s, 2H), 3.49 (s, 3H), 3.08 (q, J=7.2 Hz, 3H), 2.78 (s, 7H), 2.26 (s, 3H), 2.06 (d, J=10.4 Hz, 2H), 2.01 (d, J=11.2 Hz, 2H), 1.50 (h, J=11.2 Hz, 4H), 0.87 (t, J=7.0 Hz, 3H).

Compound 90: 5-chloro-N-((1,2-dimethyl-3-oxo-5-(trifluoromethyl)-2,3-dihydro-1H-pyrazol-4-yl)methyl)-3-(ethyl((trans)-4-(dimethylamino)cyclohexyl)amino)-2-methylbenzamide

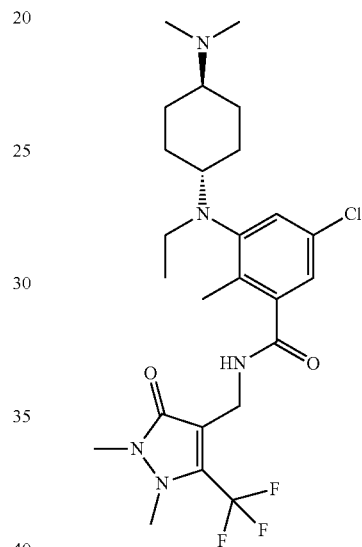

Step 1: Synthesis of 4-bromo-1-methyl-5-(trifluoromethyl)-2,3-dihydro-1H-pyrazol-3-one To a stirred solution of 1-methyl-5-(trifluoromethyl)-1H-pyrazol-3-ol (2 g, 12.0 mmol) in ethanol (15 mL) was added bromine (0.74 mL, 14.5 mmol). The resulting solution was stirred at room temperature overnight. After which time, the reaction was concentrated in vacuo and the residue was basified (pH 8) with a saturated aqueous solution of sodium hydrogen carbonate (20 mL). The product was extracted with DCM (5×15 mL) and the combined organics were washed with brine (20 mL). The aqueous phase was back-extracted with DCM (2×5 mL). The combined organics were dried over MgSO$_4$, filtered and concentrated in vacuo to afford the title compound as an off white solid (2.48 g, 83% yield), which was used directly in the next step without purification. LC-MS 99%, 1.69 min (3 minute LC-MS method), m/z=244.80, 246.85, $^1$H NMR (500 MHz, Methanol-d4) δ 3.81 (d, J=1.1 Hz, 3H).

Step 2: Synthesis of 4-bromo-1,2-dimethyl-5-(trifluoromethyl)-2,3-dihydro-1H-pyrazol-3-one A solution of 4-bromo-1-methyl-5-(trifluoromethyl)-2,3-dihydro-1H-pyrazol-3-one (0.50 g, 2.04 mmol) in DCM (10.0 mL) was cooled to 0° C. (ice/water). Trimethyloxonium tetrafluoroborate (1.51 g, 10.2 mmol) was added and the reaction mixture stirred at 0° C. for 25 min and then at room temperature over the weekend. The reaction mixture was quenched with a saturated aqueous solution of NaHCO$_3$ (20 mL) and extracted with DCM (5×15 mL), followed by a mixture of 1:1 IPA/CHCl$_3$ (1×15 mL), the combined extracts were dried over MgSO$_4$, filtered and concentrated in vacuo to afford the title compound as a waxy beige solid (520 mg, 91% yield) which was used directly in the next step without purification. LC-MS 93%, 1.36 min (3 minute LC-MS method), m/z=258.85, 260.85, $^1$H NMR (500 MHz, Methanol-d4) δ 3.63 (s, 3H), 3.56 (s, 3H).

Step 3: Synthesis of 1,2-dimethyl-3-oxo-5-(trifluoromethyl)-2,3-dihydro-1H-pyrazole-4-carbaldehyde In a 3-necked RBF, a solution of 4-bromo-1,2-dimethyl-5-(trifluoromethyl)-2,3-dihydro-1H-pyrazol-3-one (500 mg, 1.93 mmol) in anhydrous THF (8 mL) was cooled to −78° C. (dry ice/acetone) and treated with n-butyl lithium (2.5M in heptanes, 927 µL, 2.32 mmol) over 15 minutes. The resulting solution was stirred at −78° C. for 30 minutes and then treated with DMF (164 µl, 2.12 mmol). The solution was stirred at −78° C. for 1 h and then at room temperature for 1.5 h. The reaction mixture was quenched with a saturated solution of aqueous ammonium chloride (2 mL) and concentrated in vacuo. The orange solid was heated to reflux in CHCl$_3$ (20 mL), filtered and the filtrate concentrated in vacuo to afford the title compound as a brown immobile oil (349 mg, 43% yield) which was used directly in the next step without purification. LC-MS (ELS) 42%, 0.15 min (3 minute LC-MS method), m/z=208.90. Purity estimated at 50%.

Step 4: Synthesis of 1,2-dimethyl-3-oxo-5-(trifluoromethyl)-2,3-dihydro-1H-pyrazole-4-carbonitrile To a stirred solution of 1,2-dimethyl-3-oxo-5-(trifluoromethyl)-2,3-dihydro-1H-pyrazole-4-carbaldehyde (50%, 346 mg, 0.83 mmol) in DMSO (2 mL), was added hydroxylamine hydrochloride (127 mg, 1.83 mmol). The resulting mixture was stirred at 90° C. for 7 h, then the heat was removed and the reaction was left stand at room temperature overnight. The reaction mixture was diluted with water (10 mL), extracted with DCM (5×10 mL) and further extracted with a mixture of 1:1 IPA/CHCl$_3$ (2×10 mL). The combined extracts were dried over MgSO$_4$, filtered and concentrated in vacuo. The residue was purified by FCC (0-50% 90:9:1 [DCM:MeOH:NH4OH]/DCM), 25 g SNAP cartridge on the Biotage Isolera to afford the title compound as a brown oil (100 mg, 58% yield). LC-MS 100%, 2.45 min (7 min basic LC-MS method), m/z=206.1, $^1$H NMR (500 MHz, Methanol-d4) δ 3.84 (s, 3H), 3.57 (s, 3H).

Step 5: Synthesis of 4-(aminomethyl)-1,2-dimethyl-5-(trifluoromethyl)-2,3-dihydro-1H-pyrazol-3-one A solution of 1,2-dimethyl-3-oxo-5-(trifluoromethyl)-2,3-dihydro-1H-pyrazole-4-carbonitrile (97 mg, 0.47 mmol) in 2M NH$_3$/MeOH (10 mL), was passed through the H-Cube at 50 bar and 80° C. at 1 mL/min using a Raney Nickel cartridge. The resulting solution was concentrated in vacuo, and dried under high vacuum to afford the title compound as a light yellowish solid (153 mg, quant.), which was used directly in the next step without purification. LC-MS 73% and 23%, 0.90 min and 0.95 min (2.5 minute basic LC-MS method), m/z=210.2, $^1$H NMR (500 MHz, Methanol-d4) δ 3.98 (s, 2H), 3.70 (s, 3H), 3.56 (s, 3H).

Step 6: Synthesis of 5-chloro-N-((1,2-dimethyl-3-oxo-5-(trifluoromethyl)-2,3-dihydro-1H-pyrazol-4-yl)methyl)-3-(ethyl((trans)-4-(dimethylamino)cyclohexyl)amino)-2-methylbenzamide; Formic Acid In a vial, a stirred solution of 5-chloro-3-(ethyl((trans)-4-(dimethylamino)cyclohexyl) amino)-2-methylbenzoic acid (174 mg, 0.51 mmol) in DMF (2 mL) under a balloon of N$_2$ at 0° C., was treated with HATU (234 mg, 0.62 mmol) and DIPEA (179 µL, 1.03 mmol) dropwise. The resulting solution was stirred for 15 min and transferred into a pre-cooled flask (ice/water) containing 4-(aminomethyl)-1,2-dimethyl-5-(trifluoromethyl)-2,3-dihydro-1H-pyrazol-3-one (85%, 153 mg, 0.62 mmol). The resulting suspension was stirred at 0° C. for 50 min and then at room temperature over the weekend, after which the reaction was treated with further HATU (117 mg, 0.31 mmol, followed by DIPEA (89 µL, 0.51 mmol) and was stirred at room temperature for a further night. The reaction mixture was diluted with water (10 mL) and extracted with DCM (3×10 mL), followed by a mixture of 1:1 IPA:CHCl$_3$ (4×10 mL). The combined extracts were dried over MgSO$_4$, filtered and concentrated in vacuo. The crude residue was purified by FCC (0-100% [90:9:1 DCM/MeOH/NH$_4$OH]/DCM) 25 g SNAP cartridge on the Biotage Isolera, followed by preparative HPLC (low pH method) to afford the title compound as a white solid (29 mg, 10% yield).

Analytical Data:

LC-MS 99%, 2.88 min (7 min LC-MS method), m/z=530.15, 531.10, 532.15, 533.10, $^1$H NMR (500 MHz, Methanol-d4) δ 8.39 (s, 1H), 7.23 (d, J=2.1 Hz, 1H), 7.07 (d, J=2.1 Hz, 1H), 4.38 (s, 2H), 3.62 (s, 3H), 3.53 (s, 3H), 3.20-3.12 (m, 1H), 3.09 (q, J=7.0 Hz, 2H), 2.81 (s, 7H), 2.25 (s, 3H), 2.08 (d, J=8.7 Hz, 2H), 2.02 (d, J=10.0 Hz, 2H), 1.52 (q, J=11.3 Hz, 4H), 0.86 (t, J=7.0 Hz, 3H).

Compound 91: Synthesis of 5-chloro-N-((5-methoxy-1,3-dimethyl-1H-pyrazol-4-yl)methyl)-3-(((trans)-4-(dimethylamino)cyclohexyl)(ethyl)amino)-2-methylbenzamide

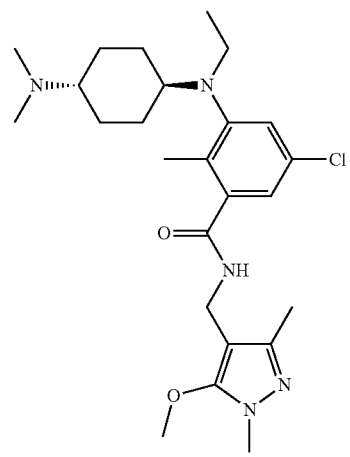 [SMILES: CCN(c1cc(Cl)cc(C(=O)NCc2c(C)nn(C)c2OC)c1C)[C@H]1CC[C@H](N(C)C)CC1]

Synthesis of 5-chloro-N-((5-methoxy-1,3-dimethyl-1H-pyrazol-4-yl)methyl)-3-(((trans)-4-(dimethylamino)cyclohexyl)(ethyl)amino)-2-methylbenzamide 5-methoxy-1,3-dimethyl-1H-pyrazole-4-carbonitrile (200 mg, 1.32 mmol) was dissolved in 2M $NH_3$ in MeOH (25 mL) making a 0.05M solution. This solution was processed using a Thales H-Cube hydrogenator using a Raney nickel cartridge and 50 Bar $H_2$ pressure and 80° C. chamber temperature. The initial reduction was incomplete and so the material was retreated again using the H-Cube and the same reaction conditions. The solution was then evaporated to dryness in vacuo to afford the title compound as a white solid (223 mg, quant) which was used in the next stage without any purification. LC-MS shows product in solvent front (3.5 minute LC-MS method), m/z=138.95 (M+H—NH2), 155.95 (M+H), $^1$H NMR (500 MHz, Methanol-d4) δ 3.18 (s, 3H), 2.87 (s, 2H), 2.76 (s, 3H), 1.36 (s, 3H).

To a stirred solution of 5-chloro-3-(ethyl((trans)-4-(dimethylamino)cyclohexyl)amino)-2-methylbenzoic acid hydrochloride (99%, 290 mg, 0.77 mmol) in DMF (3 mL) cooled to 0° C. using an ice batch was added DIPEA (400 μL, 2.30 mmol) and HATU (320 mg, 0.84 mmol), the reaction was stirred for 10 min after which time (5-methoxy-1,3-dimethyl-1H-pyrazol-4-yl)methanamine (95%, 125 mg, 0.77 mmol) was added and the reaction was then warmed to room temperature and stirred for 16 h. The reaction mixture was then poured onto water (20 mL) to which is added satd. $NaHCO_3$ (2 mL) and stirred for 10 min after which the solution was extracted with EtOAc (3×30 mL), washed with brine (30 mL), dried ($Na_2SO_4$), filtered and evaporated then azeotroped with heptane (2×100 mL) to remove residual DMF. The crude product was purified using a 50 g SNAP Isolute column on Isolera system eluting with a DCM to 1:9:90 $NH_4OH$:MeOH:DCM gradient to afford the title compound as a beige powder (161 mg, 43% yield). LC-MS 97%, 2.84 min (7 min LC-MS method), m/z=239.10 and 476.15, $^1$H NMR (500 MHz, Methanol-d4) δ 7.19 (d, J=2.1 Hz, 1H), 7.01 (d, J=2.1 Hz, 1H), 4.37 (s, 2H), 4.03 (s, 3H), 3.58 (s, 3H), 3.09 (q, J=7.0 Hz, 2H), 2.71 (tt, J=11.7, 3.4 Hz, 1H), 2.31-2.29 (m, 6H), 2.29-2.26 (m, 1H), 2.24 (s, 3H), 2.19 (s, 3H), 1.99-1.86 (m, 4H), 1.51-1.39 (m, 2H), 1.27-1.18 (m, 2H), 0.86 (t, J=7.0 Hz, 3H).

Compound 92: Synthesis of 5-chloro-3-(ethyl[(trans)-4-(dimethylamino)cyclohexyl]amino)-N-([3-methoxy-1-methyl-5-(piperidin-1-yl)-1H-pyrazol-4-yl]methyl)-2-methylbenzamide

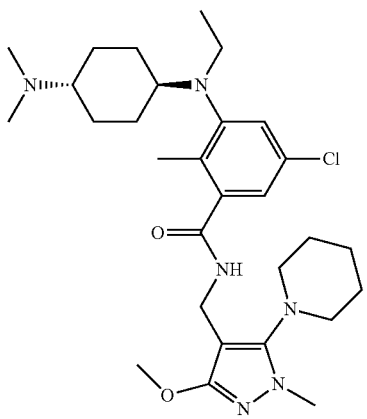 [SMILES: CCN(c1cc(Cl)cc(C(=O)NCc2c(OC)nn(C)c2N2CCCCC2)c1C)[C@H]1CC[C@H](N(C)C)CC1]

Step 1: Synthesis of ethyl (2Z)-2-cyano-3-(methylsulfanyl)-3-(piperidin-1-yl)prop-2-enoate To a stirred solution of ethyl 2-cyano-3,3-bis(methylsulfanyl)prop-2-enoate (4.0 g, 18.41 mmol, 1 eq) in MeCN (25 ml) set-up with a bleach trap (MeSH evolution, stench, toxic) and condenser was added piperidine (1.82 ml, 18.4 mmol, 1 eq) and with the reaction flask under positive $N_2$ pressure the reaction was heated to 50° C. for 3 h. The reaction was cooled to room temperature, EtOAc (50 ml) was added and the organic phase was washed with brine (2×30 ml), dried ($Na_2SO_4$), filtered and evaporated to afford the title compound (4.32 g, 92%) as a yellow crystalline solid. LCMS: 100%, 1.73 min, (3 min LCMS) m/z=255.0. $^1$H NMR (500 MHz, Chloroform-d) δ 4.17 (q, J=7.1 Hz, 2H), 3.76-3.58 (m, 4H), 2.61 (s, 3H), 1.80-1.64 (m, 6H), 1.30 (t, J=7.1 Hz, 3H).

Step 2: Synthesis of 1-methyl-3-oxo-5-(piperidin-1-yl)-2,3-dihydro-1H-pyrazole-4-carbonitrile To a stirred solution of ethyl (2Z)-2-cyano-3-(methylsulfanyl)-3-(piperidin-1-yl)prop-2-enoate (2.0 g, 7.86 mmol, 1 eq) in MeCN (30 ml) set-up with a bleach trap (MeSH evolution, stench, toxic) and condenser was added DBU (2.3 ml, 15.73 mmol) followed by methylhydrazine (455 μl, 8.65 mmol, 1.1 eq) and the reaction was then heated to 60° C. for 18 h after which time the solvent was evaporated and the crude reaction mixture was purified on a 100 g SNAP cartridge on a Biotage Isolera system eluting with 2% to 15% MeOH in DCM gradient. The mixed fractions were then purified further using 50 g SNAP cartridge on a Biotage Isolera system eluting with 2% to 20% MeOH in DCM gradient to give 1-methyl-3-oxo-5-(piperidin-1-yl)-2,3-dihydro-1H-pyrazole-4-carbonitrile (501 mg, 28%, 92% LCMS purity, 1.36 min, m/z=207.0). $^1$H NMR (500 MHz, Methanol-d4) δ 3.39 (s, 3H), 3.27-3.22 (m, 4H), 1.76-1.68 (m, 4H), 1.69-1.61 (m, 2H).

Step 3: Synthesis of 3-methoxy-1-methyl-5-(piperidin-1-yl)-1H-pyrazole-4-carbonitrile To a solution of 1-methyl-3-oxo-5-(piperidin-1-yl)-2,3-dihydro-1H-pyrazole-4-carbonitrile (250 mg, 1.21 mmol, 1.0 eq) in anhydrous THF (10 ml) was added anhydrous methanol (74 μl, 1.82 mmol, 1.5 eq), $PPh_3$ (477 mg, 1.82 mmol, 1.5 eq) and DIAD (358 μl, 1.82 mmol, 1.5 eq) sequentially. The reaction was stirred under $N_2$ for 2.5 days (note this was a weekend and other similar reactions are typically completed in ~2 hours) after which time the THF was evaporated in vacuo, DCM (50 ml) was added and the organic phase washed with saturated NaCl (2×30 ml), dried ($Na_2SO_4$), filtered and evaporated. The crude product was purified using a 25 g SNAP Isolute column on a Biotage Isolera using 0% to 60% EtOAc gradient to afford the title compound as a yellow solid (330 mg, 92% LCMS, 63% w/w purity with ~37% reduced DIAD impurity). $^1$H NMR (500 MHz, Chloroform-d) δ 3.89 (s, 3H), 3.52 (s, 3H), 3.21-3.08 (m, 4H), 1.69 (p, J=5.6 Hz, 4H), 1.65-1.57 (m, 2H).

Step 4: Synthesis of [3-methoxy-1-methyl-5-(piperidin-1-yl)-1H-pyrazol-4-yl]methanamine 3-methoxy-1-methyl-5-(piperidin-1-yl)-1H-pyrazole-4-carbonitrile (300 mg, 0.86 mmol) was dissolved in 17 ml of 2M $NH_3$ in MeOH (making a 0.05M solution). This solution was reduced using a Thales H-cube reaction using a RaNi cartridge and 80 Bar H$_2$ pressure and 80° C. chamber temperature. The solution was then evaporated to dryness in vacuo after which the product was dissolved in MeOH (10 ml) loaded onto a 10 g SCX-2 column, washed with MeOH (2×20 ml), eluted with 7M NH$_3$ in MeOH (3×30 ml) and evaporated to dryness in vacuo to afford the title compound as a colourless oil (122 mg, 59% yield) which was used in the next stage without any purification. LC-MS 93%, 0.84 min, m/z=208.00 (2 min LCMS) $^1$H NMR (500 MHz, Methanol-d4) δ 3.84 (s, 3H), 3.65 (s, 2H), 3.53 (s, 3H), 3.09-3.01 (m, 4H), 1.69 (p, J=5.5 Hz, 4H), 1.66-1.55 (m, 2H).

Step 5: Synthesis of 5-chloro-3-(ethyl[(trans)-4-(dimethylamino)cyclohexyl]amino)-N-([3-methoxy-1-methyl-5-(piperidin-1-yl)-1H-pyrazol-4-yl]methyl)-2-methylbenzamide To a stirred solution of 5-chloro-3-(ethyl[(trans)-4-(dimethylamino)cyclohexyl]amino)-2-methylbenzoic acid HCl (99% purity, SAI BB, 192 mg, 0.51 mmol) in DMF (3 ml) at 0° C. was added DIPEA (264 μl, 1.52 mmol, 3 eq) followed by HATU (212 mg, 0.56 mmol, 1.1 eq). The reaction was stirred at 0° C. for 5 min after which time [3-methoxy-1-methyl-5-(piperidin-1-yl)-1H-pyrazol-4-yl]methanamine (93%, 122 mg, 0.51 mmol, 1.0 eq) was added and the reaction was stirred at room temperature for 16 h. The reaction mixture was then poured onto water (30 ml) and the suspension stirred for 20 minutes. The suspension was then filtered, washed well with water, and dried for 4 h in a 40° C. vacuum oven to afford the title compound as a white powder (167 mg, 58%) that was sufficiently clean to take on to subsequent chemistry without any purification.

Analytical Data:
LCMS 7 min: 96%, 3.37 min, m/z=273.3, 545.25, 547.15, LCMS 2 min: 93%, 1.15 min, m/z=273.65, 545.20, 547.10. $^1$H NMR (500 MHz, Methanol-d4) δ 7.18 (d, J=2.0 Hz, 1H), 7.01 (d, J=2.0 Hz, 1H), 4.34 (s, 2H), 3.84 (s, 3H), 3.55 (s, 3H), 3.10 (q, J=6.7, 5.8 Hz, 6H), 2.78-2.64 (m, 1H), 2.41-2.29 (m, 7H), 2.25 (s, 3H), 2.02-1.87 (m, 4H), 1.70 (p, J=5.6 Hz, 4H), 1.62 (d, J=4.8 Hz, 2H), 1.46 (q, J=12.1, 11.4 Hz, 2H), 1.34-1.19 (m, 2H), 0.86 (t, J=7.0 Hz, 3H).

Compound 93: Synthesis of 5-chloro-3-(ethyl[(trans)-4-(dimethylamino)cyclohexyl]amino)-2-methyl-N-([1-methyl-3-oxo-5-(piperidin-1-yl)-2,3-dihydro-1H-pyrazol-4-yl]methyl)benzamide

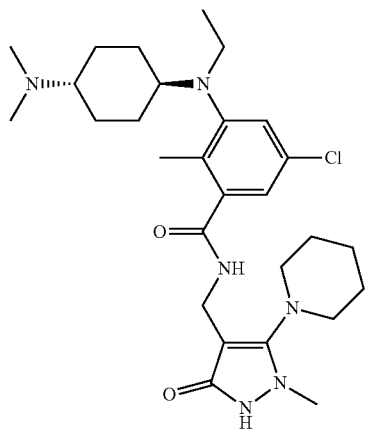 [SMILES: CCN(c1cc(Cl)cc(C(=O)NCc2c(N3CCCCC3)n(C)[nH]c2=O)c1C)[C@H]1CC[C@H](N(C)C)CC1]

Step 1: Synthesis of 5-chloro-3-(ethyl[(trans)-4-(dimethylamino)cyclohexyl]amino)-2-methyl-N-([1-methyl-3-oxo-5-(piperidin-1-yl)-2,3-dihydro-1H-pyrazol-4-yl]methyl)benzamide To a stirred solution of 5-chloro-3-(ethyl[(trans)-4-(dimethylamino)cyclohexyl]amino)-N-([3-methoxy-1-methyl-5-(piperidin-1-yl)-1H-pyrazol-4-yl]methyl)-2-methylbenzamide (93%, 50 mg, 0.09 mmol) in anhydrous DCM (3 ml) cooled to 0° C. using an ice batch was added 1M BBr$_3$ (2.13 ml) dropwise, after stirring at 0° C. for 10 min the reaction was allowed to warm to room temperature and stir for 4 days after which time more 1M BBr$_3$ (2 ml) was added, after a further 24 h at room temperature the reaction was heated to 35° C. for 1.5 days. The reaction was then cooled and quenched with MeOH (10 ml) and evaporated. The crude residue was purified using high pH prep-LCMS to afford the title compound as a beige powder (19 mg, 42%).

LCMS (7 min) 100%, 3.13 min, m/z=266.15, 266.60, 531.25, 533.30. $^1$H NMR (500 MHz, Methanol-d4) δ 7.20 (d, J=2.1 Hz, 1H), 7.05 (d, J=2.1 Hz, 1H), 4.30 (s, 2H), 3.37 (s, 3H), 3.22-3.14 (m, 4H), 3.09 (q, J=7.1 Hz, 2H), 2.80-2.65 (m, 1H), 2.52-2.43 (m, 1H), 2.41 (s, 6H), 2.25 (s, 3H), 2.01-1.88 (m, 4H), 1.75-1.59 (m, 6H), 1.54-1.40 (m, 2H), 1.36-1.21 (m, 2H), 0.86 (t, J=7.0 Hz, 3H).

Compound 94: Synthesis of 5-chloro-3-(((trans)-4-(dimethylamino)cyclohexyl)(ethyl)amino)-N-((5-methoxy-1-methyl-3-(piperidin-1-yl)-1H-pyrazol-4-yl)methyl)-2-methylbenzamide

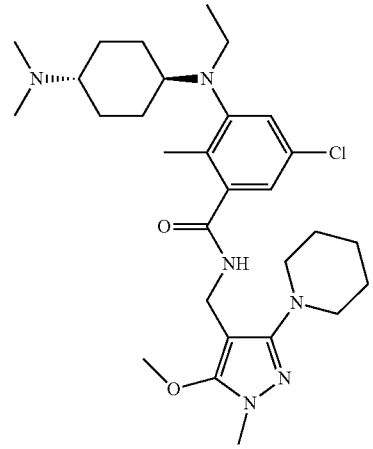 [SMILES: CCN(c1cc(Cl)cc(C(=O)NCc2c(N3CCCCC3)nn(C)c2OC)c1C)[C@H]1CC[C@H](N(C)C)CC1]

5-chloro-3-(((trans)-4-(dimethylamino)cyclohexyl)(ethyl)amino)-N-((5-methoxy-1-methyl-3-(piperidin-1-yl)-1H-pyrazol-4-yl)methyl)-2-methylbenzamide was prepared in a manner similar to that for Compound 92, using the alternate methyl isomer, 2-methyl-3-oxo-5-(piperidin-1-yl)-2,3-dihydro-1H-pyrazole-4-carbonitrile.

Analytical Data:
LCMS 7 min: 95%, 3.10 min, m/z=273.3, 545. $^1$H NMR (500 MHz, Methanol-d4) δ 7.20 (d, J=2.1 Hz, 1H), 7.09 (d, J=2.1 Hz, 1H), 4.37 (s, 2H), 3.99 (s, 3H), 3.53 (s, 3H), 3.09 (q, J=7.0 Hz, 2H), 3.05-2.99 (m, 4H), 2.74 (td, J=11.4, 9.8, 5.8 Hz, 1H), 2.54-2.45 (m, 1H), 2.42 (s, 6H), 2.27 (s, 3H), 2.05-1.89 (m, 4H), 1.73-1.64 (m, 4H), 1.61-1.52 (m, 2H), 1.48 (q, J=10.8 Hz, 2H), 1.30 (q, J=12.6 Hz, 2H), 0.86 (t, J=7.0 Hz, 3H).

Compound 95: Synthesis of 5-chloro-N-((3,5-dimethoxy-1-methyl-1H-pyrazol-4-yl)methyl)-3-(((trans)-4-(dimethylamino)cyclohexyl)(ethyl)amino)-2-methylbenzamide

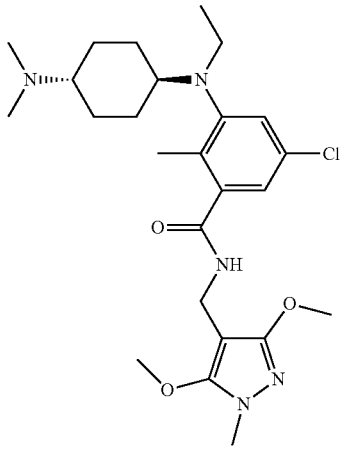

Compound 95 was synthesized in a manner similar to that for Compound 86 using symmetric 3,5-dimethoxy-1-methyl-1H-pyrazole-4-carbonitrile as the coupling partner precursor.

Analytical Data:

LCMS 7 min: 92%, 3.00 min, m/z=247, 492. $^1$H NMR (500 MHz, Methanol-d4) δ 7.18 (d, J=2.1 Hz, 1H), 7.01 (d, J=2.1 Hz, 1H), 4.31 (s, 2H), 4.06 (s, 3H), 3.85 (s, 3H), 3.50 (s, 3H), 3.09 (q, J=7.0 Hz, 2H), 2.73 (ddd, J=11.6, 8.2, 3.4 Hz, 1H), 2.47-2.39 (m, 1H), 2.38 (s, 6H), 2.24 (s, 3H), 1.95 (dd, J=26.6, 12.3 Hz, 4H), 1.46 (q, J=10.3, Hz, 2H), 1.33-1.21 (m, 2H), 0.86 (t, J=7.0 Hz, 3H).

Example 2: Bioassay Protocol and General Methods

Protocol for Wild-Type and Mutant PRC2 Enzyme Assays

General Materials.

S-adenosylmethionine (SAM), S-adenosylhomocyteine (SAH), bicine, KCl, Tween20, dimethylsulfoxide (DMSO) and bovine skin gelatin (BSG) were purchased from Sigma-Aldrich at the highest level of purity possible. Dithiothreitol (DTT) was purchased from EMD. $^3$H-SAM was purchased from American Radiolabeled Chemicals with a specific activity of 80 Ci/mmol 384-well streptavidin Flashplates were purchased from PerkinElmer.

Substrates.

Peptides representative of human histone H3 residues 21-44 containing either an unmodified lysine 27 (H3K27me0) or dimethylated lysine 27 (H3K27me2) were synthesized with a C-terminal G(K-biotin) linker-affinity tag motif and a C-terminal amide cap by 21$^{st}$ Century Biochemicals. The peptides were high-performance liquid chromatography (HPLC) purified to greater than 95% purity and confirmed by liquid chromatography mass spectrometry (LC-MS). The sequences are listed below.

H3K27me0:

(SEQ ID NO: 1)
ATKAARKSAPATGGVKKPHRYRPGGK(biotin)-amide

H3K27me2:

(SEQ ID NO: 2)
ATKAARK(me2)SAPATGGVKKPHRYRPGGK(biotin)-amide

Chicken erythrocyte oligonucleosomes were purified from chicken blood according to established procedures.

Recombinant PRC2 Enzymes.

Human PRC2 enzymes were purified as 4-component enzyme complexes co-expressed in *Spodoptera frugiperda* (sf9) cells using a baculovirus expression system. The subunits expressed were wild-type EZH2 (NM_004456) or EZH2 Y641F, N, H, S or C mutants generated from the wild-type EZH2 construct, EED (NM_003797), Suz12 (NM_015355) and RbAp48 (NM_005610). The EED subunit contained an N-terminal FLAG tag that was used to purify the entire 4-component complex from sf9 cell lysates. The purity of the complexes met or exceeded 95% as determined by SDS-PAGE and Agilent Bioanalyzer analysis. Concentrations of enzyme stock concentrations (generally 0.3-1.0 mg/mL) was determined using a Bradford assay against a bovine serum albumin (BSA) standard.

General Procedure for PRC2 Enzyme Assays on Peptide Substrates.

The assays were all performed in a buffer consisting of 20 mM bicine (pH=7.6), 0.5 mM DTT, 0.005% BSG and 0.002% Tween20, prepared on the day of use. Compounds in 100% DMSO (1 µL) were spotted into polypropylene 384-well V-bottom plates (Greiner) using a Platemate 2×3 outfitted with a 384-channel pipet head (Thermo). DMSO (1 µL) was added to columns 11, 12, 23, 24, rows A-H for the maximum signal control, and SAH, a known product and inhibitor of PRC2 (1 µL) was added to columns 11, 12, 23, 24, rows I-P for the minimum signal control. A cocktail (40 µL) containing the wild-type PRC2 enzyme and H3K27me0 peptide or any of the Y641 mutant enzymes and H3K27me2 peptide was added by Multidrop Combi (Thermo). The compounds were allowed to incubate with PRC2 for 30 min at 25° C., then a cocktail (10 µL) containing a mixture of non-radioactive and $^3$H-SAM was added to initiate the reaction (final volume=51 µL). In all cases, the final concentrations were as follows: wild-type or mutant PRC2 enzyme was 4 nM, SAH in the minimum signal control wells was 1 mM and the DMSO concentration was 1%. The final concentrations of the rest of the components are indicated in Table 6, below. The assays were stopped by the addition of non-radioactive SAM (10 µL) to a final concentration of 600 µM, which dilutes the $^3$H-SAM to a level where its incorporation into the peptide substrate is no longer detectable. 50 of the reaction in the 384-well polypropylene plate was then transferred to a 384-well Flashplate and the biotinylated peptides were allowed to bind to the streptavidin surface for at least 1 h before being washed three times with 0.1% Tween20 in a Biotek ELx405 plate washer. The plates were then read in a PerkinElmer TopCount platereader to measure the quantity of $^3$H-labeled peptide bound to the Flashplate surface, measured as disintegrations per minute (dpm) or alternatively, referred to as counts per minute (cpm).

TABLE 6

Final concentrations of components for each assay variation
based upon EZH2 identity (wild-type or Y641 mutant EZH2)

| PRC2 Enzyme (denoted by EZH2 identity) | Peptide (nM) | Non-radioactive SAM (nM) | $^3$H-SAM (nM) |
|---|---|---|---|
| Wild-type | 185 | 1800 | 150 |
| Y641F | 200 | 850 | 150 |
| Y641N | 200 | 850 | 150 |
| Y641H | 200 | 1750 | 250 |
| Y641S | 200 | 1300 | 200 |
| Y641C | 200 | 3750 | 250 |

General Procedure for Wild-Type PRC2 Enzyme Assay on Oligonucleosome Substrate.

The assays were performed in a buffer consisting of 20 mM bicine (pH=7.6), 0.5 mM DTT, 0.005% BSG, 100 mM KCl and 0.002% Tween20, prepared on the day of use. Compounds in 100% DMSO (1 µL) were spotted into polypropylene 384-well V-bottom plates (Greiner) using a Platemate 2×3 outfitted with a 384-channel pipet head (Thermo). DMSO (1 µL) was added to columns 11, 12, 23, 24, rows A-H for the maximum signal control, and SAH, a known product and inhibitor of PRC2 (1 µL) was added to columns 11, 12, 23, 24, rows I-P for the minimum signal control. A cocktail (40 µL) containing the wild-type PRC2 enzyme and chicken erythrocyte oligonucleosome was added by Multidrop Combi (Thermo). The compounds were allowed to incubate with PRC2 for 30 min at 25° C., then a cocktail (10 µL) containing a mixture of non-radioactive and $^3$H-SAM was added to initiate the reaction (final volume=51 µL). The final concentrations were as follows: wild-type PRC2 enzyme was 4 nM, non-radioactive SAM was 430 nM, $^3$H-SAM was 120 nM, chicken erythrocyte oligonucleosome was 120 nM, SAH in the minimum signal control wells was 1 mM and the DMSO concentration was 1%. The assay was stopped by the addition of non-radioactive SAM (10 µL) to a final concentration of 600 µM, which dilutes the $^3$H-SAM to a level where its incorporation into the chicken erythrocyte olignonucleosome substrate is no longer detectable. 50 µL of the reaction in the 384-well polypropylene plate was then transferred to a 384-well Flashplate and the chicken erythrocyte nucleosomes were immobilized to the surface of the plate, which was then washed three times with 0.1% Tween20 in a Biotek ELx405 plate washer. The plates were then read in a PerkinElmer TopCount platereader to measure the quantity of $^3$H-labeled chicken erythrocyte oligonucleosome bound to the Flashplate surface, measured as disintegrations per minute (dpm) or alternatively, referred to as counts per minute (cpm).

% Inhibition Calculation $$\% \; inh = 100 - \left(\frac{dpm_{cmpd} - dpm_{min}}{dpm_{max} - dpm_{min}}\right) \times 100$$

Where dpm=disintegrations per minute, cmpd=signal in assay well, and min and max are the respective minimum and maximum signal controls.

Four-Parameter $IC_{50}$ Fit $$Y = Bottom + \frac{(Top-Bottom)}{1+\left(\frac{X}{IC_{50}}\right)^{Hill\;Coefficient}}$$

Where top and bottom are the normally allowed to float, but may be fixed at 100 or 0 respectively in a 3-parameter fit. The Hill Coefficient normally allowed to float but may also be fixed at 1 in a 3-parameter fit. Y is the % inhibition and X is the compound concentration.

$IC_{50}$ values for the PRC2 enzyme assays on peptide substrates (e.g., EZH2 wild type and Y641F) are presented in Table 7 below.

WSU-DLCL2 Methylation Assay

WSU-DLCL2 suspension cells were purchased from DSMZ (German Collection of Microorganisms and Cell Cultures, Braunschweig, Germany). RPMI/Glutamax Medium, Penicillin-Streptomycin, Heat Inactivated Fetal Bovine Serum, and D-PBS were purchased from Life Technologies, Grand Island, N.Y., USA. Extraction Buffer and Neutralization Buffer (5×) were purchased from Active Motif, Carlsbad, Calif., USA. Rabbit anti-Histone H3 antibody was purchased from Abcam, Cambridge, Mass., USA. Rabbit anti-H3K27me3 and HRP-conjugated anti-rabbit-IgG were purchased from Cell Signaling Technology, Danvers, Mass., USA. TMB "Super Sensitive" substrate was sourced from BioFX Laboratories, Owings Mills, Md., USA. IgG-free Bovine Serum Albumin was purchased from Jackson ImmunoResearch, West Grove, Pa., USA. PBS with Tween (10×PBST) was purchased from KPL, Gaithersburg, Md., USA. Sulfuric Acid was purchased from Ricca Chemical, Arlington, Tex., USA. Immulon ELISA plates were purchased from Thermo, Rochester, N.Y., USA. V-bottom cell culture plates were purchased from Corning Inc., Corning, N.Y., USA. V-bottom polypropylene plates were purchased from Greiner Bio-One, Monroe, N.C., USA.

WSU-DLCL2 suspension cells were maintained in growth medium (RPMI 1640 supplemented with 10% v/v heat inactivated fetal bovine serum and 100 units/mL penicillin-streptomycin) and cultured at 37° C. under 5% $CO_2$. Under assay conditions, cells were incubated in Assay Medium (RPMI 1640 supplemented with 20% v/v heat inactivated fetal bovine serum and 100 units/mL penicillin-streptomycin) at 37° C. under 5% $CO_2$ on a plate shaker.

WSU-DLCL2 cells were seeded in assay medium at a concentration of 50,000 cells per mL to a 96-well V-bottom cell culture plate with 200 µL per well. Compound (1 µL) from 96 well source plates was added directly to V-bottom cell plate. Plates were incubated on a titer-plate shaker at 37° C., 5% $CO_2$ for 96 hours. After four days of incubation, plates were spun at 241×g for five minutes and medium was aspirated gently from each well of cell plate without disturbing cell pellet. Pellet was resuspended in: 200 µL DPBS and plates were spun again at 241×g for five minutes. The supernatant was aspirated and cold (4° C.) Extraction buffer (100 µL) was added per well. Plates were incubated at 4° C. on orbital shaker for two hours. Plates were spun at 3427×g×10 minutes. Supernatant (80 µL per well) was transferred to its respective well in 96 well V-bottom polypropylene plate. Neutralization Buffer 5× (20 µL per well) was added to V-bottom polypropylene plate containing supernatant. V-bottom polypropylene plates containing crude histone preparation (CHP) were incubated on orbital shaker×five minutes. Crude Histone Preparations were added (2 µL per well) to each respective well into duplicate 96 well ELISA plates containing 100 µL Coating Buffer (1×PBS+BSA 0.05% w/v). Plates were sealed and incubated overnight at 4° C. The following day, plates were washed three times with 300 µL per well 1×PBST. Wells were blocked for two hours with 300 µL per well ELISA Diluent ((PBS (1×) BSA (2% w/v) and Tween20 (0.05% v/v)). Plates were washed three times with 1×PBST. For the Histone H3 detection plate, 100 μL per well were added of anti-Histone-H3 antibody (Abcam, ab1791) diluted 1:10,000 in ELISA Diluent. For H3K27 trimethylation detection plate, 100 μL per well were added of anti-H3K27me3 diluted 1:2000 in ELISA diluent. Plates were incubated for 90 minutes at room temperature. Plates were washed three times with 300 μL 1×PBST per well. For Histone H3 detection, 100 μL of HRP-conjugated anti-rabbit IgG antibody diluted to 1:6000 in ELISA diluent was added per well. For H3K27me3 detection, 100 μL of HRP conjugated anti-rabbit IgG antibody diluted to 1:4000 in ELISA diluent was added per well. Plates were incubated at room temperature for 90 minutes. Plates were washed four times with 1×PBST 300 μL per well. TMB substrate 100 μL was added per well. Histone H3 plates were incubated for five minutes at room temperature. H3K27me3 plates were incubated for 10 minutes at room temperature. The reaction was stopped with sulfuric acid 1N (100 μL per well). Absorbance for each plate was read at 450 nm.

First, the ratio for each well was determined by:

$$\left(\frac{H3K27me3\ OD450\ \text{value}}{\text{Histone } H3\ OD450\ \text{value}}\right)$$

Each plate included eight control wells DMSO only treatment (Minimum Inhibition) as well as eight control wells for maximum inhibition (Background wells).

The average of the ratio values for each control type was calculated and used to determine the percent inhibition for each test well in the plate. Test compound was serially diluted three-fold in DMSO for a total of ten test concentrations, beginning at 25 μM. Percent inhibition was determined and IC$_{50}$ curves were generated using duplicate wells per concentration of compound. IC$_{50}$ values for this assay are presented in Table 7 below.

Percent Inhibition = 100 −

$$\left(\left(\frac{(\text{Individual Test Sample Ratio})\ (\text{Background } Avg\ \text{Ratio})}{(\text{Minimum Inhibition Ratio}) - (\text{Background Average Ratio})}\right) * 100\right)$$

Cell Proliferation Analysis

WSU-DLCL2 suspension cells were purchased from DSMZ (German Collection of Microorganisms and Cell Cultures, Braunschweig, Germany), RPMI/Glutamax Medium, Penicillin-Streptomycin, Heat Inactivated Fetal Bovine Serum were purchased from Life Technologies, Grand Island, N.Y., USA, V-bottom polypropylene 384-well plates were purchased from Greiner Bio-One, Monroe, N.C., USA. Cell culture 384-well white opaque plates were purchased from Perkin Elmer, Waltham, Mass., USA. Cell-Titer Glo® was purchased from Promega Corporation, Madison, Wis., USA. SpectraMax M5 plate reader was purchased from Molecular Devices LLC, Sunnyvale, Calif., USA.

WSU-DLCL2 suspension cells were maintained in growth medium (RPMI 1640 supplemented with 10% v/v heat inactivated fetal bovine serum and cultured at 37° C. under 5% $CO_2$. Under assay conditions, cells were incubated in Assay Medium (RPMI 1640 supplemented with 20% v/v heat inactivated fetal bovine serum and 100 units/mL penicillin-streptomycin) at 37° C. under 5% $CO_2$.

For the assessment of the effect of compounds on the proliferation of the WSU-DLCL2 cell line, exponentially growing cells were plated in 384-well white opaque plates at a density of 1250 cell/ml in a final volume of 50 μl of assay medium. A compound source plate was prepared by performing triplicate nine-point 3-fold serial dilutions in DMSO, beginning at 10 mM (final top concentration of compound in the assay was 20 μM and the DMSO was 0.2%). A 100 nL aliquot from the compound stock plate was added to its respective well in the cell plate. The 100% inhibition control consisted of cells treated with 200 nM final concentration of staurosporine and the 0% inhibition control consisted of DMSO treated cells. After addition of compounds, assay plates were incubated for 6 days at 37° C., 5% $CO_2$, relative humidity >90% for 6 days. Cell viability was measured by quantization of ATP present in the cell cultures, adding 35 μl of Cell Titer Glo® reagent to the cell plates. Luminescence was read in the SpectraMax M5. The concentration inhibiting cell viability by 50% was determined using a 4-parametric fit of the normalized dose response curves. IC$_{50}$ values for this assay are also presented in Table 7 below.

TABLE 7

| Cpd # | WT EZH2 IC$_{50}$ (μM) | Mutant Y641F IC$_{50}$ (μM) | H3K27Me3 ELISA IC$_{50}$ (μM) | WSU proliferation IC$_{50}$ (μM) |
|---|---|---|---|---|
| 1 | 0.075 | 0.149 | 0.75 | 0.85 |
| 2 | 15.118 | 8.345 | | |
| 8 | 20.029 | 5.820 | | |
| 9 | 34.507 | 11.481 | | |
| 30 | 0.024 | 0.007 | 29.013 | |
| 31a | 0.505 | 0.230 | | |
| 31b | 1.238 | 1.069 | | |
| 32 | 0.068 | 0.015 | 15.376 | 11.51 |
| 33a | 0.038 | 0.013 | 2.431 | |
| 33b | 0.975 | 0.479 | >50 | |
| 34 | 0.223 | 0.110 | 18.644 | 6.918 |
| 35 | 0.267 | 0.063 | 17.887 | >20 |
| 36 | 0.829 | 0.114 | 7.971 | >20 |
| 37 | 15.626 | 2.665 | | |
| 38 | 3.370 | 0.265 | 18.069 | >20 |
| 39 | 6.584 | 2.229 | | |
| 40 | 0.689 | 0.166 | | |
| 41 | 37.209 | 26.166 | >50 | |
| 42 | >50 | | | >20 |
| 43 | >50 | >50 | | |
| 44 | >50 | | | |
| 45 | >50 | >50 | | |
| 46 | 3.252 | 0.682 | >50 | |
| 47 | 0.348 | 0.382 | >50 | |
| 48 | >50 | >50 | | |
| 49 | 10.354 | 5.165 | | |
| 50 | 27.571 | 2.709 | | |
| 51 | 2.870 | 0.573 | | >20 |
| 52 | 0.367 | 0.030 | 3.036 | 7.342 |
| 53 | 2.175 | 0.625 | | |
| 54 | 0.194 | 0.039 | | |
| 55 | 0.695 | 0.418 | 30.550 | |
| 56 | 0.025 | 0.011 | 4.676 | 10.665 |
| 57 | 0.020 | 0.010 | 6.160 | 6.050 |
| 58 | 1.540 | 0.342 | | 14.260 |
| 59 | | | >50 | >20 |
| 60 | 2.110 | 0.695 | | 13.483 |
| 61 | 0.857 | 0.188 | | |
| 62 | 0.745 | 0.193 | >50 | |
| 63 | 0.046 | 0.012 | >50 | 1.550 |
| 64 | 17.481 | 4.475 | | |
| 65 | 1.140 | 0.442 | | |
| 66 | 10.250 | 2.343 | | |
| 67 | 0.319 | 0.060 | | |
| 68 | 2.587 | | | |
| 69 | 0.136 | 0.031 | | |
| 70 | 0.039 | 0.012 | 4.057 | 3.606 |
| 71 | 1.918 | 0.504 | | |
| 72 | >50 | 5.675 | | |
| 73 | 1.289 | 0.149 | | |

TABLE 7-continued

| Cpd # | WT EZH2 IC$_{50}$ (µM) | Mutant Y641F IC$_{50}$ (µM) | H3K27Me3 ELISA IC$_{50}$ (µM) | WSU proliferation IC$_{50}$ (µM) |
|---|---|---|---|---|
| 74 | 12.609 | 7.252 | | |
| 75 | >50 | >50 | | |
| 76 | >50 | >50 | | |
| 77 | 12.621 | 4.692 | | |
| 78 | 17.561 | 4.265 | | |
| 79 | 0.485 | 0.100 | | |
| 80 | >50 | 49.392 | | |
| 81 | 0.018 | 0.005 | 2.188 | 1.264 |
| 82 | 22.902 | 27.007 | | |
| 83 | 45.786 | 18.270 | | |
| 84 | 1.441 | 1.216 | 16.700 | |
| 85 | 35.182 | 7.525 | >50 | 6.383 |
| 86 | 0.021 | 0.001 | 1.787 | 1.134 |
| 87 | 0.335 | 0.253 | | |
| 88 | >50 | 46.447 | | |
| 89 | >50 | >50 | | |
| 90 | 1.907 | 0.502 | | |
| 91 | 7.454 | 1.173 | >50 | |
| 92 | >50 | >50.0 | | |
| 93 | 0.00971 | 0.0144 | 3.553 | |
| 94 | >50 | >50 | | |
| 95 | >50 | 17.650 | | |

Example 3: Derivation of the Lowest Cytotoxic Concentration (LCC)

It is well established that cellular proliferation proceeds through cell division that results in a doubling of the number of cells after division, relative to the number of cells prior to division. Under a fixed set of environmental conditions (e.g., pH, ionic strength, temperature, cell density, medium content of proteins and growth factors, and the like) cells will proliferate by consecutive doubling (i.e., division) according to the following equation, provided that sufficient nutrients and other required factors are available.

$$N_t = N_0 \times 2^{\frac{t}{t_D}} \quad (A.1)$$

where $N_t$ is the cell number at a time point (t) after initiation of the observation period, $N_0$ is the cell number at the initiation of the observation period, t is the time after initiation of the observation period and $t_D$ is the time interval required for cell doubling, also referred to as the doubling time. Equation A.1 can be converted into the more convenient form of an exponential equation in base e, taking advantage of the equality, 0.693=ln(2).

$$N_t = N_0 \times e^{\frac{0.693t}{t_D}} \quad (A.2)$$

The rate constant for cell proliferation ($k_p$) is inversely related to the doubling time as follows.

$$k_p = \frac{0.693}{t_D} \quad (A.3)$$

Combining equation A.2 and A.3 yields, $$N_t = N_0 e^{k_p t} \quad (A.4)$$

Thus, according to equation A.4 cell number is expected to increase exponentially with time during the early period of cell growth referred to as log-phase growth. Exponential equations like equation A.4 can be linearized by taking the natural logarithm of each side.

$$\ln(N_t) = \ln(N_0) + k_p t \quad (A.5)$$

Thus a plot of $\ln(N_t)$ as a function of time is expected to yield an ascending straight line with slope equal to $k_p$ and y-intercept equal to $\ln(N_0)$.

Changes in environmental conditions can result in a change in the rate of cellular proliferation that is quantifiable as changes in the proliferation rate constant $k_p$. Among conditions that may result in a change in proliferation rate is the introduction to the system of an antiproliferative compound at the initiation of the observation period (i.e., at t=0). When an antiproliferative compound has an immediate impact on cell proliferation, one expects that plots of $\ln(N_t)$ as a function of time will continue to be linear at all compound concentrations, with diminishing values of $k_p$ at increasing concentrations of compound.

Depending on the mechanistic basis of antiproliferative action, some compounds may not immediately effect a change in proliferation rate. Instead, there may be a period of latency before the impact of the compound is realized. In such cases a plot of $\ln(N_t)$ as a function of time will appear biphasic, and a time point at which the impact of the compound begins can be identified as the breakpoint between phases. Regardless of whether a compound's impact on proliferation is immediate or begins after a latency period, the rate constant for proliferation at each compound concentration is best defined by the slope of the $\ln(N_t)$ vs. time curve from the time point at which compound impact begins to the end of the observation period of the experiment.

A compound applied to growing cells may affect the observed proliferation in one of two general ways: by inhibiting further cell division (cytostasis) or by cell killing (cytotoxicity). If a compound is cytostatic, increasing concentration of compound will reduce the value of $k_p$ until there is no further cell division. At this point, the rate of cell growth, and therefore the value of $k_p$, will be zero. If, on the other hand, the compound is cytotoxic, then the value of $k_p$ will be composed of two rate constants: a rate constant for continued cell growth in the presence of the compound ($k_g$) and a rate constant for cell killing by the compound ($k_d$). The overall rate constant for proliferation at a fixed concentration of compound will thus be the difference between the absolute values of these opposing rate constants.

$$k_p = |k_g| - |k_d| \quad (A.6)$$

At compound concentrations for which the rate of cell growth exceeds that of cell killing, the value of $k_p$ will have a positive value (i.e., $k_p > 0$). At compound concentrations for which the rate of cell growth is less than that for cell killing, the value of $k_p$ will have a negative value (i.e., $k_p < 0$) and the cell number will decrease with time, indicative of robust cytotoxicity. When $k_g$ exactly matches $k_d$ then the overall proliferation rate constant, $k_p$, will have a value of zero. We can thus define the lowest cytotoxic concentration (LCC) as that concentration of compound that results in a value of $k_p$ equal to zero, because any concentration greater than this will result in clearly observable cytotoxicity. Nota bene: at concentrations below the LCC there is likely to be cell killing occurring, but at a rate that is less than that of residual cell proliferation. The treatment here is not intended to define the biological details of compound action. Rather, the goal here is to merely define a practical parameter with which to objectively quantify the concentration of compound at which the rate of cell killing exceeds new cell growth. Indeed, the LCC represents a breakpoint or critical concentration above which frank cytotoxicity is observed, rather than a cytotoxic concentration per se. In this regard, the LCC can be viewed similar to other physical breakpoint metrics, such as the critical micelle concentration (CMC) used to define the concentration of lipid, detergent or other surfactant species above which all molecules incorporate into micellar structures.

Traditionally, the impact of antiproliferative compounds on cell growth has been most commonly quantified by the $IC_{50}$ value, which is defined as that concentration of compound that reduces the rate of cell proliferation to one half that observed in the absence of compound (i.e., for the vehicle or solvent control sample). The $IC_{50}$, however, does not allow the investigator to differentiate between cytostatic and cytotoxic compounds. The LCC, in contrast, readily allows one to make such a differentiation and to further quantify the concentration at which the transition to robust cytotoxic behavior occurs.

If one limits the observation time window to between the start of impact and the end of the experiment, then the data will generally fit well to a linear equation when plotted as $\ln(N_t)$ as a function of time (vide supra). From fits of this type, the value of $k_p$ can be determined at each concentration of compound tested. A replot of the value of $k_p$ as a function of compound concentration ([I]) will have the form of a descending isotherm, with a maximum value at [I]=0 of $k_{max}$ (defined by the vehicle or solvent control sample) and a minimum value at infinite compound concentration of $k_{min}$.

$$k_p = \frac{(k_{max} - k_{min})}{1 + \frac{[I]}{I_{mid}}} + k_{min} \quad (A.7)$$

where $I_{mid}$ is the concentration of compound yielding a value of $k_p$ that is midway between the values of $k_{max}$ and $k_{min}$ (note that the value of $I_{mid}$ is not the same as the $IC_{50}$, except in the case of a complete and purely cytostatic compound). Thus, fitting the replot data to equation A.7 provides estimates of $k_{max}$, $k_{min}$ and $I_{mid}$. If a compound is cytostatic (as defined here), the value of $k_{min}$ cannot be less than zero. For cytotoxic compounds, $k_{min}$ will be less than zero and the absolute value of $k_{min}$ will relate directly to the effectiveness of the compound in killing cells.

The fitted values derived from equation A.7 can also be used to determine the value of the LCC. By definition, when [I]=LCC, $k_p$=0. Thus, under these conditions equation A.7 becomes.

$$0 = \frac{(k_{max} - k_{min})}{1 + \frac{LCC}{I_{mid}}} + k_{min} \quad (A.8)$$

Algebraic rearrangement of equation A.8 yields an equation for the LCC.

$$LCC = I_{mid}\left[\left(\frac{k_{max} - k_{min}}{-k_{min}}\right) - 1\right] \quad (A.9)$$

This analysis is simple to implement with nonlinear curve fitting software and may be applied during cellular assays of compound activity throughout the drug discovery and development process. In this manner, the LCC may provide a valuable metric for the assessment of compound SAR (structure-activity relationship).

Example 4: In Vivo Assays

Mice

Female Fox Chase SCID® Mice (CB17/Icr-Prkdc$_{scid}$/IcrIcoCrl, Charles River Laboratories) or athymic nude mice (Crl:NU(Ncr)-Foxn1$_{nu}$, Charles River Laboratories) are 8 weeks old and had a body-weight (BW) range of 16.0-21.1 g on D1 of the study. The animals are fed ad libitum water (reverse osmosis 1 ppm Cl) and NIH 31 Modified and Irradiated Lab Diet® consisting of 18.0% crude protein, 5.0% crude fat, and 5.0% crude fiber. The mice are housed on irradiated Enrich-o'Cobs™ bedding in static microisolators on a 12-hour light cycle at 20-22° C. (68-72° F.) and 40-60% humidity. All procedures comply with the recommendations of the *Guide for Care and Use of Laboratory Animals* with respect to restraint, husbandry, surgical procedures, feed and fluid regulation, and veterinary care.

Tumor Cell Culture

Human lymphoma cell lines line are obtained from different sources (ATCC, DSMZ), e.g., WSU-DLCL2 obtained from DSMZ. The cell lines are maintained at Piedmont as suspension cultures in RPMI-1640 medium containing 100 units/mL penicillin G sodium salt, 100 g/mL streptomycin, and 25 g/mL gentamicin. The medium is supplemented with 10% fetal bovine serum and 2 mM glutamine. The cells are cultured in tissue culture flasks in a humidified incubator at 37° C., in an atmosphere of 5% $CO_2$ and 95% air.

In Vivo Tumor Implantation

Human lymphoma cell lines, e.g., WSU-DLCL2 cells, are harvested during mid-log phase growth, and re-suspended in PBS with 50% Matrigel™ (BD Biosciences). Each mouse receives $1\times10^7$ cells (0.2 mL cell suspension) subcutaneously in the right flank. Tumors are calipered in two dimensions to monitor growth as the mean volume approached the desired 80-120 mm³ range. Tumor size, in mm³, is calculated from:

$$\text{Tumor volume} = \frac{w^2 \times l}{2}$$

where w=width and l=length, in mm, of the tumor. Tumor weight can be estimated with the assumption that 1 mg is equivalent to 1 mm³ of tumor volume. After 10-30 days mice with 108-126 mm³ tumors are sorted into treatment groups with mean tumor volumes of 117-119 mm³.

Test Articles

Test compounds are stored at room temperature and protected from light. On each treatment day, fresh compound formulations are prepared by suspending the powders in 0.5% sodium carboxymethylcellulose (NaCMC) and 0.1% Tween® 80 in deionized water. Compound 141 (free base) is dissolved in sterile saline and the pH is adjusted to 4.5 with HCl fresh every day. The vehicles, 0.5% NaCMC and 0.1% Tween® 80 in deionized water or sterile saline pH 4.5, are used to treat the control groups at the same schedules. Formulations are stored away from light at 4° C. prior to administration. Unless otherwise specified, compounds referred to and tested in this experiment are in their specific salt forms mentioned in this paragraph.

Treatment Plan

Mice are treated at compound doses ranging from 12.5-600 mg/kg and at TID (three time a day every 8 h), BID (2 times a day every 12 h) or QD (once a day) schedules for various amounts of days by oral gavage or injections via the intraperitoneal route. Each dose is delivered in a volume of 0.2 mL/20 g mouse (10 mL/kg), and adjusted for the last recorded weight of individual animals. The maximal treatment length is 28 days.

Median Tumor Volume (MTV) and Tumor Growth Inhibition (TGI) Analysis

Treatment efficacy is determined on the last treatment day. MTV(n), the median tumor volume for the number of animals, n, evaluable on the last day, is determined for each group. Percent tumor growth inhibition (% TGI) can be defined several ways. First, the difference between the MTV(n) of the designated control group and the MTV(n) of the drug-treated group is expressed as a percentage of the MTV(n) of the control group:

$$\% \ TGI = \left( \frac{MTV(n)_{control} - MTV(n)_{treated}}{MTV(n)_{control}} \right) \times 100$$

Another way of calculating % TGI is taking the change of tumor size from day 1 to day n into account with n being the last treatment day.

$$\% \ TGI = \left( \frac{\Delta MTV_{control} - \Delta MTV_{treated}}{\Delta MTV_{control}} \right) \times 100$$

$$\Delta MTV_{control} = MTV(n)_{control} - MTV(1)_{control}$$

$$\Delta MTV_{treated} = MTV(n)_{treated} - MTV(1)_{treated}$$

Toxicity

Animals are weighed daily on Days 1-5, and then twice weekly until the completion of the study. The mice are examined frequently for overt signs of any adverse, treatment related side effects, which are documented. Acceptable toxicity for the maximum tolerated dose (MTD) is defined as a group mean BW loss of less than 20% during the test, and not more than 10% mortality due to TR deaths. A death is to be classified as TR if it is attributable to treatment side effects as evidenced by clinical signs and/or necropsy, or due to unknown causes during the dosing period. A death is to be classified as NTR if there is evidence that the death is unrelated to treatment side effects. NTR deaths during the dosing interval would typically be categorized as NTRa (due to an accident or human error) or NTRm (due to necropsy-confirmed tumor dissemination by invasion and/or metastasis). Orally treated animals that die from unknown causes during the dosing period may be classified as NTRu when group performance does not support a TR classification and necropsy, to rule out a dosing error, is not feasible.

Sampling

On days 7 or 28 during the studies mice are sampled in a pre-specified fashion to assess target inhibition in tumors. Tumors are harvested from specified mice under RNAse free conditions and bisected. Frozen tumor tissue from each animal is snap frozen in liquid $N_2$ and pulverized with a mortar and pestle.

Statistical and Graphical Analyses

All statistical and graphical analyses are performed with Prism 3.03 (GraphPad) for Windows. To test statistical significance between the control and treated groups over the whole treatment time course a repeated measures ANOVA test followed by Dunnets multiple comparison post test or a 2 way ANOVA test are employed. Prism reports results as non-significant (ns) at P>0.05, significant (symbolized by "*") at 0.01<P<0.05, very significant ("") at 0.001<P<0.01 and extremely significant ("*") at P<0.001.

Histone Extraction

For isolation of histones, 60-90 mg tumor tissue is homogenized in 1.5 ml nuclear extraction buffer (10 mM Tris-HCl, 10 mM $MgCl_2$, 25 mM KCl, 1% Triton X-100, 8.6% Sucrose, plus a Roche protease inhibitor tablet 1836145) and incubated on ice for 5 minutes. Nuclei are collected by centrifugation at 600 g for 5 minutes at 4° C. and washed once in PBS. Supernatant is removed and histones extracted for one hour, with vortexing every 15 minutes, with 0.4N cold sulfuric acid. Extracts are clarified by centrifugation at 10,000 g for 10 minutes at 4° C. and transferred to a fresh microcentrifuge tube containing 10× volume of ice cold acetone. Histones are precipitated at −20° C. for 2 hours-overnight, pelleted by centrifugation at 10,000 g for 10 minutes, and resuspended in water.

ELISA

Histones are prepared in equivalent concentrations in coating buffer (PBS+0.05% BSA) yielding 0.5 ng/ul of sample, and 100 ul of sample or standard is added in duplicate to 2 96-well ELISA plates (Thermo Labsystems, Immulon 4HBX #3885). The plates are sealed and incubated overnight at 4° C. The following day, plates are washed 3× with 300 ul/well PBST (PBS+0.05% Tween 20; 10×PBST, KPL #51-14-02) on a Bio Tek plate washer. Plates are blocked with 300 ul/well of diluent (PBS+2% BSA+0.05% Tween 20), incubated at RT for 2 hours, and washed 3× with PBST. All antibodies are diluted in diluent. 100 ul/well of anti-H3K27me3 (CST #9733, 50% glycerol stock 1:1,000) or anti-total H3 (Abcam ab1791, 50% glycerol 1:10,000) is added to each plate. Plates are incubated for 90 min at RT and washed 3× with PBST. 100 ul/well of anti-Rb-IgG-HRP (Cell Signaling Technology, 7074) is added 1:2,000 to the H3K27Me3 plate and 1:6,000 to the H3 plate and incubated for 90 min at RT. Plates are washed 4× with PBST. For detection, 100 ul/well of TMB substrate (BioFx Laboratories, #TMBS) is added and plates incubated in the dark at RT for 5 min. Reaction is stopped with 100 ul/well 1N $H_2SO_4$. Absorbance at 450 nm is read on SpectaMax M5 Microplate reader.

7 Day PD Study

In order to test whether a compound can modulate the H3K27me3 histone mark in tumors in vivo, WSU-DLCL2 xenograft tumor bearing mice are treated with the compound at either 200 mg/kg BID or 400 mg/kg QD or vehicle (BID schedule) for 7 days. There are 4 animals per group. Animals are euthanized 3 h after the last dose and tumor is preserved in a frozen state as described above. Following histone extraction the samples are applied to ELISA assays using antibodies directed against the trimethylated state of histone H3K27 (H3K27me3) or total histone H3. Based on these data the ratio of globally methylated to total H3K27 is calculated. The mean global methylation ratios for all groups as measured by ELISA indicate target inhibition range compared to vehicle.

28 Day Efficacy Study in WSU-DLCL2 Xenograft Model

In order to test whether a compound could induce a tumor growth inhibition in vivo WSU-DLCL2 xenograft tumor bearing mice are treated with the compound at 12.5, 25 or 50 mg/kg QD for 28 days via intraperitoneal injection. Tumor volume and body weights are determined twice a week. A parallel cohort of mice (n=4 per group) is treated at the same doses for 7 days, and mice are euthanized on day 7, 3 h after the last dose for tumor sampling and assessment of target inhibition. The result of the ELISA measuring global methylation of H3K27me3 normalized to total H3 is determined.

Efficacy Study with Increasing Doses in WSU-DLCL2 Xenograft Model

In order to test whether a compound could induce an anti-tumor effect in vivo, WSU-DLCL2 xenograft tumor bearing mice are treated with a compound at, e.g., 37.5, 75 or 150 mg/kg TID for 28 days. There are 12 mice per group for the efficacy arm of the experiment. A parallel cohort is dosed for 7 days at the same doses and schedules for assessment of target inhibition after 7 days (n=6 per group). The tumor growth over the treatment course of 28 days for vehicle and compound treated groups is measured.

Histones are extracted from tumors collected after 7 days of dosing (parallel PD cohort) and at the end of the study on day 28 for the efficacy cohort (3 h after the last dose for both cohorts). The H3K27me3 methyl mark is assessed for modulation with treatment in a dose dependent matter.

Efficacy Study at Different Dose Schedules

To assess whether a compound would lead to tumor growth inhibition at other dosing schedules but TID a WSU-DLCL2 xenograft efficacy study is performed where TID, BID and QD schedules are compared side by side. There are 12 animals per group, and mice are treated for 28 days. The tumor growth over the treatment course of 28 days for vehicle and compound treated groups is measured.

On day 28 mice are euthanized and tumors are collected 3 h after the last dose for assessment of target inhibition.

Example 5: Anti-Cancer Effect on the KARPAS-422 Human Diffused Large B-Cell Lymphoma Mouse Xenograft Model A test compound is analyzed for its anti-cancer activity in KARPAS-422 mouse xenograft model, which is a human diffused large B-Cell lymphoma xenograft model. 45 female of CAnN.Cg-Foxn1nu/CrlCrlj mice (Charles River Laboratories Japan) with KARPAS-422 tumors whose mean tumor volume (TV) reached approximately 150 mm³ are selected based on their TVs, and are randomly divided into five groups. The oral administration of compound (e.g., 80.5, 161, 322, and 644 mg/kg) or vehicle is started on day 1. Compound is given once daily on day 1 and day 29 and twice daily everyday from day 2 to day 28. The administration volume (0.1 mL/10 g body weight) is calculated from the body weight before administration. The TV and body weight are measured twice a week. The design for this experiment is shown in Table 8.

TABLE 8

Dosing Scheme

| Group | No. of Animals | Treatment (twice a day) | Route and Schedule |
|---|---|---|---|
| 1 | 9 | Vehicle (0.5% Methyl Cellulose, 0.1% Tween-80) | PO; BID × 28 days |
| 2 | 9 | 80.5 mg/kg Compound | PO; BID × 28 days |
| 3 | 9 | 161 mg/kg Compound | PO; BID × 28 days |
| 4 | 9 | 322 mg/kg Compound | PO; BID × 28 days |
| 5 | 9 | 644 mg/kg Compound | PO; bid × 28 days |

TV is calculated from caliper measurements by the formula for the volume of a prolate ellipsoid $(L \times W^2)/2$ where L and W are the respective orthogonal length and width measurements (mm).

Data are expressed as the mean±standard deviation (SD). The differences in TV between the vehicle-treated and compound-treated groups are analyzed by a repeated measures analysis of variance (ANOVA) followed by the Dunnett-type multiple comparison test. A value of $P<0.05$ (two sided) is considered statistically significant. Statistical analyses are performed using the Prism 5 software package version 5.04 (GraphPad Software, Inc., CA, USA).

The invention can be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:

1. A compound of Formula (I) or a pharmaceutically acceptable salt thereof:

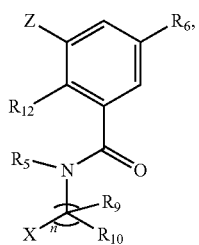

(I)

wherein
X is

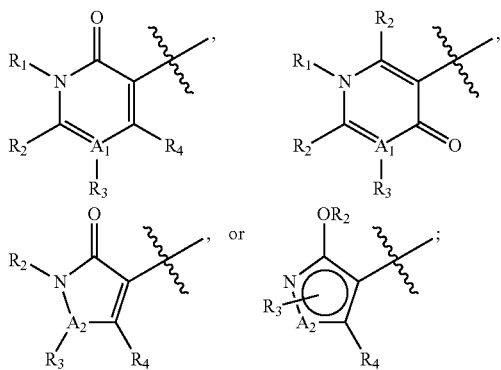

$A_1$ is C or N and when $A_1$ is N, $R_3$ is absent;
$A_2$ is N, O, or S and when $A_2$ is O or S, $R_3$ is absent;
Z is $NR_7R_8$, $OR_7$, $S(O)_aR_7$, or $CR_7R_8R_{14}$, in which a is 0, 1, or 2;
$R_1$ is $-Q_0-T_0$, in which $Q_0$ is $NR_{1a}$, O or S, $R_{1a}$ being H, OH, $C_1$-$C_6$ alkyl, or $C_1$-$C_6$ alkoxyl, and $T_0$ is H or $R_{S0}$, in which $R_{S0}$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 12-membered heterocycloalkyl, or 5- or 6-membered heteroaryl, and $R_{S0}$ is optionally substituted with one or more substituents selected from the group consisting of halo, hydroxyl, oxo, C(O)OH, C(O)O—$C_1$-$C_6$ alkyl, cyano, $C_1$-$C_6$ alkyl, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl;

each of $R_2$, $R_3$, and $R_4$, independently, is $-Q_1-T_1$, in which $Q_1$ is a bond or $C_1$-$C_3$ alkyl linker optionally substituted with halo, cyano, hydroxyl or $C_1$-$C_6$ alkoxy, and $T_1$ is H, halo, hydroxyl, C(O)OH, cyano, azido, or $R_{S1}$, in which $R_{S1}$ is $C_1$-$C_3$ alkyl, $C_2$-$C_6$ alkenyl, $C_2$-$C_6$ alkynyl, $C_1$-$C_6$ alkoxyl, $C_1$-$C_6$ thioalkyl, C(O)O—$C_1$-$C_6$ alkyl, $CONH_2$, $SO_2NH_2$, —C(O)—NH($C_1$-$C_6$ alkyl), —C(O)—N($C_1$-$C_6$ alkyl)$_2$, —$SO_2$—NH($C_1$-$C_6$ alkyl), —$SO_2$—N($C_1$-$C_6$ alkyl)$_2$, $C_3$-$C_8$ cycloalkyl, $C_6$-$C_{10}$ aryl, $C_6$-$C_{10}$ aryloxy, amino, mono-$C_1$-$C_6$ alkylamino, di-$C_1$-$C_6$ alkylamino, 4 to 12-membered heterocycloalkyl, or 5- or 6-membered heteroaryl, and $R_{S1}$ is optionally substituted with one or more substituents selected from the group consisting of halo, hydroxyl, oxo, C(O)OH, C(O)O—$C_1$-$C_6$ alkyl, cyano, $C_1$-$C_6$ alkyl, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl; or neighboring $R_1$ and $R_2$, together with the atoms to which they are attached, form a 5- or 6-membered heteroaryl having 0 to 2 additional heteroatoms or a 5 to 12-membered heterocycloalkyl ring having 0 to 2 additional heteroatoms; or neighboring $R_1$ and $R_4$, together with the atoms to which they are attached, form a 5- or 6-membered heteroaryl having 0 to 2 additional heteroatoms or a 5 to 12-membered heterocycloalkyl ring having 0 to 2 additional heteroatoms; or neighboring $R_2$ and $R_3$, together with the atoms to which they are attached, form $C_5$-$C_8$ cycloalkyl, $C_6$-$C_{10}$ aryl, or a 5- or 6-membered heteroaryl having 1 to 3 heteroatoms, or a 5 to 12-membered heterocycloalkyl ring having 1 to 3 heteroatoms; or neighboring $R_3$ and $R_4$, together with the atoms to which they are attached, form $C_5$-$C_8$ cycloalkyl, $C_6$-$C_{10}$ aryl, or a 5- or 6-membered heteroaryl having 1 to 3 heteroatoms, or a 5 to 12-membered heterocycloalkyl ring having 1 to 3 heteroatoms; in which each of the ring structures formed by $R_1$ and $R_2$, by $R_1$ and $R_4$, by $R_2$ and $R_3$, or by $R_3$ and $R_4$, independently is optionally substituted with one or more substituents selected from the group consisting of halo, hydroxyl, oxo, $C_1$-$C_6$ alkyl, $C_1$-$C_6$ haloalkyl, C(O)OH, C(O)O—$C_1$-$C_6$ alkyl, C(O)O—$C_1$-$C_6$ haloalkyl, cyano, $C_1$-$C_6$ alkoxyl, $C_1$-$C_6$ haloalkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl;

each of $R_5$, $R_9$, and $R_{10}$, independently, is H or $C_1$-$C_6$ alkyl optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl;

$R_6$ is halo, cyano, azido, $OR_a$, —$NR_aR_b$, —$C(O)R_a$, —$C(O)OR_a$, —$C(O)NR_aR_b$, —$NR_bC(O)R_a$, —$S(O)_bR_a$, —$S(O)_bNR_aR_b$, or $R_{S2}$, in which $R_{S2}$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 5- or 6-membered heteroaryl, or 4 to 12-membered heterocycloalkyl, b is 0, 1, or 2, each of $R_a$ and $R_b$, independently is H or $R_{S3}$, and $R_{S3}$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 12-membered heterocycloalkyl, or 5- or 6-membered heteroaryl; or $R_a$ and $R_b$, together with the N atom to which they are attached, form a 4 to 12-membered heterocycloalkyl ring having 0 or 1 additional heteroatom; and each of $R_{S2}$, $R_{S3}$, and the 4 to 12-membered heterocycloalkyl ring formed by $R_a$ and $R_b$, is optionally substituted with one or more -$Q_2$-$T_2$, wherein $Q_2$ is a bond or $C_1$-$C_3$ alkyl linker each optionally substituted with halo, cyano, hydroxyl or $C_1$-$C_6$ alkoxy, and $T_2$ is H, halo, cyano, —$OR_c$, —$NR_cR_d$, —$C(O)R_c$, —$C(O)OR_c$, —$C(O)NR_cR_d$, —$NR_dC(O)R_c$, —$NR_dC(O)OR_c$, —$S(O)_2R_c$, —$S(O)_2NR_cR_d$, or $R_{S4}$, in which each of $R_c$ and $R_d$, independently is H or $R_{S5}$, each of $R_{S4}$ and $R_{S5}$, independently, is $C_1$-$C_6$ alkyl, $C_3$-$C_8$ cycloalkyl, $C_6$-$C_{10}$ aryl, 4 to 12-membered heterocycloalkyl, or 5- or 6-membered heteroaryl, or $R_c$ and $R_d$, together with the N atom to which they are attached, form a 4 to 12-membered heterocycloalkyl ring having 0 or 1 additional heteroatom, and each of $R_{S4}$, $R_{S5}$, and the 4 to 12-membered heterocycloalkyl ring formed by $R_c$ and $R_d$, is optionally substituted with one or more -$Q_3$-$T_3$, wherein $Q_3$ is a bond or $C_1$-$C_3$ alkyl linker each optionally substituted with halo, cyano, hydroxyl or $C_1$-$C_6$ alkoxy, and $T_3$ is selected from the group consisting of H, halo, cyano, $C_1$-$C_6$ alkyl, $C_3$-$C_8$ cycloalkyl, $C_6$-$C_{10}$ aryl, 4 to 12-membered heterocycloalkyl, 5- or 6-membered heteroaryl, $OR_e$, $COOR_e$, —$S(O)_2R_e$, —$NR_eR_f$ and —$C(O)NR_eR_f$ each of $R_e$ and $R_f$ independently being H or $C_1$-$C_6$ alkyl optionally substituted with OH, O—$C_1$-$C_6$ alkyl, or NH—$C_1$-$C_6$ alkyl, or -$Q_3$-$T_3$ is oxo; or -$Q_2$-$T_2$ is oxo; or any two neighboring -$Q_2$-$T_2$, when $R_6$ is $C_6$-$C_{10}$ aryl or 5- or 6-membered heteroaryl, together with the atoms to which they are attached form a 5- or 6-membered ring optionally containing 1-4 heteroatoms selected from N, O and S and optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl;

$R_7$ is -$Q_4$-$T_4$, in which $Q_4$ is a bond, $C_1$-$C_4$ alkyl linker, or $C_2$-$C_4$ alkenyl linker, each linker optionally substituted with halo, cyano, hydroxyl or $C_1$-$C_6$ alkoxy, and $T_4$ is H, halo, cyano, $NR_gR_h$, —$OR_g$, —$C(O)R_g$, —$C(O)OR_g$, —$C(O)NR_gR_h$, —$C(O)NR_gOR_h$, —$NR_gC(O)R_h$, —$S(O)_2R_g$, or $R_{S6}$, in which each of $R_g$ and $R_h$, independently is H or $R_{S7}$, each of $R_{S6}$ and $R_{S7}$, independently is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 14-membered heterocycloalkyl, or 5- or 6-membered heteroaryl, and each of $R_{S6}$ and $R_{S7}$ is optionally substituted with one or more -$Q_5$-$T_5$, wherein $Q_5$ is a bond, C(O), C(O)$NR_k$, $NR_kC(O)$, $NR_k$, $S(O)_2$, $NR_kS(O)_2$, or $C_1$-$C_3$ alkyl linker, $R_k$ being H or $C_1$-$C_6$ alkyl, and $T_5$ is H, halo, $C_1$-$C_6$ alkyl, $C_2$-$C_6$ alkenyl, $C_2$-$C_6$ alkynyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_1$-$C_6$ alkylene-$C_3$-$C_8$ cycloalkyl, $C_6$-$C_{10}$ aryl, $C_1$-$C_6$ alkylene-$C_6$-$C_{10}$ aryl, 4 to 12-membered heterocycloalkyl, $C_1$-$C_6$ alkylene-4 to 12-membered heterocycloalkyl, 5- or 6-membered heteroaryl, $C_1$-$C_6$ alkylene-5- or 6-membered heteroaryl, or $S(O)_qR_q$ in which q is 0, 1, or 2 and $R_q$ is $C_1$-$C_6$ alkyl, $C_2$-$C_6$ alkenyl, $C_2$-$C_6$ alkynyl, $C_3$-$C_5$ cycloalkyl, $C_6$-$C_{10}$ aryl, 4 to 12-membered heterocycloalkyl, or 5- or 6-membered heteroaryl, and $T_5$ is optionally substituted with one or more substituents selected from the group consisting of halo, $C_1$-$C_6$ alkyl, hydroxyl, cyano, $C_1$-$C_6$ alkoxyl, O—$C_1$-$C_4$ alkylene-$C_1$-$C_4$ alkoxy, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl except when $T_5$ is H, halo, hydroxyl, or cyano; or -$Q_5$-$T_5$ is oxo;

each of $R_8$, and $R_{12}$, independently, is H, halo, hydroxyl, COOH, cyano, $R_{S8}$, $OR_{S8}$, or $COOR_{S8}$, in which $R_{S8}$ is $C_1$-$C_6$ alkyl, $C_2$-$C_6$ alkenyl, $C_2$-$C_6$ alkynyl, $C_3$-$C_8$ cycloalkyl, 4 to 12-membered heterocycloalkyl, amino, mono-$C_1$-$C_6$ alkylamino, or di-$C_1$-$C_6$ alkylamino, and $R_{S8}$ is optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, and di-$C_1$-$C_6$ alkylamino; or $R_7$ and $R_8$, together with the N atom to which they are attached, form a 4 to 12-membered heterocycloalkyl ring having 0 to 2 additional heteroatoms, or $R_7$ and $R_8$, together with the C atom to which they are attached, form $C_3$-$C_8$ cycloalkyl or a 4 to 12-membered heterocycloalkyl ring having 1 to 3 heteroatoms, and each of the 4 to 12-membered heterocycloalkyl rings or $C_3$-$C_8$ cycloalkyl formed by $R_7$ and $R_8$ is optionally substituted with one or more -$Q_6$-$T_6$, wherein $Q_6$ is a bond, C(O), C(O)$NR_m$, $NR_mC(O)$, $S(O)_2$, or $C_1$-$C_3$ alkyl linker, $R_m$ being H or $C_1$-$C_6$ alkyl, and $T_6$ is H, halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, 5- or 6-membered heteroaryl, or $S(O)_pR_p$ in which p is 0, 1, or 2 and $R_p$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 12-membered heterocycloalkyl, or 5- or 6-membered heteroaryl, and $T_6$ is optionally substituted with one or more substituents selected from the group consisting of halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl except when $T_6$ is H, halo, hydroxyl, or cyano; or -$Q_6$-$T_6$ is oxo;

$R_{14}$ is absent, H, or $C_1$-$C_6$ alkyl optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl; and n is 1, 2, 3, 4, or 5.

2. The compound of claim 1, wherein the compound is of Formula (Ia):

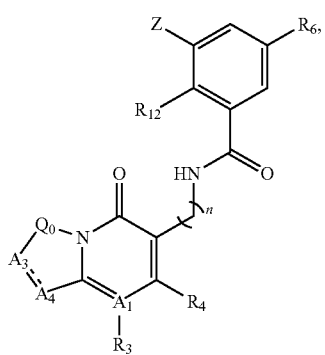

(Ia)

wherein $Q_0$ is NH or O;

==== between $A_3$ and $A_4$ is a single or double bond, each of $A_3$ and $A_4$, independently, is $CR_{15}R_{16}$, $NR_{15}$, O, or S;

each of $R_{15}$ and $R_{16}$, independently is absent, H, halo, hydroxyl, $C_1$-$C_6$ alkyl, $C_1$-$C_6$ haloalkyl, C(O)OH, C(O)O—$C_1$-$C_6$ alkyl, C(O)O—$C_1$-$C_6$ haloalkyl, cyano, $C_1$-$C_6$ alkoxyl, $C_1$-$C_6$ haloalkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, or 5- or 6-membered heteroaryl; and (i) when $Q_0$ is NH and ==== is a single bond, each of $A_3$ and $A_4$ independently is $CR_{15}R_{16}$, $NR_{15}$, O, or S;

(ii) when $Q_0$ is NH and ==== is a double bond, each of $A_3$ and $A_4$ independently is $CR_{15}$ or N;

(iii) when $Q_0$ is O and ==== is a single bond, each of $A_3$ and $A_4$ independently is $CR_{15}R_{16}$ or $NR_{15}$; or (iv) when $Q_0$ is O and ==== is a double bond, each of $A_3$ and $A_4$ independently is $CR_{15}$ or N.

3. The compound of claim 1, wherein the compound is of Formula (Ib):

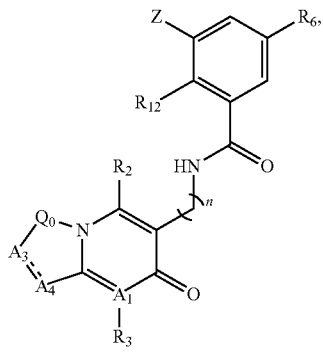

(Ib)

wherein $Q_0$ is NH or O;

==== between $A_3$ and $A_4$ is a single or double bond, each of $A_3$ and $A_4$, independently, is $CR_{15}R_{16}$, $NR_{15}$, O, or S;

each of $R_{15}$ and $R_{16}$, independently is absent, H, halo, hydroxyl, $C_1$-$C_6$ alkyl, $C_1$-$C_6$ haloalkyl, C(O)OH, C(O)O—$C_1$-$C_6$ alkyl, C(O)O—$C_1$-$C_6$ haloalkyl, cyano, $C_1$-$C_6$ alkoxyl, $C_1$-$C_6$ haloalkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, or 5- or 6-membered heteroaryl; and (i) when $Q_0$ is NH and ==== is a single bond, each of $A_3$ and $A_4$ independently is $CR_{15}R_{16}$, $NR_{15}$, O, or S;

(ii) when $Q_0$ is NH and ==== is a double bond, each of $A_3$ and $A_4$ independently is $CR_{15}$ or N;

(iii) when $Q_0$ is O and ==== is a single bond, each of $A_3$ and $A_4$ independently is $CR_{15}R_{16}$ or $NR_{15}$; or (iv) when $Q_0$ is O and ==== is a double bond, each of $A_3$ and $A_4$ independently is $CR_{15}$ or N.

4. The compound of claim 1, wherein the compound is of Formula (Ic), (Id1) or (Id2):

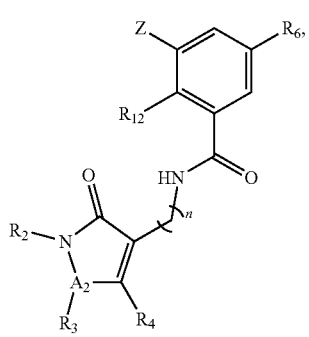

(Ic)

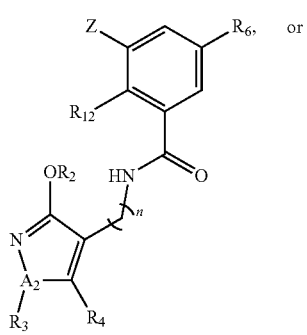

(Id1) or

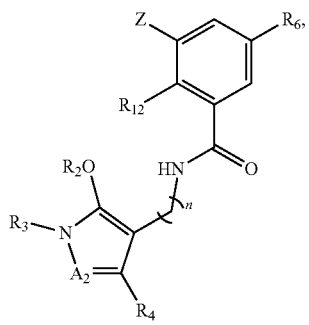

(Id2)

wherein

A$_2$ is N or O, and when A$_2$ is O, R$_3$ is absent;

each of R$_2$, R$_3$, and R$_4$, independently, is -Q$_1$-T$_1$, in which Q$_1$ is a bond or C$_1$-C$_3$ alkyl linker optionally substituted with halo, and T$_1$ is H, halo, hydroxyl, C(O)OH, cyano, azido, or R$_{S1}$, in which R$_{S1}$ is C$_1$-C$_3$ alkyl, C$_1$-C$_6$ alkoxyl, C$_3$-C$_8$ cycloalkyl, C$_6$-C$_{10}$ aryl, C$_6$-C$_{10}$ aryloxy, amino, mono-C$_1$-C$_6$ alkylamino, di-C$_1$-C$_6$ alkylamino, 4 to 12-membered heterocycloalkyl, or 5- or 6-membered heteroaryl, and R$_{S1}$ is optionally substituted with one or more substituents selected from the group consisting of halo, hydroxyl, C(O)OH, C(O)O—C$_1$-C$_6$ alkyl, cyano, C$_1$-C$_6$ alkyl, C$_1$-C$_6$ alkoxyl, amino, mono-C$_1$-C$_6$ alkylamino, di-C$_1$-C$_6$ alkylamino, C$_3$-C$_8$ cycloalkyl, C$_6$-C$_{10}$ aryl, 4 to 12-membered heterocycloalkyl, and 5- or 6-membered heteroaryl; or neighboring R$_2$ and R$_3$, together with the atoms to which they are attached, form a 6 to 12-membered heterocycloalkyl ring having 2 to 3 heteroatoms; or neighboring R$_3$ and R$_4$, together with the atoms to which they are attached, form a 6-membered heteroaryl having 1 to 3 heteroatoms, or a 6 to 12-membered heterocycloalkyl ring having 1 to 3 heteroatoms; in which each of the ring structures formed by R$_2$ and R$_3$, or by R$_3$ and R$_4$, independently is optionally substituted with one or more substituents selected from the group consisting of halo, hydroxyl, oxo, C$_1$-C$_6$ alkyl, C$_1$-C$_6$ haloalkyl, cyano, C$_1$-C$_6$ alkoxyl, C$_1$-C$_6$ haloalkoxyl, amino, mono-C$_1$-C$_6$ alkylamino, or di-C$_1$-C$_6$ alkylamino.

5. The compound of claim 1, X is

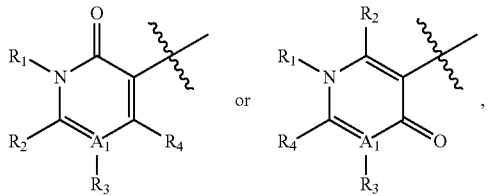

and R$_1$ is —OH.

6. The compound of claim 1, Z is NR$_7$R$_8$.

7. The compound of claim 1, wherein i) R$_6$ is C$_6$-C$_{10}$ aryl or 5- or 6-membered heteroaryl, each of which is optionally, independently substituted with one or more -Q$_2$-T$_2$, wherein Q$_2$ is a bond or C$_1$-C$_3$ alkyl linker, and T$_2$ is H, halo, cyano, —OR$_c$, —NR$_c$R$_d$, —C(O)NR$_c$R$_d$, —NR$_d$C(O)R$_c$, —S(O)$_2$R$_c$, —S(O)$_2$NR$_c$R$_d$, or R$_{S4}$, in which each of R$_c$ and R$_d$, independently is H or R$_{S5}$, each of R$_{S4}$ and R$_{S5}$, independently, is C$_1$-C$_6$ alkyl, or R$_c$ and R$_d$, together with the N atom to which they are attached, form a 4 to 7-membered heterocycloalkyl ring having 0 or 1 additional heteroatom, and each of R$_{S4}$, R$_{S5}$, and the 4 to 7-membered heterocycloalkyl ring formed by R$_c$ and R$_d$, is optionally, independently substituted with one or more -Q$_3$-T$_3$, wherein Q$_3$ is a bond or C$_1$-C$_3$ alkyl linker and T$_3$ is selected from the group consisting of H, halo, C$_1$-C$_6$ alkyl, 4 to 7-membered heterocycloalkyl, OR$_e$, —S(O)$_2$R$_e$, and —NR$_e$R$_f$, each of R$_e$ and R$_f$ independently being H or C$_1$-C$_6$ alkyl optionally substituted with OH, O—C$_1$-C$_6$ alkyl, or NH—C$_1$-C$_6$ alkyl, or -Q$_3$-T$_3$ is oxo; or any two neighboring -Q$_2$-T$_2$, together with the atoms to which they are attached form a 5- or 6-membered ring optionally containing 1-4 heteroatoms selected from N, O and S; or ii) R$_6$ is halo, C$_1$-C$_3$ alkyl, C$_2$-C$_6$ alkenyl, C$_3$-C$_6$ cycloalkyl, C(O)H, or —C(O)R$_a$, in which R$_a$ is C$_1$-C$_6$ alkyl or 4 to 12-membered heterocycloalkyl; or iii) R$_6$ is ethynyl substituted with one or more -Q$_2$-T$_2$, in which Q$_2$ is a bond or C$_1$-C$_3$ alkyl linker and T$_2$ is C$_1$-C$_6$ alkyl, C$_3$-C$_6$ cycloalkyl, or 4 to 7-membered heterocycloalkyl optionally substituted with one or more -Q$_3$-T$_3$.

8. The compound of claim 7, wherein i) R$_6$ is phenyl or pyridyl, Q$_2$ is a bond or methyl linker, and T$_2$ is H, halo, —OR$_c$, —NR$_c$R$_d$, or —S(O)$_2$NR$_c$R$_d$; or ii) R$_6$ is F, Br, or Cl; or iii) R$_6$ is

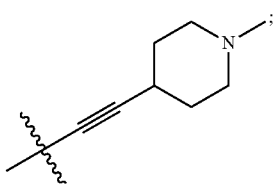 [SMILES: *C#CC1CCN(C)CC1]

or iv) R$_6$ is selected from the group consisting of CH$_3$, OCH

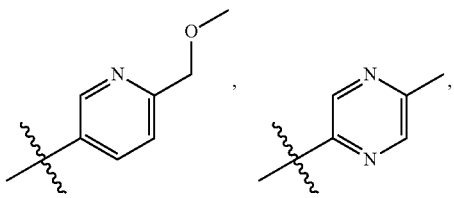

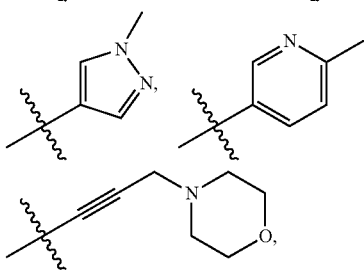

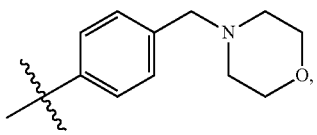

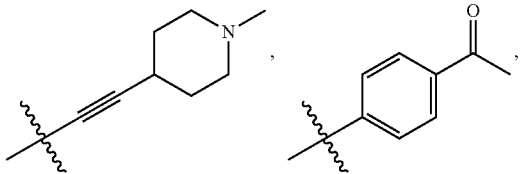

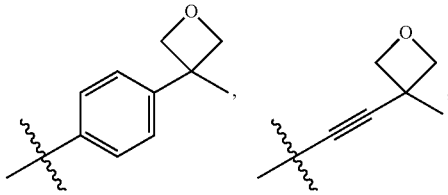

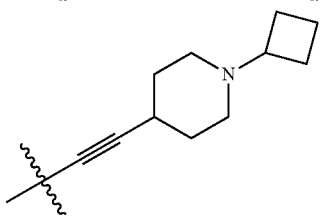

-continued

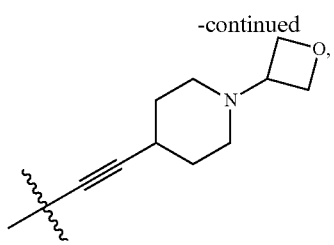

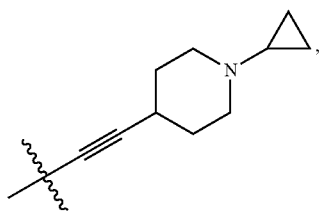

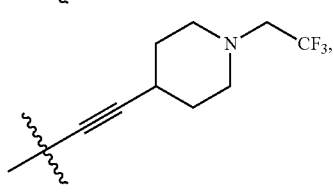

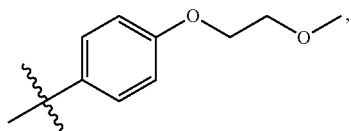

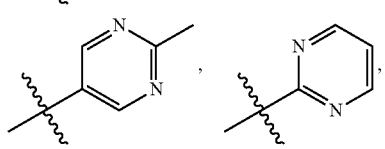

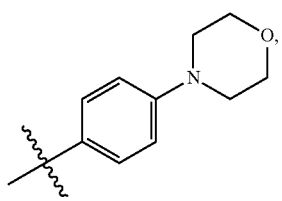

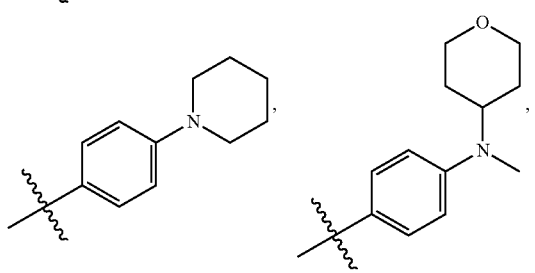

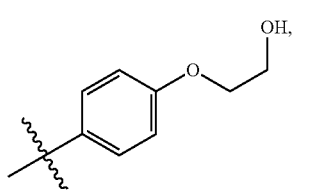

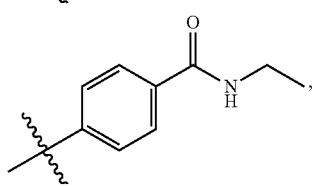

-continued

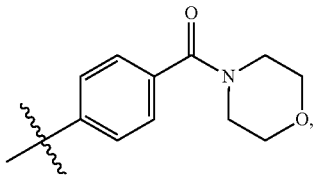

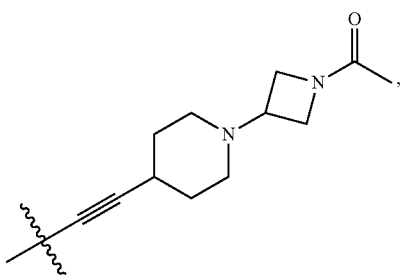

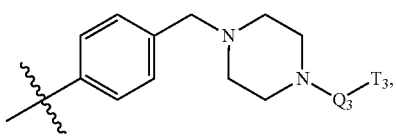

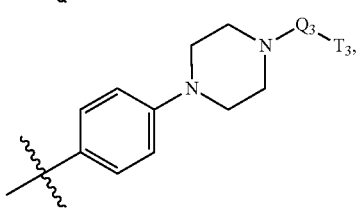

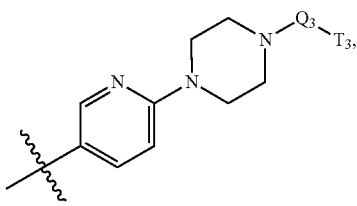

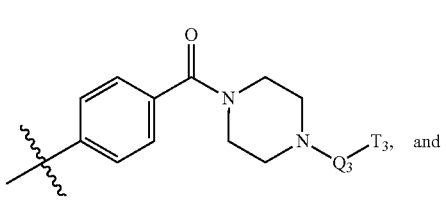

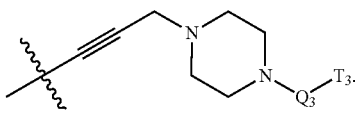

9. The compound of claim 1, wherein $R_7$ is $C_3$-$C_8$ cycloalkyl or 4 to 7-membered heterocycloalkyl, each optionally substituted with one or more -$Q_5$-$T_5$.

10. The compound of claim 9, wherein i) $R_7$ is piperidinyl, tetrahydropyran, tetrahydro-2H-thiopyranyl, piperazinyl, cyclopentyl, cyclohexyl, pyrrolidinyl, or cycloheptyl, each optionally substituted with one or more -$Q_5$-$T_5$; or ii) $R_7$ is tetrahydropyran,

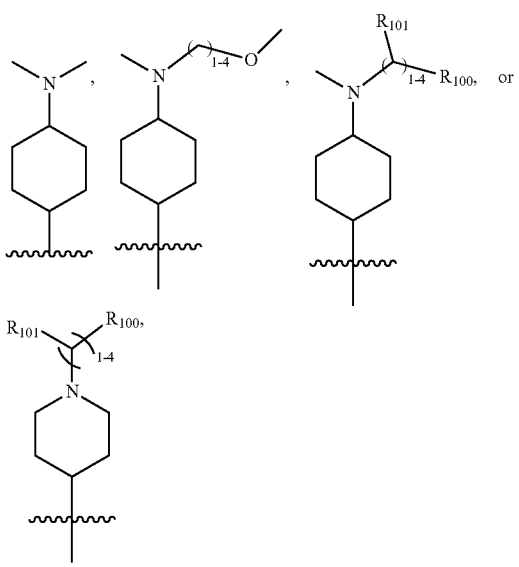

wherein $R_{100}$ is phenyl, 5- or 6-membered heteroaryl, or 4 to 12-membered heterocycloalkyl, each optionally substituted with one or more $T_{5a}$ in which each $T_{5a}$ is independently $C_1$-$C_6$ alkoxyl or O—$C_1$-$C_4$ alkylene-$C_1$-$C_4$ alkoxy, and $R_{101}$ is H or $C_1$-$C_4$ alkyl; or iii) $R_7$ is

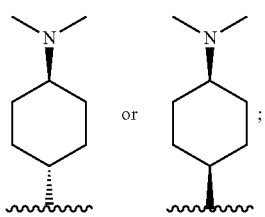

or iv) $R_7$ is

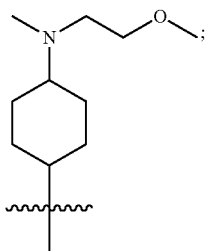 [SMILES: *C1CCC(N(C)CCOC)CC1]

or v) $R_7$ is

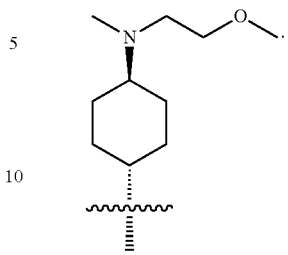

11. The compound of claim 1, wherein $R_8$ is H or $C_1$-$C_6$ alkyl which is optionally substituted with one or more substituents selected from the group consisting of halo, hydroxyl, C(O)OH, C(O)O—$C_1$-$C_6$ alkyl, cyano, $C_1$-$C_6$ alkoxyl, amino, mono-$C_1$-$C_6$ alkylamino, and di-$C_1$-$C_6$ alkylamino.

12. The compound of claim 1, wherein $R_7$ is piperidinyl, tetrahydropyran, cyclopentyl, or cyclohexyl, each optionally substituted with one -$Q_5$-$T_5$ and $R_8$ is ethyl.

13. The compound of claim 1, wherein n is 1 or 2.

14. The compound of claim 13, wherein n is 1.

15. The compound of claim 1, wherein the compound is selected from those in Tables 1-5, and pharmaceutically acceptable salts thereof.

16. A pharmaceutical composition comprising a compound of claim 1 or a pharmaceutically acceptable salt thereof and a pharmaceutically acceptable carrier.

17. A method of treating cancer wherein the cancer is lymphoma, leukemia or melanoma comprising administering to a subject in need thereof a therapeutically effective amount of a compound of claim 1 or a pharmaceutically acceptable salt thereof.

18. The method of claim 17, wherein the cancer is diffuse large B-cell lymphoma (DLBCL), non-Hodgkin's lymphoma (NHL), follicular lymphoma or diffuse large B-cell lymphoma, chronic myelogenous leukemia (CML), acute myeloid leukemia, acute lymphocytic leukemia or mixed lineage leukemia, or myelodysplastic syndromes (MDS).

19. The method of claim 17, wherein the cancer is malignant rhabdoid tumor or INI1-defecient tumor.

* * * * *

UNITED STATES PATENT AND TRADEMARK OFFICE
CERTIFICATE OF CORRECTION

PATENT NO. : 10,150,764 B2
APPLICATION NO. : 14/904801
DATED : December 11, 2018
INVENTOR(S) : John Emmerson Campbell It is certified that error appears in the above-identified patent and that said Letters Patent is hereby corrected as shown below:

In the Claims

At Column 271, Lines 43-49, second structure, in Claim 1:

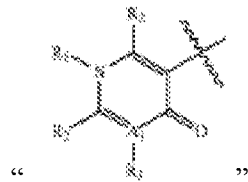
" "

Should read:

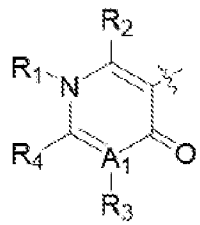
, --

At Column 274, Line number 23, in Claim 1:
"alkynyl, $C_3$-$C_5$ cycloalkyl, $C_6$-$C_{10}$ aryl, 4 to 12-mem-"
Should read:
-- alkynyl, $C_3$-$C_8$ cycloalkyl, $C_6$-$C_{10}$ aryl, 4 to 12-mem- --

At Column 278, Line number 19, in Claim 8:
"or iv) $R_6$ is selected from the group consisting of $CH_3$, OCH"
Should read:
-- or iv) $R_6$ is selected from the group consisting of $CH_3$, $OCH_3$, --

Signed and Sealed this
Fifth Day of February, 2019

Andrei Iancu
*Director of the United States Patent and Trademark Office*

SEQUENCE LISTING

```
<160> NUMBER OF SEQ ID NOS: 2

<210> SEQ ID NO 1
<211> LENGTH: 26
<212> TYPE: PRT
<213> ORGANISM: Artificial Sequence
<220> FEATURE:
<223> OTHER INFORMATION: Chemically synthesized polypeptide
<220> FEATURE:
<221> NAME/KEY: MISC_FEATURE
<222> LOCATION: (26)..(26)
<223> OTHER INFORMATION: wherein a biotin and an amide are conjugated

<400> SEQUENCE: 1

Ala Thr Lys Ala Ala Arg Lys Ser Ala Pro Ala Thr Gly Gly Val Lys
1               5                   10                  15

Lys Pro His Arg Tyr Arg Pro Gly Gly Lys
            20                  25
```

```
<210> SEQ ID NO 2
<211> LENGTH: 26
<212> TYPE: PRT
<213> ORGANISM: Artificial Sequence
<220> FEATURE:
<223> OTHER INFORMATION: Chemically synthesized polypeptide
<220> FEATURE:
<221> NAME/KEY: MISC_FEATURE
<222> LOCATION: (7)..(7)
<223> OTHER INFORMATION: wherein the lysine is dimethylated
<220> FEATURE:
<221> NAME/KEY: MISC_FEATURE
<222> LOCATION: (26)..(26)
<223> OTHER INFORMATION: wherein a biotin and an amide are conjugated

<400> SEQUENCE: 2

Ala Thr Lys Ala Ala Arg Lys Ser Ala Pro Ala Thr Gly Gly Val Lys
1               5                   10                  15

Lys Pro His Arg Tyr Arg Pro Gly Gly Lys
            20                  25
```